(12) United States Patent
Haddach et al.

(10) Patent No.: US 8,124,649 B2
(45) Date of Patent: Feb. 28, 2012

(54) OXINDOLE COMPOUNDS

(75) Inventors: Mustapha Haddach, San Diego, CA (US); Johnny Yasuo Nagasawa, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 139 days.

(21) Appl. No.: 12/495,666

(22) Filed: Jun. 30, 2009

(65) Prior Publication Data
US 2010/0041635 A1 Feb. 18, 2010

Related U.S. Application Data

(60) Provisional application No. 61/077,091, filed on Jun. 30, 2008, provisional application No. 61/156,426, filed on Feb. 27, 2009, provisional application No. 61/180,095, filed on May 20, 2009.

(51) Int. Cl.
*A61K 31/195* (2006.01)
*A61K 31/341* (2006.01)
*C07D 307/32* (2006.01)
*C07D 409/04* (2006.01)

(52) U.S. Cl. ........... 514/444; 514/473; 549/60; 549/479

(58) Field of Classification Search .................. 514/444, 514/473; 549/60, 479
See application file for complete search history.

(56) References Cited

FOREIGN PATENT DOCUMENTS

| JP | 2007-84494 A | * | 4/2007 |
|----|--------------|---|--------|
| WO | WO 2007/085188 A1 | | 8/2007 |
| WO | WO 2007/087429 A2 | | 8/2007 |

OTHER PUBLICATIONS

Bullock et al. "Structure and Substrate Specificity of the Pim-1 Kinase," J. Biol. Chem. 280(50):41675-41682 (2005).
Young, "International Search Report," 2 pages, from International Appl. No. PCT/US09/49318, United States Patent and Trademark Office, Alexandria, Virginia, USA (mailed Sep. 23, 2009).
Young, "Written Opinion of the International Searching Authority," 5 pages, from International Appl. No. PCT/US09/49318, United States Patent and Trademark Office, Alexandria, Virginia, USA (mailed Sep. 23, 2009).

* cited by examiner

*Primary Examiner* — Susannah Chung
(74) *Attorney, Agent, or Firm* — Cooley LLP

(57) ABSTRACT

The invention provides compounds that inhibit PIM kinases and Flt3 kinase, and compositions containing such compounds. These compounds and compositions are useful for treating proliferative disorders such as cancer, as well as other kinase-associated conditions including inflammation.

21 Claims, 2 Drawing Sheets

|  | @0.5μM |  | @0.5μM |  | @0.5μM |
|---|---|---|---|---|---|
| Pim-1(h) | 1 | FGFR1(h) | 90 | MST1(h) | 101 |
| Pim-2(h) | 13 | Flt1(h) | 90 | Rse(h) | 101 |
| Pim-3(h) | 13 | CDK2/cyclinA(h) | 91 | CHK1(h) | 102 |
| Flt3(h) | 19 | DYRK2(h) | 91 | GSK3β(h) | 102 |
| Flt3(D835Y)(h) | 21 | ZIPK(h) | 91 | PKCα(h) | 102 |
| DRAK1(h) | 27 | CK1γ3(h) | 92 | Ret(h) | 102 |
| HIPK2(h) | 30 | EGFR(L861Q)(h) | 93 | JAK2(h) | 103 |
| cKit(V560G)(h) | 31 | MAPKAP-K2(h) | 93 | CK2(h) | 104 |
| PKG1α(h) | 46 | EGFR(h) | 94 | CDK1/cyclinB(h) | 105 |
| Flt4(h) | 47 | EphA5(h) | 94 | Fyn(h) | 105 |
| TrkA(h) | 54 | Fer(h) | 94 | eEF-2K(h) | 106 |
| MELK(h) | 57 | KDR(h) | 94 | ASK1(h) | 107 |
| Mer(h) | 58 | Lck(h) | 94 | c-RAF(h) | 107 |
| cKit(h) | 63 | EGFR(T790M, L858R)(h) | 95 | Snk(h) | 107 |
| ARK5(h) | 65 | FAK(h) | 95 | EGFR(T790M)(h) | 108 |
| HIPK3(h) | 65 | Ron(h) | 95 | Fes(h) | 108 |
| Rsk4(h) | 67 | PDGFRα(D842V)(h) | 96 | Mnk2(h) | 108 |
| MKK7β(h) | 70 | CK1γ1(h) | 97 | TAK1(h) | 108 |
| Yes(h) | 70 | CK1γ2(h) | 97 | EphA7(h) | 109 |
| cKit(D816H)(h) | 72 | ROCK-I(h) | 97 | mTOR(h) | 110 |
| EGFR(L858R)(h) | 74 | ALK(h) | 99 | NEK2(h) | 110 |
| Rsk2(h) | 75 | DDR2(h) | 99 | P1k1(h) | 111 |
| FGFR2(h) | 78 | EphB4(h) | 99 | SRPK1(h) | 111 |
| MSK2(h) | 79 | Hck(h) | 99 | CDK6/cyclinD3(h) | 112 |
| Aurora-A(h) | 80 | MAPK1(h) | 99 | IKKα(h) | 114 |
| Rsk1(h) | 82 | PDGFRα(h) | 99 | PDK1(h) | 114 |
| Fms(h) | 83 | PKCθ(h) | 99 | Lyn(h) | 115 |
| PRAK(h) | 85 | IGF-1R(h) | 100 | Met(h) | 118 |
| MLK1(h) | 87 | IRAK4(h) | 100 | ZAP-70(h) | 118 |
| p70S6K(h) | 87 | LOK(h) | 100 | PAK2(h) | 119 |
| Rsk3(h) | 87 | MEK1(h) | 100 | PDGFRβ(h) | 119 |
| cSRC(h) | 88 | PKBα(h) | 100 | Plk3(h) | 123 |
| PKA(h) | 88 | PKD2(h) | 100 | Tie2(h) | 123 |
| Ab1(h) | 90 | CaMKI(h) | 101 | CSK(h) | 130 |
| CDK9/cyclin T1(h) | 90 | DK7/cyclinH/MAT1(h) | 101 | Ros(h) | 132 |
| CK2α2(h) | 90 | IR(h) | 101 | ErbB4(h) | 134 |

*FIG. 1*

OXINDOLE COMPOUNDS

CROSS REFERENCE TO RELATED APPLICATIONS

This application claims priority from U.S. Provisional Application Ser. No. 61/077,091, filed 30 Jun. 2008; U.S. Provisional Application Ser. No. 61/156,426, filed 27 Feb. 2009; and U.S. Provisional Application Ser. No. 61/180,095, filed 20 May 2009. The content of each of these documents is incorporated by reference herein in its entirety.

TECHNICAL FIELD

The invention relates to compounds that inhibit PIM-1, PIM-2, and/or PIM-3, and are useful for treating cancers and other conditions associated with excessive activity of one or more of these kinases, like inflammation. In addition, these compounds are also active inhibitors of Flt3 kinase, and compounds having activity against both PIM and Flt3 are provided by the invention. These novel oxindole compounds and pharmaceutical compositions containing these compounds are useful in methods of treating diseases or conditions responsive to inhibition of PIM kinases and/or Flt3 kinase, such as cancers or inflammation.

BACKGROUND ART

The PIM protein kinases which include the closely related PIM-1, -2, and -3, have been implicated in diverse biological processes such as cell survival, proliferation, and differentiation. PIM-1 is involved in a number of signaling pathways that are highly relevant to tumorigenesis [reviewed in Bachmann & Moroy, *Internat. J. Biochem. Cell Biol.*, 37, 726-730 (2005)]. Many of these are involved in cell cycle progression and apoptosis. It has been shown that PIM-1 acts as an anti-apoptotic factor via inactivation of the pro-apoptotic factor BAD (Bcl2 associated death promoter, an apoptosis initiator). This finding suggested a direct role of PIM-1 in preventing cell death, since the inactivation of BAD can enhance Bcl-2 activity and can thereby promote cell survival [Aho et al., *FEBS Letters*, 571, 43-49 (2004)]. PIM-1 has also been recognized as a positive regulator of cell cycle progression. PIM-1 binds and phosphorylates Cdc25A, which leads to an increase in its phosphatase activity and promotion of G1/S transition [reviewed in Losman et al., *JBC*, 278, 4800-4805 (1999)]. In addition, the cyclin kinase inhibitor p21$^{Waf}$ which inhibits G1/S progression, was found to be inactivated by PIM-1 [Wang et al., *Biochim. Biophys. Act.* 1593, 45-55 (2002)]. Furthermore, by means of phosphorylation, PIM-1 inactivates C-TAK1 and activates Cdc25C which results in acceleration of G2/M transition [Bachman et al., *JBC*, 279, 48319-48 (2004)].

PIM-1 appears to be an essential player in hematopoietic proliferation. Kinase active PIM-1 is required for the gp130-mediated STAT3 proliferation signal [Hirano et al., *Oncogene* 19, 2548-2556, (2000)]. PIM-1 is overexpressed or even mutated in a number of tumors and different types of tumor cell lines and leads to genomic instability. Fedorov, et al., concluded that a Phase III compound in development for treating leukemia, LY333'531, is a selective PIM-1 inhibitor. O. Fedorov, et al., *PNAS* 104(51), 20523-28 (December 2007). Evidence has been published to show that PIM-1 is involved in human tumors including prostate cancer, oral cancer, and Burkitt lymphoma (Gaidano & Dalla Faver, 1993). All these findings point to an important role of PIM-1 in the initiation and progression of human cancers, including various tumors and hematopoietic cancers, thus small molecule inhibitors of PIM-1 activity are a promising therapeutic strategy.

Additionally, PIM-2 and PIM-3 have overlapping functions with PIM-1 and inhibition of more than one isoform may provide additional therapeutic benefits. However, it is sometimes preferable for inhibitors of PIM to have little or no in vivo impact through their inhibition of various other kinases, since such effects are likely to cause side effects or unpredictable results. See, e.g., O. Fedorov, et al., *PNAS* 104(51), 20523-28 (December 2007), discussing the effects that non-specific kinase inhibitors can produce. Accordingly, in some embodiments, the invention provides compounds that are selective inhibitors of at least one of PIM-1, PIM-2, and PIM-3, or some combination of these, while having substantially less activity on certain other human kinases, as described further herein.

The implication of a role for PIM-3 in cancer was first suggested by transcriptional profiling experiments showing that PIM3 gene transcription was upregulated in EWS/ETS-induced malignant transformation of NIH 3T3 cells. These results were extended to show that PIM-3 is selectively expressed in human and mouse hepatocellular and pancreatic carcinomas but not in normal liver or pancreatic tissues. In addition, PIM-3 mRNA and protein are constitutively expressed in multiple human pancreatic and hepatocellular cancer cell lines.

The link between PIM-3 overexpression and a functional role in promoting tumorigenesis came from RNAi studies in human pancreatic and hepatocellular cancer cell lines overexpressing PIM-3. In these studies the ablation of endogenous PIM-3 protein promoted apoptosis of these cells. The molecular mechanism by which PIM-3 suppresses apoptosis is in part carried out through the modulation of phosphorylation of the pro-apoptotic protein BAD. Similar to both PIM-1 and PIM-2 which phosphorylate BAD protein, the knock-down of PIM-3 protein by siRNA results in a decrease in BAD phosphorylation at Ser112. Thus, similar to PIM-1 and 2, PIM-3 acts a suppressor of apoptosis in cancers of endodermal origin, e.g., pancreatic and liver cancers. Moreover, as conventional therapies in pancreatic cancer have a poor clinical outcome, PIM-3 could represent a new important molecular target towards successful control of this incurable disease.

At the 2008 AACR Annual Meeting, SuperGen announced that it has identified a lead PIM kinase inhibitor, SGI-1776, that causes tumor regression in acute myelogenous leukemia (AML) xenograft models (Abstract No. 4974). In an oral presentation entitled, "A potent small molecule PIM kinase inhibitor with activity in cell lines from hematological and solid malignancies," Dr. Steven Warner detailed how scientists used SuperGen's CLIMB™ technology to build a model that allowed for the creation of small molecule PIM kinase inhibitors. SGI-1776 was identified as a potent and selective inhibitor of the PIM kinases, inducing apoptosis and cell cycle arrest, thereby causing a reduction in phospho-BAD levels and enhancement of mTOR inhibition in vitro. Most notably, SGI-1776 induced significant tumor regression in MV-4-11 (AML) and MOLM-13 (AML) xenograft models. This demonstrates that inhibitors of PIM kinases can be used to treat leukemias.

Fedorov, et al., in *PNAS* vol. 104(51), 20523-28, showed that a selective inhibitor of PIM-1 kinase (Ly5333'531) suppressed cell growth and induced cell death in leukemic cells from AML patients. PIM-3 has been shown to be expressed in pancreatic cancer cells, while it is not expressed in normal pancreas cells, demonstrating that it should be a good target for pancreatic cancer. Li, et al., *Cancer Res.* 66(13), 6741-47 (2006).

Another kinase shown to be a useful target for certain cancers, including leukemia, is Flt3 kinase (FMS-like tyrosine kinase 3). Flt3 is prevalent in refractory AML patients, so inhibitors of Flt3 are useful to treat such patients. Smith, et al., reported an alkaloid called CEP-701 that is a potent inhibitor of Flt3 and provided clinical responses in tested subjects with minimal dose-related toxicity. *Blood*, vol. 103(10), 3669-76 (2004). Dual inhibitors that are active against both PIM and Flt3 may be advantageous over inhibitors of either target alone. In particular, excessive Flt3 activity is associated with refractory AML, so dual inhibitors of PIM and Flt3 such as compounds disclosed herein are useful to treat refractory AML.

In addition, Flt3 inhibitors are useful to treat inflammation. Inhibitors of Flt3 have been shown to be effective to treat airway inflammation in mice, using a murine asthma model. Edwan, et al., *J. Immunologoy*, 5016-23 (2004). Accordingly, the compounds of the invention, and particularly compounds of formula (II) and formula (III) are useful to treat conditions associated with excessive activity of Flt3, including inflammation such as airway inflammation and asthma.

Collectively, these results demonstrate that inhibitors of PIM kinases and Flt3 kinase are useful for treating certain types of cancers. Accordingly, the identification of compounds that specifically inhibit, regulate and/or modulate the signal transduction of PIM-1, PIM-2, PIM-3, and/or Flt3 is desirable as a means to treat or prevent disease states associated with abnormal cell proliferation, such as cancer. The invention provides compounds, compositions and methods that address this need and are useful for treating cancers.

EMBODIMENTS OF THE INVENTION

The present invention in part provides chemical compounds having certain biological activities that include, but are not limited to, inhibiting cell proliferation, inhibiting angiogenesis, and modulating protein kinase activities. The present invention provides compounds that inhibit PIM-1, PIM-2 and/or PIM-3, and may also inhibit Flt3. The present invention also in part provides methods for preparing novel chemical compounds, and analogs thereof, and methods of using these compounds. Also provided are compositions comprising the above-described molecules in combination with other materials, including other therapeutic agents, and methods for using such compositions.

Certain compounds of the invention have general structural formula (I):

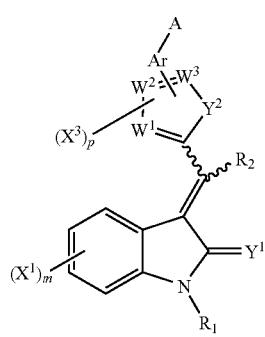

(I)

wherein:
$R^1$ is selected from H, alkyl, substituted alkyl, —$SO_2NR_2$, and —C(=O)R;
$R^2$ is selected from H, D, alkyl, and substituted alkyl;
$Y^1$ is O or S;
$Y^2$ is O, S or $NR^1$;
each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;
m, n and p each independently represent 0, 1 or 2;
$W^1$, $W^2$ and $W^3$ are each independently C or N, wherein each C is substituted with H or $X^3$ or Ar, provided that either $W^2$ or $W^3$ is the point of attachment for Ar;
Ar is a 5-10 membered aromatic or heteroaromatic group that is optionally substituted with $(X^2)_n$;
A is selected from the group consisting of $CH_2Q$, —O—Z, —NRZ, $SO_qZ$, $SO_qNRZ$, $NRSO_qZ$, NR—C(O)Z, NRC(O)—OZ, NRC(O)—NRZ, NRC(O)—OZ, OC(O)NRZ, —C(=O)OZ and —C(=O)NRZ,
where Z is H, alkyl, substituted alkyl, heterocyclyl, substituted heterocyclyl, aryl, or substituted aryl,
and Q is OZ or NRZ;
R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member,
and R and Z, when both present on A or Q, can optionally cyclize to form a 5-7 membered ring that can be substituted and can include an additional O, N or S as a ring member; and
each q is independently 0, 1 or 2;
or a pharmaceutically acceptable salt or labeled form thereof.

Other compounds of the invention have general structural formula (I'):

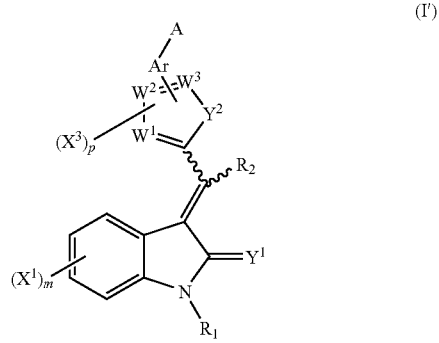

(I')

wherein:
$R^1$ is selected from H, alkyl, substituted alkyl, —$SO_2NR_2$, and —C(=O)R;
$R^2$ is selected from H, alkyl, and substituted alkyl;
$Y^1$ is O or S;
$Y^2$ is O, S or $NR^1$;
each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;
m, n and p each independently represent 0, 1 or 2;
$W^1$, $W^2$ and $W^3$ are each independently C or N, wherein each C is substituted with H or $X^3$ or Ar, provided that either $W^2$ or $W^3$ is the point of attachment for Ar;
Ar is a 5-10 membered aromatic or heteroaromatic group that is optionally substituted with $(X^2)_n$;
A is selected from the group consisting of $CH_2Q$, —O—Z, —NRZ, $SO_qZ$, $NRSO_qZ$, NR—C(O)Z, NRC(O)—OZ, NRC(O)—NRZ, NRC(O)—OZ, OC(O)NRZ, —C(=O)OZ and —C(=O)NRZ, where Z is H, alkyl, substituted alkyl, heterocyclyl, substituted heterocyclyl, aryl, or substituted aryl, and Q is OZ or NRZ;

R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and each q is independently 0, 1 or 2;

or a pharmaceutically acceptable salt thereof.

In specific embodiments, the compounds of Formula III have the formula (IIIa):

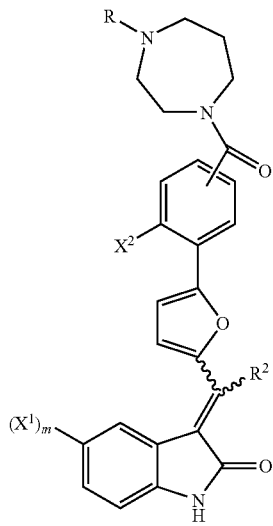

wherein m is 0 or 1, and $X^1$ is Cl or F;

$X^2$ is selected from H, Cl, OH, OMe, $NH_2$, NHMe, Me, and F;

$R^2$ is H, D or Me; and

R is H, Me, Et, or isopropyl;

or a pharmaceutically acceptable salt or labeled form thereof.

Other compounds of the invention have general structural formula (IV):

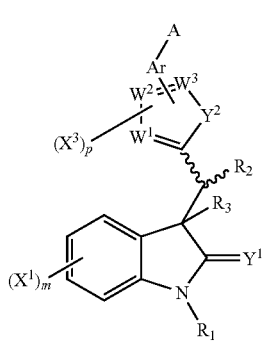

wherein:

$R^1$ is selected from H, alkyl, substituted alkyl, —$SO_2NR_2$, and —C(=O)R;

$R^2$ is selected from H, D, alkyl and substituted alkyl;

$R^3$ is selected from H, D, F, OH, alkyl, and substituted alkyl;

$Y^1$ is O or S;

$Y^2$ is O, S or $NR^1$;

each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;

m, n and p each independently represent 0, 1 or 2;

$W^1$, $W^2$ and $W^3$ are each independently C or N, wherein each C is substituted with H or $X^3$ or Ar, provided that either $W^2$ or $W^3$ is the point of attachment for Ar;

Ar is a 5-10 membered aromatic or heteroaromatic group that is optionally substituted with $(X^2)_n$;

A is selected from the group consisting of $CH_2Q$, —O—Z, —NRZ, $SO_qZ$, $SO_qNRZ$, $NRSO_qZ$, NR—C(O)Z, NRC(O)—OZ, NRC(O)—NRZ, NRC(O)—OZ, OC(O)NRZ, —C(=O)OZ and —C(=O)NRZ, where Z is H, alkyl, substituted alkyl, heterocyclyl, substituted heterocyclyl, aryl, or substituted aryl, and Q is OZ or NRZ;

R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and each q is independently 0, 1 or 2;

or a pharmaceutically acceptable salt or labeled form thereof.

Other compounds of the invention have general structural formula (IV'):

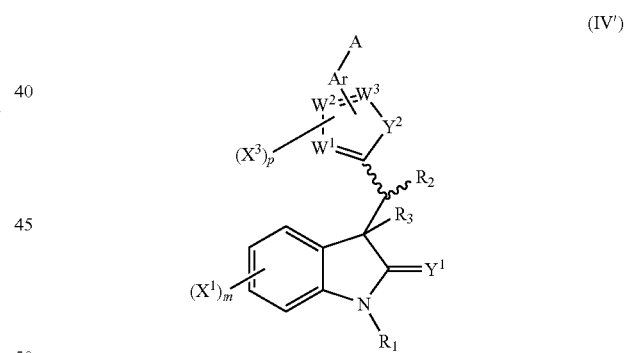

wherein:

$R^1$ is selected from H, alkyl, substituted alkyl, —$SO_2NR_2$, and —C(=O)R;

$R^2$ is selected from H, alkyl, and substituted alkyl;

$R^3$ is selected from H, F, OH, alkyl, and substituted alkyl;

$Y^1$ is O or S;

$Y^2$ is O, S or $NR^1$;

each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;

m, n and p each independently represent 0, 1 or 2;

$W^1$, $W^2$ and $W^3$ are each independently C or N, wherein each C is substituted with H or $X^3$ or Ar, provided that either $W^2$ or $W^3$ is the point of attachment for Ar;

Ar is a 5-10 membered aromatic or heteroaromatic group that is optionally substituted with $(X^2)_n$;

A is selected from the group consisting of $CH_2Q$, —O—Z, —NRZ, $SO_qZ$, $NRSO_qZ$, NR—C(O)Z, NRC(O)—OZ, NRC(O)—NRZ, NRC(O)—OZ, OC(O)NRZ, —C(=O)OZ and —C(=O)NRZ, where Z is H, alkyl, substituted alkyl, heterocyclyl, substituted heterocyclyl, aryl, or substituted aryl, and Q is OZ or NRZ;

R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and each q is independently 0, 1 or 2;

or a pharmaceutically acceptable salt thereof.

Specific compounds useful for the methods described below are exemplified throughout the specification, and each of these compounds that corresponds to Formula I is a preferred species, useful in the compositions and methods described herein.

In other aspects, the invention provides a pharmaceutical composition comprising a compound of one of the formulae provided herein, a method of inhibiting the in vivo activity of PIM-1, PIM-2, PIM-3 and/or Flt3 using a compound of one of the formulae described herein, and a method of treating proliferative diseases and inflammatory conditions with a compound of one of the formulae described herein.

Also provided are methods for modulating the activity of a Pim protein, which comprise contacting a system comprising the protein with a compound described herein in an amount effective for modulating the activity of the protein. In certain embodiments, the system is a cell, and in other embodiments the system is a cell-free system. In certain embodiments, the activity of the Pim protein is inhibited.

Provided also are methods for inhibiting cell proliferation, which comprise contacting cells with a compound described herein in an amount effective to inhibit proliferation of the cells. The cells sometimes are in a cell line, such as a cancer cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer. The cancer sometimes is cancer of the breast, prostate, pancreas, lung, colorectum, skin, or ovary. In some embodiments, the cell proliferative condition is a non-tumor cancer, such as a hematopoietic cancer, for example, including leukemias and lymphomas. The cell proliferative condition is macular degeneration in some embodiments.

The invention also includes methods for treating cancer or an inflammatory disorder in a subject in need of such treatment, comprising: administering to the subject a therapeutically effective amount of a therapeutic agent useful for treating such disorder; and administering to the subject a molecule that inhibits Pim and/or Flt in an amount that is effective to enhance a desired effect of the therapeutic agent. In certain embodiments, the molecule that inhibits Pim and/or Flt is a compound of Formula I, or a pharmaceutically acceptable salt thereof. In certain embodiments, the desired effect of the therapeutic agent that is enhanced by the molecule that inhibits Pim and/or Flt is an increase in apoptosis in at least one type of cell.

In some embodiments, the therapeutic agent and the molecule that inhibits Pim and/or Flt are administered at substantially the same time. The therapeutic agent and molecule that inhibits Pim and/or Flt sometimes are used concurrently by the subject. The therapeutic agent and the molecule that inhibits Pim and/or Flt can be combined into one pharmaceutical composition in certain embodiments; in other embodiments that are administered as separate compositions.

Also provided are compositions of matter comprising a compound described herein and an isolated protein. The protein sometimes is a Pim protein. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hematopoietic cancer, colorectal cancer, skin cancer, of ovary cancer cell line.

The foregoing merely summarizes certain aspects of the invention and is not intended to be limiting in nature. These aspects and other aspects and embodiments are described more fully below. The patent and scientific literature referred to herein establishes knowledge that is available to those with skill in the art.

BRIEF DESCRIPTION OF THE DRAWINGS

FIG. 1 shows activity of a compound of Formula (III) against a panel of over 100 kinases. The compound was tested for activity at 0.5 micromolar concentration. The chart demonstrates that compounds of the invention are more active on PIM than on many other known kinases, and are selective by a significant margin over a group of kinases that includes AST1, MST1, Ab1, CDK2, EGFR, PDGFRa, MAPK, CK1g, PKD2, GSK3b, PKCa, JAK2, CK2, CDK1, c-RAF, mTOR, PDK1, and PAK2. Note that the compound also exhibits activity against a few other kinases, including Flt3.

MODES OF CARRYING OUT THE INVENTION

Figure 2:
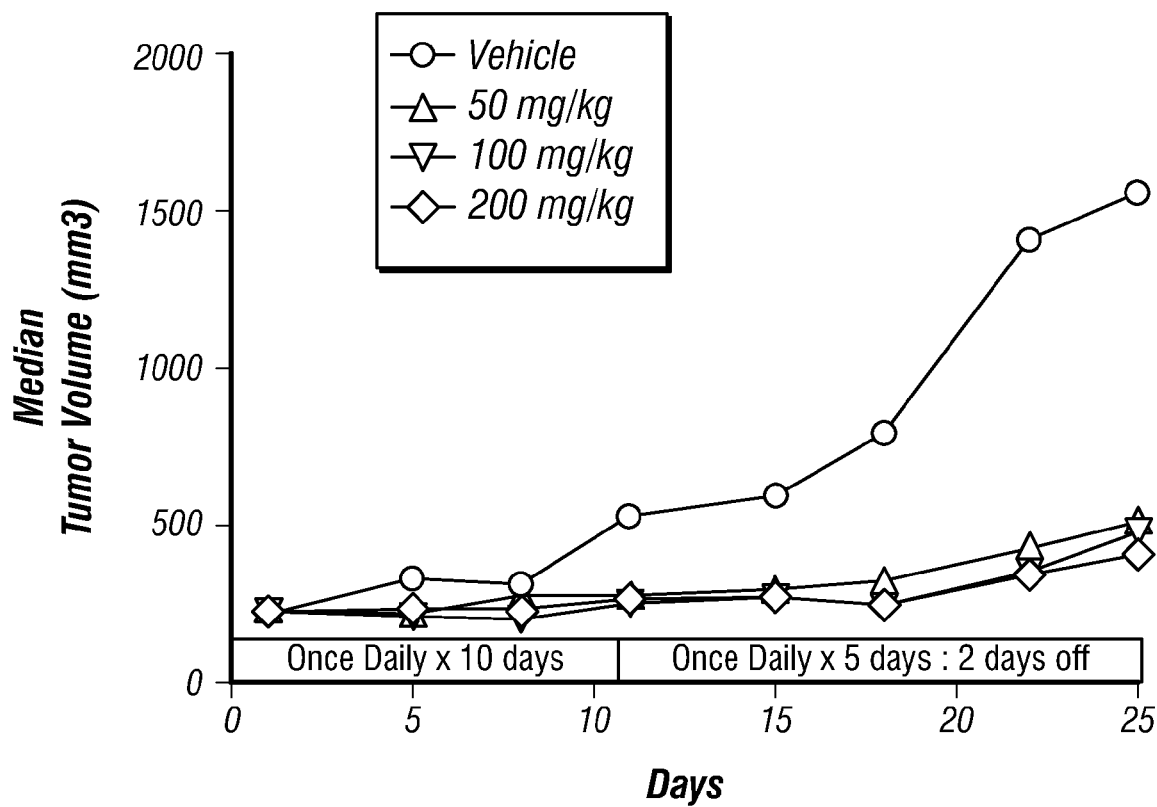
FIG. 2 shows activity of a compound of Formula (III) in the MV4-11 xenograft model of acute lymphocytic leukemia.

Compounds of Formula I exert biological activities that include, but are not limited to, inhibiting cell proliferation, reducing angiogenesis, preventing or reducing inflammatory responses and pain, and modulating certain immune responses. Compounds of this Formula can modulate Pim activity, Flt activity or both, as demonstrated by the data herein. Such compounds therefore can be utilized in multiple applications by a person of ordinary skill in the art. For example, compounds described herein can be used, for example, for (i) modulation of Pim activity (e.g., PIM-1 activity), (ii) modulation of Flt activity (e.g., Flt3 activity), (iii) modulation of cell proliferation, (iv) modulation of apoptosis, and (v) treatments of cell proliferation related disorders (e.g., administration alone or co-administration with another molecule).

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed, including both E and Z isomers of double bonds that are not in rings. The compounds of the invention may also exist in more than one tautomeric form; the depiction herein of one tautomer is for convenience only, and is also understood to encompass other tautomers of the form shown.

As an example, only, the compounds of Formula I have a Carbon-Carbon double bond to which group $R^2$ is attached. The Formula is depicted to indicate it can represent either the E isomer or the Z isomer, or both. Other structures may appear to depict a specific isomer, but that is merely for convenience, and is not intended to limit the invention to the depicted olefin isomer.

As used herein, "hydrocarbyl residue" refers to a residue which contains only carbon and hydrogen. The residue may be aliphatic or aromatic, straight-chain, cyclic, branched, saturated or unsaturated, or any combination of these. The hydrocarbyl residue, when so stated however, may contain heteroatoms in addition to or instead of the carbon and hydrogen members of the hydrocarbyl group itself. Thus, when specifically noted as containing heteroatoms the hydrocarbyl group may contain heteroatoms within the "backbone" of the hydrocarbyl residue, and when optionally substituted, the hydrocarbyl residue may also have one or more carbonyl groups, amino groups, hydroxyl groups and the like in place of one or more hydrogens of the parent hydrocarbyl residue.

As used herein, "inorganic substituent" refers to a group that does not contain carbon. Examples include, but are not limited to, halo, hydroxy, $NO_2$ or $NH_2$.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Alternatively, they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, $NR'COOR'$, $NR'COR'$, CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., $-NR_2$, or —NR—C(O)R), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Where these terms are used, the alkyl, alkenyl, or alkynyl group still includes at least one carbon in its backbone, i.e., a single heteroatom linker such as —O— is not intended to be within the scope of these terms, while —O—$CH_2$— would be included. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom (i.e., its open valence for connecting to a molecule is on a ring carbon), and "cycloalkylalkyl" may be used to describe a carbocyclic non-aromatic group that is connected to the molecule through an alkylene linker. Similarly, "heterocyclyl" may be used to describe a non-aromatic cyclic group that contains at least one heteroatom (typically selected from N, O and S) as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (—C(O)—), and heteroacyl refers to the corresponding groups wherein at least one carbon other than the carbonyl carbon has been replaced by a heteroatom chosen from N, O and S. The other open valence of the carbonyl is available to connect the acyl group or heteroacyl group to a base molecule. Thus heteroacyl includes, for example, —C(=O)OR and —C(=O)$NR_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups. Where a substituent group contains two R or R' groups on the same or adjacent atoms (e.g., —$NR_2$, or —NR—C(O)R), the two R or R' groups can optionally be taken together with the atoms in the substituent group to which they are attached to form a ring having 5-8 ring members, which can be substituted as allowed for the R or R' itself, and can contain an additional heteroatom (N, O or S) as a ring member.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Sometimes it refers to —$(CH_2)_n$— where n is 1-8 and preferably n is 1-4, though where specified, an alkylene can also be substituted by other groups, and can be of other lengths. The open valences of an alkylene need not be at opposite ends of a chain. Thus —CH(Me)- and —$C(Me)_2$- are also included within the scope of the term 'alkylenes', as are cyclic groups such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. In some embodiments, the number of substituents permitted on a group is equal to the number of carbon atoms in the group. Where an optional substituent is attached via a double bond, such as a carbonyl oxygen (=O), the group occupies two available valences, so the total number of other substituents that may be included is reduced according to the number of other available valences.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

In one aspect, the invention provides novel compounds that are inhibitors of PIM kinases; such compounds are effective to treat cancers. The compounds may be inhibitors of one or more of PIM-1, PIM-2, and PIM-3. In some embodiments, the compounds are selective inhibitors of one or more of these three targets, and are significantly less active as inhibitors of other kinases such as AST1, MST1, Ab1, CDK2, EGFR, PDGFRa, MAPK, CK1g, PKD2, GSK3b, PKCa, JAK2, CK2, CDK1, c-RAF, mTOR, PDK1, and PAK2. In other embodiments, the compounds may inhibit other kinases in addition to one or more PIM kinases.

In one aspect, the novel compounds of the invention are compounds having the structure shown in formula (I):

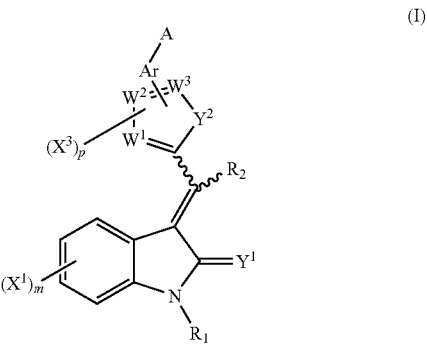

wherein:

$R^1$ is selected from H, alkyl, substituted alkyl, $-SO_2NR_2$, and $-C(=O)R$;

$R^2$ is selected from H, D, alkyl, and substituted alkyl;

$Y^1$ is O or S;

$Y^2$ is O, S or $NR^1$;

each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;

m, n and p each independently represent 0, 1 or 2;

$W^1$, $W^2$ and $W^3$ are each independently C or N, wherein each C is substituted with H or $X^3$ or Ar, provided that either $W^2$ or $W^3$ is the point of attachment for Ar;

Ar is a 5-10 membered aromatic or heteroaromatic group that is optionally substituted with $(X^2)_n$;

A is selected from the group consisting of $CH_2Q$, $-O-Z$, $-NRZ$, $SO_qZ$, $SO_qNRZ$, $NRSO_qZ$, $NR-C(O)Z$, NRC(O)-OZ, NRC(O)-NRZ, NRC(O)-OZ, OC(O)NRZ, $-C(=O)OZ$ and $-C(=O)NRZ$, where Z is H, alkyl, substituted alkyl, heterocyclyl, substituted heterocyclyl, aryl, or substituted aryl, and Q is OZ or NRZ;

R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and each q is independently 0, 1 or 2;

or a pharmaceutically acceptable salt or labeled form thereof.

In another aspect, the novel compounds of the invention are compounds having the structure shown in formula (I'):

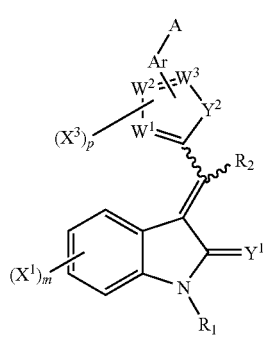
(I')

wherein:

$R^1$ is selected from H, alkyl, substituted alkyl, —$SO_2NR_2$, and —C(=O)R;

$R^2$ is selected from H, alkyl, and substituted alkyl;

$Y^1$ is O or S;

$Y^2$ is O, S or $NR^1$;

each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;

m, n and p each independently represent 0, 1 or 2;

$W^1$, $W^2$ and $W^3$ are each independently C or N, wherein each C is substituted with H or $X^3$ or Ar, provided that either $W^2$ or $W^3$ is the point of attachment for Ar;

Ar is a 5-10 membered aromatic or heteroaromatic group that is optionally substituted with $(X^2)_n$;

A is selected from the group consisting of $CH_2Q$, —O—Z, —NRZ, $SO_qZ$, $NRSO_qZ$, NR—C(O)Z, NRC(O)—OZ, NRC(O)—NRZ, NRC(O)—OZ, OC(O)NRZ, —C(=O)OZ and —C(=O)NRZ, where Z is H, alkyl, substituted alkyl, heterocyclyl, substituted heterocyclyl, aryl, or substituted aryl, and Q is OZ or NRZ;

R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and each q is independently 0, 1 or 2;

or a pharmaceutically acceptable salt thereof.

In some embodiments of compounds of formula (I) and (I'), $Y^1$ is O. In some embodiments, $R^1$ is H, Me or —C(=O)R. In preferred embodiments, $R^1$ is H.

In some embodiments, $Y^2$ is O. In other embodiments, $Y^2$ is S. In still other embodiments, $Y^2$ is $NR^1$.

In some embodiments of formula (I), $R^2$ is H, D, Me, Et, cyclopropyl, isopropyl, or $CH_2OH$. In preferred embodiments, $R^2$ is H or D.

In some embodiments of formula (I'), $R^2$ is H, Me, Et, cyclopropyl, isopropyl, or $CH_2OH$. In preferred embodiments, $R^2$ is H.

In some embodiments of formula (I) and (I'), $W^1$ and $W^2$ are each independently CH or CMe. In preferred embodiments, both $W^1$ and $W^2$ are CH.

In some of the foregoing embodiments, m is 1. When m is 1, in some embodiments $X^1$ is halo.

In formula (I) and (I'), $W^1$, $W^2$ and $W^3$ are each independently C or N, wherein each C is substituted with H or $X^3$ or Ar, provided that either $W^2$ or $W^3$ is C and is the point of attachment for Ar. Since Ar is attached to one position of this ring, no more than two of $W^1$, $W^2$ and $W^3$ can be N, and preferably at most one of $W^1$, $W^2$ and $W^3$ is N and the other two are both carbon. In some preferred embodiments, $W^1$, $W^2$ and $W^3$ are each carbon.

In some embodiments, $W^1$ is C, and one of $W^2$ and $W^3$ is N.

In the foregoing compounds, sometimes $W^3$ is the point of attachment for Ar. In other embodiments of these compounds, $W^2$ is the point of attachment for Ar. Preferably, $W^3$ is C and is the point of attachment for Ar.

In some embodiments of the foregoing compounds, Ar is phenyl or pyridyl or pyrazinyl, each of which can be substituted. In some embodiments, Ar is 3-pyridyl; or Ar is phenyl; or Ar is 2-pyrazinyl.

In some embodiments of the foregoing compounds, A comprises an amide linkage. In some embodiments of the foregoing compounds, Ar is preferably phenyl or 3-pyridyl. Preferably, A is attached to Ar at a position that is meta or para relative to the point where Ar attaches to $W^2$ or $W^3$, i.e., A and $W^2$ (or $W^3$) are not attached at adjacent atoms of the ring Ar in such embodiments.

Ar in the foregoing embodiments can be substituted. In some embodiments, Ar is substituted with one group selected from halo, amino, alkyl, and hydroxyl, in addition to A.

In some embodiments of the foregoing compounds, A is selected from the group consisting of $CH_2Q$, —O—Z, —NRZ, $SO_qZ$, $SO_qNRZ$, $NRSO_qZ$, NR—C(O)Z, NRC(O)—OZ, NRC(O)—NRZ, NRC(O)—OZ, OC(O)NRZ, —C(=O)OZ and —C(=O)NRZ, where q, R and Z are defined as further described herein. In some embodiments of the foregoing compounds, A is —NR—C(O)Z or —C(=O)NRZ, wherein R is H or Me. In other embodiments wherein R and Z of the group A are linked together to form an optionally substituted ring, such as an optionally substituted pyrrolidine, piperidine, piperazine, homopiperazine, morpholine, or thiomorpholine. In some such embodiments wherein A is —NR—C(O)Z or —C(=O)NRZ. In still other embodiments, A is —NRZ or —OZ.

In some embodiments of the compounds described above, Z is a group of the formula —$(CH_2)_rZ'$, wherein r is 0, 1, 2, 3, or 4, and Z' is —$NR^1R^2$ or a 5-6 membered heteroaryl or heterocyclic ring containing at least one N as a ring member, and optionally substituted. In some embodiments, Z' is 1-pyrrolidinyl, 2-pyridinyl, 3-pyridinyl, 4-pyridinyl, 2-pyrazinyl, 1-imidazolyl, 2-imidazolyl, 4-imidazolyl, 3-piperidinyl, 1-piperidinyl, 4-morpholinyl, 2-thiazolinyl, and 2-thiazolidinyl.

In some embodiments, the compound of formula (I) is a compound of formula (II):

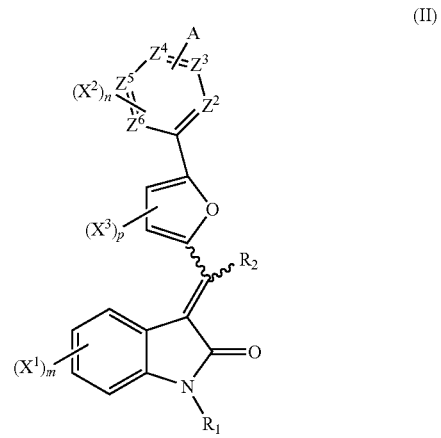
(II)

wherein A, $R^1$, $R^2$, $X^1$, $X^2$, $X^3$, m, n, and p are as defined above for compounds of formula (I), and each of $Z^3$, $Z^4$, $Z^4$, $Z^5$ and $Z^6$ is independently C or N, provided not more than two of $Z^2$, $Z^3$, $Z^4$, $Z^5$ and $Z^6$ are N, and wherein each C is CH or $CX^2$ or is the point of attachment for A, or a pharmaceutically acceptable salt or labeled form thereof.

In some embodiments, the compound of formula (I') is a compound of formula (II'):

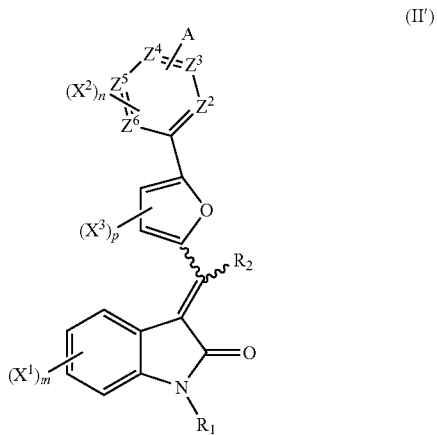

(II')

wherein A, $R^1$, $R^2$, $X^1$, $X^2$, $X^3$, m, n, and p are as defined above for compounds of formula (I'), and each of $Z^2$, $Z^3$, $Z^4$, $Z^5$ and $Z^6$ is independently C or N, provided not more than two of $Z^2$, $Z^3$, $Z^4$, $Z^5$ and $Z^6$ are N, and wherein each C is CH or $CX^2$ or is the point of attachment for A.

In some embodiments of formula (II) and (II'), $Z^3$ is C-A.

In some embodiments of formula (II) and (II'), $Z^6$ is N and $Z^3$ is N. A in such embodiments can be attached at $Z^5$.

In some embodiments of formula (II) and (II'), A is —C(=O)—NRZ or —NRC(O)Z, wherein R is H or Me; or A is —NRZ or —OZ. In some such embodiments wherein A is —NR—C(O)Z or —C(=O)NRZ, R and Z of the group A are linked together to form an optionally substituted ring, such as an optionally substituted pyrrolidine, piperidine, piperazine, homopiperazine, morpholine, or thiomorpholine.

In compounds of formula (II) and (II'), sometimes m is 1; and when m is 1, in some embodiments $X^1$ is halo.

In some embodiments of the compounds of formula (II) and (II'), $Z^4$ and $Z^5$ are both C.

In some embodiments of the compounds of formula (II) and (II'), $Z^4$ is C-A. In these embodiments, sometimes $Z^3$ is N.

In some embodiments of the compounds of formula (II) and (II') described above, $Z^2$ and $Z^6$ are both CH.

In some embodiments of the compounds of formula (II) and (II') described above, p is 0.

In some embodiments of the compounds of formula (II) and (II') described above, n is 0.

In another aspect, the invention provides a compound of the formula (III):

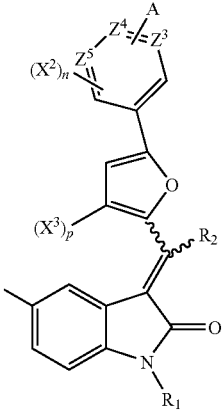

(III)

wherein $X^1$ is Cl or F, and m is 0 or 1;
$R^2$ is selected from H, D, alkyl, and substituted alkyl;
$X^2$ is halo, $NH_2$, OH, or $CH_2OH$, and n is 0 or 1;
$X^3$ is Me, and p is 0 or 1;
one of $Z^3$ and $Z^4$ is CH and the other of $Z^3$ and $Z^4$ is CA;
$Z^5$ is N or CH, or $Z^5$ can be CX if n is 1;
$R^1$ is H or —C(O)R;
A is COOH, OH, $CH_2OH$, $NH_2$, $CONH_2$, —$SO_2NH_2$, —$NHSO_2CF_3$, tetrazole, or a group of the formula -L-Az, wherein L is a linker selected from the group consisting of —NR—, —C(O)—, —O—, —NRC(O)—, —C(O)NR—, —$NRSO_2$—, —$SO_2NR$—, —NRC(O)—$(CH_2)_r$—, and —C(O)NR—$(CH_2)_r$, where each r is independently 1-3;
each R is independently H, alkyl or substituted alkyl; and
Az represents a 5-7-membered nitrogen-containing heterocyclic or heteroaryl group;
or a pharmaceutically acceptable salt or labeled form thereof.

In another aspect, the invention provides a compound of the formula (III'):

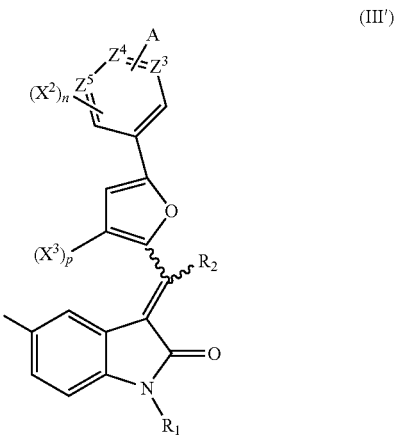

(III')

wherein $X^1$ is Cl or F, and m is 0 or 1;
$R^2$ is selected from H, alkyl, and substituted alkyl;
$X^2$ is halo, $NH_2$, OH, or $CH_2OH$, and n is 0 or 1;
$X^3$ is Me, and p is 0 or 1;
one of $Z^3$ and $Z^4$ is CH and the other of $Z^3$ and $Z^4$ is CA;
$Z^5$ is N or CH, or $Z^5$ can be CX if n is 1;
$R^1$ is H or —C(O)R;
and A is COOH, OH, $CH_2OH$, $NH_2$, $CONH_2$, —$SO_2NH_2$, —$NHSO_2CF_3$, tetrazole, or a group of the formula -L-Az, wherein L is a linker selected from the group consisting of —NR—, —C(O)—, —O—, —NRC(O)—, —C(O)NR—, —NRC(O)—$(CH_2)_r$, and —C(O)NR—$(CH_2)_r$, where each r is independently 1-3;

each R is independently H, alkyl or substituted alkyl; and

Az represents a 5-7-membered nitrogen-containing heterocyclic or heteroaryl group.

In some embodiments of the compounds of formula (III) and (III') described above, m is 0. In other embodiments, m is 1.

In some embodiments of the compounds of formula (III) and (III') described above, p is 0.

In some embodiments of the compounds of formula (III) and (III') described above, $Z^3$ is CA. In other embodiments of the compounds of formula (III) and (III') described above, $Z^4$ is CA.

In some embodiments of the compounds of formula (III) and (III') described above, n is 1 and $Z^5$ is CX. In other embodiments of the compounds of formula (III) and (III'), $Z^5$ is N. In other embodiments of the compounds of formula (III) and (III'), $Z^5$ is CH.

In preferred embodiments of formula (III) and (III'), $R^1$ is H.

In some embodiments of formula (III), $R^2$ is H. In some embodiments, $R^2$ is selected from H, D and Me. In some embodiments, $R^2$ is selected from H, D, Me, Et, cyclopropyl, isopropyl and $CH_2OH$.

In some embodiments of formula (III'), $R^2$ is H. In some embodiments, $R^2$ is selected from H and Me. In some embodiments, $R^2$ is selected from H, Me, Et, cyclopropyl, isopropyl and $CH_2OH$.

In some embodiments of the compounds of formula (III) and (III') described above, A is a group -L-Az. In some embodiments of formula (III), L is a linker selected from the group consisting of —NR—, —C(O)—, —O—, —NRC(O)—, —C(O)NR—, —NRSO$_2$—, —SO$_2$NR—, —NRC(O)—(CH$_2$)$_r$, and —C(O)NR—(CH$_2$)$_r$—. In some embodiments of formula (III) and (III'), L is a linker selected from the group consisting of —NR—, —NRC(O)—, and —C(O)NR—. In other such embodiments of formula (III) and (III'), L is selected from —NRC(O)—(CH$_2$)$_r$, and —C(O)NR—(CH$_2$)$_r$—, where each r is independently 1-3.

In specific embodiments, the compounds of Formula (III) have the formula (IIIa):

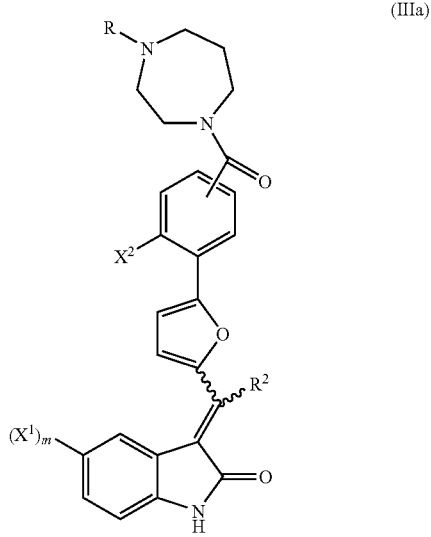

(IIIa)

wherein m is 0 or 1, and $X^1$ is Cl or F;

$X^2$ is selected from H, Cl, OH, OMe, NH$_2$, NHMe, Me, and F;

$R^2$ is H, D or Me; and

R is H, Me, Et, or isopropyl;

or a pharmaceutically acceptable salt or labeled form thereof.

In specific embodiments, the compounds of Formula (III') have the formula (IIIa'):

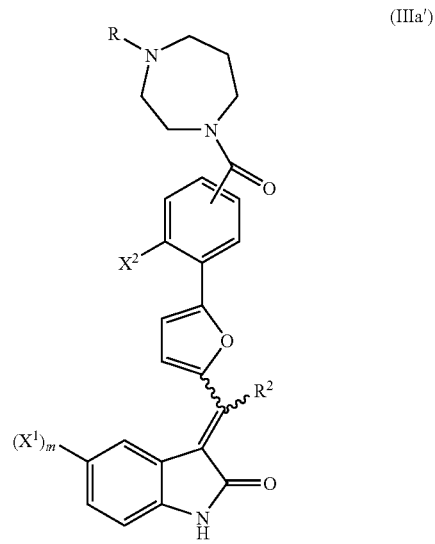

(IIIa')

wherein m is 0 or 1, and $X^1$ is Cl or F;

$X^2$ is selected from H, Cl, OH, OMe, NH$_2$, NHMe, Me, and F;

$R^2$ is H or Me; and

R is H, Me, Et, or isopropyl;

or a pharmaceutically acceptable salt thereof.

In formula IIIa and IIIa', the acyl group attached to the phenyl ring bearing $X^2$ can be at any position on the phenyl ring; preferably it is not ortho to the phenyl-furan linking bond. In specific embodiments, the acyl group is attached at the position para to (i.e., farthest from) $X^2$. In specific embodiments, the acyl group is attached at the position para to (i.e., farthest from) the bond linking the phenyl ring to the furan in Formula IIIa and IIIa'. In the compounds of Formula IIIa and IIIa', $X^2$ can sometimes be H, F or Cl. In some embodiments, R is Me or H, and Me is sometimes preferred. In many embodiments of these compounds, $R^2$ is H. In some embodiments of formula IIIa, R is D. In compounds of formula IIIa and IIIa', m can be 0, in which case $X^1$ is absent; or m can be 1, in which case $X^1$ is F or Cl. Preferably, m is 1.

In another aspect, the invention provides a compound of the formula (IV):

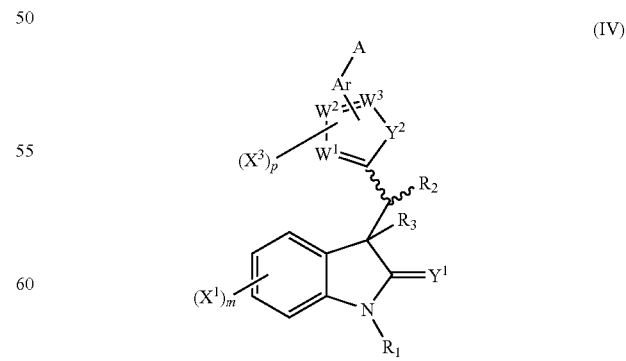

(IV)

wherein:

$R^1$ is selected from H, alkyl, substituted alkyl, —SO$_2$NR$_2$, and —C(=O)R;

$R^2$ is selected from H, D, alkyl and substituted alkyl;
$R^3$ is selected from H, D, F, OH, alkyl, and substituted alkyl;
$Y^1$ is O or S;
$Y^2$ is O, S or $NR^1$;
each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;
m, n and p each independently represent 0, 1 or 2;
$W^1$, $W^2$ and $W^3$ are each independently C or N, wherein each C is substituted with H or $X^3$ or Ar, provided that either $W^2$ or $W^3$ is the point of attachment for Ar;
Ar is a 5-10 membered aromatic or heteroaromatic group that is optionally substituted with $(X^2)_n$;
A is selected from the group consisting of $CH_2Q$, —O—Z, —NRZ, $SO_qZ$, $SO_qNRZ$, $NRSO_qZ$, NR—C(O)Z, NRC(O)—OZ, NRC(O)—NRZ, NRC(O)—OZ, OC(O)NRZ, —C(=O)OZ and —C(=O)NRZ,
where Z is H, alkyl, substituted alkyl, heterocyclyl, substituted heterocyclyl, aryl, or substituted aryl,
and Q is OZ or NRZ;
R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member,
and R and Z, when both present on A or Q, can optionally cyclize to form a 5-7 membered ring that can be substituted and can include an additional O, N or S as a ring member; and
each q is independently 0, 1 or 2;
or a pharmaceutically acceptable salt or labeled form thereof.

In another aspect, the invention provides a compound of the formula (IV'):

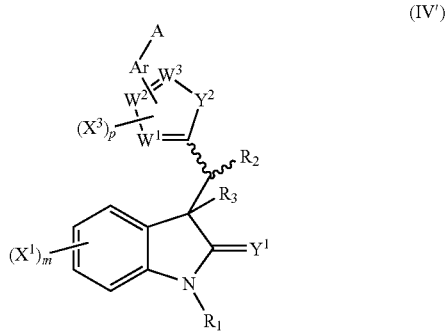

(IV')

wherein:
$R^1$ is selected from H, alkyl, substituted alkyl, —$SO_2NR_2$, and —C(=O)R;
$R^2$ is selected from H, alkyl, and substituted alkyl;
$R^3$ is selected from H, F, OH, alkyl and substituted alkyl;
$Y^1$ is O or S;
$Y^2$ is O, S or $NR^1$;
each $X^1$, $X^2$, and $X^3$ is independently selected from halo, CN, $CF_3$, $NO_2$, alkyl, substituted alkyl, OR, and $NR_2$, COR, CONR, $SO_qR$, $NSO_qR$, NRCONR, and NRC(O)OR;
m, n and p each independently represent 0, 1 or 2;
$W^1$, $W^2$ and $W^3$ are each independently C or N, wherein each C is substituted with H or $X^3$ or Ar, provided that either $W^2$ or $W^3$ is the point of attachment for Ar;
Ar is a 5-10 membered aromatic or heteroaromatic group that is optionally substituted with $(X^2)_n$;

A is selected from the group consisting of $CH_2Q$, —O—Z, —NRZ, $SO_qZ$, $NRSO_qZ$, NR—C(O)Z, NRC(O)—OZ, NRC(O)—NRZ, NRC(O)—OZ, OC(O)NRZ, —C(=O)OZ and —C(=O)NRZ,
where Z is H, alkyl, substituted alkyl, heterocyclyl, substituted heterocyclyl, aryl, or substituted aryl,
and Q is OZ or NRZ;
R is independently selected at each occurrence from the group consisting of H, alkyl or substituted alkyl, and two R on $NR_2$ can cyclize to form a 5-7 membered ring that can be substituted and may optionally contain one additional heteroatom selected from N, O and S as a ring member,
and R and Z, when both present on A or Q, can optionally cyclize to form a 5-7 membered ring that can be substituted and can include an additional O, N or S as a ring member; and
each q is independently 0, 1 or 2;
or a pharmaceutically acceptable salt thereof.

In some embodiments of compounds of formula (IV) and (IV'), $Y^1$ is O. In some embodiments, $R^1$ is H, Me or —C(=O)R. In preferred embodiments, $R^1$ is H.

In some embodiments, $Y^2$ is O. In other embodiments, $Y^2$ is S. In still other embodiments, $Y^2$ is $NR^1$.

In some embodiments of formula (IV), $R^2$ is H, D, Me, Et, cyclopropyl, isopropyl, or $CH_2OH$. In certain preferred embodiments, $R^2$ is H. In other preferred embodiments, $R^2$ is D.

In some embodiments of formula (IV'), $R^2$ is H, Me, Et, cyclopropyl, isopropyl, or $CH_2OH$. In preferred embodiments, $R^2$ is H.

In compounds of formula (IV), $R^3$ is selected from H, D, F, OH, alkyl, and substituted alkyl. In some embodiments of $R^3$ is H. In other embodiments, $R^3$ is D. In other embodiments, $R^3$ is F or OH. In further embodiments, $R^3$ is alkyl or substituted alkyl; sometimes $R^3$ is methyl. In certain embodiments of formula (IV), each of $R^2$ and $R^3$ is H. In other embodiments, each of $R^2$ and $R^3$ is D.

In compounds of formula (IV'), $R^3$ is selected from H, F, OH, alkyl, and substituted alkyl. In some embodiments of $R^3$ is H. In other embodiments, $R^3$ is F or OH. In further embodiments, $R^3$ is alkyl or substituted alkyl; sometimes $R^3$ is methyl.

In some embodiments of the foregoing compounds of formula (IV) and (IV'), $W^1$ and $W^2$ are each independently CH or CMe. In preferred embodiments, both $W^1$ and $W^2$ are CH.

In some of the foregoing embodiments, m is 1. When m is 1, in some embodiments $X^1$ is halo.

In formula (IV) and (IV'), $W^1$, $W^2$ and $W^3$ are each independently C or N, wherein each C is substituted with H or $X^3$ or Ar, provided that either $W^2$ or $W^3$ is C and is the point of attachment for Ar. Since Ar is attached to one position of this ring, no more than two of $W^1$, $W^2$ and $W^3$ can be N, and preferably at most one of $W^1$, $W^2$ and $W^3$ is N and the other two are both carbon. In some preferred embodiments, $W^1$, $W^2$ and $W^3$ are each carbon.

In some embodiments, $W^1$ is C, and one of $W^2$ and $W^3$ is N.

In the foregoing compounds, sometimes $W^3$ is the point of attachment for Ar. In other embodiments of these compounds, $W^2$ is the point of attachment for Ar. Preferably, $W^3$ is C and is the point of attachment for Ar.

In some embodiments of the foregoing compounds, Ar is phenyl or pyridyl or pyrazinyl, each of which can be substituted. In some embodiments, Ar is 3-pyridyl; or Ar is phenyl; or Ar is 2-pyrazinyl.

In some embodiments of the foregoing compounds, A comprises an amide linkage. In some embodiments of the foregoing compounds, Ar is preferably phenyl or 3-pyridyl. Preferably, A is attached to Ar at a position that is meta or para relative to the point where Ar attaches to $W^2$ or $W^3$, i.e., A and $W^2$ (or $W^3$) are not attached at adjacent atoms of the ring Ar in such embodiments.

Ar in the foregoing embodiments can be substituted. In some embodiments, Ar is substituted with one group selected from halo, amino, alkyl, and hydroxyl, in addition to A.

In compounds of formula (IV), A is selected from the group consisting of $CH_2Q$, —O—Z, —NRZ, $SO_qZ$, $SO_qNRZ$, $NRSO_qZ$, NR—C(O)Z, NRC(O)—OZ, NRC(O)—NRZ, NRC(O)—OZ, OC(O)NRZ, —C(=O)OZ and —C(=O)NRZ. In some embodiments of the foregoing compounds, A is —NR—C(O)Z or —C(=O)NRZ, wherein R is H or Me. In other embodiments wherein A is —NR—C(O)Z or —C(=O)NRZ, R and Z of the group A are linked together to form an optionally substituted ring, such as an optionally substituted pyrrolidine, piperidine, piperazine, homopiperazine, morpholine, or thiomorpholine. In still other embodiments, A is —NRZ or —OZ.

In some embodiments of the compounds described above, Z is a group of the formula —$(CH_2)_rZ'$, wherein r is 0, 1, 2, 3, or 4, and Z' is —$NR^1R^2$ or a 5-6 membered heteroaryl or heterocyclic ring containing at least one N as a ring member, and optionally substituted. In some embodiments, Z' is 1-pyrrolidinyl, 2-pyridinyl, 3-pyridinyl, 4-pyridinyl, 2-pyrazinyl, 1-imidazolyl, 2-imidazolyl, 4-imidazolyl, 3-piperidinyl, 1-piperidinyl, 4-morpholinyl, 2-thiazolinyl, and 2-thiazolidinyl.

In selected embodiments, the invention provides a compound selected from the compounds in Table 1. In further embodiments, the invention provides a compound selected from the compounds in any one of the tables provided herein.

In another aspect, the invention provides a method to treat a condition associated with excessive activity of a PIM kinase or Flt3. These conditions include cancer; thus in certain embodiments, the invention provides a method to treat cancer, comprising administering to a subject in need of treatment for cancer an effective amount of a compound as described above, of Formula (I), (I'), (II), (II'), (III), (III'), (IV) and/or (IV'). In certain embodiments, the cancer is selected from the group consisting of colon cancer, pancreatic cancer, prostate cancer, and leukemia. In specific embodiments, the cancer is acute myelogenous leukemia. Optionally, the leukemia may be refractory AML or AML associated with a mutated Flt3.

In another aspect, the invention provides a method to manufacture a medicament, wherein the medicament comprises a compound of one of the formulae as described above.

In another aspect, the invention provides a pharmaceutical composition comprising at least one compound from among the compounds described above, admixed with at least one pharmaceutically acceptable excipient. Preferably, the excipient(s) include at least one excipient other than water, ethanol or DMSO.

In yet another aspect, the invention provides a method to treat inflammation or pain, comprising administering to a subject in need of such treatment an effective amount of a compound described above. For example, methods are provided for treating pain in a subject, which comprise administering a compound described herein to a subject in need thereof in an amount effective to treat the pain. Provided also are methods of treating inflammation in a subject, which comprise administering a compound described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and allergen sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, glomerulonephritis (GN), juvenile cystic kidney disease, and type I nephronophthisis (NPHP), osteoporosis, Parkinson's disease, Guam-Parkinson dementia, supranuclear palsy, Kuf's disease, and Pick's disease, as well as memory impairment, brain ischemia, and schizophrenia, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like.

Methods for determining and monitoring effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal.

Provided also are methods for identifying a compound that reduces inflammation or pain, which comprise: contacting a system with a compound of Formula I; and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule. The invention thus in part pertains to methods for modulating angiogenesis in a subject, and methods for treating a condition associated with aberrant angiogenesis in a subject. proliferative diabetic retinopathy.

Also provided are methods for treating a condition associated with an aberrant immune response in a subject, which comprise administering a compound described herein to a subject in need thereof in an amount effective to treat the condition. Conditions characterized by an aberrant immune response include without limitation, organ transplant rejection, asthma, autoimmune disorders, including rheumatoid arthritis, multiple sclerosis, myasthenia gravis, systemic lupus erythematosus, scleroderma, polymyositis, mixed connective tissue disease (MCTD), Crohn's disease, and ulcerative colitis. In certain embodiments, an immune response may be modulated by administering a compound herein in combination with a molecule that modulates (e.g., inhibits) the biological activity of an mTOR pathway member or member of a related pathway (e.g., mTOR, PI3 kinase, AKT). In certain embodiments the molecule that modulates the biological activity of an mTOR pathway member or member of a related pathway is rapamycin. In certain embodiments, provided herein is a composition comprising a compound described herein in combination with a molecule that modulates the biological activity of an mTOR pathway member or member of a related pathway, such as rapamycin, for example.

The compounds are inhibitors of at least one PIM kinase, and frequently they are selective inhibitors that inhibit one or more of PIM-1, PIM-2 and PIM-3, while exerting less inhibition of other kinases. Other kinases for this purpose include AST1, MST1, Ab1, CDK2, EGFR, PDGFRa, MAPK, CK1g, PKD2, GSK3b, PKCa, JAK2, CK2, CDK1, c-RAF, mTOR, PDK1, and PAK2. In some embodiments, compounds of the invention are at least 3 times more active as measured by $IC_{50}$ against one or more of the PIM kinases than against any of the other kinases of interest.

The compounds of the formulae described herein may exist as tautomers of the depicted structure, and may exist as a single isomer about the carbon-carbon double bond or as a mixture of isomers. In some embodiments, the compounds may include one or more stereocenters, and thus may exist as enantiomers or diastereomers. They may also exist as rotamers (rotational isomers) wherein rotation about a bond such as an aryl-aryl bond is sufficiently hindered for two rotational isomers to be separable and relatively stable at room temperature. The invention includes each tautomer, isomer, enantiomer, diastereomer and rotational isomer, and mixtures thereof. In some embodiments, the compound of formula (I) is preferably in the E configuration with respect to the C—C double bond, meaning the ring containing $W^1$-$W^3$ is on the opposite side of the double bond (i.e, in a trans configuration) relative to the C=$Y^1$ carbon atom of the oxindole ring.

The compounds of the invention may have ionizable groups so as to be capable of preparation as pharmaceutically acceptable salts. These salts may be acid addition salts involving inorganic or organic acids, or the salts may, in the case of acidic forms of the compounds of the invention be prepared from inorganic or organic bases. Suitable pharmaceutically acceptable acids and bases are well-known in the art. Exemplary but not exclusive examples of suitable acids for forming pharmaceutically acceptable salts includes hydrochloric, sulphuric, hydrobromic, methanesulfonic, toluenesulfonic, phosphoric, lactic, succinic, benzoic, citric, acetic, or tartaric acids. Exemplary bases for forming pharmaceutically acceptable base addition salts include potassium hydroxide, sodium hydroxide, ammonium hydroxide, caffeine, various amines, and the like; other counterions such as magnesium, zinc, calcium, and iron may also be used. Methods for preparation of the appropriate salts are well-established in the art.

Compounds according to the present invention may optionally be in labeled form. Labeled forms of the compounds described herein include compounds that have been modified to be detectable by some analytic technique. Representative labeled forms of the compounds described herein include isotopically-labeled compounds which are otherwise identical to those defined in the general formulae provided herein, but for the fact that one or more atoms are replaced by an atom having an atomic mass or mass number different from the atomic mass or mass number found usually in nature. Examples of isotopes that can be incorporated into compounds of the invention include isotopes of hydrogen, carbon, nitrogen, oxygen, phosphorus, sulfur, fluorine, chlorine, iodine, bromine and technetium, exemplified by $^2$H, $^3$H, $^{11}$C, $^{13}$C, $^{14}$C, $^{13}$N, $^{15}$N, $^{15}$O, $^{18}$F, $^{99}$Tc, $^{31}$P, $^{34}$S, $^{123}$I and $^{125}$I, and the like. Such labeled compounds can be prepared using methods known to those of skill in the art. Compounds of present invention and pharmaceutically acceptable salts and prodrugs of said compounds that contain the aforementioned isotopes and/or other isotopes of other atoms are within the scope of this invention. Other suitable labels include radioactive labels, fluorescent labels, paramagnetic labels, heavy elements or rare earth ions.

The present invention also provides prodrugs of the compounds of this invention. Prodrugs refer to compounds that are readily convertible in vivo into a compound of formula (I). Conventional procedures for the selection and preparation of suitable prodrug derivatives are described, for example, in "Design of Prodrugs", ed. H. Bundgaard, Elsevier, 1985.

In another aspect, the invention provides a method of inhibiting the in vivo activity of PIM-1, PIM-2, and/or PIM-3, the method comprising administering to a subject in need of such treatment a therapeutically effective amount of a compound or salt of formula (I) or (I'), or a pharmaceutical composition thereof.

The compounds of the invention have been shown to inhibit PIM kinases as demonstrated in the examples provided herein. Representative compounds of the formulae provided herein have been tested for their efficacy against PIM kinases and against other kinases, and have been shown to be effective inhibitors of at least one of PIM-1, PIM-2, and PIM-3; and in many cases, they are also selective with respect to other kinases.

FIG. 1 provides results of testing one compound of formula (III) against a panel of over 100 kinases. When tested at a single concentration (0.5 micromolar) that inhibited three PIM kinases by more than 85%, most other kinases in the panel were inhibited by less than 50%, and a group of other kinases that include ASK1, MST1, Ab1, CDK2, EGFR, PDGFRa, MAPK, CK1g, PKD2, GSK3b, PKCa, JAK2, CK2, CDK1, c-RAF, mTOR, PDK1, and PAK2, were inhibited by 10% or less. ASK1 and MST1 were not inhibited measurably by this concentration of a compound of formula (III), which is particularly significant since inhibition of these kinases can cause unanticipated side effects. O. Fedorov, et al., *PNAS* 104(51), 20523-28 (December 2007). Accordingly, in one aspect the invention provides an inhibitor of PIM kinases that is selective for PIM over these other kinases. Compounds of formula (III) may be more active on PIM-1 than other PIM kinases, as illustrated in FIG. 1; thus the invention also provides compounds that are selective for PIM-1 kinase over PIM-2 or PIM-3.

In addition to their demonstrated activity on PIM kinases, the compounds of the invention have been shown to inhibit growth or cause death of cancer cells in cell cultures. Representative compounds of the formulae provided herein have been shown to be effective inhibitors of cell growth in HCT116 (colon cancer), K-562 (chronic myelogenous leukemia), MV-4-11 (acute myelogenous leukemia), MiaPaca (pancreatic cancer), PC3 (prostate cancer), and THP-1 (acute myelogenous leukemia) cell cultures. Accordingly, these compounds are shown to be useful for treatment of cancers. Without being bound by theory, it is believed that this anticancer activity correlates with and results from inhibition of PIM kinases by the compounds of the formulae provided herein.

Accordingly, in yet another aspect, the invention provides a method of treating diseases or disorders associated with uncontrolled, abnormal, and/or unwanted cellular activities effected directly or indirectly by PIM-1, PIM-2, and/or PIM-3, the method comprising administering to a mammal in need of such treatment a therapeutically effective amount of a compound or salt of any of the formulae provided herein, or a pharmaceutical composition thereof.

In addition to their activity on PIM kinases, the compounds described herein may also be active as inhibitors of Flt3. Inhibitors of Flt3 have shown clinical efficacy for treating refractory AML. Accordingly, in another aspect, the invention also provides compounds and compositions for treating disorders associated with excessive or undesired levels of Flt3 activity. In particular embodiments, these compounds are useful to treat patients with relapsed or refractory AML, as demonstrated by Smith, et al. Smith, et al. demonstrated that mutated Flt3 is associated with many refractory AML conditions, and that inhibitors of Flt3 were effective to treat such conditions. In some embodiments, the invention thus includes a further step of identifying a suitable patient for treatment by determining whether the patient (subject) has excessive activity of Flt3 kinase, or if the cancer involved includes a mutated Flt3 kinase that is activated more than normal.

In another aspect, the invention provides a method of inhibiting proliferative activity of cells when such activity is undesired or excessive, the method comprising administering to a cell or a plurality of cells an effective amount of a compound or salt of one of the formulae provided herein, or a pharmaceutical composition thereof.

In still another aspect, the invention provides a method of treating cancer, comprising administering a therapeutically effective amount of a compound of any of the formulae provided herein, or a pharmaceutically acceptable salt or a pharmaceutical composition comprising a compound or salt of one of these formulae to a patient in need of such treatment.

A further aspect of the invention is a method of treating malignancies such as ovarian cancer, cervical cancer, breast cancer, colorectal cancer, and glioblastomas, among others, in a patient in need of such treatment, by administering a compound or salt of formula 1, or a pharmaceutical composition thereof. In some embodiments, the malignancy is selected from colon cancer, pancreatic cancer, prostate cancer, and leukemia, such as acute myelogeneous leukemia (AML) and/or chronic myelogenous leukemia (CML). In one embodiment, the invention provides a method to treat refractory AML.

Compounds and compositions of the invention may be used alone or in combination with anticancer or other agents, such as palliative agents, that are generally administered to a patient being treated for cancer, as further described herein.

In another aspect, the invention provides a method to treat inflammation, which method comprises administering to a subject in need of such treatment an effective amount of a compound of one of the formulae provided herein, or a pharmaceutically acceptable salt or pharmaceutical composition thereof, as described herein.

In yet another aspect, the invention provides a method to inhibit a PIM kinase in vitro. This method may be used for screening of compounds or antibodies to assess their binding to a PIM kinase, i.e., as a standard for an assay or as a binding agent in a displacement assay, or it can be used to verify the functioning of an in vitro assay method, or it can be used to reduce or prevent activity of PIM kinase in a cell-free in vitro mixture that is used to assess a pathway for overall activity, when the pathway includes or depends upon the activity of a PIM kinase.

In another aspect, the invention provides compounds that are inhibitors of Flt3. These compounds and pharmaceutical compositions containing such compounds, are useful to treat conditions associated with excessive or undesired activity of Flt3, including inflammation. Thus the invention also provides a method to treat inflammation, which method comprises administering to a subject in need of such treatment an effective amount of a compound of any of the formulae provided herein. The condition can be an airway inflammation disorder; in one embodiment, the condition is asthma.

"Subject" for the purposes of the present invention includes humans and other animals, particularly mammals. Thus the methods are applicable to both human therapy and veterinary applications. In certain embodiments the subject is a mammal, and in a preferred embodiment the subject is human.

Where the invention includes administering a compound of one of the formulae described herein to a subject, it may also include the step of identifying a subject in need of such treatment. Methods for identifying a subject in need of treatment for cancer are known in the art to those of ordinary skill. In some of these embodiments, the subject is a human who has been diagnosed with at least one form of cancer. In some embodiments the subject is a human who has previously been treated for cancer, and in some embodiments the subject is a human who is undergoing current treatment for a cancer.

"Therapeutically effective amount" or "effective amount" as used herein is an amount of a compound of the invention, that when administered to a subject, ameliorates at least one symptom of the disease. It may, for example, slow or stop proliferation of cancerous cells, or induce cell death or otherwise reduce the number of cancerous cells. The amount of a compound of the invention which constitutes a "therapeutically effective amount" will vary depending on the compound, the disease state and its severity, the age and weight of the patient to be treated, and the like. The therapeutically effective amount can be determined routinely by one of ordinary skill in the art having regard to their knowledge and to this disclosure. Methods for determining a therapeutically effective amount include initiating treatment with a known dose and adjusting the dose until a therapeutic effect is observable. The adjusting step may be an increase or a decrease in dosage, and typically it is an increase in dosage from a relatively low initial dose.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal gland: neuroblastoma. Thus, the term "cancerous cell" as provided herein, includes a cell afflicted by any one of the above-identified conditions.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor).

"Treating" or "treatment" as used herein with respect to cancers or cell proliferative disorders covers the treatment of a disease-state in a human, which disease-state is characterized by abnormal, excessive and/or undesired cellular proliferation, and includes at least one of: (i) preventing the disease-state from occurring in a human, in particular, when such human is predisposed to the disease-state but has not yet been diagnosed as having it; (ii) inhibiting the disease-state, i.e., arresting its development; (iii) inhibiting spread of the disease state to new loci, e.g., slowing or preventing metastasis of a tumor; and (iv) relieving the disease-state, i.e., causing regression of the disease-state.

'Treating' or 'treatment' with regard to inflammatory conditions includes prevention of inflammation in a subject where inflammation is expected to occur, or reduction of the extent or duration of one or more of the symptoms of inflammation in a subject having symptoms of inflammation such as redness, swelling, pain associated with these, or elevated temperature.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Representative compounds of the invention are shown in Table 1, which includes the mass of a molecular ion detected in the LC-mass spectral analysis of the compound, its $IC_{50}$ for inhibition of PIM-1 kinase for compounds that achieved an $IC_{50}$ at or below 2 micromolar; and the % inhibition of PIM-1 kinase at the high dose (2 micromolar) tested in a single screening assay. Tables 2-8 contain cell-based activity data for representative compounds of the invention. As further described herein, these compounds may also inhibit Flt3. FIG. 1 further illustrates that such compounds are active as inhibitors of other PIM kinases, and that they are selective for PIM kinases over an array of other kinases.

TABLE 1

Compounds of the invention and their activity against PIM-1 kinase.

| Entry No. | Structure | M + 1 | $IC_{50}$ (µM) | PIM-1 Inhibition @ 15 µMATP |
|---|---|---|---|---|
| 1 | 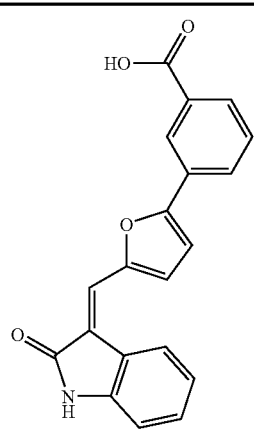 | 332 | | <2 |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 2 | 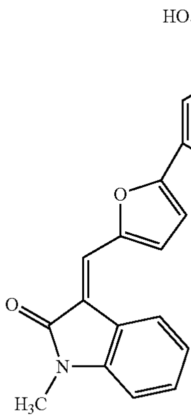 | 346 | | 31.60% |
| 3 | 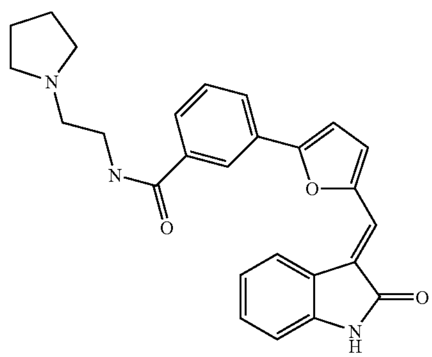 | 428 | <1 | |
| 4 | 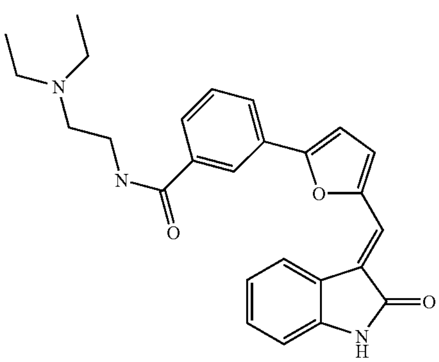 | 430 | <1 | |
| 5 | 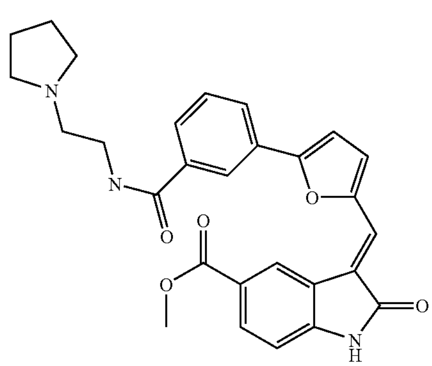 | 486 | <1 | |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 6 | 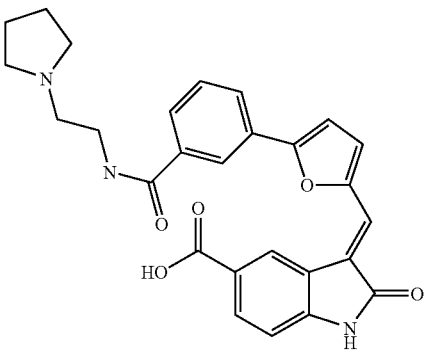 | 472 | | 32.30% |
| 7 | 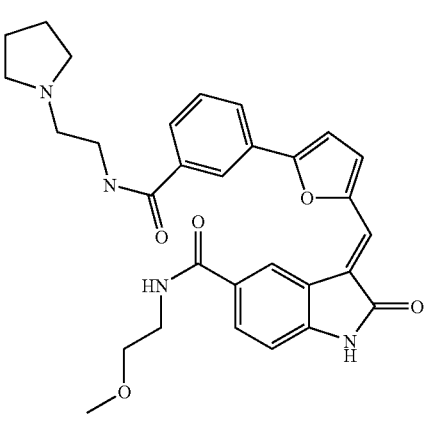 | 529 | | 32.70% |
| 8 | 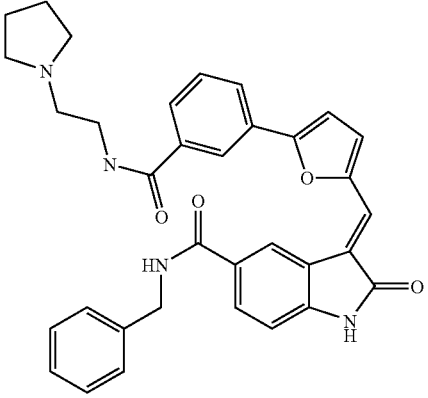 | 561 | | 11.50% |
| 9 | 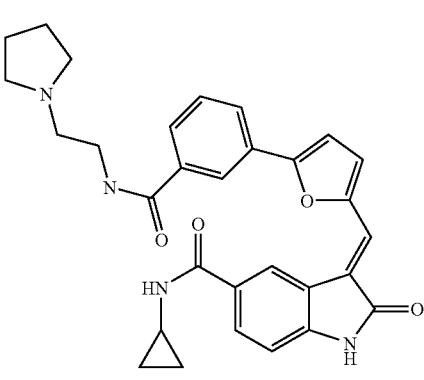 | 511 | | 37.20% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 10 | 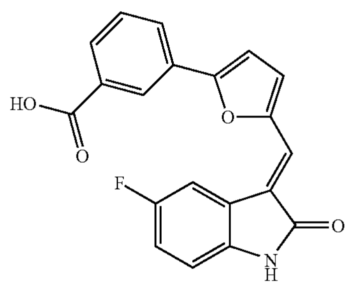 | 350 | <2 | |
| 11 | 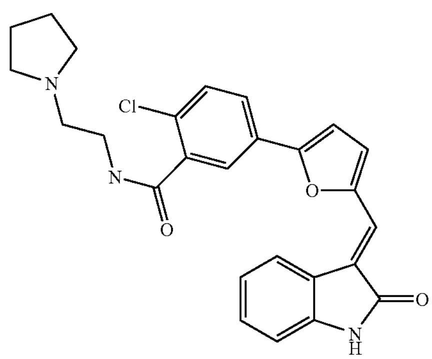 | 462 | | 5.60% |
| 12 | 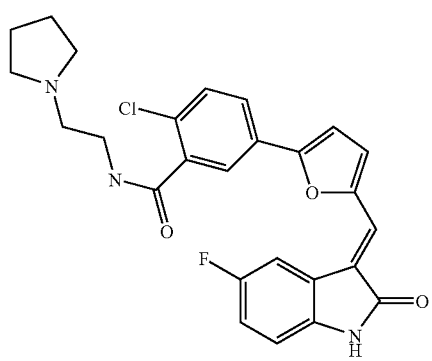 | 480 | | 35.20% |
| 13 | 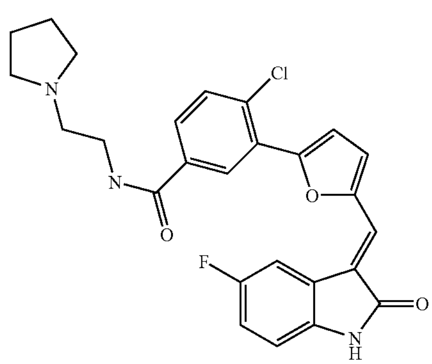 | 480 | <2 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 14 | 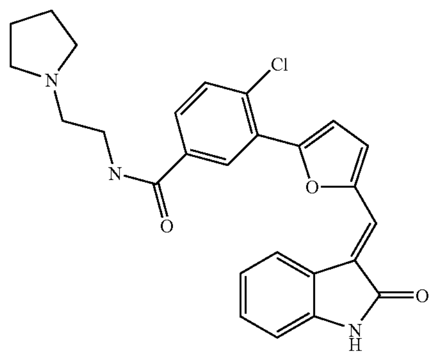 | 462 | <2 | |
| 15 | 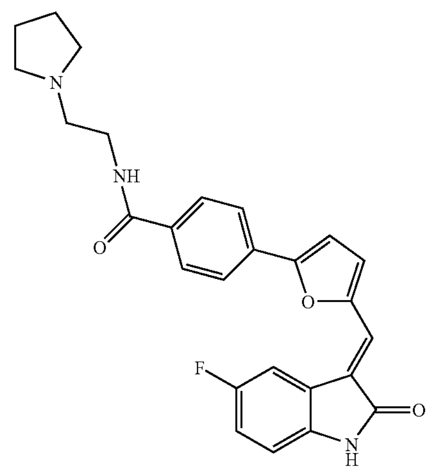 | 428 | <1 | |
| 16 | 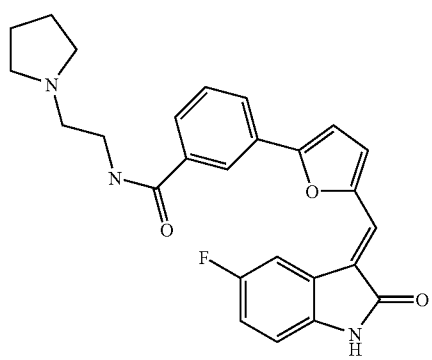 | 446 | <1 | |
| 17 | 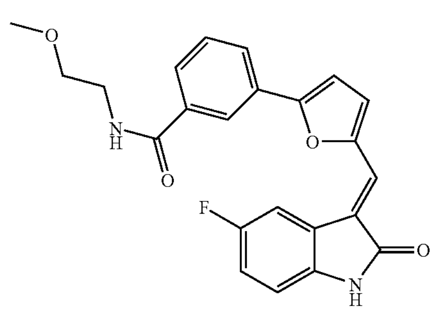 | 407 | | 49.60% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 18 | 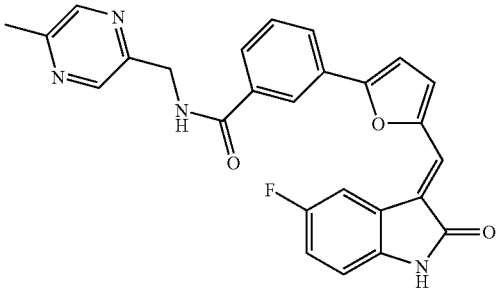 | 455 | | 42.30% |
| 19 | 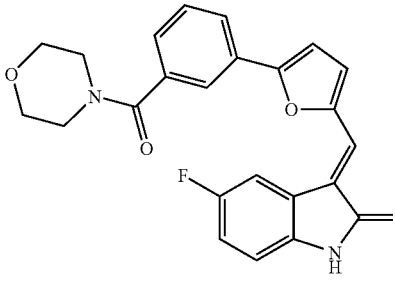 | 419 | | 42.20% |
| 20 | 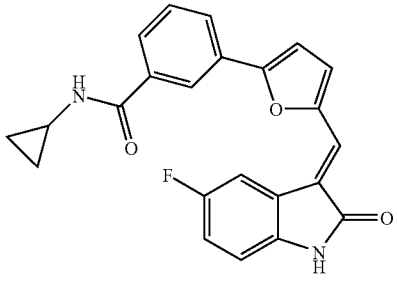 | 389 | | 46% |
| 21 | 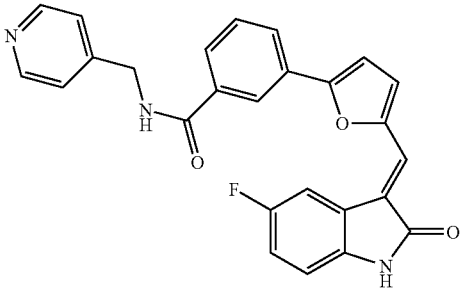 | 440 | <2 | |
| 22 | 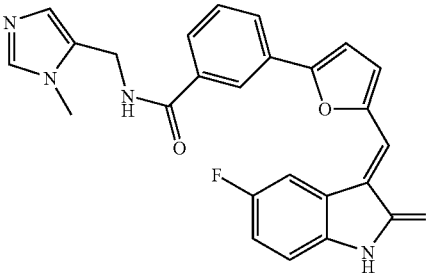 | 443 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 23 | 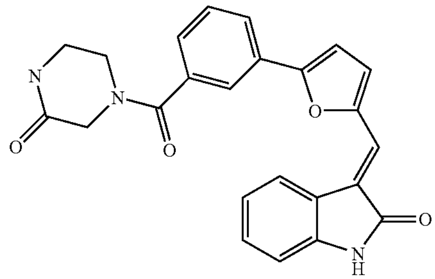 | 448 | | −14.20% |
| 24 | 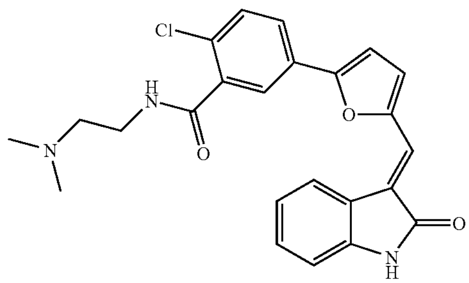 | 436 | | 36.70% |
| 25 | 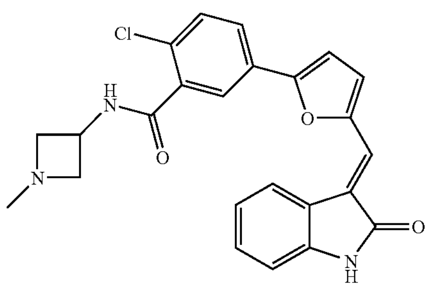 | 434 | | −15.80% |
| 26 | 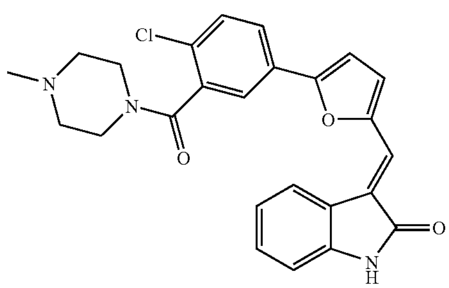 | 448 | | −18.80% |
| 27 | 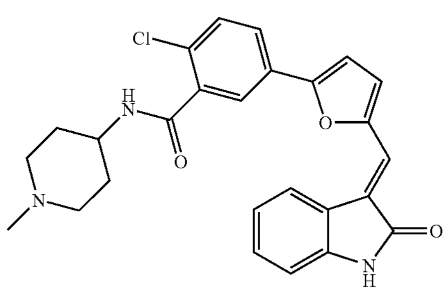 | 462 | | −16.90% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 28 | 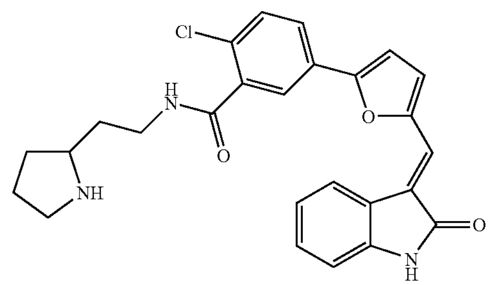 | 462 | | −37.63% |
| 29 | 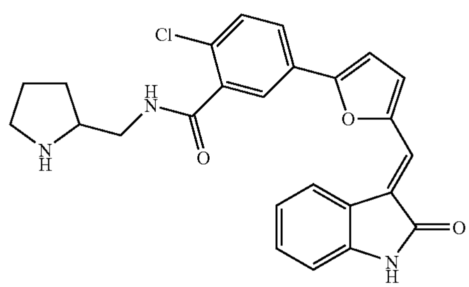 | 448 | | −33.40% |
| 30 | 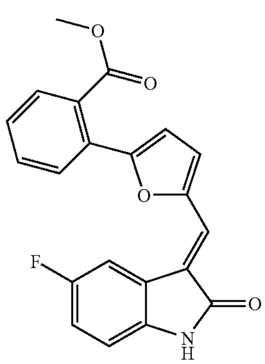 | 364 | | −6.80% |
| 31 | 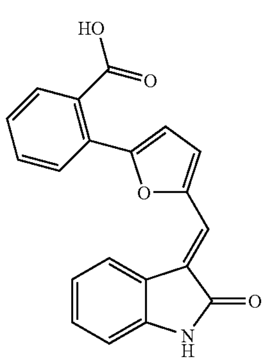 | 332 | | 11.43% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 32 | 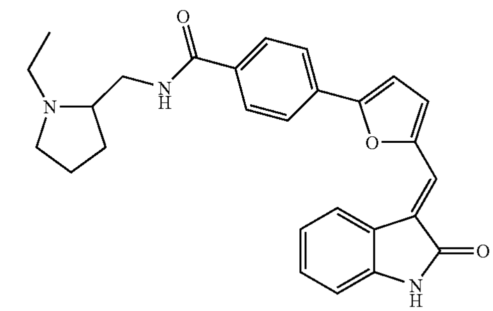 | 442 | <1 | |
| 33 | 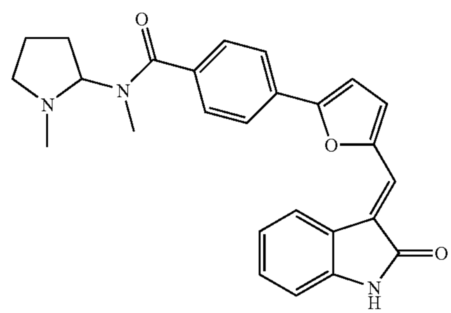 | 428 | <1 | |
| 34 | 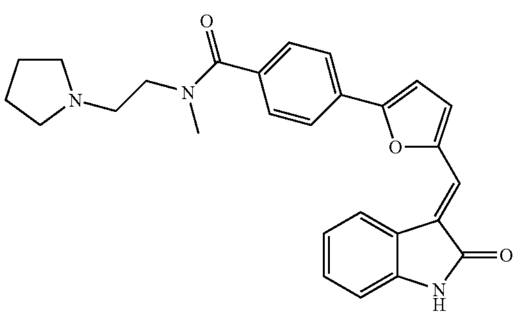 | 442 | <1 | |
| 35 | 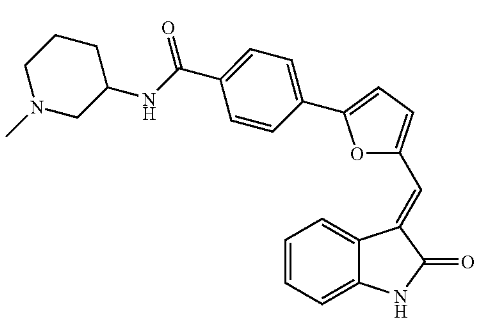 | 428 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 36 | 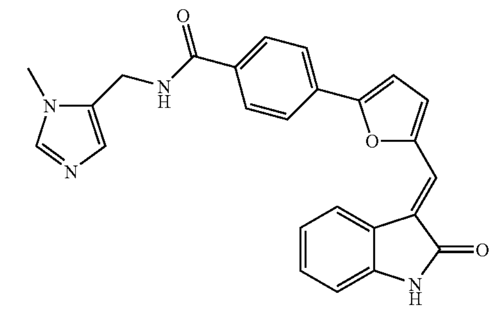 | 425 | <1 | |
| 37 | 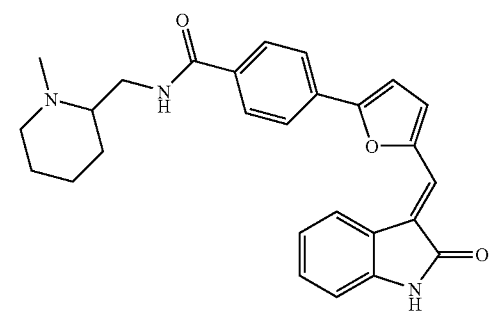 | 442 | <2 | |
| 38 | 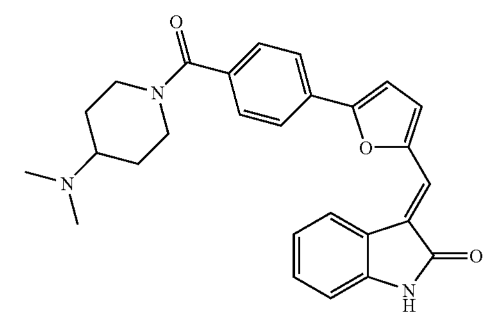 | 442 | <2 | |
| 39 | 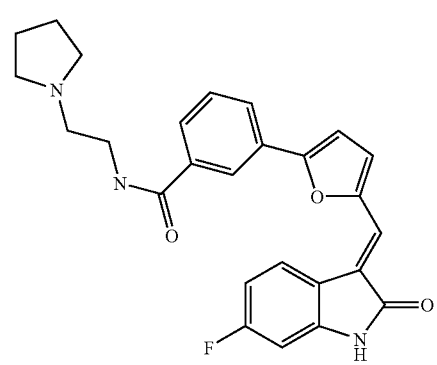 | 446 | | 21.02% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 40 | 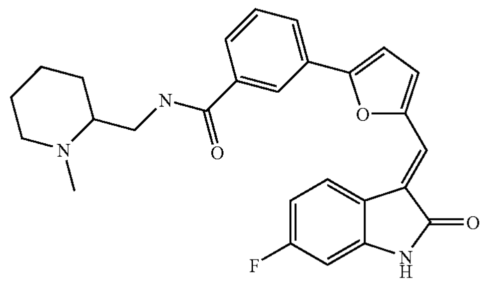 | 460 | | 33.93% |
| 41 | 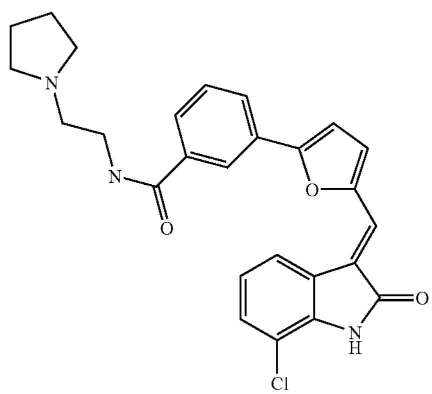 | 462 | | 19.04% |
| 42 | 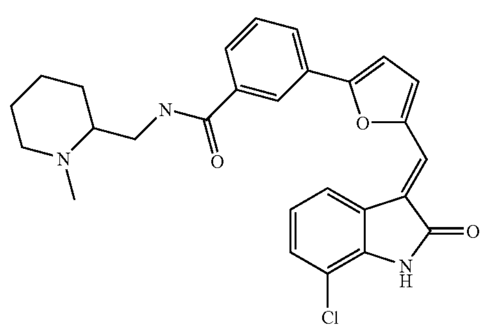 | 476 | | 9.73% |
| 43 | 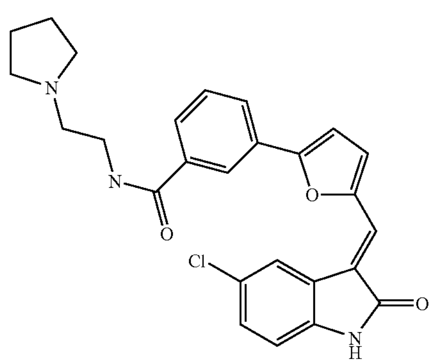 | 462 | | 32.71% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 44 | 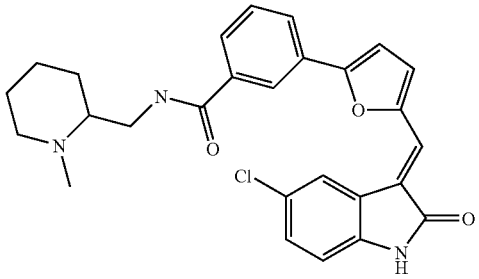 | 476 | | −9.22% |
| 45 | 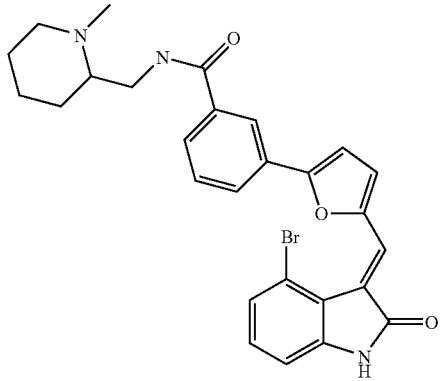 | 520 | | −21.95% |
| 46 | 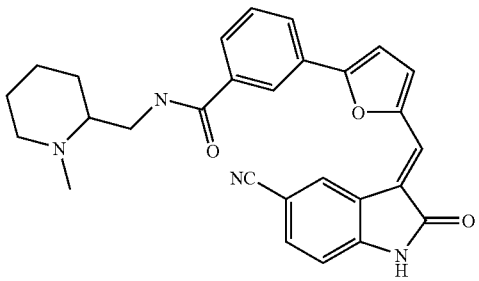 | 467 | | −0.36% |
| 47 | 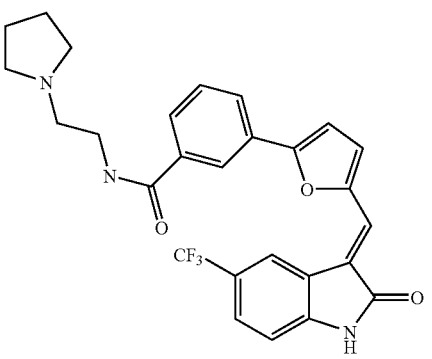 | 496 | | 22.93% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 48 | 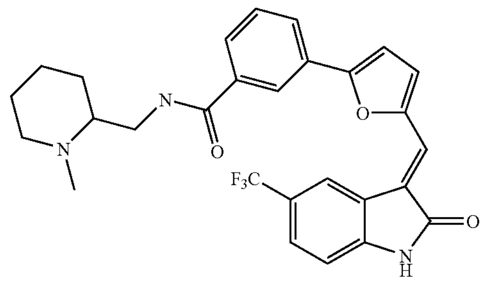 | 510 | | −4.56% |
| 49 | 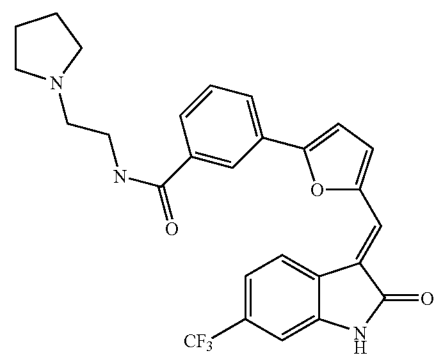 | 496 | | 2.70% |
| 50 | 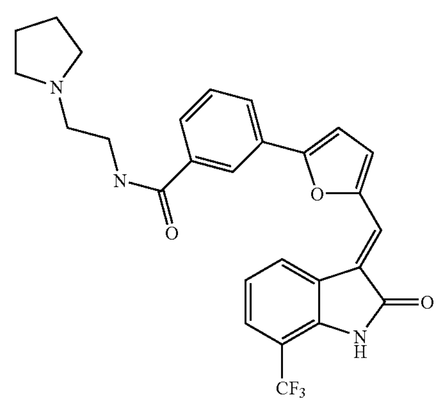 | 496 | | 8.16% |
| 51 | 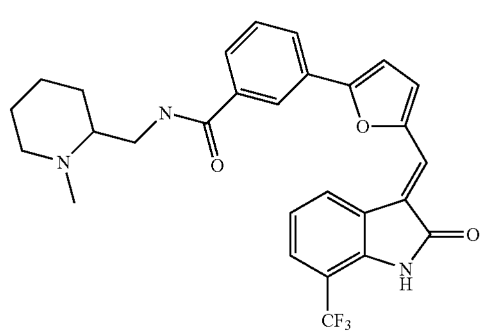 | 510 | | 2.32% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 52 | 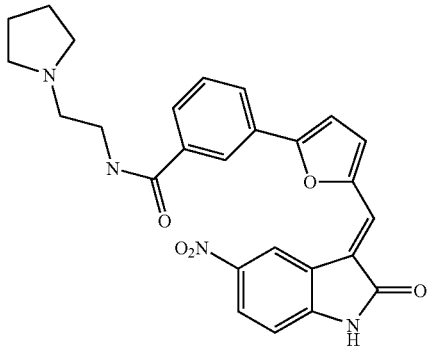 | 473 | | 20.37% |
| 53 | 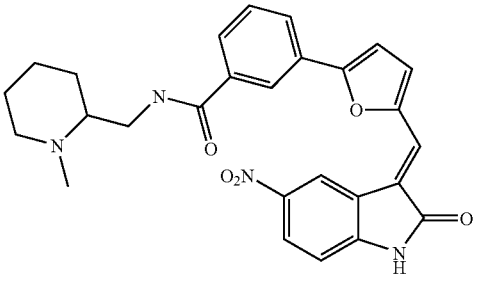 | 487 | | 23.50% |
| 54 | 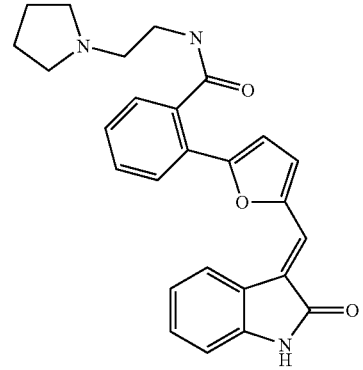 | 428 | | 3.52% |
| 55 | 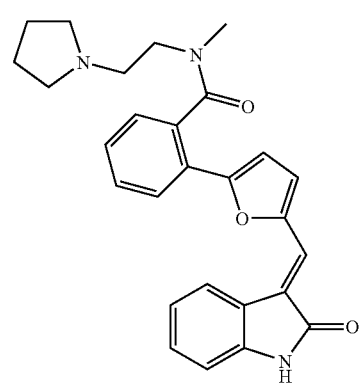 | 442 | | 2.91% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 56 | 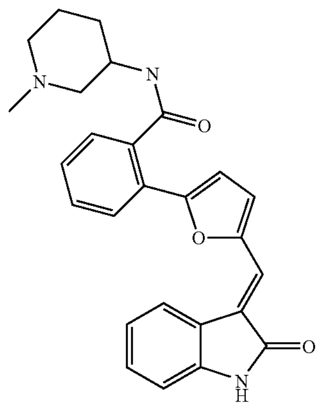 | 428 | | 13.75% |
| 57 | 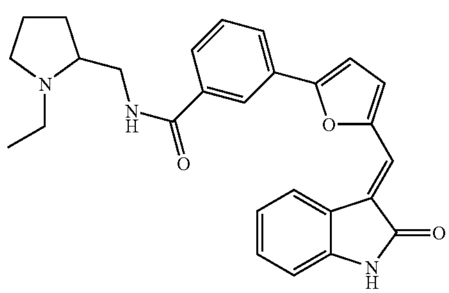 | 442 | | 10.57% |
| 58 | 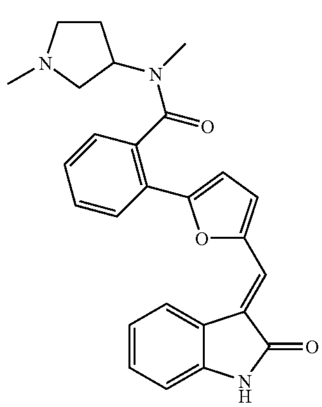 | 428 | | 7.15% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 59 | 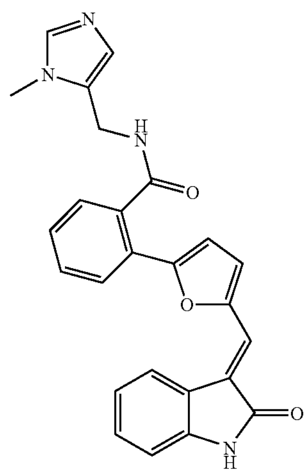 | 425 | | −4.35% |
| 60 | 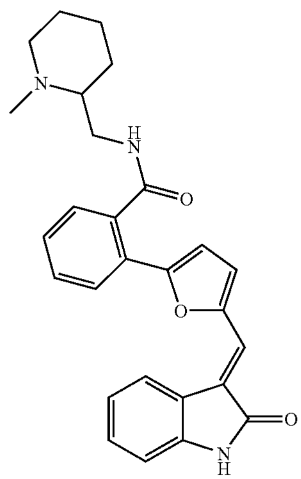 | 442 | | 0.33% |
| 61 | 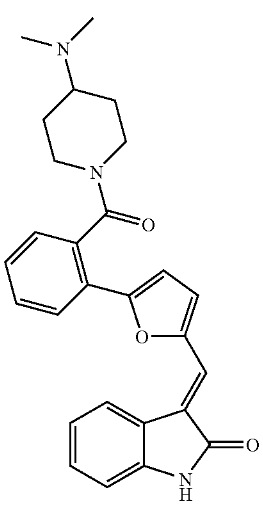 | 442 | | −2.65% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 62 | 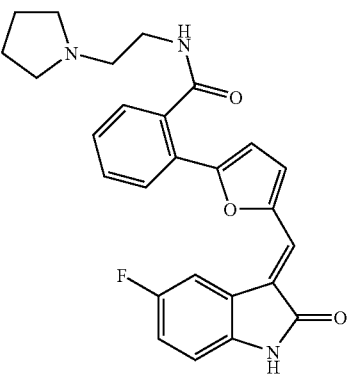 | 446 | | 0.28% |
| 63 | 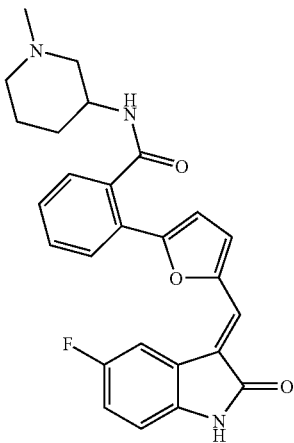 | 446 | | 10.26% |
| 64 | 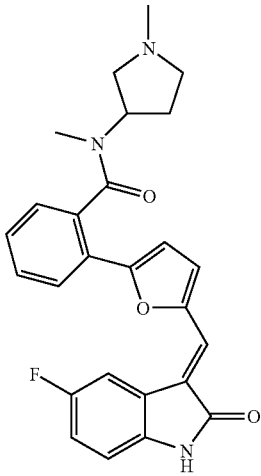 | 446 | | 18.25% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 65 | 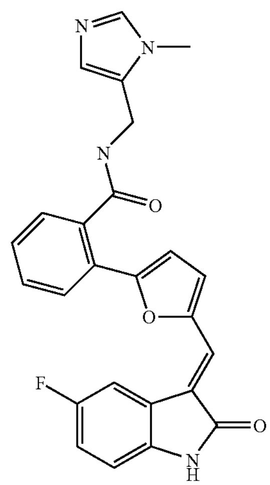 | 443 | | −2.39% |
| 66 | 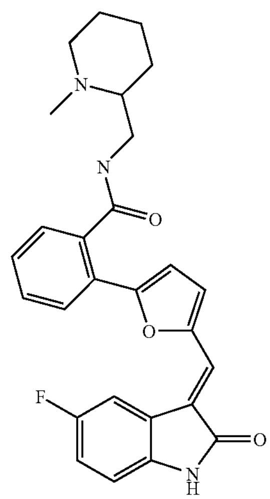 | 460 | | 4.53% |
| 67 | 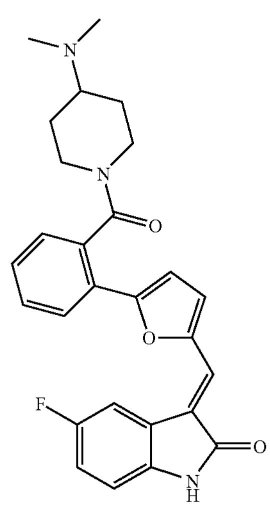 | 460 | | 8.84% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 68 | 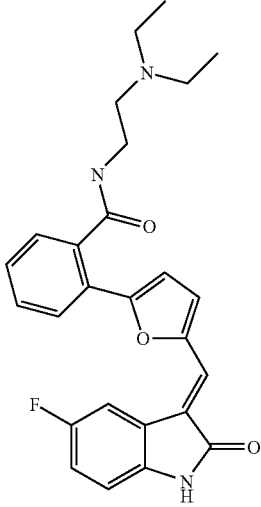 | 448 | | 11.21% |
| 69 | 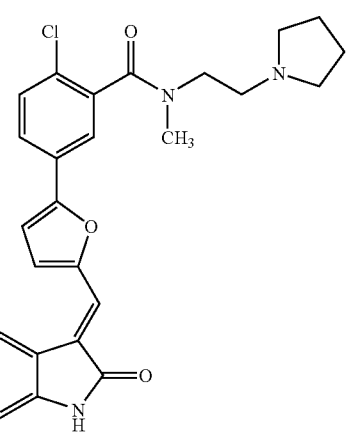 | 494 | | |
| 70 | 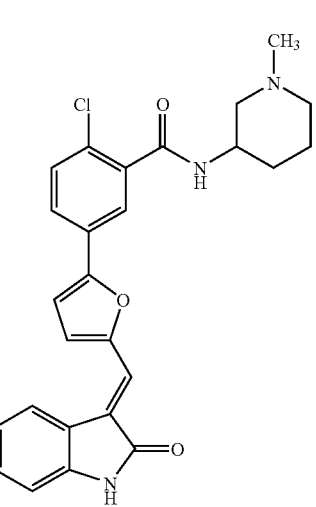 | 480 | | 27.85% |

TABLE 1-continued

Compounds of the invention and their activity against PIM-1 kinase.

| Entry No. | Structure | M + 1 | IC$_{50}$ (μM) | PIM-1 Inhibition @ 15 μM ATP |
|---|---|---|---|---|
| 71 | 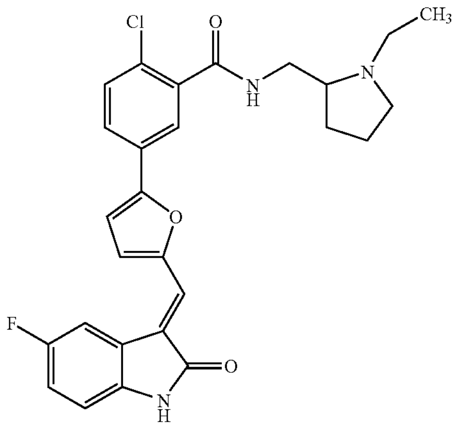 | 494 | | 5.32% |
| 72 | 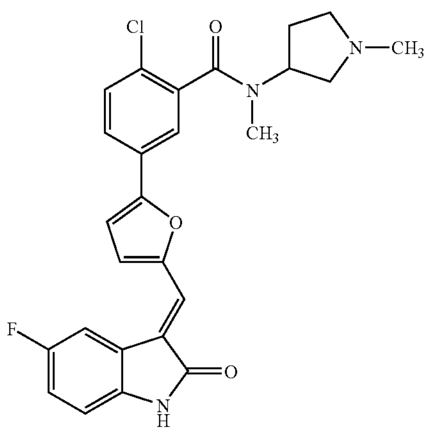 | 480 | | 37.14% |
| 73 | 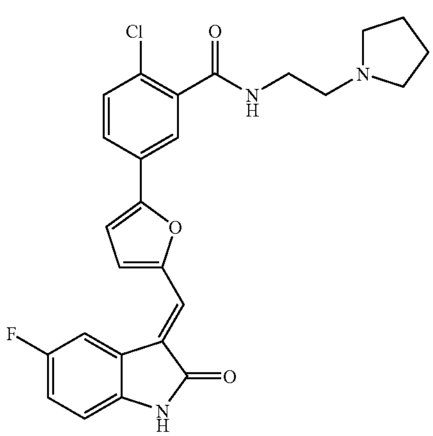 | 480 | | 20.89% |

TABLE 1-continued

Compounds of the invention and their activity against PIM-1 kinase.

| Entry No. | Structure | M + 1 | IC$_{50}$ (μM) | PIM-1 Inhibition @ 15 μM ATP |
|---|---|---|---|---|
| 74 | 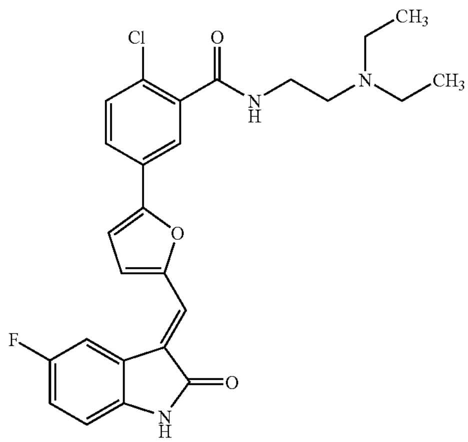 | 482 | | 15.62% |
| 75 | 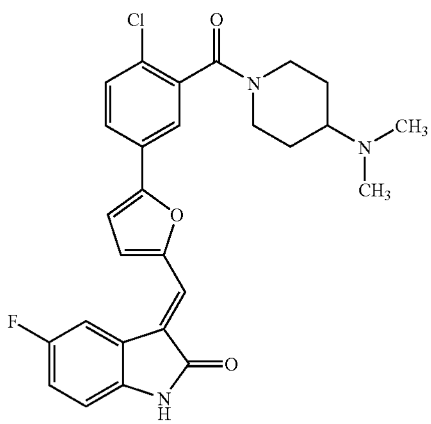 | 494 | | 27.78% |
| 76 | 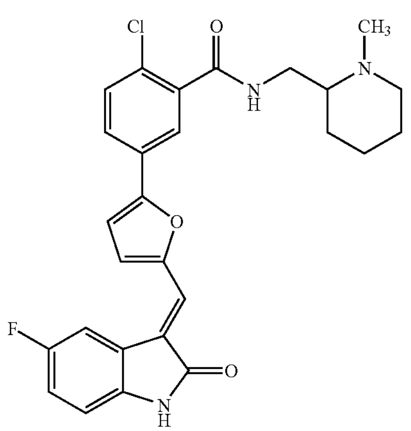 | 494 | | 15.66% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 77 | 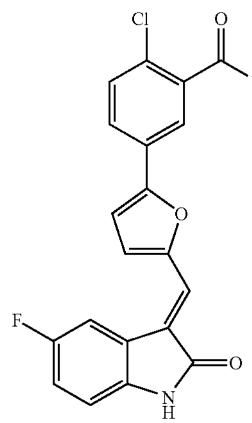 | 451 | | −16.96% |
| 78 | 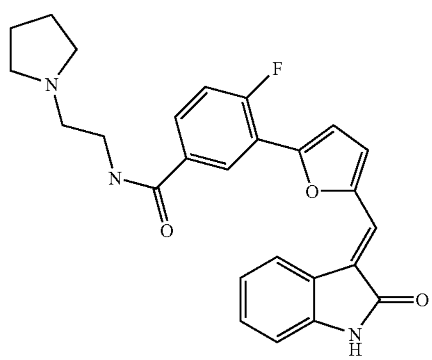 | 446 | <1 | 88.257 |
| 79 | 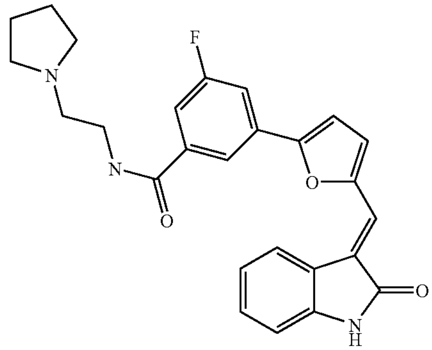 | 446 | <2 | 43.326 |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 80 | 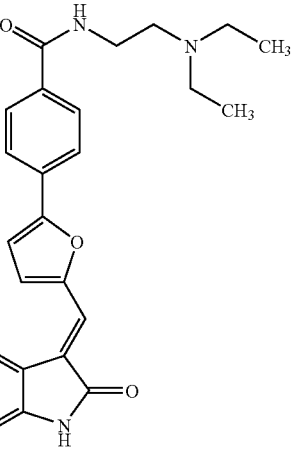 | 448 | <1 | 94.164 |
| 81 | 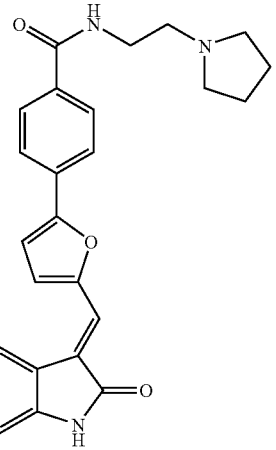 | 446 | <1 | 94.83 |
| 82 | 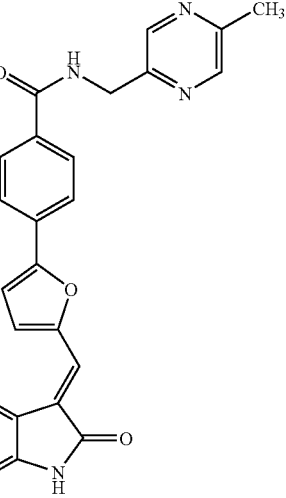 | 455 | | 26.58% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 83 | 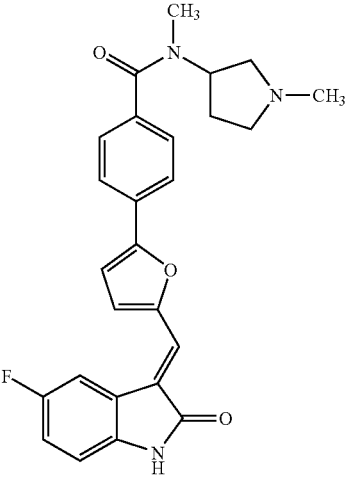 | 446 | <1 | 54.842 |
| 84 | 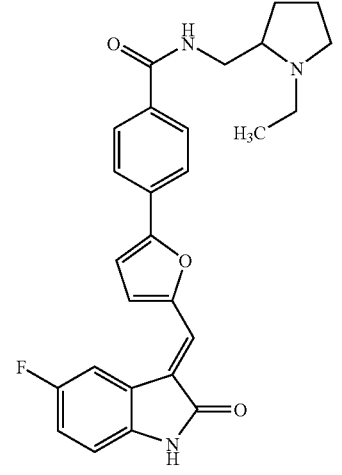 | 460 | <1 | 91.286 |
| 85 | 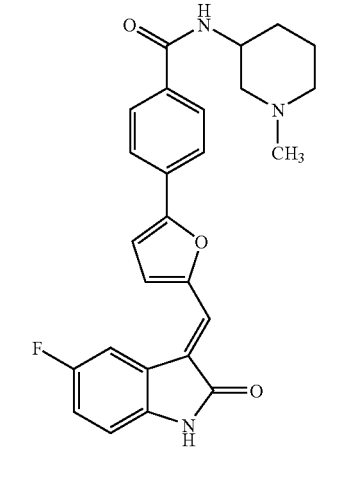 | 446 | <2 | 84.54 |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 86 | 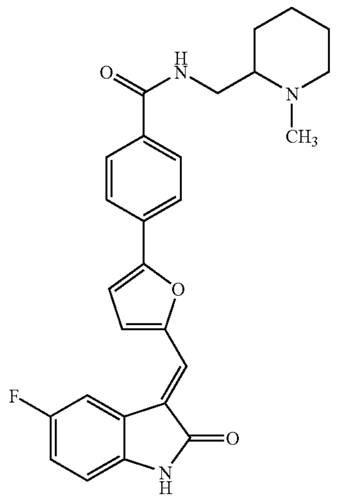 | 460 | <1 | 90.563 |
| 87 | 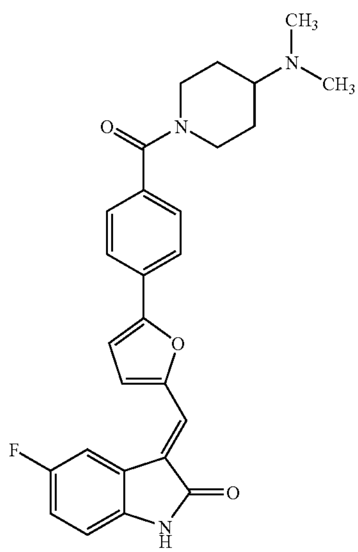 | 460 | <2 | 51.921 |
| 88 | 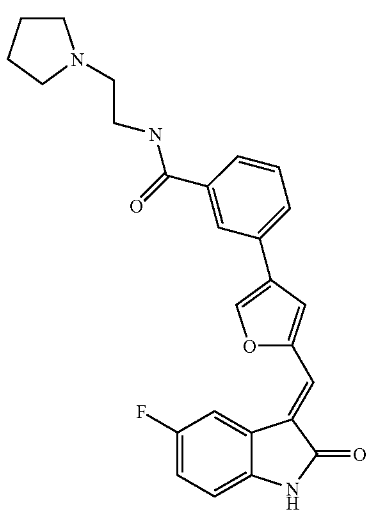 | 446 | | 9% |

TABLE 1-continued

Compounds of the invention and their activity against PIM-1 kinase.

| Entry No. | Structure | M + 1 | IC$_{50}$ (μM) | PIM-1 Inhibition @ 15 μM ATP |
|---|---|---|---|---|
| 89 | 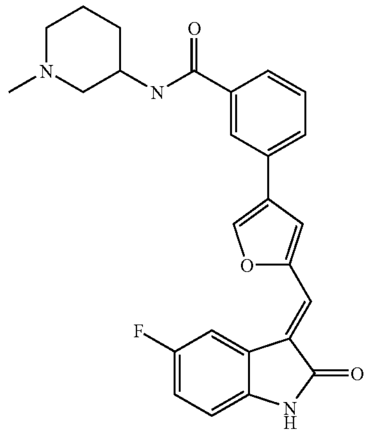 | 446 | | 6.10% |
| 90 | 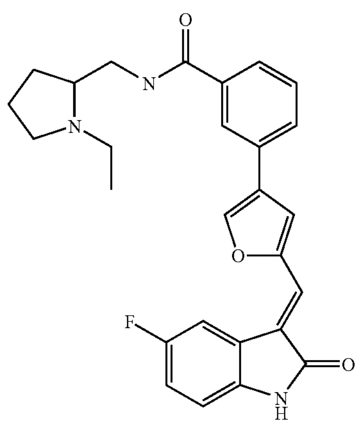 | 460 | | 17.05% |
| 91 | 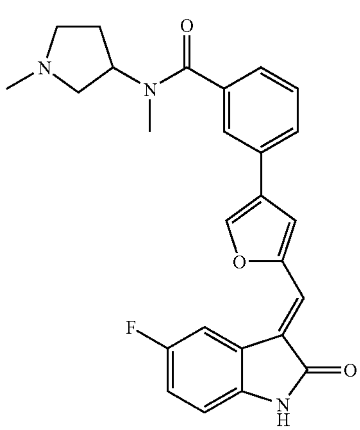 | 446 | | 2.87% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 92 | 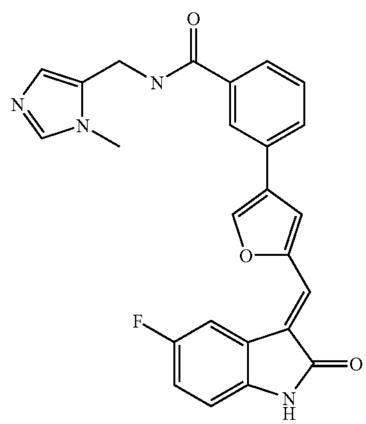 | 443 | | 12.70% |
| 93 | 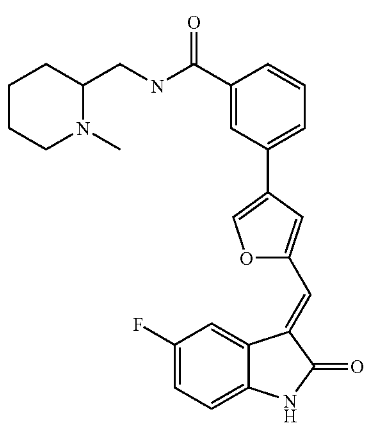 | 460 | | 9.42% |
| 94 | 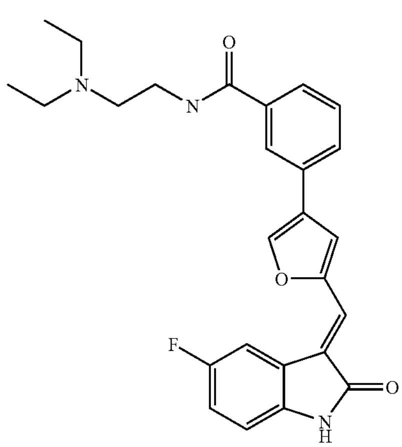 | 448 | | 11.52% |

TABLE 1-continued

Compounds of the invention and their activity against PIM-1 kinase.

| Entry No. | Structure | M + 1 | IC$_{50}$ (μM) | PIM-1 Inhibition @ 15 μM ATP |
|---|---|---|---|---|
| 95 | 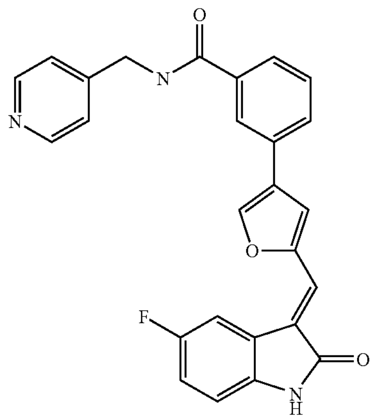 | 440 | | −19.13% |
| 96 | 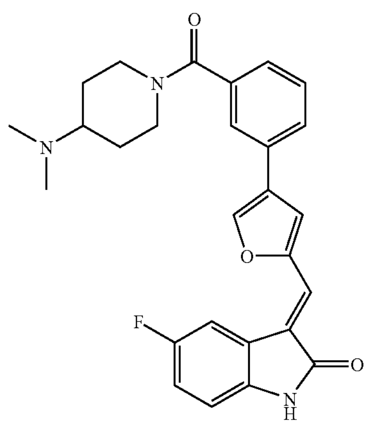 | 460 | | 10.80% |
| 97 | 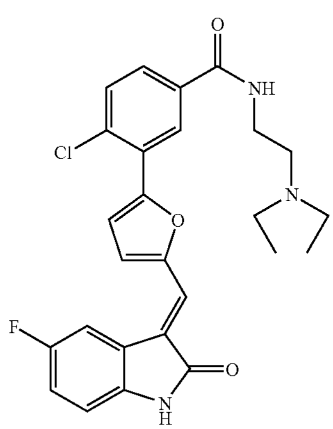 | 482 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 98 | 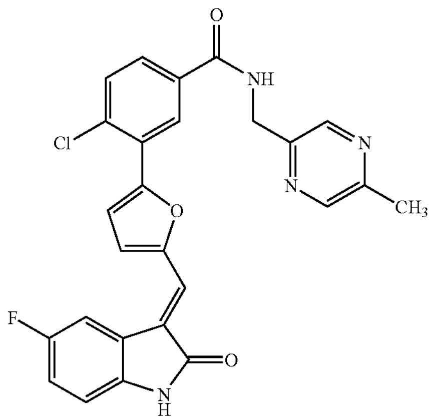 | 489 | | |
| 99 | 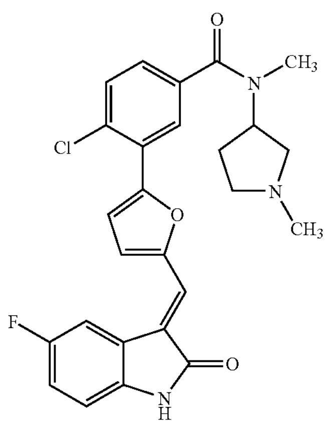 | 480 | | <1 |
| 100 | 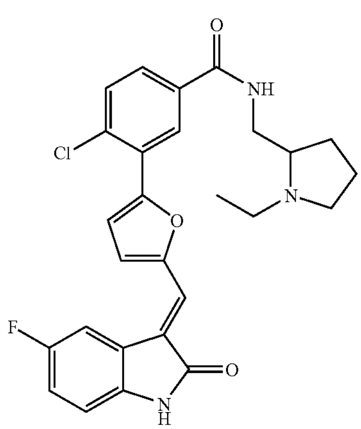 | 494 | | <1 |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 101 | 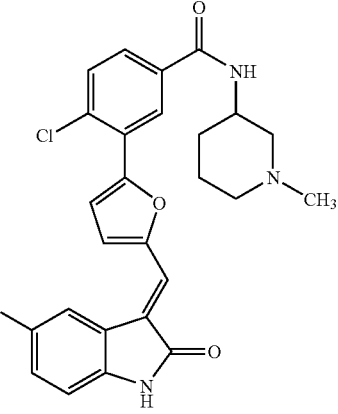 | 480 | | <2 |
| 102 | 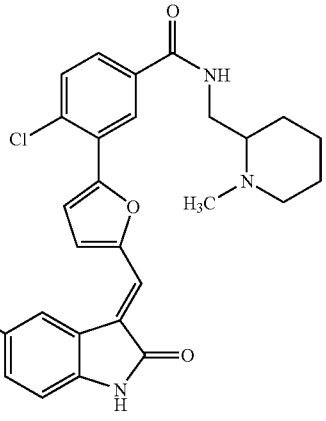 | 494 | | <2 |
| 103 | 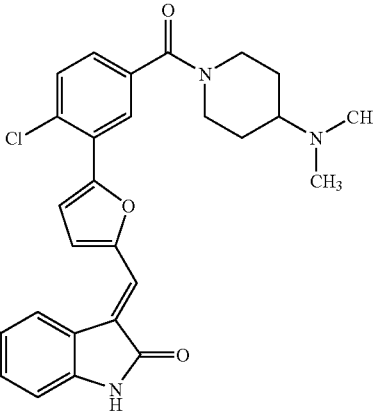 | 494 | | <2 |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 104 | 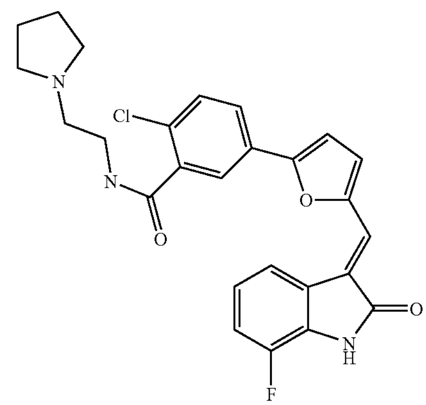 | 480 | | −5.30% |
| 105 | 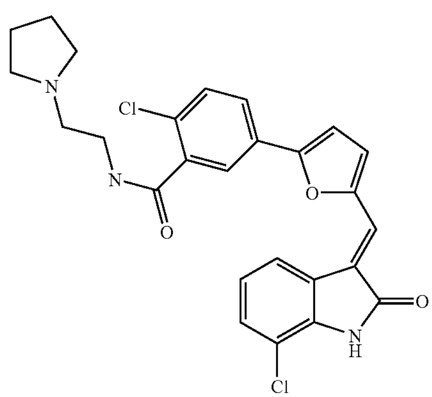 | 496 | | −16.73% |
| 106 | 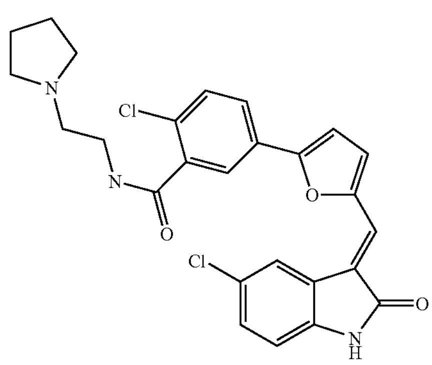 | 496 | | 22.22% |
| 107 | 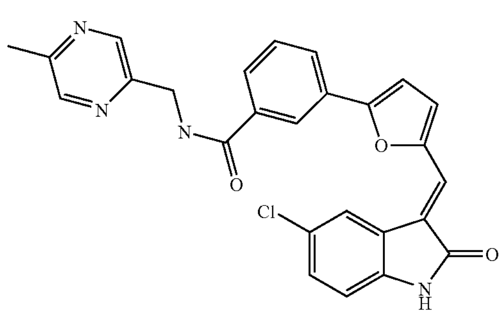 | 471 | | 21.00% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 108 | 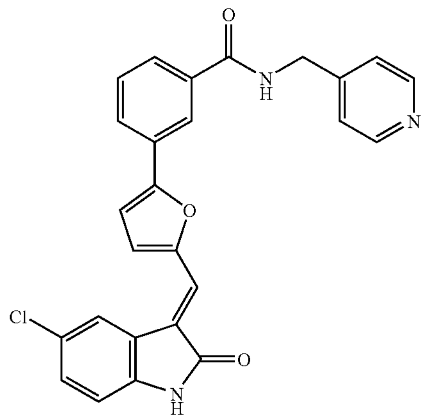 | 456 | <1 | |
| 109 | 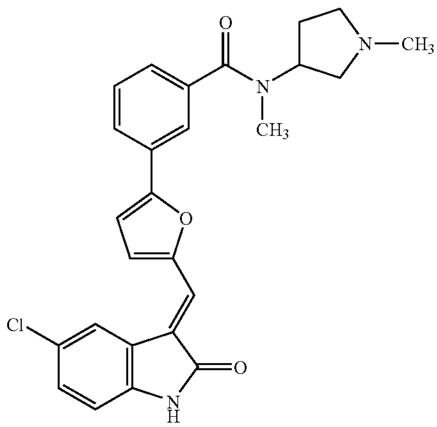 | 462 | <2 | |
| 110 | 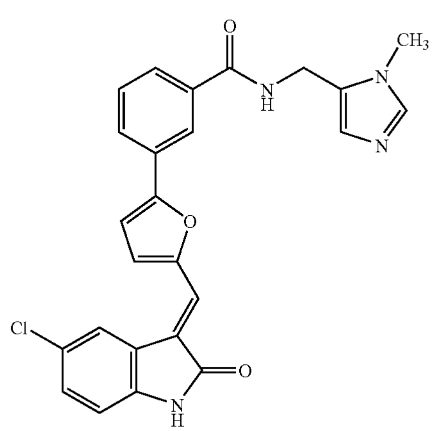 | 459 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 111 | 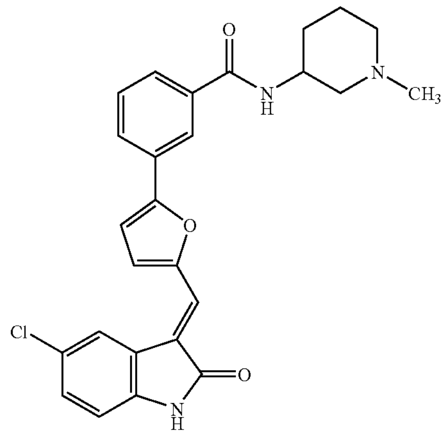 | 462 | | 42.64% |
| 112 | 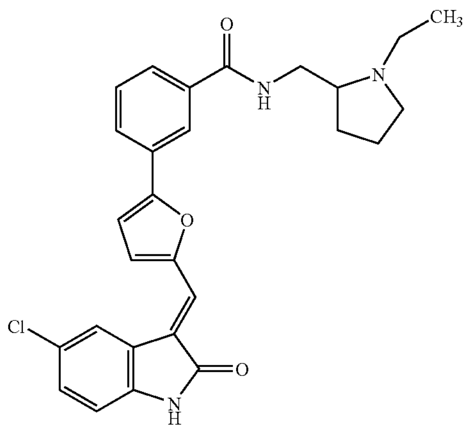 | 476 | <1 | |
| 113 | 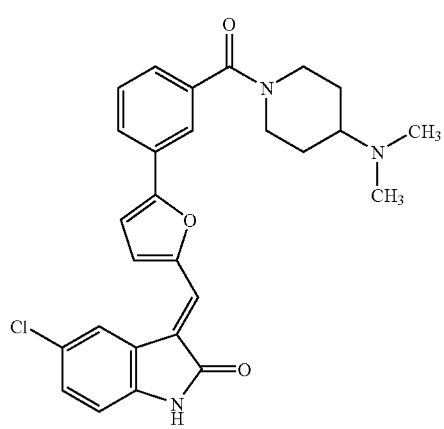 | 476 | | 38.08% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 114 | 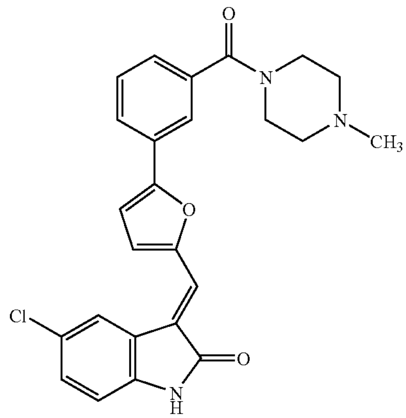 | 448 | | 22.99% |
| 115 | 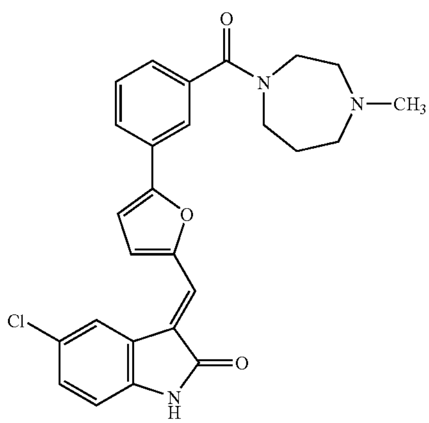 | 462 | <1 | |
| 116 | 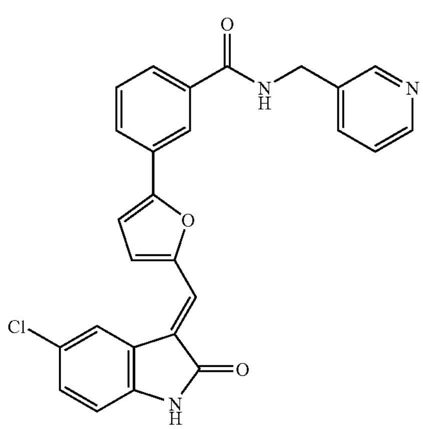 | 456 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 117 | 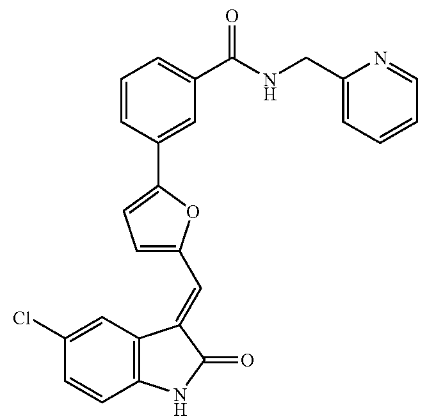 | 456 | | 19.24% |
| 118 | 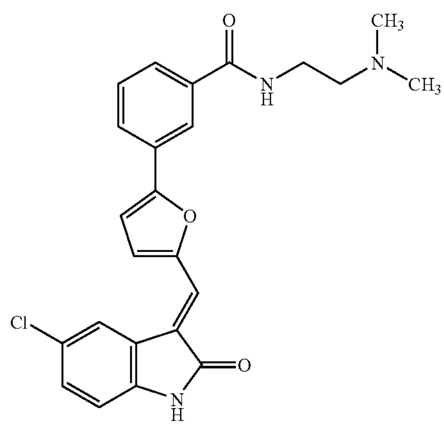 | 436 | <1 | |
| 119 | 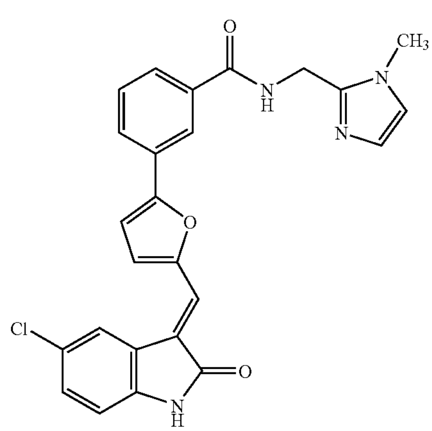 | 459 | | 37.01% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 120 | 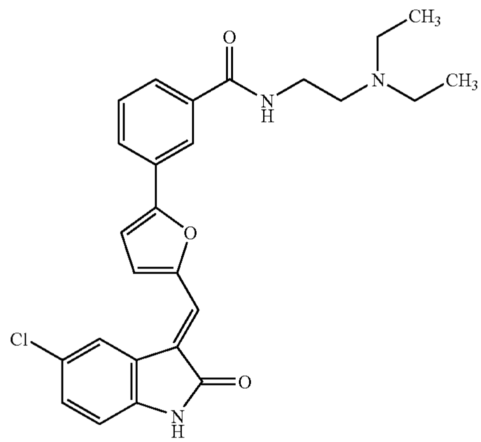 | 464 | <2 | |
| 121 | 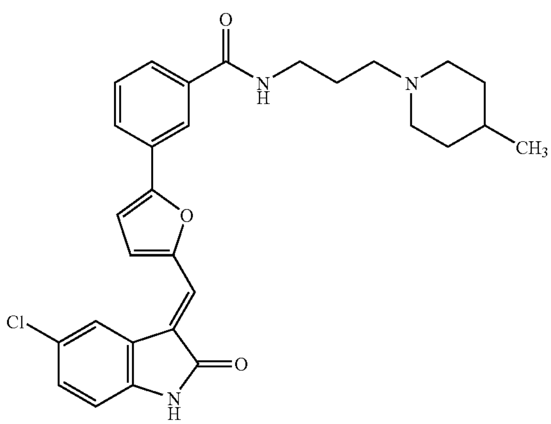 | 504 | | 25.17% |
| 122 | 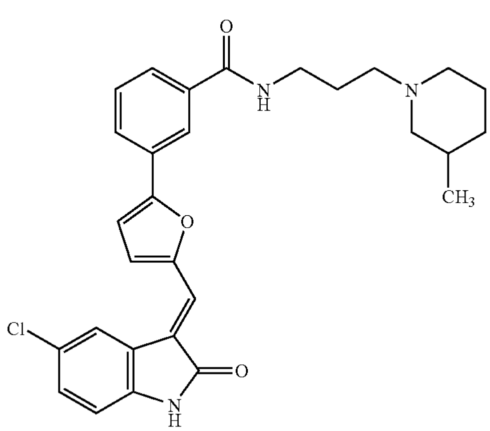 | 504 | | 39.32% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 123 | 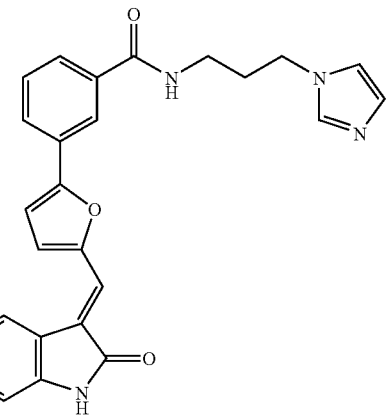 | 473 | <1 | |
| 124 | 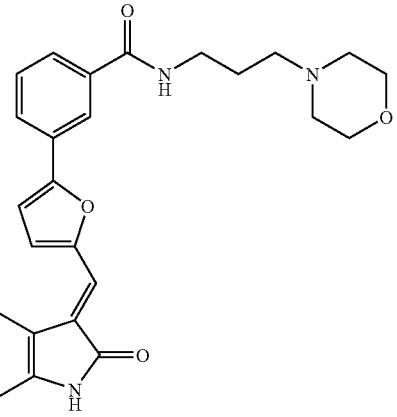 | 492 | <1 | |
| 125 | 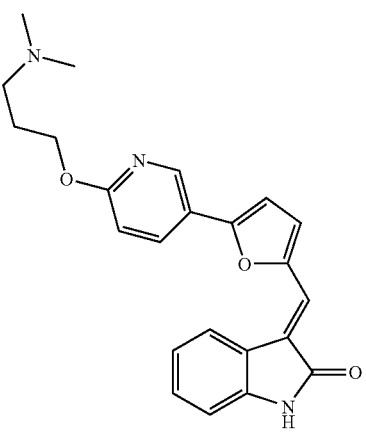 | 390 | | 41.51% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 126 | 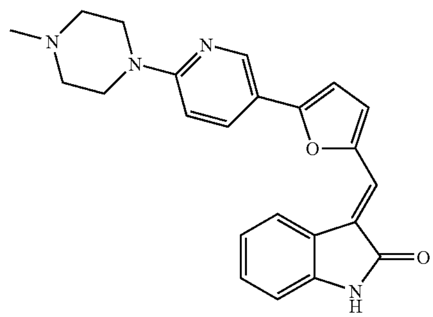 | 387 | | 19.53% |
| 127 | 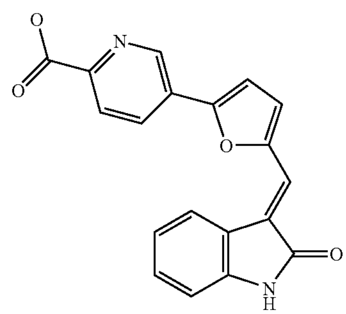 | 333 | <1 | |
| 128 | 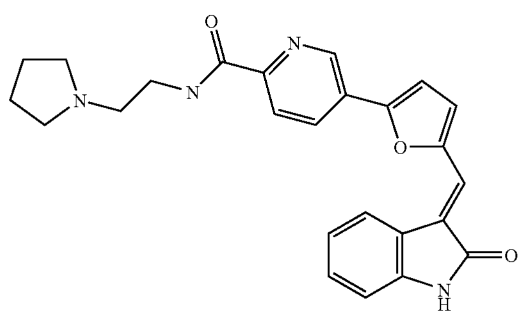 | 429 | | 27.22% |
| 129 | 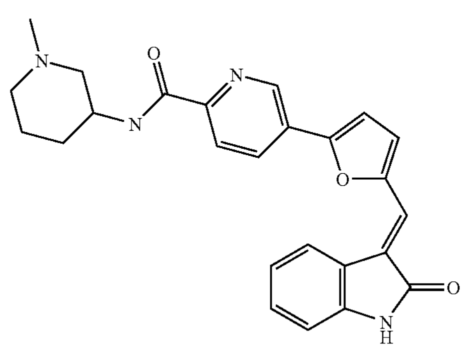 | 429 | | 1.44% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 130 | 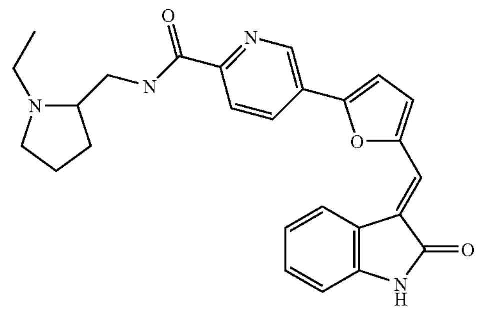 | 443 | | 24.28% |
| 131 | 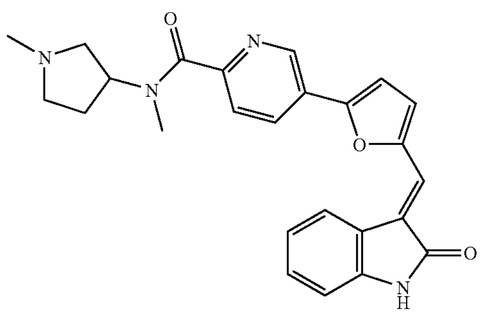 | 429 | | 5.08% |
| 132 | 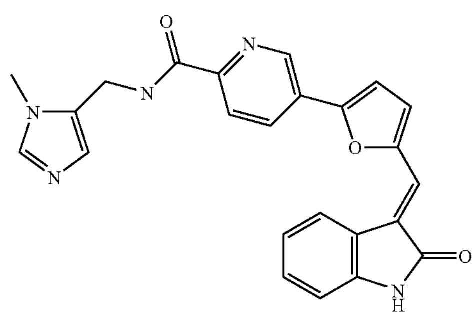 | 426 | <1 | |
| 133 | 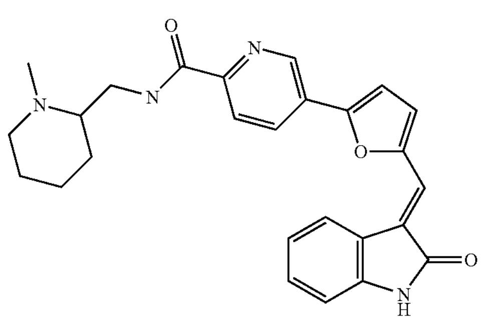 | 443 | 7.61 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 134 | 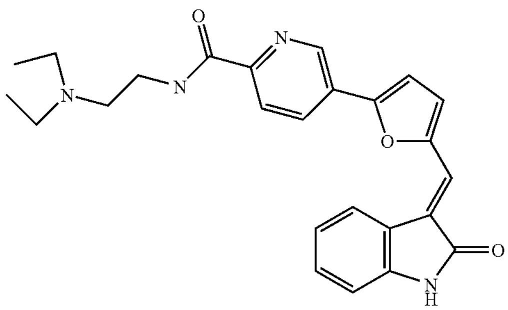 | 431 | | 32.352 |
| 135 | 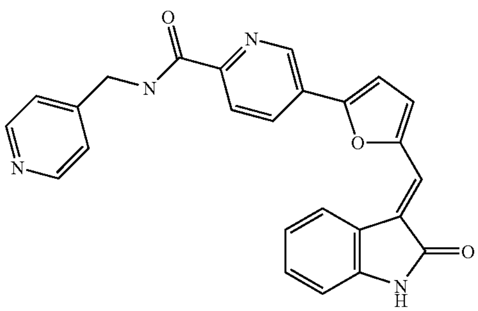 | 423 | | 43.551 |
| 136 | 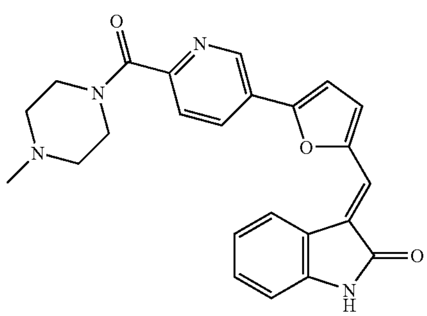 | 415 | | 15.23% |
| 137 | 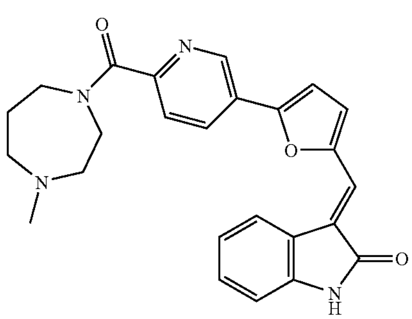 | 429 | | 20.65% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 138 | 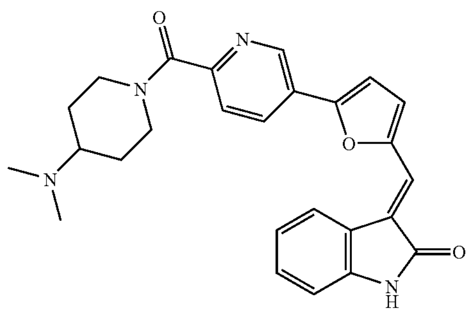 | 443 | | 30.48% |
| 139 | 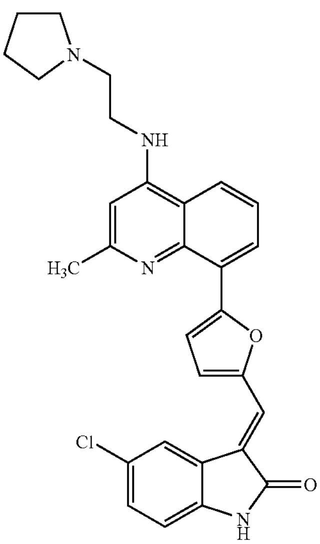 | 500 | | −23.35% |
| 140 | 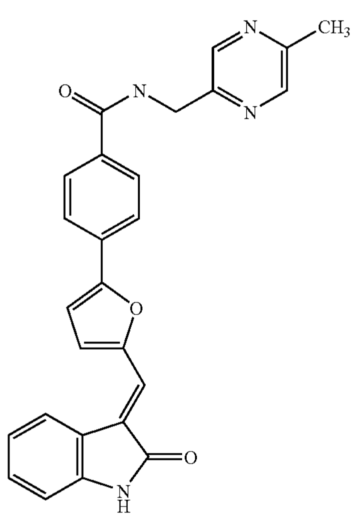 | 437 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 141 | 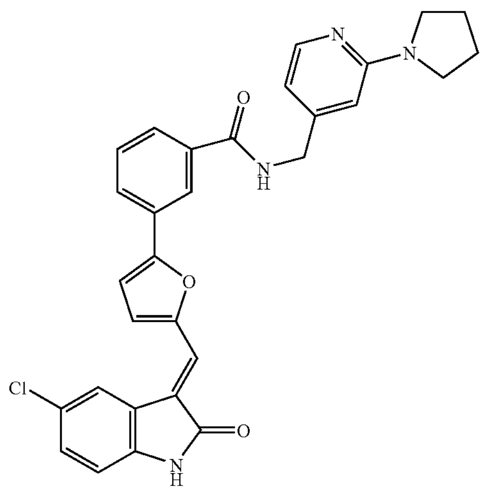 | 525 | | 26.33% |
| 142 | 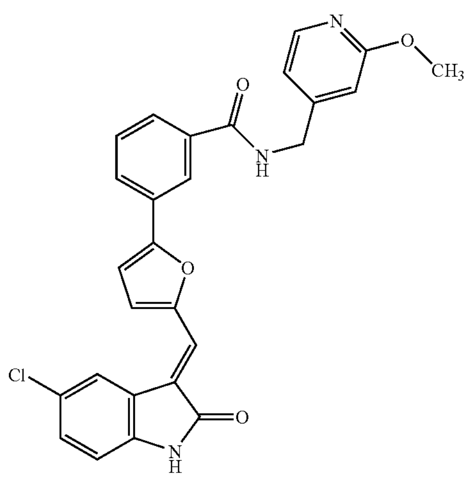 | 486 | | 32.67% |
| 143 | 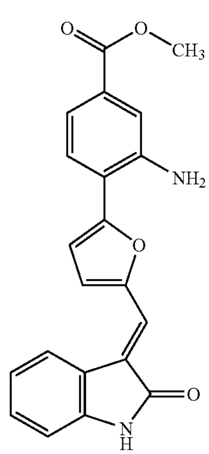 | 361 | | 30.61% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 144 | 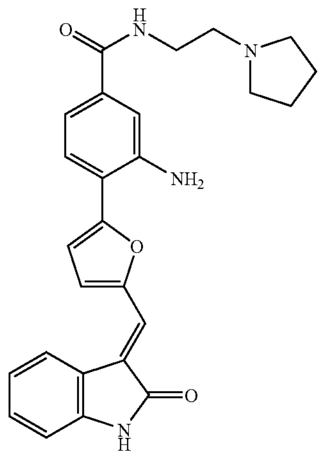 | 443 | <1 | |
| 145 | 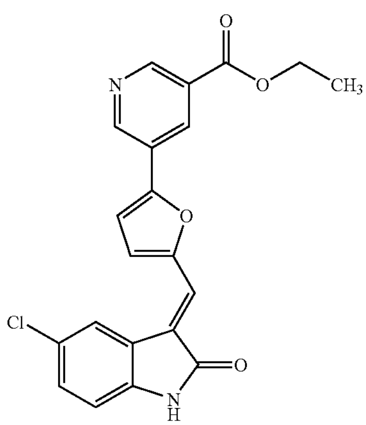 | 395 | | 34.55% |
| 146 | 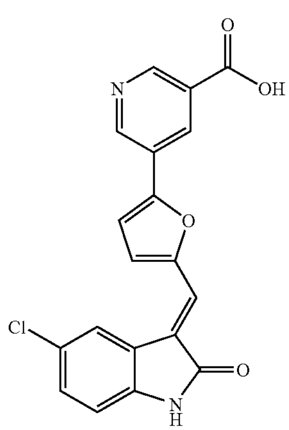 | 367 | <2 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 147 | 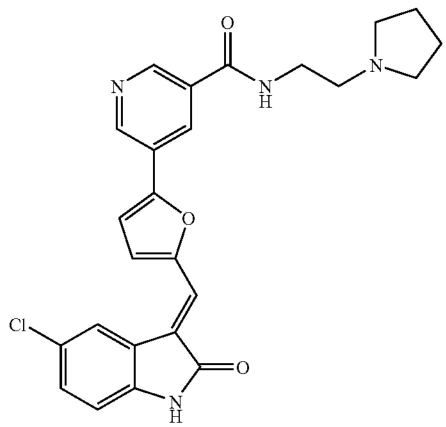 | 463 | | <1 |
| 148 | 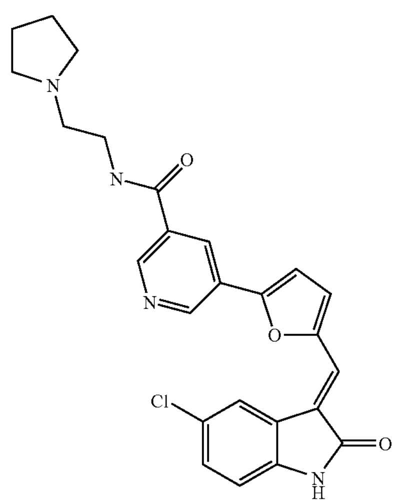 | 463 | | <1 |
| 149 | 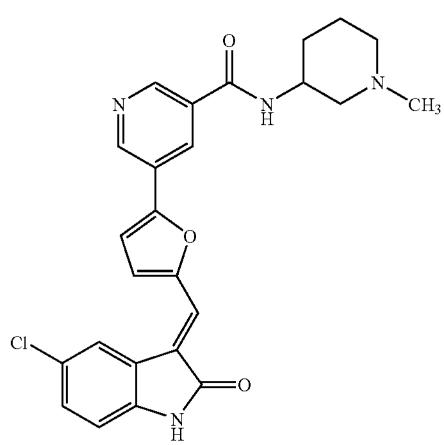 | 463 | | <1 |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 150 | 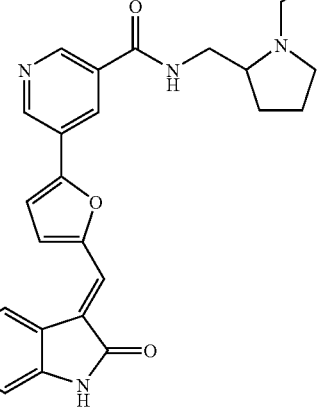 | 477 | <1 | |
| 151 | 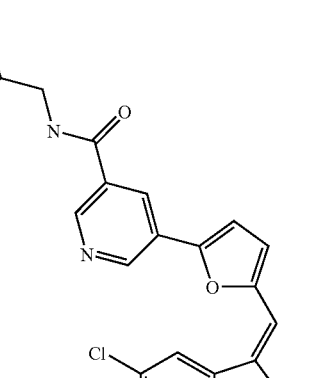 | 477 | <1 | |
| 152 | 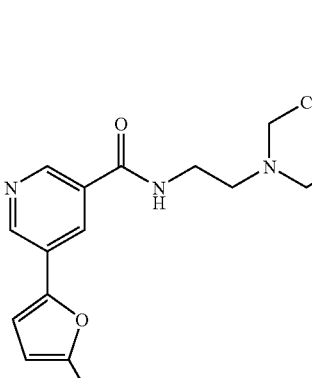 | 465 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 153 | 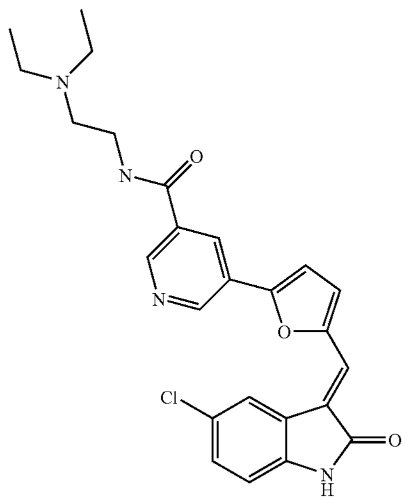 | 465 | <1 | |
| 154 | 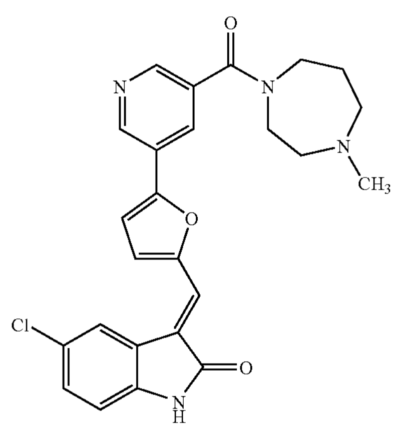 | 463 | <1 | |
| 155 | 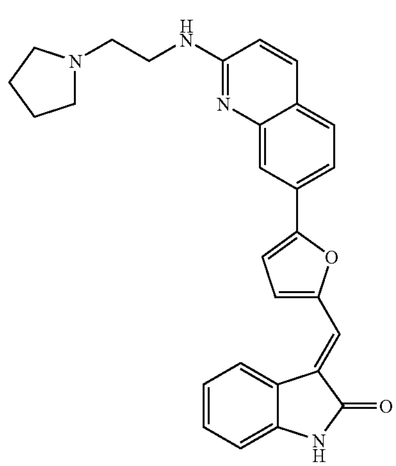 | 451 | <1 | |

TABLE 1-continued

Compounds of the invention and their activity against PIM-1 kinase.

| Entry No. | Structure | M + 1 | IC$_{50}$ (µM) | PIM-1 Inhibition @ 15 µMATP |
|---|---|---|---|---|
| 156 | 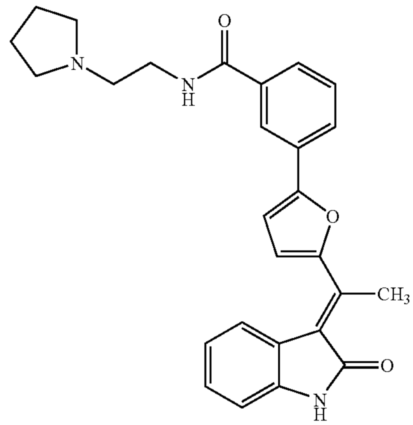 | 442 | | <2 |
| 157 | 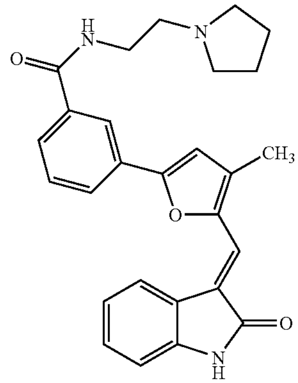 | 442 | | <2 |
| 158 | 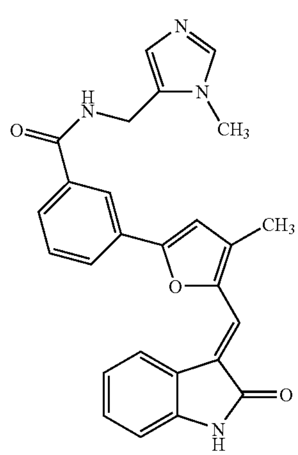 | 439 | | <2 |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 159 | 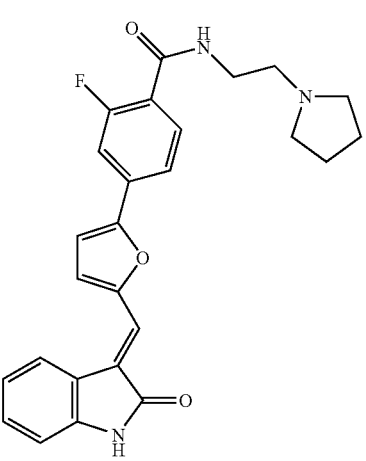 | 446 | | 11.35% |
| 160 | 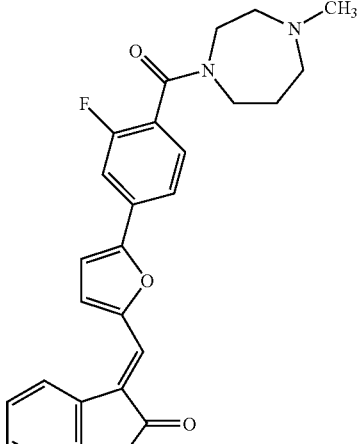 | 446 | | −17.05% |
| 161 | 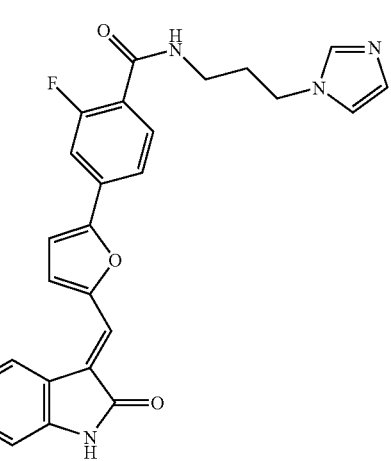 | 457 | | 28.40% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 162 | 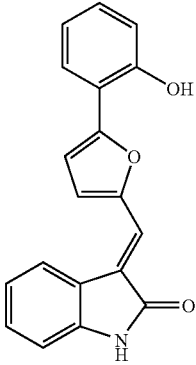 | 304 | <2 | |
| 163 | 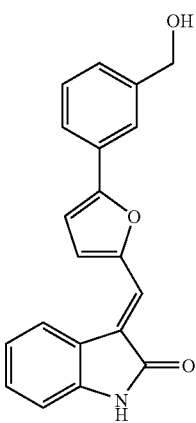 | 318 | <2 | |
| 164 | 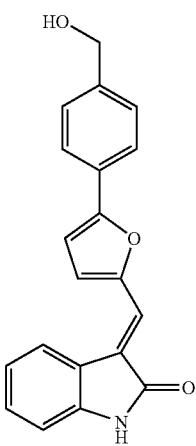 | 319 | <2 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 165 | 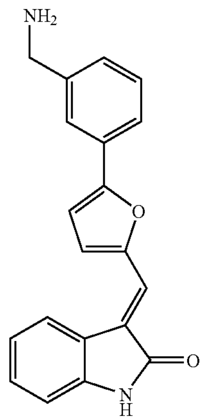 | 317 | | 19.36% |
| 166 | 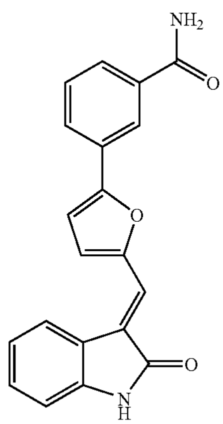 | 332 | <1 | |
| 167 | 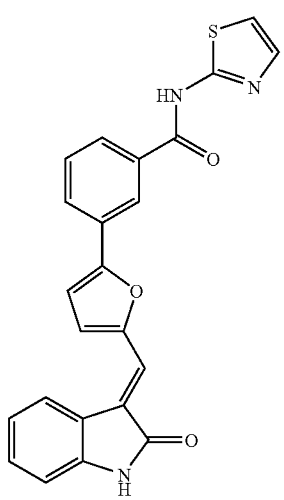 | 414 | | −3.02;% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 168 | 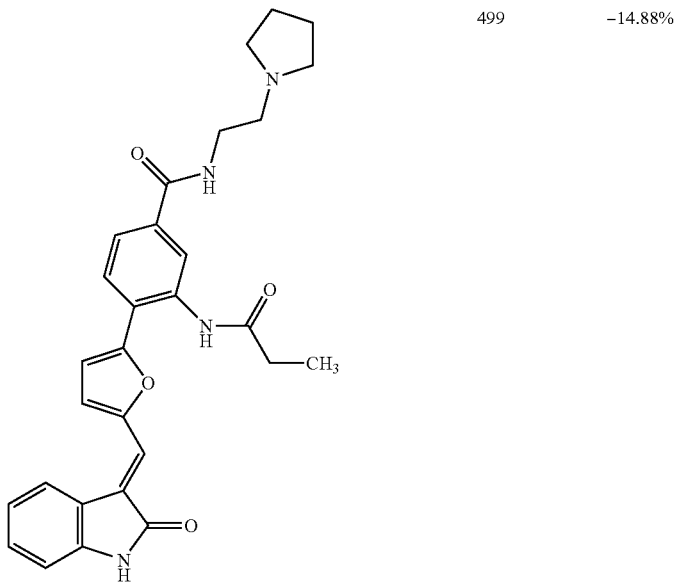 | 499 | | −14.88% |
| 169 | 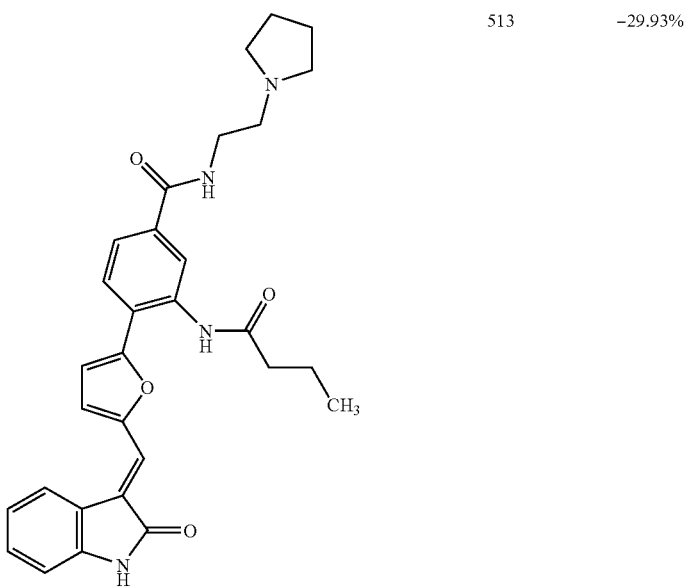 | 513 | | −29.93% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 170 | 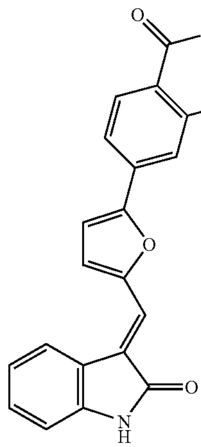 | 348 | | 42.96% |
| 171 | 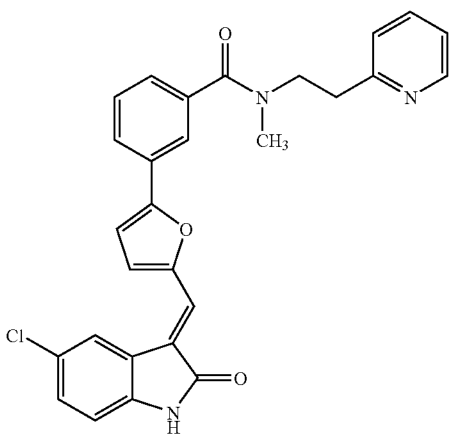 | 484 | | −0.11% |
| 172 | 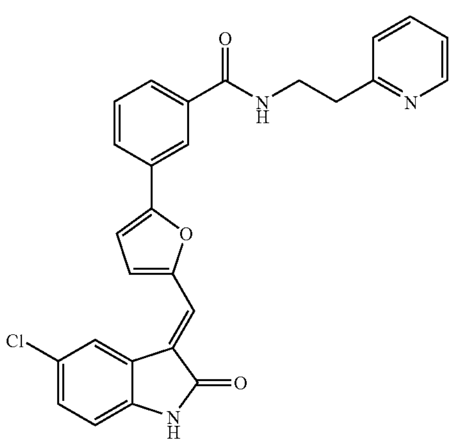 | 470 | | 29.27% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 173 | 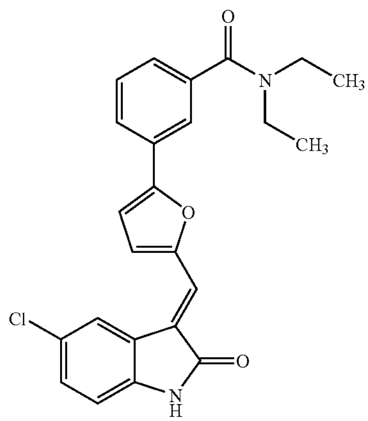 | 421 | | 29.20% |
| 174 | 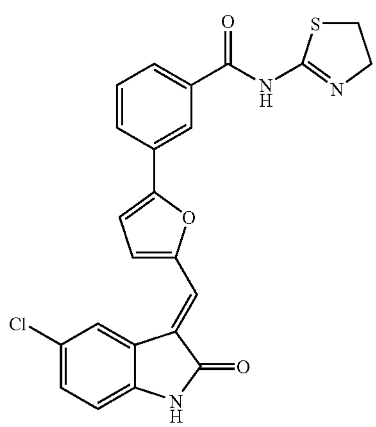 | 450 | <1 | |
| 175 | 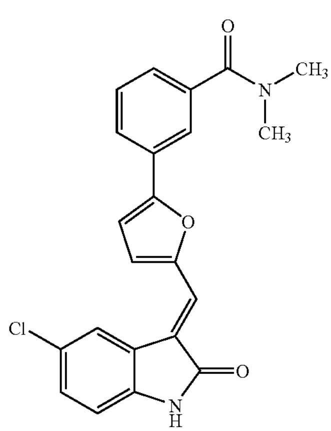 | 393 | | 21.21% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 176 | 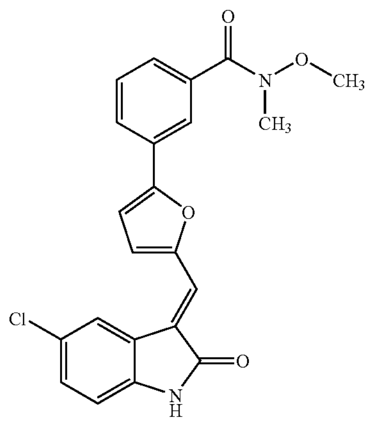 | 409 | | −59.63% |
| 177 | 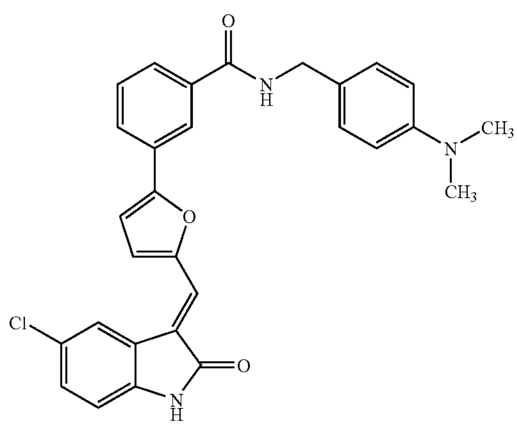 | 498 | | 10.92% |
| 178 | 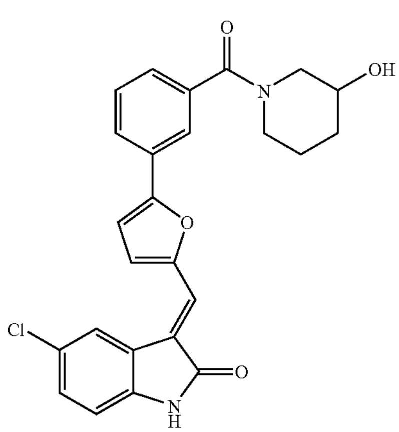 | 449 | | −19.44% |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 179 | 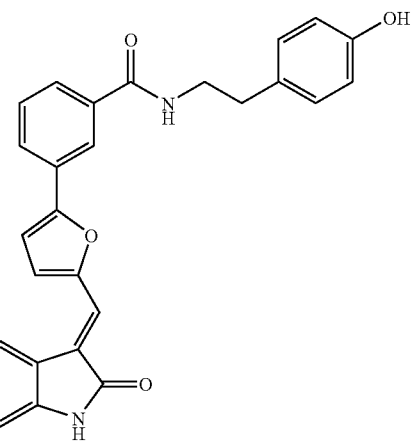 | 485 | | 18.39% |
| 180 | 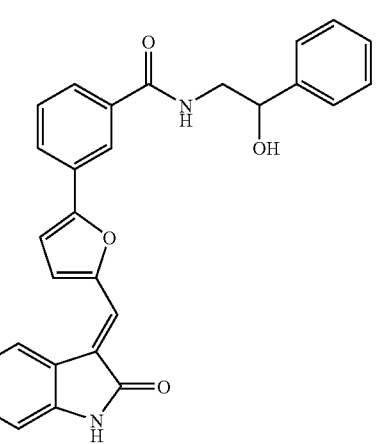 | 485 | <1 | |
| 181 | 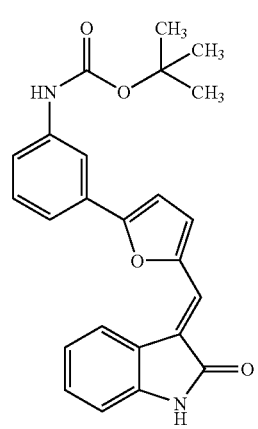 | 403 | | 14.48% |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 182 | 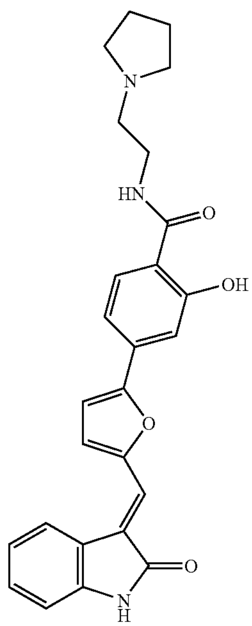 | 444 | <2 | |
| 183 | 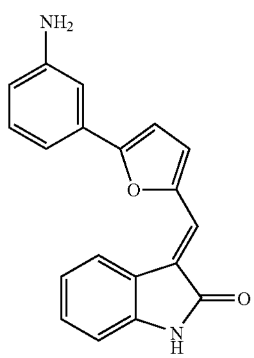 | 303 | <2 | |
| 184 | 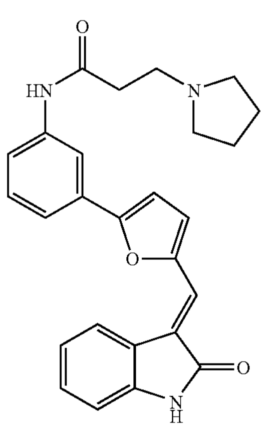 | 428 | <1 | |

TABLE 1-continued
Compounds of the invention and their activity against PIM-1 kinase.
| Entry No. | Structure | M + 1 | IC$_{50}$ (µM) | PIM-1 Inhibition @ 15 µMATP |
|---|---|---|---|---|
| 185 | 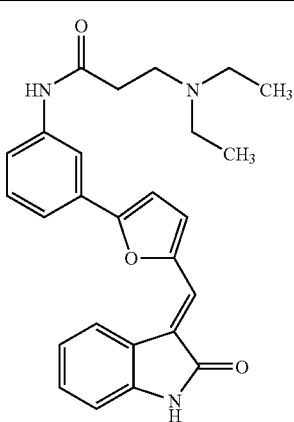 | 430 | <1 | |
| 186 | 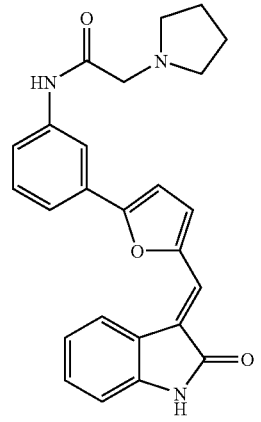 | 414 | <1 | |
| 187 | 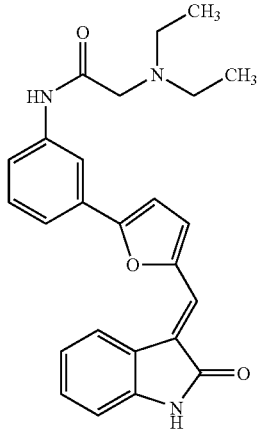 | 416 | <1 | |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 188 | 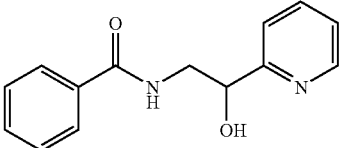 | 486 | <1 | |
| 189 | 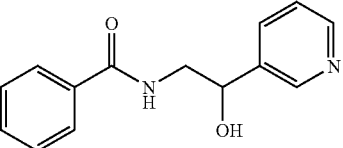 | 486 | <1 | |
| 190 | 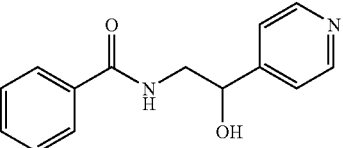 | 486 | <1 | |

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 191 | 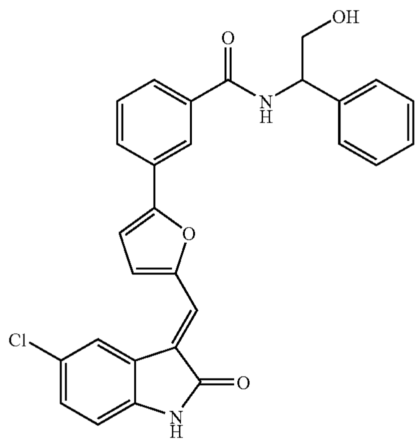 | 485 | | |
| 192 | 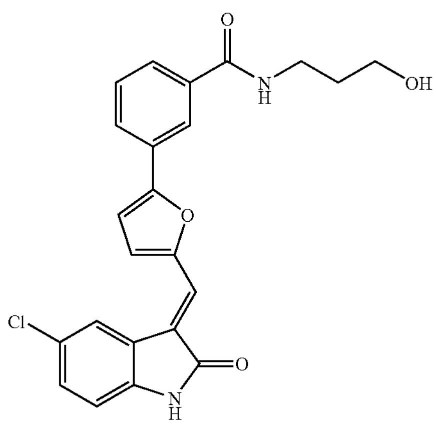 | 423 | | <1 |
| 193 | 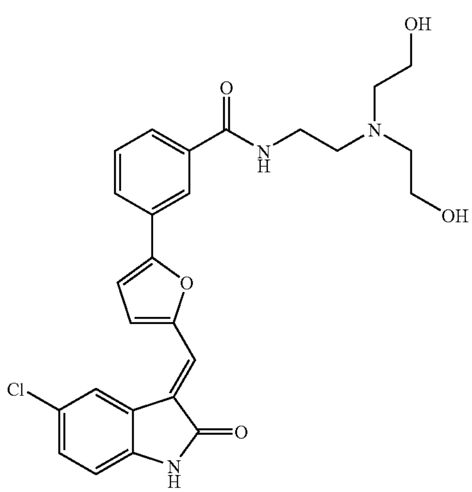 | 496 | | <1 |

TABLE 1-continued
Compounds of the invention and their activity against PIM-1 kinase.
| Entry No. | Structure | M + 1 | IC$_{50}$ (μM) | PIM-1 Inhibition @ 15 μMATP |
|---|---|---|---|---|
| 194 | 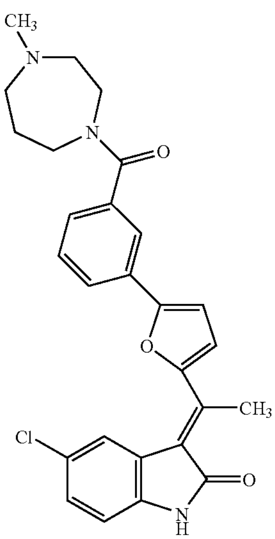 | 476 | <1 | |
| 195 | 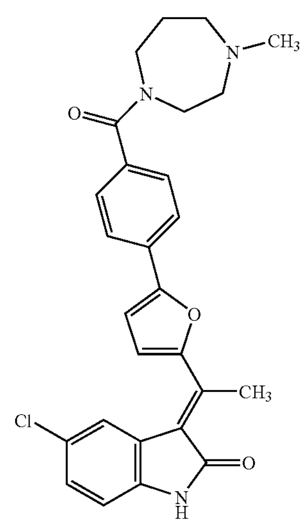 | 476 | <1 | |
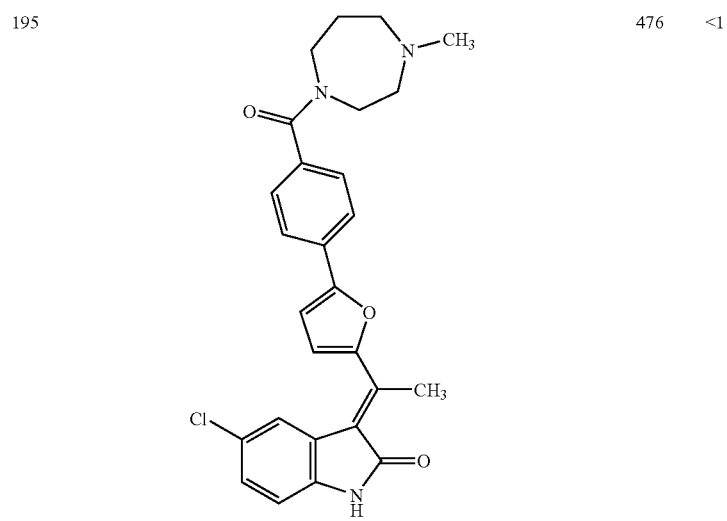

TABLE 1-continued

Compounds of the invention and their activity against PIM-1 kinase.

| Entry No. | Structure | M + 1 | IC$_{50}$ (μM) | PIM-1 Inhibition @ 15 μMATP |
|---|---|---|---|---|
| 196 | 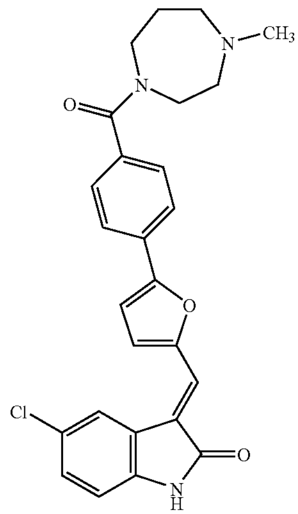 | 462 | <1 | |
| 197 | 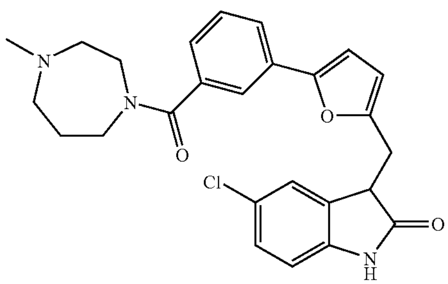 | 464 | <1 | |

The following tables (Table 2 and Table 3) provide cell based data for selected compounds. All the data is reported in μM.

TABLE 2

| Cell based Activity of Selected Compounds in μM. | | | | |
|---|---|---|---|---|
| Structure | AB: K-562 | AB: MiaPaCa | AB: PC3 | PIM1: IC50 |
| | 0.24 μM | 0.559 μM | 15.357 μM | <0.1 μM |

TABLE 3
Cell-based Activity of Selected Compounds in μM.
| Structure | AB: MiaPaCa | AB: MDAMB-231 | AB: PC3 | AB: K-562 | AB: MV-4-11 | PIM1: IC50 (DMSO 4%) | LCMS (ES): m/z [M + 1]+ |
|---|---|---|---|---|---|---|---|
| 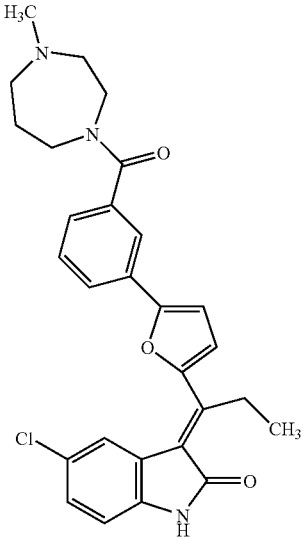 | 0.302 | >10 | >30 | 0.153 | 0.109 | <1 | 491 |
| 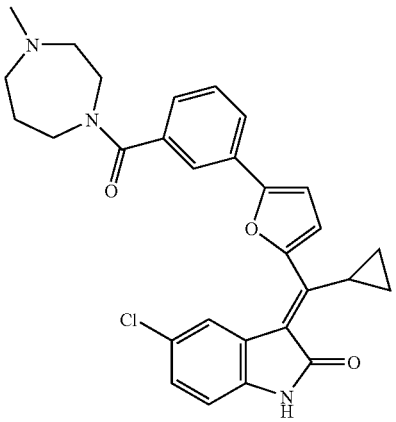 | | | | | | >1.1 | 502 |
| 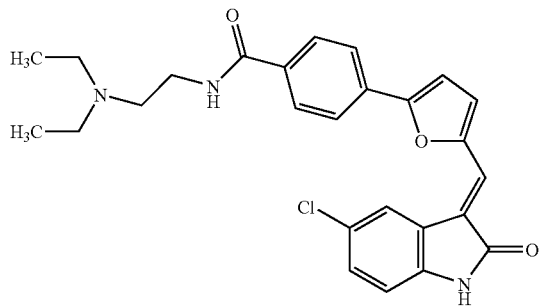 | >10 | >10 | >10 | >1 | <1 | | 464 |

TABLE 3-continued

Cell-based Activity of Selected Compounds in μM.

| Structure | AB: MiaPaCa | AB: MDAMB-231 | AB: PC3 | AB: K-562 | AB: MV-4-11 | PIM1: IC50 (DMSO 4%) | LCMS (ES): m/z [M + 1]+ |
|---|---|---|---|---|---|---|---|
| | >10 | >10 | >30 | >10 | >10 | <1 | 451 |
| | >10 | >10 | >30 | >10 | >10 | <1 | 389 |
| 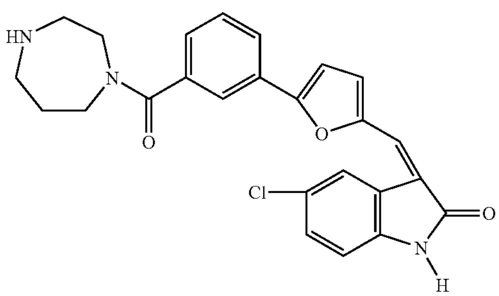 | 0.815 | 3.152 | 9.615 | 0.342 | | <1 | 448 |
| | >10 | >10 | >30 | 2.32 | 0.198 | <1 | 425 |
| | >10 | >10 | 11.013 | 2.88 | 2.219 | <1 | 415 |

TABLE 3-continued

Cell-based Activity of Selected Compounds in μM.

| Structure | AB: MiaPaCa | AB: MDAMB-231 | AB: PC3 | AB: K-562 | AB: MV-4-11 | PIM1: IC50 (DMSO 4%) | LCMS (ES): m/z [M + 1]+ |
|---|---|---|---|---|---|---|---|
| | >10 | >10 | 11.996 | >10 | 0.189 | <1 | 388 |
| | >10 | >10 | >30 | >10 | | <1 | 365 |
| | >10 | >10 | >30 | >10 | 1.912 | <1 | 365 |
| | | | | | | <1 | 421 |
| | >10 | >10 | 2.679 | >10 | 0.748 | <1 | 379 |
| | | | | | | <1 | 480 |

TABLE 3-continued

Cell-based Activity of Selected Compounds in μM.

| Structure | AB: MiaPaCa | AB: MDAMB-231 | AB: PC3 | AB: K-562 | AB: MV-4-11 | PIM1: IC50 (DMSO 4%) | LCMS (ES): m/z [M + 1]+ |
|---|---|---|---|---|---|---|---|
| | | | | >10 | | <1 | 446 |
| | | | | >10 | | <1 | 401 |
| | | | | | | | 480 |

TABLE 3-continued

Cell-based Activity of Selected Compounds in μM.

| Structure | AB: MiaPaCa | AB: MDAMB-231 | AB: PC3 | AB: K-562 | AB: MV-4-11 | PIM1: IC50 (DMSO 4%) | LCMS (ES): m/z [M + 1]+ |
|---|---|---|---|---|---|---|---|
| 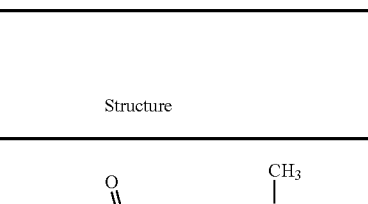 | | | | | | | 480 |

The following is a table (Table 4) of compounds with cell based data and phospho Flt3 and phospho BAD data. All the data is in μM.

TABLE 4

Cell-based Activity of Selected Compounds in μM.

| Structure | AB: K-562 | AB: MV-4-11 | AB: HCT-116 | AB: MiaPaCa | PIM1: IC50 (15 um ATP) | phospho FLT3 |
|---|---|---|---|---|---|---|
| 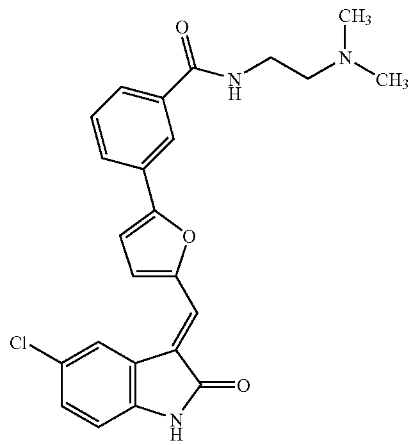 | 0.367 | 2.987 | 1.188 | 1.94 | 0.289 | 5.295 |

TABLE 4-continued
Cell-based Activity of Selected Compounds in μM.
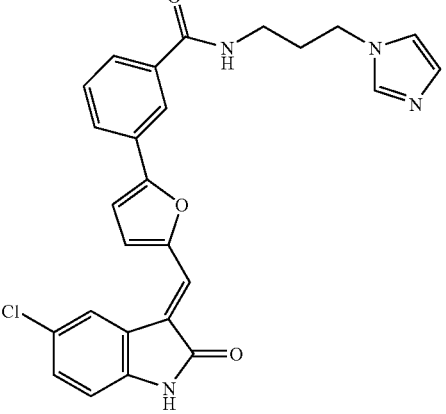
| | | | | | |
|---|---|---|---|---|---|
| 0.288 | 0.067 | 0.314 | 0.233 | 0.376 | >10 |
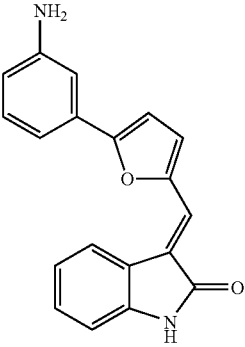
| | | | |
|---|---|---|---|
| 5.129 | 2.437 | | 0.992 |
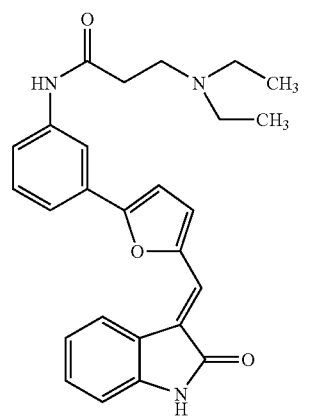
| | | | | |
|---|---|---|---|---|
| 0.472 | 0.349 | 0.101 | 0.259 | >10 |

TABLE 4-continued
Cell-based Activity of Selected Compounds in μM.
| | | | | | |
|---|---|---|---|---|---|
| 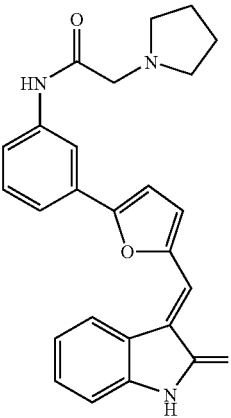 | 1.367 | 0.35 | >10 | 0.549 | >10 |
| 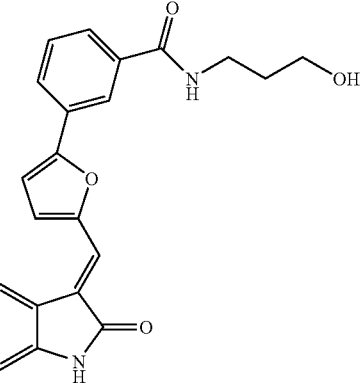 | >10 | 0.608 | >30 | 0.132 | >10 |
| 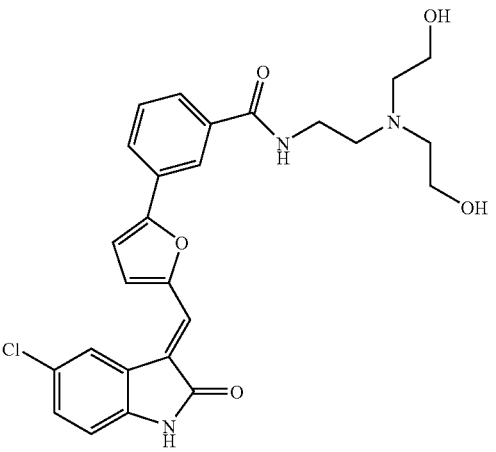 | 1.61 | 0.288 | >30 | 0.081 | >10 |

TABLE 4-continued
Cell-based Activity of Selected Compounds in μM.
| Structure | phospho BAD | AB: PC3 | AB: THP-1 | AB: MDAMB231 | AB: BxPC3 |
|---|---|---|---|---|---|
| 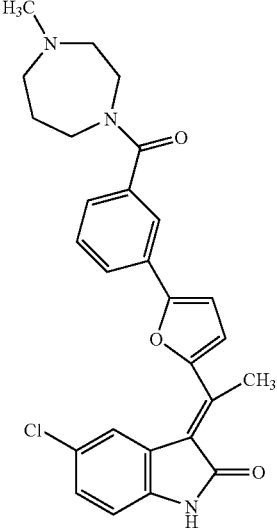 | 0.777 | 0.178 | | 0.106 | 9.063 |
| 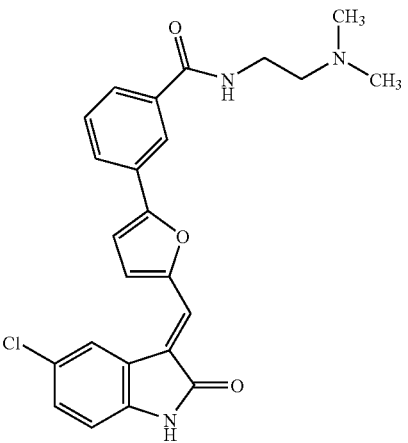 | 0.444 | | | | |
| 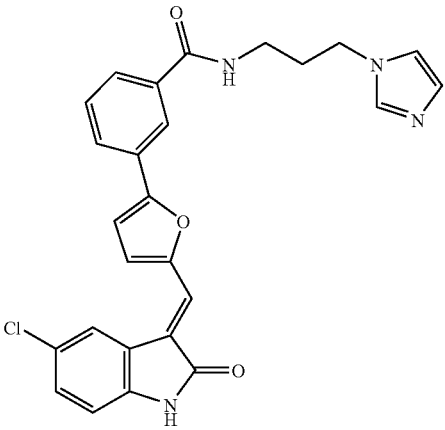 | 1.864 | | | | |

TABLE 4-continued
Cell-based Activity of Selected Compounds in μM.
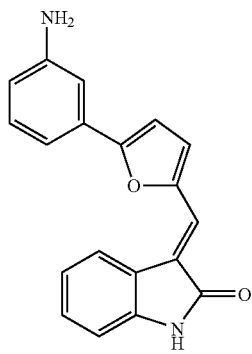
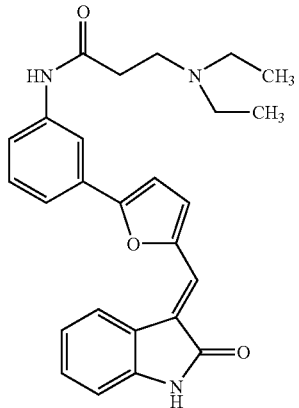
1.414   3.927   3.774
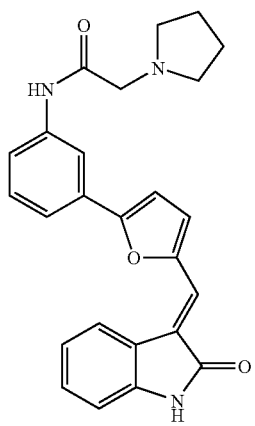
2.129   1.351   3.862
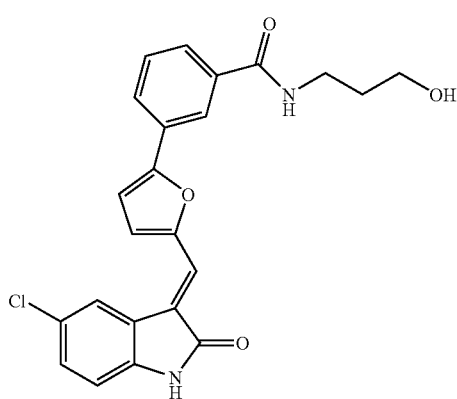
3.501   >30   >30

TABLE 4-continued
Cell-based Activity of Selected Compounds in μM.
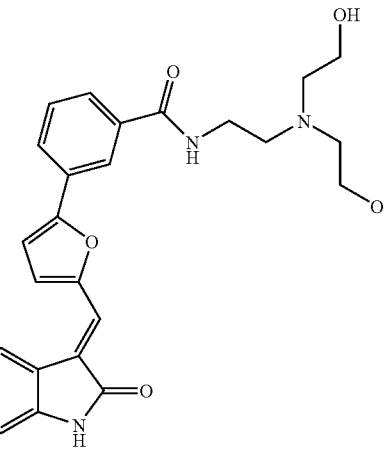
| | | |
|---|---|---|
| 0.609 | >30 | 2.903 |
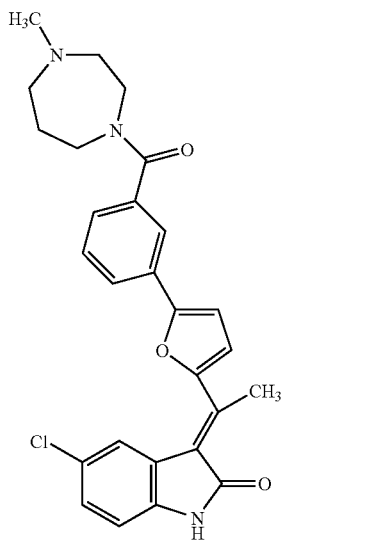
| | | |
|---|---|---|
| 1.764 | 0.816 | 0.785 |
The following table (Table 5) contains additional cell-based screening data. All data is reported in μM.
TABLE 5
| Structure | AB: MiaPaCa IC50 (uM) | AB: HCT-116 IC50 (uM) | AB: PC3 IC50 (uM) | AB: K-562 IC50 (uM) | AB: MV-4-11 IC50 (uM) | PIM1: % inh 500 nM | M + 1 |
|---|---|---|---|---|---|---|---|
| 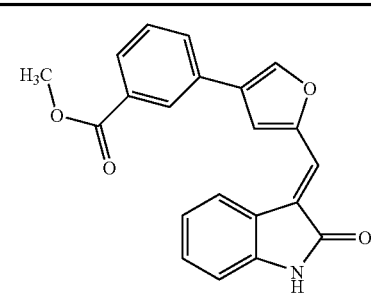 | 4.34 | 2.326 | 1.889 | 1.306 | >10 | −18.367 | 346 |

TABLE 5-continued

| Structure | AB: MiaPaCa IC50 (uM) | AB: HCT-116 IC50 (uM) | AB: PC3 IC50 (uM) | AB: K-562 IC50 (uM) | AB: MV-4-11 IC50 (uM) | PIM1: % inh 500 nM | M + 1 |
|---|---|---|---|---|---|---|---|
| | >10 | 4.306 | >10 | >10 | 0.315 | −22.653 | 428 |
| 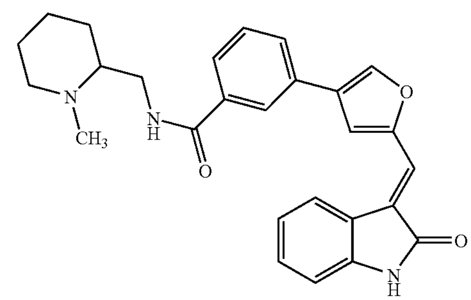 | 2.404 | 2.488 | 1.653 | 0.099 | 0.12 | −28.904 | 442 |
| 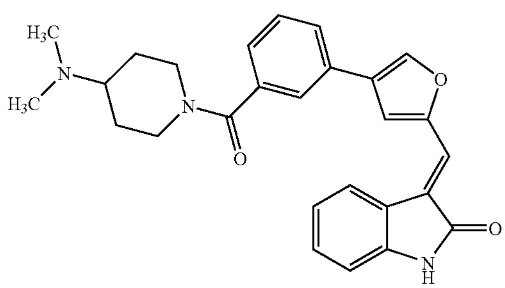 | 9.374 | 7.012 | >10 | 0.077 | 2.141 | −38.769 | 442 |
| 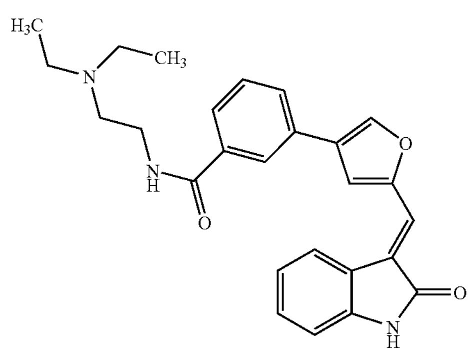 | 9.232 | 7.824 | >10 | >10 | 0.761 | −10.861 | 430 |
| | >10 | >10 | >10 | >10 | 1.072 | −22.375 | 442 |

TABLE 5-continued

| Structure | AB: MiaPaCa IC50 (uM) | AB: HCT-116 IC50 (uM) | AB: PC3 IC50 (uM) | AB: K-562 IC50 (uM) | AB: MV-4-11 IC50 (uM) | PIM1: % inh 500 nM | M + 1 |
|---|---|---|---|---|---|---|---|
| | >10 | >10 | >10 | >10 | 1.184 | −17.401 | 428 |
| | >10 | >10 | >10 | >10 | 0.998 | −14.607 | 425 |
| | >10 | >10 | >10 | >10 | 0.168 | −4.22 | 422 |
| | >10 | 4.65 | 6.999 | 3.12 | 1.012 | 6.108 | 446 |
| | >10 | 5.233 | >10 | 0.941 | 0.485 | 17.059 | 460 |

TABLE 5-continued

| Structure | AB: MiaPaCa IC50 (uM) | AB: HCT-116 IC50 (uM) | AB: PC3 IC50 (uM) | AB: K-562 IC50 (uM) | AB: MV-4-11 IC50 (uM) | PIM1: % inh 500 nM | M + 1 |
|---|---|---|---|---|---|---|---|
| (1-methylpyrrolidin-2-yl structure) | >10 | 5.161 | >10 | >10 | 0.93 | 2.87 | 446 |
| (1-methylimidazol-5-yl structure) | >10 | >10 | >10 | >10 | 1.379 | 12.701 | 443 |
| (1-methylpiperidin-2-yl structure) | >10 | 4.473 | >10 | 1.649 | 0.627 | 9.422 | 460 |
| (diethylaminoethyl structure) | >10 | 3.596 | >10 | 2.438 | 0.271 | 11.525 | 448 |
| (pyridin-4-ylmethyl structure) | >10 | >10 | | >10 | 1.567 | −19.133 | 440 |

TABLE 5-continued
| Structure | AB: MiaPaCa IC50 (uM) | AB: HCT-116 IC50 (uM) | AB: PC3 IC50 (uM) | AB: K-562 IC50 (uM) | AB: MV-4-11 IC50 (uM) | PIM1: % inh 500 nM | M + 1 |
|---|---|---|---|---|---|---|---|
| 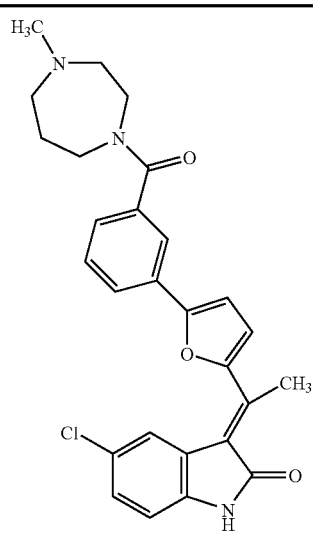 | >10 | 3.848 | 7.526 | 3.698 | 0.516 | 10.802 | 460 |
The following table (Table 6) provides IC$_{50}$ data for activity on PIM-2 for selected compounds.
TABLE 6
PIM-2 Activity of selected compounds
| Structure | PIM2: IC50 (15 μm ATP) |
|---|---|
| 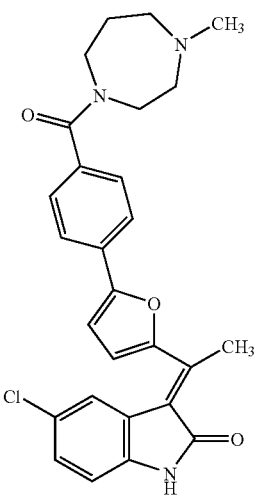 | <1 μM |
| | <1 μM |

TABLE 6-continued

| PIM-2 Activity of selected compounds | |
|---|---|
| Structure | PIM2: IC50 (15 μm ATP) |
| *(structure: 4-methyl-1,4-diazepane-carbonyl-phenyl-furan-methylidene-5-chlorooxindole)* | <1 μM |
| *(structure: N,N-diethylaminoethyl-amide-phenyl-furan-methylidene-5-chlorooxindole)* | <1 μM |

Examples of compounds of formula (I) were shown to be active inhibitors of Flt3. Table 7 provides exemplary compounds and their activity on Flt3.

TABLE 7

| Flt3 activity of selected compounds. | |
|---|---|
| Structure | FLT3_RB: IC50 (μM) |
| *(structure: pyrrolidinyl-ethyl-amide-chlorophenyl-furan-methylidene-oxindole)* | 0.211 |

TABLE 7-continued

Flt3 activity of selected compounds.

| Structure | FLT3_RB: IC50 (μM) |
|---|---|
| 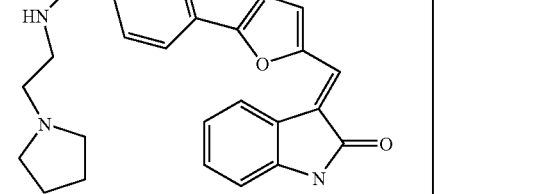 | 0.099 |
| 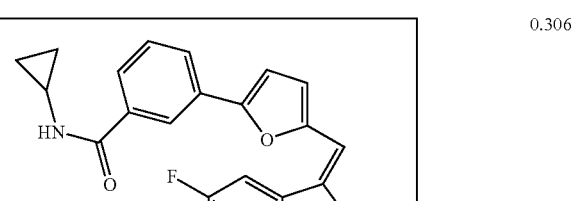 | 0.306 |
| 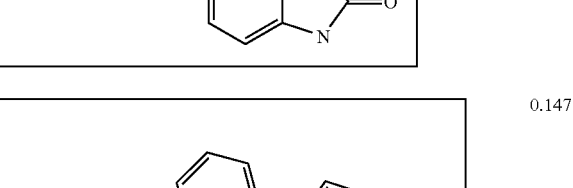 | 0.147 |
| 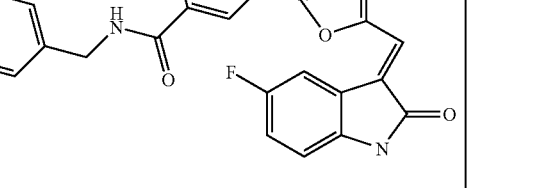 | 0.1 |

Formulation and Methods of Administration

Administration of the compounds of the invention, or their pharmaceutically acceptable salts, in pure form or in an appropriate pharmaceutical composition, can be carried out via any of the accepted modes of administration of agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, gel, ointment, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. In some embodiments, the dosage form is a solution that is suitable for administration by injection, such as intramuscular, subcutaneous, or intravenous injection. Such dosage forms may be administered in a single bolus or by an infusion, or by other methods known in the art such as using depot delivery.

In some embodiments, the compounds or compositions of the invention are administered about once per week. In some embodiments, they are administered about once per day, or at least once per day. In some embodiments, the compounds and compositions may suitably be administered in two or more dosages per day. Selection of the timing and frequency of administration, and determining the duration of treatment, is generally within the level of an ordinarily skilled practitioner.

The pharmaceutical compositions discussed herein include a conventional pharmaceutical carrier or excipient and a compound of the invention as the/an active agent. Typically, the compositions include at least one pharmaceutically acceptable carrier, and in some embodiments the carrier is an excipient other than or in addition to water, DMSO and ethanol. In addition, they may include other medicinal agents, pharmaceutical agents, carriers, adjuvants, buffers, etc. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate.

One preferable route of administration is oral, using a convenient dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients. In solid dosages, a compound of one of the formulae described herein or a pharmaceutically acceptable salt thereof will sometimes comprise 10-90% of the solid dosage form, or between about 20% and 80%. In liquid dosage forms, the compound or a pharmaceutically acceptable salt thereof will often comprise from about 1% to about 10% of the weight of the liquid dosage.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. For administration to animal or human subjects, the appropriate dosage of a compound described above often is 0.01-15 mg/kg, and sometimes 0.1-10 mg/kg. In some embodiments, a suitable dosage of the compound of the invention for an adult patient will be between 1 and 500 mg per dose, frequently between 10 and 300 mg, and the dosage may be administered 1-4 times per day. Dosage levels are dependent on the nature of the condition, drug efficacy, the condition of the patient, the judgment of the practitioner, and the frequency and mode of administration; however, optimization of such parameters is within the ordinary level of skill in the art.

The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Therapeutic Combinations

Compounds and compositions of the invention may be used in combination with anticancer or other agents, such as palliative agents, that are typically administered to a patient being treated for cancer. Such "anticancer agents" include, e.g., classic chemotherapeutic agents, as well as molecular targeted therapeutic agents, biologic therapy agents, and radiotherapeutic agents.

When a compound or composition of the invention is used in combination with an anticancer agent to another agent, the present invention provides, for example, simultaneous, staggered, or alternating treatment. Thus, the compound of the invention may be administered at the same time as an anticancer agent, in the same pharmaceutical composition; the compound of the invention may be administered at the same time as the anticancer agent, in separate pharmaceutical compositions; the compound of the invention may be administered before the anticancer agent, or the anticancer agent may be administered before the compound of the invention, for example, with a time difference of seconds, minutes, hours, days, or weeks.

In examples of a staggered treatment, a course of therapy with the compound of the invention may be administered, followed by a course of therapy with the anticancer agent, or the reverse order of treatment may be used, and more than one series of treatments with each component may also be used. In certain examples of the present invention, one component, for example, the compound of the invention or the anticancer agent, is administered to a mammal while the other component, or its derivative products, remains in the bloodstream of the mammal. For example, a compound for formulae (I)-(IV) may be administered while the anticancer agent or its derivative products remains in the bloodstream, or the anticancer agent may be administered while the compound of formulae (I)-(IV) or its derivatives remains in the bloodstream. In other examples, the second component is administered after all, or most of the first component, or its derivatives, have left the bloodstream of the mammal.

The compound of the invention and the anticancer agent may be administered in the same dosage form, e.g., both administered as intravenous solutions, or they may be administered in different dosage forms, e.g., one compound may be administered topically and the other orally. A person of ordinary skill in the art would be able to discern which combinations of agents would be useful based on the particular characteristics of the drugs and the cancer involved.

Anticancer agents useful in combination with the compounds of the present invention may include agents selected from any of the classes known to those of ordinary skill in the art, including, but not limited to, antimicrotubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; pro-apoptotic agents; and cell cycle signaling inhibitors; other agents.

Anti-microtubule or anti-mitotic agents are phase specific agents that are typically active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that are believed to operate at the G2/M phases of the cell cycle. It is believed that the diterpenoids stabilize the p-tubulin subunit of the microtubules, by binding with this protein. Disassembly of the protein appears then to be inhibited with mitosis being arrested and cell death following.

Examples of diterpenoids include, but are not limited to, taxanes such as paclitaxel, docetaxel, larotaxel, ortataxel, and tesetaxel. Paclitaxel is a natural diterpene product isolated from the Pacific yew tree *Taxus brevifolia* and is commercially available as an injectable solution TAXOL®. Docetaxel is a semisynthetic derivative of paclitaxel q. v., prepared using a natural precursor, 10-deacetyl-baccatin III, extracted from the needle of the European Yew tree. Docetaxel is commercially available as an injectable solution as TAXOTERE®.

Vinca alkaloids are phase specific anti-neoplastic agents derived from the periwinkle plant. Vinca alkaloids that are believed to act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, vindesine, and vinorelbine. Vinblastine, vincaleukoblastine sulfate, is commercially available as VELBAN® as an injectable solution. Vincristine, vincaleukoblastine 22-oxo-sulfate, is commercially available as ONCOVIN® as an injectable solution. Vinorelbine, is commercially available as an injectable solution of vinorelbine tartrate (NAVELBINE®), and is a semisynthetic vinca alkaloid derivative.

Platinum coordination complexes are non-phase specific anti-cancer agents, which are interactive with DNA. The platinum complexes are believed to enter tumor cells, undergo, aquation and form intra- and interstrand crosslinks with DNA causing adverse biological effects to the tumor. Platinum-based coordination complexes include, but are not limited to cisplatin, carboplatin, nedaplatin, oxaliplatin, satraplatin, and (SP-4-3)-(cis)-amminedichloro-[2-methylpyridine]platinum(II). Cisplatin, cis-diamminedichloroplatinum, is commercially available as PLATINOL® as an injectable solution. Carboplatin, platinum, diammine[1,1-cyclobutane-dicarboxylate(2-)-0,0'], is commercially available as PARAPLATIN® as an injectable solution.

Alkylating agents are generally non-phase specific agents and typically are strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, alkyl sulfonates such as busulfan; ethyleneimine and methylmelamine derivatives such as altretamine and thiotepa; nitrogen mustards such as chlorambucil, cyclophosphamide, estramustine, ifosfamide, mechlorethamine, melphalan, and uramustine; nitrosoureas such as carmustine, lomustine, and streptozocin; triazenes and imidazotetrazines such as dacarbazine, procarbazine, temozolamide, and temozolomide. Cyclophosphamide, 2-[bis(2-chloroethyl)-amino] tetrahydro-2H-1,3,2-oxazaphosphorine 2-oxide monohydrate, is commercially available as an injectable solution or tablets as CYTOXAN®. Melphalan, 4-[bis(2-chloroethyl) amino]-L-phenylalanine, is commercially available as an injectable solution or tablets as ALKERAN®. Chlorambucil, 4-[bis(2-chloroethyl)amino]-benzenebutanoic acid, is commercially available as LEUKERAN® tablets. Busulfan, 1,4-butanediol dimethanesulfonate, is commercially available as MYLERAN® TABLETS. Carmustine, 1,3-[bis(2-chloroethyl)-1-nitrosourea, is commercially available as single vials of lyophilized material as BiCNU®, 5-(3,3-dimethyl-1-triazeno)-imidazole-4-carboxamide, is commercially available as single vials of material as DTIC-Dome®.

Anti-tumor antibiotics are non-phase specific agents which are believed to bind or intercalate with DNA. This may result in stable DNA complexes or strand breakage, which disrupts ordinary function of the nucleic acids, leading to cell death. Examples of anti-tumor antibiotic agents include, but are not limited to, anthracyclines such as daunorubicin (including liposomal daunorubicin), doxorubicin (including liposomal doxorubicin), epirubicin, idarubicin, and valrubicin; streptomyces-related agents such as bleomycin, actinomycin, mithramycin, mitomycin, porfiromycin; and mitoxantrone. Dactinomycin, also know as Actinomycin D, is commercially available in injectable form as COSMEGEN®. Daunorubicin, (8S-cis-)-8-acetyl-10-[(3-amino-2,3,6-trideoxy-a-L-lyxohexopyranosyl)oxy]-7,8,9,10-tetrahydro-6,8,11-trihydroxy-1-methoxy-5,12-naphthacenedione hydrochloride, is commercially available as a liposomal injectable form as DAUNOXOME® or as an injectable as CERUBIDINE®. Doxorubicin, (8S,10S)-10-[(3-amino-2,3,6-trideoxy-α-L-lyxohexopyranosyl)oxy]-8-glycoloyl, 7,8,9,10-tetrahydro-6, 8,11-trihydroxy-1-methoxy-5,12-naphthacenedione hydrochloride, is commercially available in an injectable form as RUBEX® or ADRIAMYCIN RDF®. Bleomycin, a mixture of cytotoxic glycopeptide antibiotics isolated from a strain of *Streptomyces verticil/us*, is commercially available as BLENOXANE®.

Topoisomerase II inhibitors include, but are not limited to, epipodophyllotoxins, which are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide, teniposide, and amsacrine. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Teniposide, 4'-demethyl-epipodophyllotoxin 9[4,6-0-(R)-thenylidene-β-D-glucopyranoside], is commercially available as an injectable solution as VUMON® and is commonly known as VM-26.

Antimetabolite neoplastic agents are phase specific antineoplastic agents that typically act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Anti-metabolites, include purine analogs, such as fludarabine, cladribine, chlorodeoxyadenosine, clofarabine, mercaptopurine, pentostatin, erythrohydroxynonyladenine, fludarabine phosphate and thioguanine; pyrimidine analogs such as fluorouracil, gemcitabine, capecitabine, cytarabine, azacitidine, edatrexate, floxuridine, and troxacitabine; antifolates, such as methotrexate, pemetrexed, raltitrexed, and trimetrexate. Cytarabine, 4-amino-1-p-D-arabinofuranosyl-2(1H)-pyrimidinone, is commercially available as CYTOSAR-U® and is commonly known as Ara-C. Mercaptopurine, 1,7-dihydro-6H-purine-6-thione monohydrate, is commercially available as PURINETHOL®. Thioguanine, 2-amino-1,7-dihydro-6H-purine-6-thione, is commercially available as TABLOID®. Gemcitabine, 2'-deoxy-2',2'-difluorocytidine monohydrochloride (p-isomer), is commercially available as GEMZAR®.

Topoisomerase I inhibitors including, camptothecin and camptothecin derivatives. Examples of topoisomerase I inhibitors include, but are not limited to camptothecin, topotecan, irinotecan, rubitecan, belotecan and the various optical forms (i.e., (R), (S) or (R,S)) of 7-(4-methylpiperazino-methylene)-10,11-ethylenedioxy-camptothecin, as described in U.S. Pat. Nos. 6,063,923; 5,342,947; 5,559,235; 5,491,237 and pending U.S. patent application Ser. No. 08/977,217 filed Nov. 24, 1997. Irinotecan HCl, (4S)-4,11-diethyl-4-hydroxy-9-[(4-piperidinopiperidino)-carbonyloxy]-1H-pyrano[3',4', 6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite 8N-38, to the topoisomerase I-DNA complex. Topotecan HCl, (S)-10-[(dimethylamino)methyl]-4-ethyl-4,9-dihydroxy-1H-pyrano [3',4',6,7]indolizino[1,2-b]quinoline-3,14-(4H,12H)-dione monohydrochloride, is commercially available as the injectable solution HYCAMTIN®.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, androgens such as fluoxymesterone and testolactone; antiandrogens such as bicalutamide, cyproterone, flutamide, and nilutamide; aromatase inhibitors such as aminoglutethimide, anastrozole, exemestane, formestane, vorazole, and letrozole; corticosteroids such as dexamethasone, prednisone and prednisolone; estrogens such as diethylstilbestrol; antiestrogens such as fulvestrant, raloxifene, tamoxifen, toremifine, droloxifene, and iodoxyfene, as well as selective estrogen receptor modulators (SERMS) such those described in U.S. Pat. Nos. 5,681,835, 5,877,219, and 6,207,716; 5α-reductases such as finasteride and dutasteride; gonadotropin-releasing hormone (GnRH) and analogues thereof which stimulate the release of leutinizing hormone (LH) and/or follicle stimulating hormone (FSH), for example LHRH agonists and antagonists such as buserelin, goserelin, leuprolide, and triptorelin; progestins such as medroxyprogesterone acetate and megestrol acetate; and thyroid hormones such as levothyroxine and liothyronine.

Signal transduction pathway inhibitors are those inhibitors, which block or inhibit a chemical process which evokes an intracellular change, such as cell proliferation or differentiation. Signal tranduction inhibitors useful in the present invention include, e.g., inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors.

Inappropriate or uncontrolled activation of many of these kinases, for example by over-expression or mutation, has been shown to result in uncontrolled cell growth. Accordingly, the aberrant activity of such kinases has been linked to malignant tissue growth. Consequently, inhibitors of such kinases could provide cancer treatment methods.

Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene.

Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., *Exp. Opin. Ther. Patents* (2000) 10(6):803-818; Shawver et al., *Drug Discov. Today* (1997), 2(2):50-63; and Lofts, F. J. et al., "Growth factor receptors as targets", New Molecular Targets for Cancer Chemotherapy, ed. Workman, Paul and Kerr, David, CRC press 1994, London. Specific examples of receptor tyrosine kinase inhibitors include, but are not limited to, sunitinib, erlotinib, gefitinib, and imatinib.

Tyrosine kinases which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAb1, FAK (Focal adhesion kinase), Brutons tyrosine kinase, and Bcr-Ab1. Such non-receptor kinases and agents which inhibit non-receptor tyrosine kinase function are described in Sinh, S. and Corey, S. J., *J. Hematotherapy & Stem Cell Res.* (1999) 8(5): 465-80; and Bolen, J. B., Brugge, J. S., *Annual Review of Immunology*. (1997) 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E., *J. Pharmacol. Toxicol. Methods*. (1995), 34(3): 125-32. Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., *J. Biochemistry*. (1999)126 (5): 799-803; Brodt, P, Samani, A, & Navab, R, *Biochem. Pharmacol.* (2000)60:1101-1107; Massague, J., Weis-Garcia, F., *Cancer Surv*. (1996)27:41-64; Philip, P. A, and Harris, A L, *Cancer Treat. Res*. (1995) 78: 3-27; Lackey, K. et al. *Bioorg. Med. Chem. Letters*, (2000) 10(3): 223-226; U.S. Pat. No. 6,268, 391; and Martinez-Lacaci, I., et al., *Int. J. Cancer* (2000), 88(1): 44-52. Inhibitors of Phosphotidyl inositol-3 Kinase family members including blockers of PI3-kinase, ATM, DNA-PK, and Ku are also useful in the present invention. Such kinases are discussed in Abraham, R T. *Current Opin. Immunol*. (1996), 8(3): 412-8; Canman, C. E., Lim, D. S., *Oncogene* (1998) 17(25): 3301-8; Jackson, S. P., *Int. J. Biochem. Cell Biol*. (1997) 29(7):935-8; and Zhong, H. et al., *Cancer Res*. (2000) 60(6):1541-5. Also useful in the present invention are Myo-inositol signaling inhibitors such as phospholipase C blockers and Myoinositol analogues. Such signal inhibitors are described in Powis, G., and Kozikowski A, (1994) New Molecular Targets for Cancer Chemotherapy, ed., Paul Workman and David Kerr, CRC Press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R, Gervasoni, S I, Matar, P., *J. Biomed. Sci*. (2000) 7(4): 292-8; Ashby, M. N., *Curr. Opin. Lipidol*. (1998) 9(2): 99-102; and Oliff, A., *Biochim. Biophys. Acta*, (1999) 1423 (3):C19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al., *Cancer Treat. Rev*., (2000) 26(4): 269-286); Herceptin® erbB2 antibody (see Stern, D F, *Breast Cancer Res*. (2000) 2(3):176-183); and 2CB VEGFR2 specific antibody (see Brekken, R. A. et al., *Cancer Res*. (2000) 60(18): 5117-24).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed erb family inhibitors. (See Bruns, C J et al., *Cancer Res*. (2000), 60(11): 2926-2935; Schreiber A B, Winkler M E, & Derynck R., *Science* (1986) 232(4755):1250-53; Yen L. et al., *Oncogene* (2000) 19(31): 3460-9).

Agents used in immunotherapeutic regimens may also be useful in combination with the compounds of formula (I)-(IV). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T, et al., *Cancer Res.* (2000) 60(13):3569-76; and Chen Y, et al., *Cancer Res.* (1998) 58(9): 1965-71.

Agents used in pro-apoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family. Therefore, strategies designed to downregulate the expression of bcl-2 in tumors have demonstrated clinical benefit and are now in Phase II/III trials, namely Genta's G3139 bcl-2 antisense oligonucleotide. Such pro-apoptotic strategies using the antisense oligonucleotide strategy for bcl-2 are discussed in Waters J S, et al., *J. Clin. Oncol.* (2000) 18(9): 1812-23; and Kitada S, et al. *Antisense Res. Dev.* (1994) 4(2): 71-9.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G R & Chang Y-T., *Exp. Opin. Ther. Patents* (2000) 10(2):215-30.

Other molecular targeted agents include FKBP binding agents, such as the immunosuppressive macrolide antibiotic, rapamycin; gene therapy agents, antisense therapy agents, and gene expression modulators such as the retinoids and rexinoids, e.g. adapalene, bexarotene, trans-retinoic acid, 9-cisretinoic acid, and N-(4 hydroxyphenyl)retinamide; phenotype-directed therapy agents, including: monoclonal antibodies such as alemtuzumab, bevacizumab, cetuximab, ibritumomab tiuxetan, rituximab, and trastuzumab; immunotoxins such as gemtuzumab ozogamicin, radioimmunoconjugates such as 131-tositumomab; and cancer vaccines.

Miscellaneous agents include altretamine, arsenic trioxide, gallium nitrate, hydroxyurea, levamisole, mitotane, octreotide, procarbazine, suramin, thalidomide, photodynamic compounds such as methoxsalen and sodium porfimer, and proteasome inhibitors such as bortezomib.

Biologic therapy agents include: interferons such as interferon-u2a and interferon-u2b, and interleukins such as aldesleukin, denileukin diftitox, and oprelvekin.

In addition to these anticancer agents intended to act against cancer cells, combination therapies including the use of protective or adjunctive agents, including: cytoprotective agents such as armifostine, dexrazonxane, and mesna, phosphonates such as parmidronate and zoledronic acid, and stimulating factors such as epoetin, darbeopetin, filgrastim, PEG-filgrastim, and sargramostim, are also envisioned.

The following examples are offered to illustrate but not to limit the invention. Compounds of the formulae provided herein can be made using known transformations, beginning with available starting materials. A general reaction scheme for such compounds is exemplified by the following examples, which have been used to make certain of the compounds disclosed herein. Compounds of the invention can be tested by conventional known methods; exemplary methods are provided herein. Some of the cell types used for testing of these compounds include:
HCT116: Colon
K-562: CML
MV-4-11: AML
MiaPaca: Pancreatic cancer
PC3: Prostate cancer
THP-1: AML Example 1

Synthesis of Compound 3

General Condensation Procedure

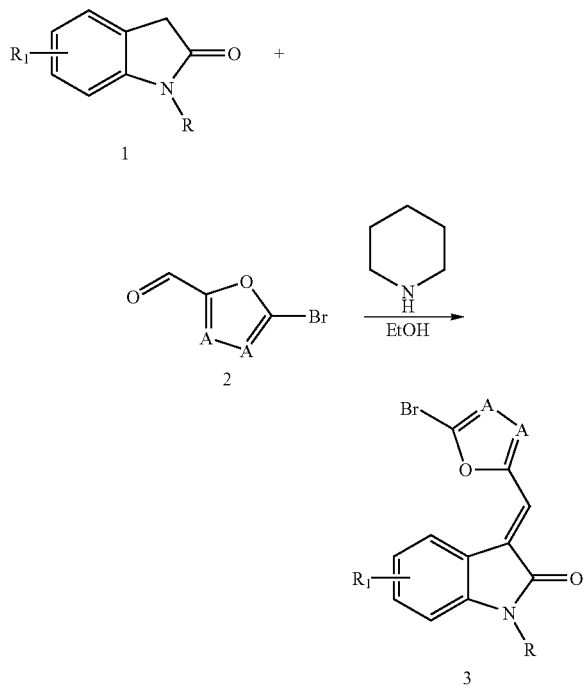

Known and readily available oxindoles of formula 1 react with heteroaryl aldehydes such as 2 to provide intermediates of formula 3; this reaction can be promoted by an amine such as piperidine in an alcoholic solvent. As a general example, a solution of oxindole 1 (1.54 mmol), aldehyde 2 (1.24 mmol) and piperidine (1.52 mmol) in EtOH (4.0 mL) was stirred at rt 30 min. The resulting precipitate was collected by filtration to yield desired compound 3.

Example 2

Synthesis of Compound 4

General Arylation Procedure

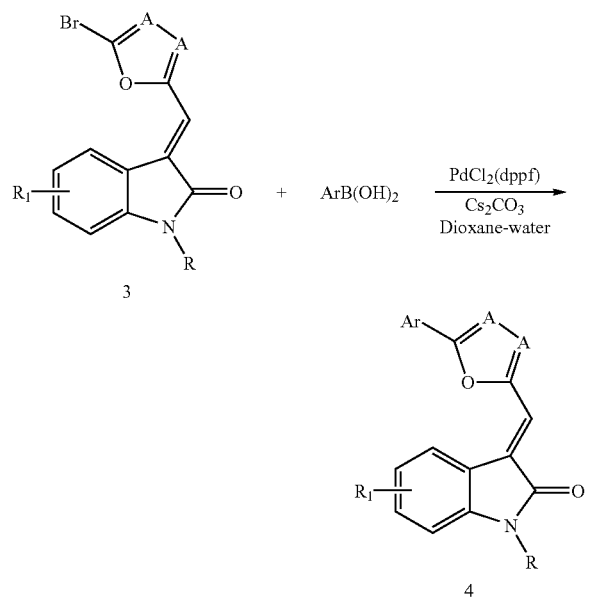

A solution of compound 3 (0.41 mmol), arylboronic acid (0.64 mmol), Cs2CO3 (270 mg, 0.83 mmol) and PdCl2(dppf) (16 mg, 0.02 mmol) in H2O/dioxane (5%, 5 mL) was heated at reflux for 6 h. The reaction mixture was diluted with H2O (150 mL) and extracted with EtOAc (3×100 mL). The organic layer was washed with brine (100 mL) and dried over Na2SO4 and concentrated to yield the desired compound 4.

Example 3

Synthesis of Compound 4

General Procedure—Arylation Followed by Condensation

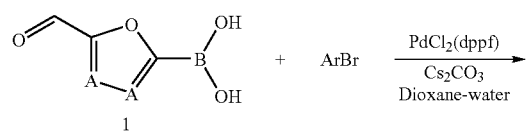

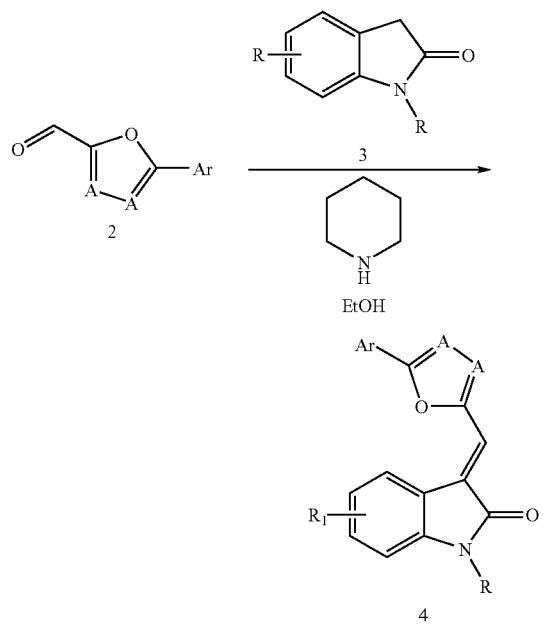

A solution of compound 1 (0.64 mmol), arylbromide (0.41 mmol), Cs2CO3 (270 mg, 0.83 mmol) and PdCl2(dppf) (16 mg, 0.02 mmol) in H2O/dioxane (5%, 5 mL) was heated at reflux for 6 h. The reaction mixture was diluted with H2O (150 mL) and extracted with EtOAc (3×100 mL). The organic layer was washed with brine (100 mL) and dried over Na2SO4 and concentrated to yield the desired compound 2. A solution of compound 2 (0.12 mmol), aldehyde 2 (0.12 mmol) and piperidine (0.12 mmol) in EtOH (2.0 mL) was stirred at rt 30 min. The resulting precipitate was collected by filtration to yield desired compound 4.

Example 4

Synthesis of Compound 3

General Procedure for Making Intermediates

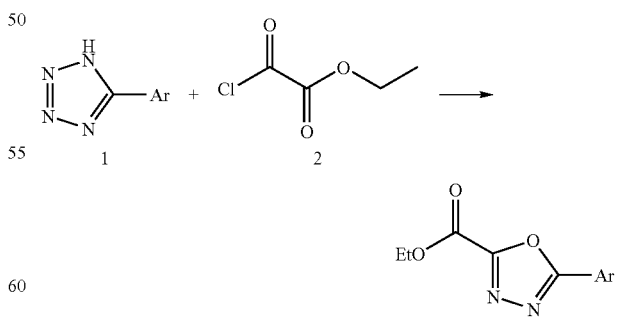

5-aryltetrazole 1 (45 mmol) and ethyl oxalyl chloride 2 (45 mmol) in dry toluene (150 mL) are refluxed for 90 min. The solvent is evaporated in vacuo and the residue is purified by flash column chromatography (silica gel, hexane/ethyl acetate 4:1 v/v) to give compound 3.

Example 5

Synthesis of Aryl Tetrazole 2

General Procedure for Making Aryl Tetrazoles

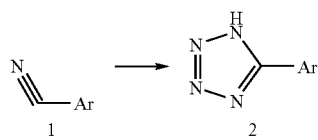

A solution of compound 1 (0.13 mmol) and azidotrimethylsilane (0.1 mL, 0.76 mmol), and ammonium chloride (21 mg, 0.39 mmol) in DMF (2 mL) was heated to 90° C. for 3 days. The mixture was cooled to room temperature, diluted with dichloromethane, washed with 1N HCl, with water, dried with Na2SO4, filtered and concentrated. The residue was purified on silica gel (eluted with dichloromethane) to give the desired compound 2.

Example 6

Synthesis of Aldehyde from Ester

General Procedure

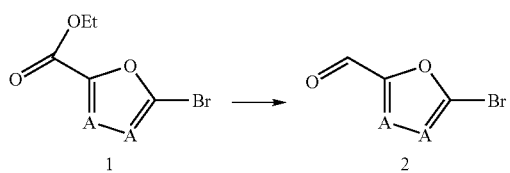

Compound 1 (2.4 mmol) was dissolved in 10 mL of anhydrous THF and then 1.2 mL of 1M solution of LiAlH4 was added to the resulting solution at 0° C. After the reaction was continued at room temperature for 30 min, 8 mL of 1N HCL was added to the reaction system, the mixture was concentrated under reduced pressure to a volume about 8 mL, the resulting concentrate was extracted with ethyl acetate and then the extract was concentrated under reduced pressure to thus give the corresponding alcohol. This alcohol was dissolved in 20 mL of methylene chloride, 1 g Molecular Sieves 4A and pyridinium chlorochromate (0.63 mmol) was added to the solution at 0° C., the mixture was stirred at 0° C. for 3 hours, the mixture was passed through a plug of Celite, followed by elution with 100 mL of diethyl ether and concentrated under reduced pressure to give compound 2.

Example 7

Synthesis of Compound 3

General Procedure

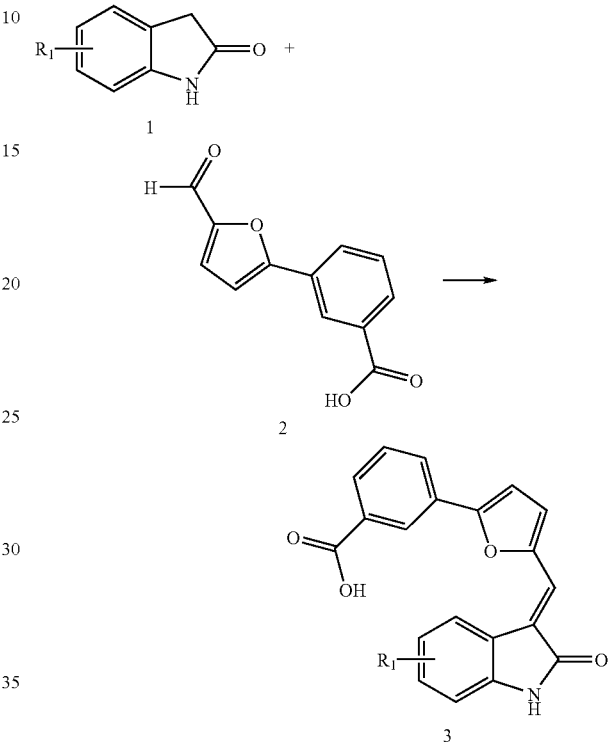

A solution of oxindole 1 (1.54 mmol), methyl 3-(5-formyl-furan-3-yl)benzoate 2 (350 mg, 1.24 mmol) and piperidine (0.15 mL, 1.52 mmol) in EtOH (4.0 mL) was stirred at rt for 30 min. The resulting precipitate was collected by filtration to yield desired compound 3.

Example 8

Synthesis of Compound 5

General Procedure

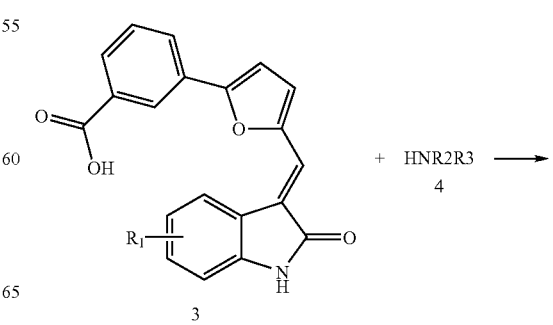

-continued

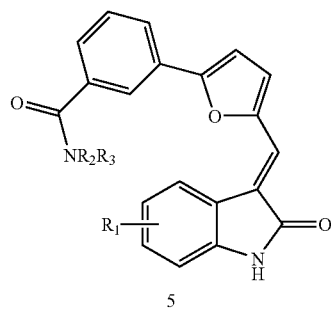

To a solution of compound 3 (0.06 mmol) and HOBt (16 mg, 0.14 mmol) in NMP (0.5 mL) was added EDCI (22 mg, 0.12 mmol). The reaction was stirred at rt for 10 min and then added amine 4 (0.24 mmol) followed by DIEA (0.05 mL). The reaction mixture was stirred at rt for 1 h and diluted with H2O (10 mL). The mixture was extracted with EtOAc, dried over Na2SO4 and concentrated. The crude was purified by RHPLC to give compound 5.

Example 9

Synthesis of (E)-3-(5-((2-oxoindolin-3-ylidene)methyl)furan-2-yl)benzoic acid

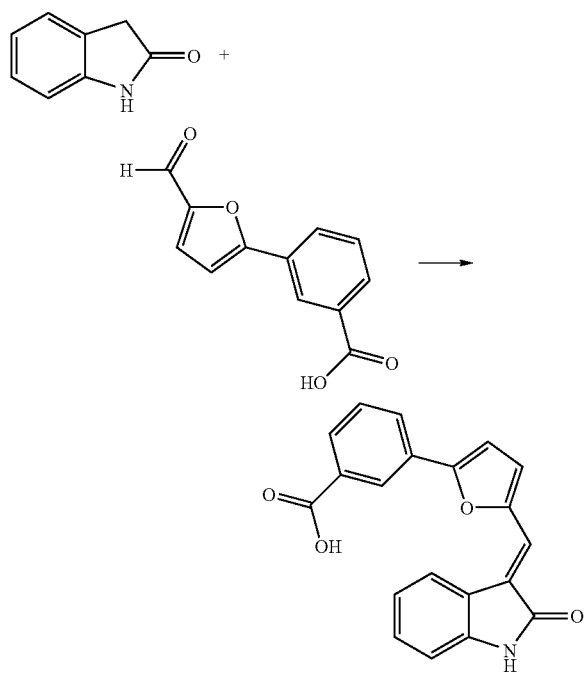

A solution of oxindole (205 mg, 1.54 mmol), methyl 3-(5-formylfuran-3-yl)benzoate (350 mg, 1.24 mmol) and piperidine (0.15 mL, 1.52 mmol) in EtOH (4.0 mL) was stirred at rt 30 min. The resulting precipitate was collected by filtration to yield desired (E)-3-(5-((2-oxoindolin-3-ylidene)methyl)furan-2-yl)benzoate (370 mg). LCMS (ES): m/z 346 [M+1]+.

Example 10

Synthesis of (E)-3-(5-((2-oxoindolin-3-ylidene)methyl)furan-2-yl)-N-(2-(pyrrolidin-1yl)ethyl)benzamide

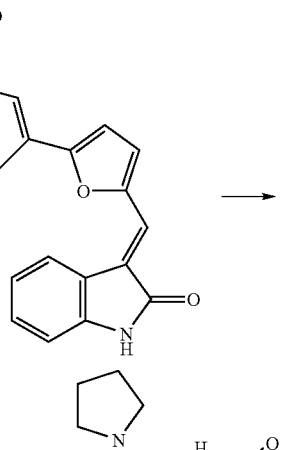

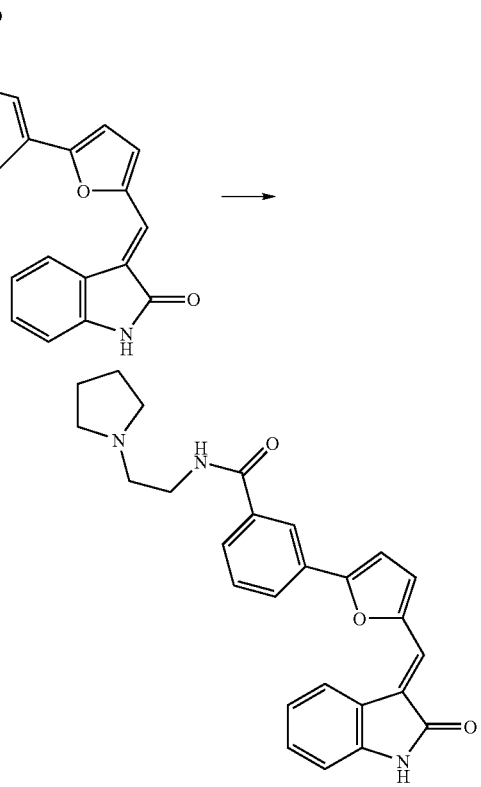

To a solution of (E)-3-(5-((2-oxoindolin-3-ylidene)methyl)furan-2-yl)benzoate (20 mg, 0.06 mmol) and HOBt (16 mg, 0.14 mmol) in NMP (0.5 mL) was added EDCI (22 mg, 0.12 mmol). The reaction was stirred at rt for 10 min and then added 2-(pyrrolidin-1-yl)ethanamine (0.05 mL) followed by DIEA (0.05 mL). The reaction mixture was stirred at rt for 1 h and diluted with H2O (10 mL). The mixture was extracted with EtOAc (3×20 mL), dried over Na2SO4 and concentrated. The crude was purified by RHPLC to give (E)-3-(5-((2-oxoindolin-3-ylidene)methyl)furan-2-yl)-N-(2-(pyrrolidin-1-yl)ethyl)benzamide. LCMS (ES): m/z 463 [M+1]+.

Example 11

Synthesis of (E)-3-(5-chloro-2-oxoindolin-3-ylidene)methyl)furan-2-yl)benzoic acid

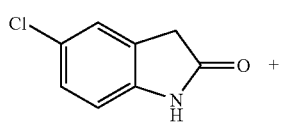

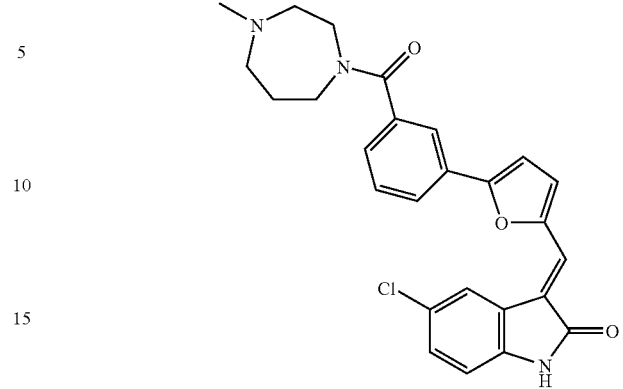

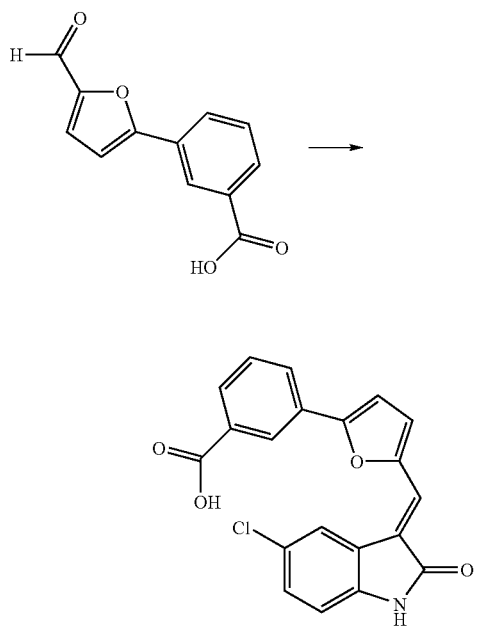

A solution of oxindole (400 mg, 2.4 mmol), methyl 3-(5-formylfuran-3-yl)benzoate (518 mg, 2.4 mmol) and piperidine (0.24 mL, 2.4 mmol) in EtOH (10 mL) was stirred at rt 30 min. The resulting precipitate was collected by filtration to yield desired (E)-3-(5-chloro-2-oxoindolin-3-ylidene)methyl)furan-2-yl)benzoic acid (541 mg). LCMS (ES): m/z 366 [M+1]+.

Example 12

Synthesis of (E)-5-chloro-3-(5-(3-(4-methyl-1,4-diazepane-1-carbonyl)phenyl)furan-2-yl)methylene)indolin-2-one

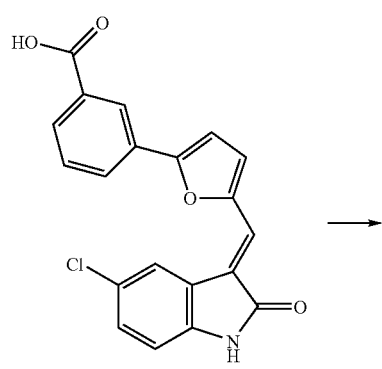

To a solution of (E)-3-(5-chloro-2-oxoindolin-3-ylidene)methyl)furan-2-yl)benzoic acid (541 mg, 1.48 mmol) and HOBt (400 mg, 2.96 mmol) in DMF (2 mL) was added EDCI (565 mg, 2.96 mmol). The reaction was stirred at rt for 10 min and then added 1-methyl homopiperazine (0.734 mL, 5.92 mmol) followed by DIEA (1 mL). The reaction mixture was stirred at rt for 1 h and diluted with H$_2$O (10 mL). The mixture was extracted with EtOAc, dried over Na$_2$SO$_4$ and concentrated. The crude was purified by preparative TLC eluting with 2% methanol in dichloromethane to give (E)-5-chloro-3-(5-(3-(4-methyl-1,4-diazepane-1-carbonyl)phenyl)furan-2-yl)methylene)indolin-2-one. LCMS (ES): m/z 462 [M+1]+.

Example 13

Synthesis of (E)-3-(5-((5-chloro-2-oxoindolin-3-ylidene)methyl)furan-2-yl)-N-(2-hydroxy-2-phenylethyl)benzamide

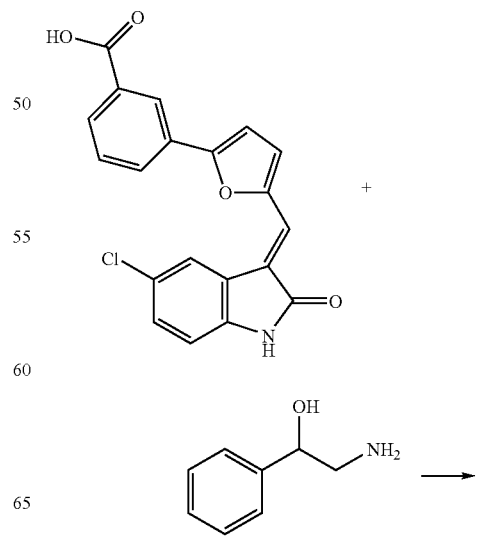

-continued

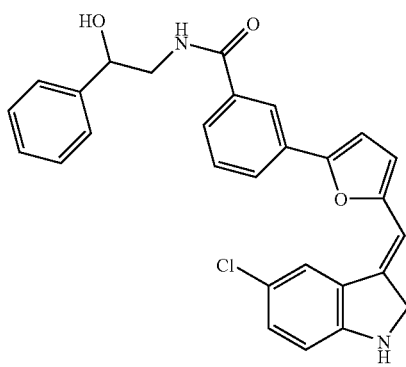

Same procedure as in example 12.

Example 14

Synthesis of (E)-3-(5-((5-chloro-2-oxoindolin-3-ylidene)methyl)furan-2-yl)-N-(3-hydroxypropyl)benzamide

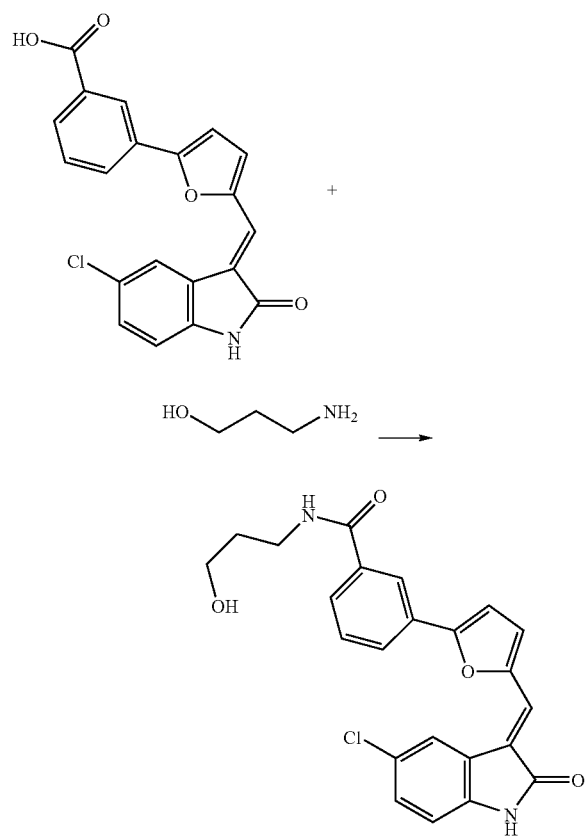

Same procedure as in example 12.

Example 15

Synthesis of 3-((3-methylfuran-2-yl)methylene)indolin-2-one

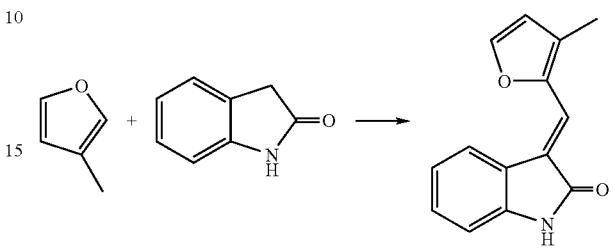

A solution of POCl3 (0.60 mL, 7.08 mmol) in DMF (0.65 mL, 8.431 mmol) was stirred at rt for 1 h. The reaction was cooled to 0° C. and added 3-methylfuran (490 mg, 5.97 mmol) dropwise. The mixture was stirred at 0 C for 1 h and at 40 C for additional 40 min. The reaction mixture was poured into H2O (25 mL), neutralized (Na2CO3), and extracted with EtOAc (25 mL×5). The organic layer was washed with brine, dried over Na2SO4 and concentrated. The crude material was heated at reflux with oxindole (800 mg, 6.02 mmol) and piperidine (0.60 mL, 8.08 mmol) in EtOH (5 mL) for 3 h. The resulting precipitate was collected by filtration to yield the desired 3-((3-methylfuran-2-yl)methylene)indolin-2-one (340 mg). LCMS (ES): m/z 226 [M+1]+.

Example 16

Synthesis of 3-((5-bromo-3-methylfuran-2-yl)methylene)indolin-2-one

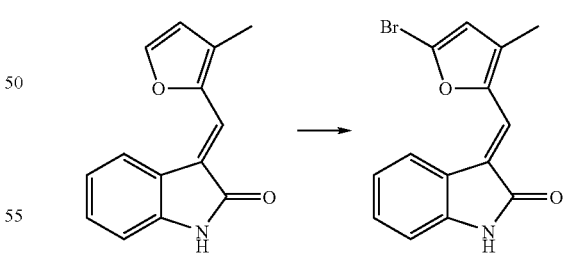

To a solution of 3-((3-methylfuran-2-yl)methylene)indolin-2-one (330 mg, 1.47 mmol) in DMF (7.0 mL) was added NBS (265 mg, 1.49 mmol) in DMF (1.0 mL) at 0° C. The reaction was stirred at 0° C. for 1 h and added H$_2$O (13 mL). The resulting precipitate was collected by filtration to yield desired 3-((5-bromo-3-methylfuran-2-yl)methylene)indolin-2-one (320 mg). LCMS (ES): m/z 304 [M+1]$^+$.

Example 17

Synthesis of methyl 3-(4-methyl-5-((2-oxoindolin-3-ylidene)methyl)furan-2-yl)benzoate

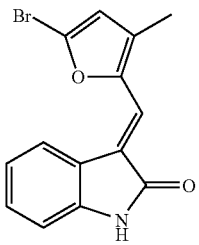

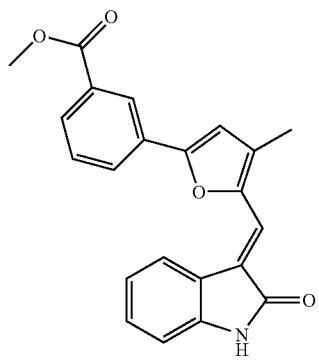

A solution of 3-((5-bromo-3-methylfuran-2-yl)methylene)indolin-2-one (125 mg, 0.41 mmol), 3-(methoxycarbonyl)phenylboronic acid (115 mg, 0.64 mmol), Cs$_2$CO$_3$ (270 mg, 0.83 mmol) and PdCl$_2$(dppf) (16 mg, 0.02 mmol) in H$_2$O/dioxane (5%, 5 mL) was heated at reflux for 1 h. The reaction mixture was diluted with H$_2$O (150 mL) and extracted with EtOAc (3×100 mL). The organic layer was washed with brine (100 mL) and dried over Na$_2$SO$_4$ and concentrated to yield the desired methyl 3-(4-methyl-5-((2-oxoindolin-3-ylidene)methyl)furan-2-yl)benzoate. LCMS (ES): m/z 360 [M+1]$^+$.

Example 18

Synthesis of 3-(4-methyl-5-((2-oxoindolin-3-ylidene)methyl)furan-2-yl)benzoic acid

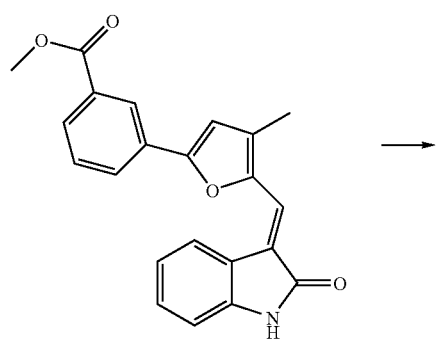

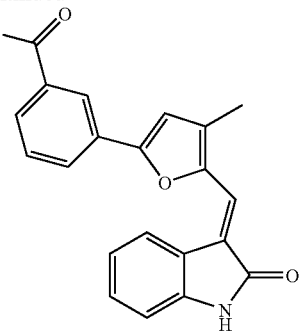

A solution of methyl 3-(4-methyl-5-((2-oxoindolin-3-ylidene)methyl)furan-2-yl)benzoate (125 mg, 0.35 mmol) in EtOH (5.0 mL) and NaOH (3N, 3.0 mL) was heated at 80° C. for 30 min. The reaction mixture was cooled to rt and pH was adjusted (pH=4) with HCl (6N). The resulting precipitate was collected by filtration to give the desired 3-(4-methyl-5-((2-oxoindolin-3-ylidene)methyl)furan-2-yl)benzoic acid (95 mg). LCMS (ES): m/z 346 [M+1]$^+$.

Example 19

Synthesis of 3-(4-methyl-5-((2-oxoindolin-3-ylidene)methyl)furan-2-yl)-N-(2-(pyrrolidin-1-yl)ethyl)benzamide

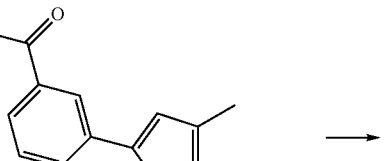

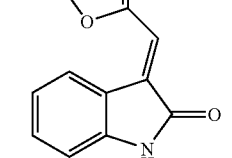

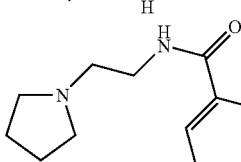

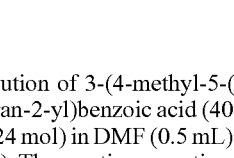

To a solution of 3-(4-methyl-5-((2-oxoindolin-3-ylidene)methyl)furan-2-yl)benzoic acid (40 mg, 0.12 mol) and HOBt (32 mg, 0.24 mol) in DMF (0.5 mL) was added EDCI (46 mg, 0.24 mmol). The reaction was stirred at rt for 10 min and then added 2-(pyrrolidin-1-yl)ethanamine (0.05 mL) followed by DIEA (0.05 mL). The reaction mixture was stirred at rt for 1 h and diluted with H$_2$O (10 mL). The mixture was extracted with EtOAc (3×20 mL), dried over Na$_2$SO$_4$ and concentrated.

The crude was purified by prep TLC (5%/MeOH, 1% TEA/DCM) to give 3-(4-methyl-5-((2-oxoindolin-3-ylidene)methyl)furan-2-yl)-N-(2-(pyrrolidin-1-yl)ethyl)benzamide (25 mg) LCMS (ES): m/z 442 [M+1]$^+$.

Example 20

Synthesis of ethyl 5-(5-formylfuran-2-yl)nicotinate

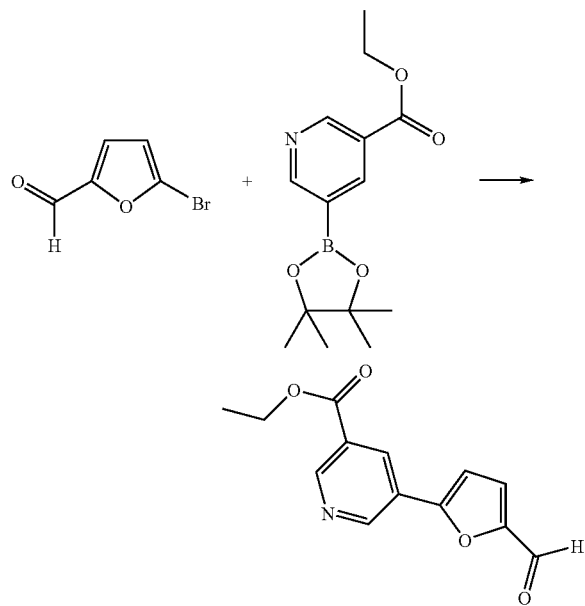

A solution of ethyl 5-(4,4,5,5-tetramethyl-1,3,2-dioxaborolan-2-yl)nicotinate (570 mg, 2.06 mmol), 5-bromofuran-2-carbaldehyde (300 mg, 1.71 mmol), Cs$_2$CO$_3$ (1.125 g, 3.46 mmol) and PdCl$_2$(dppf) (65 mg, 0.09 mmol) in H$_2$O/dioxane (5%, 10 mL) was heated at reflux for 15 min. The reaction mixture was cooled to rt and diluted with H$_2$O (100 mL). The resulting precipitate was collected by filtration to yield the desired ethyl 5-(5-formylfuran-2-yl)nicotinate (420 mg). LCMS (ES): m/z 246 [M+1]$^+$.

Example 21

Synthesis of (E)-ethyl 5-(5-((5-chloro-2-oxoindolin-3-ylidene)methyl)furan-2-yl)nicotinate

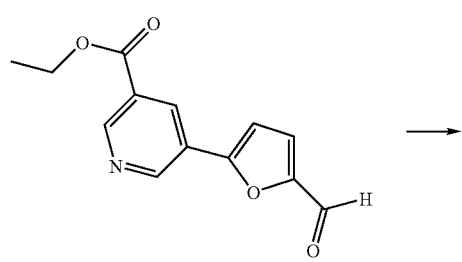

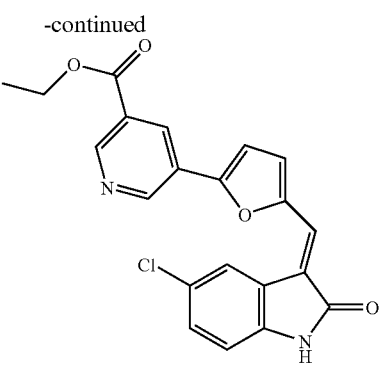

A solution of ethyl 5-(5-formylfuran-2-yl)nicotinate (235 mg, 0.96 mmol), 5-chloroindolin-2-one (161 mg, 0.96 mmol), and piperidine (0.10 mL, 1.01 mmol) in EtOH (5.0 mL) was stirred at rt for 2 h. The precipitate was collected by filtration to yield the desired crude material was heated at reflux with oxindole (800 mg, 6.02 mmol) and piperidine (0.60 mL, 8.08 mmol) in EtOH (5 mL) for 3 h. The resulting precipitate was collected by filtration to yield the desired (E)-ethyl 5-(5-((5-chloro-2-oxoindolin-3-ylidene)methyl)furan-2-yl)nicotinate (290 mg). LCMS (ES): m/z 395 [M+1]$^+$.

Example 22

Synthesis of (E)-3-(4-methyl-5-((2-oxoindolin-3-ylidene)methyl)furan-2-yl)benzoic acid

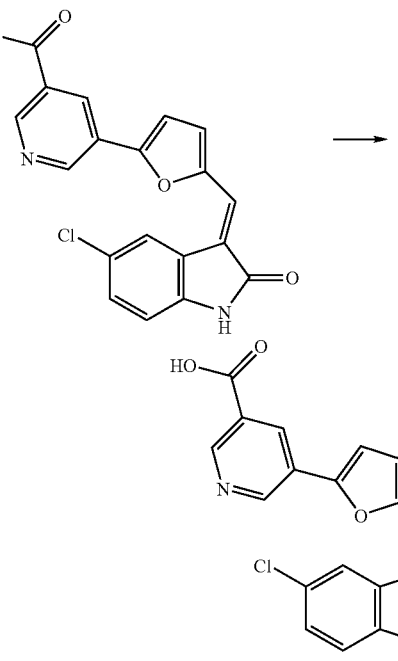

A solution of (E)-ethyl 5-(5-((5-chloro-2-oxoindolin-3-ylidene)methyl)furan-2-yl)nicotinate (280 mg, 0.71 mmol) in EtOH (5.0 mL) and NaOH (3N, 3.0 mL) was heated at 80° C. for 30 min. The reaction mixture was cooled to rt and pH was adjusted (pH=4) with HCl (6N). The resulting precipitate was collected by filtration to give the desired (E)-3-(4-methyl-5-((2-oxoindolin-3-ylidene)methyl)furan-2-yl)benzoic acid (260 mg). LCMS (ES): m/z 367 [M+1]$^+$.

Example 23

Synthesis of (E)-5-(5-((5-chloro-2-oxoindolin-3-ylidene)methyl)furan-2-yl)-N-(2-(pyrrolidin-1-yl)ethyl)nicotinamide

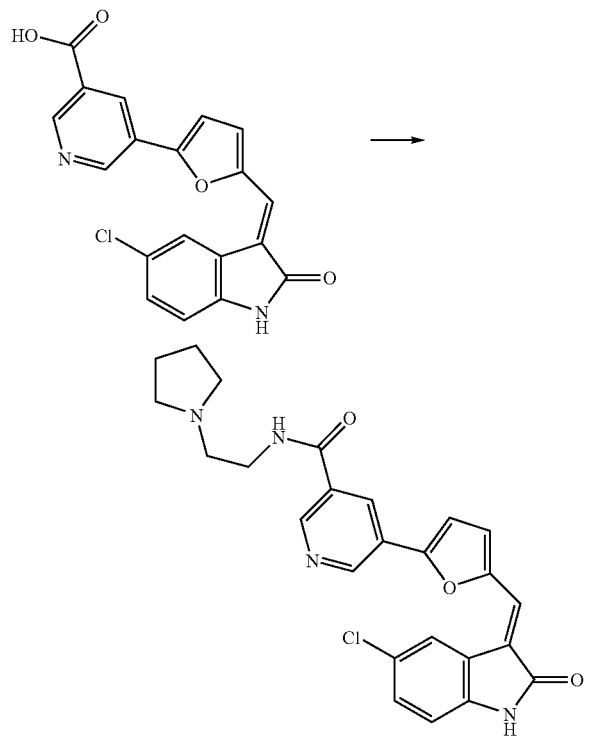

To a solution of (E)-3-(4-methyl-5-((2-oxoindolin-3-ylidene)methyl)furan-2-yl)benzoic acid (20 mg, 0.06 mol) and HOBt (16 mg, 0.14 mmol) in NMP (0.5 mL) was added EDCI (22 mg, 0.12 mmol). The reaction was stirred at rt for 10 min and then added 2-(pyrrolidin-1-yl)ethanamine (0.05 mL) followed by DIEA (0.05 mL). The reaction mixture was stirred at rt for 1 h and diluted with H$_2$O (10 mL). The mixture was extracted with EtOAc (3×20 mL), dried over Na$_2$SO$_4$ and concentrated. The crude was purified by RHPLC to give (E)-5-(5-((5-chloro-2-oxoindolin-3-ylidene)methyl)furan-2-yl)-N-(2-(pyrrolidin-1-yl)ethyl)nicotinamide. LCMS (ES): m/z 463 [M+1]$^+$.

Example 24

Synthesis of (E)-tert-butyl 3-(5-((2-oxoindolin-3-ylidene)methyl)furan-2-yl)phenylcarbamate

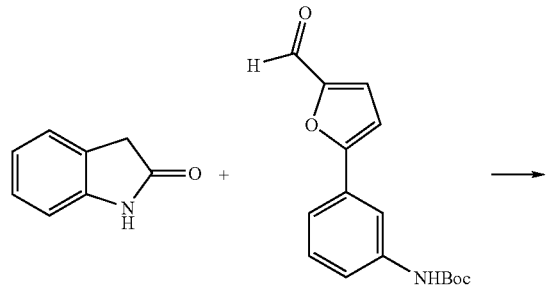

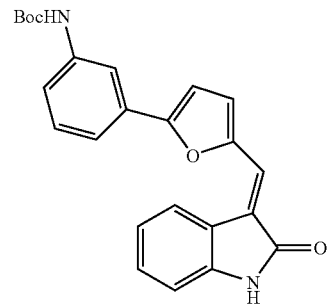

A solution of oxindole (235 mg, 1.76 mmol), tert-butyl 3-(5-formylfuran-2-yl)phenylcarbamate (500 mg, 1.74 mmol) and piperidine (0.18 mL, 1.80 mmol) in EtOH (5.0 mL) was stirred at rt overnight. The resulting precipitate was collected by filtration to yield desired (E)-tert-butyl 3-(5-((2-oxoindolin-3-ylidene)methyl)furan-2-yl)phenylcarbamate (640 mg). LCMS (ES): m/z 403 [M+1]$^+$.

Example 25

Synthesis of (E)-3-((5-(3-aminophenyl)furan-2-yl)methylene)indolin-2-one

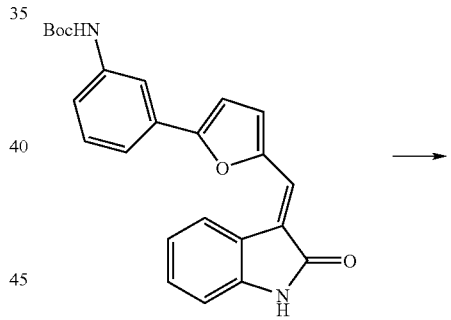

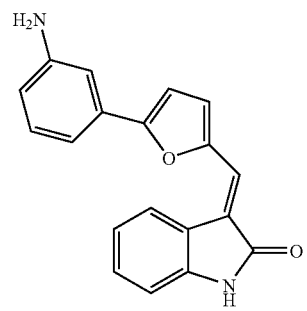

A solution of (E)-tert-butyl 3-(5-((2-oxoindolin-3-ylidene)methyl)furan-2-yl)phenylcarbamate (600 mg, 1.49 mmol) in HCl/dioxane (4M, 3.0 mL) was stirred over night. The resulting precipitate was collected by filtration to yield desired (E)-3-((5-(3-aminophenyl)furan-2-yl)methylene)indolin-2-one (503 mg). LCMS (ES): m/z 303 [M+1]$^+$.

Example 26

Synthesis of (E)-3-chloro-N-(3-(5-((2-oxoindolin-3-ylidene)methyl)furan-2-yl)phenyl)propanamide

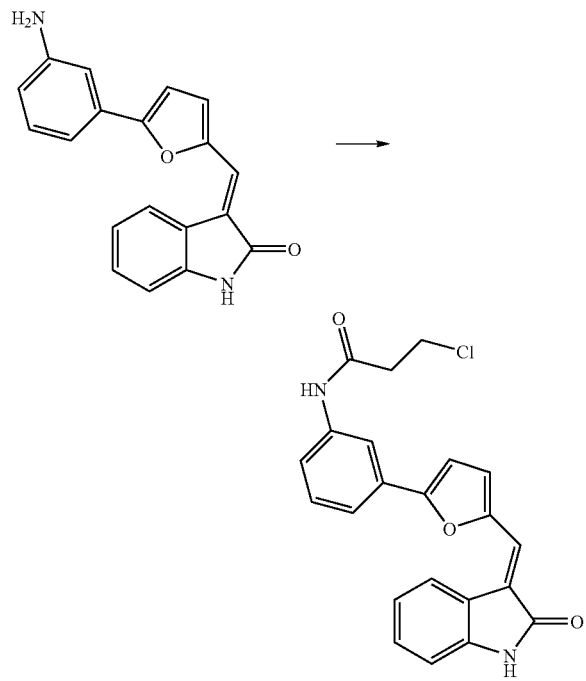

To a solution of (E)-3-((5-(3-aminophenyl)furan-2-yl)methylene)indolin-2-one (80 mg, 0.26 mmol) and TEA (0.11 mL, 0.79 mol) in DCM (5.0 mL) was added 3-chloropropanoyl chloride (0.04 mL, 0.42 mmol). The reaction was stirred for 20 min and the precipitate was collected by filtration to yield desired (E)-3-chloro-N-(3-(5-((2-oxoindolin-3-ylidene)methyl)furan-2-yl)phenyl)propanamide. LCMS (ES): m/z 357 [M+1-Cl]+.

Example 27

Synthesis of (E)-N-(3-(5-((2-oxoindolin-3-ylidene)methyl)furan-2-yl)phenyl)-3-(pyrrolidin-1-yl)propanamide

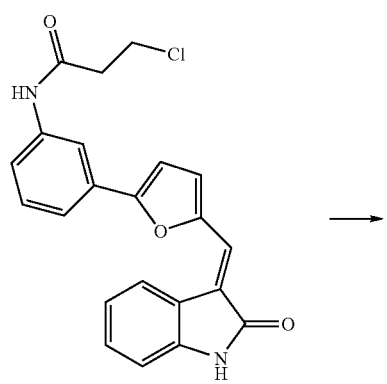

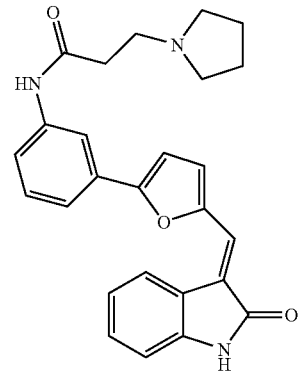

A solution of (E)-3-chloro-N-(3-(5-((2-oxoindolin-3-ylidene)methyl)furan-2-yl)phenyl)propanamide (25 mg, 0.06 mmol) and pyrrolidine (0.025 mL) in NMP (0.75 mL) was heated in microwave (100° C., 5 min). The reaction mixture was purified by RHPLC to yield the desired (E)-N-(3-(5-((2-oxoindolin-3-ylidene)methyl)furan-2-yl)phenyl)-3-(pyrrolidin-1-yl)propanamide LCMS (ES): m/z 428 [M+1]+.

Example 28

Synthesis of methyl 3-(5-acetylfuran-2-yl)benzoate

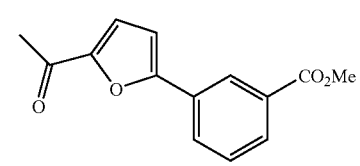

To a solution of 1-(5-bromofuran-2-yl)ethanone (2 g, 10.58 mmol) and cesium carbonate (10.35 g, 31.74 mmol in water/dioxane (5%, 20 mL), flushed with nitrogen for 15 minutes, was added 3-methoxycarbonylphenyl boronic acid (2.09 g, 11.64 mmol), followed by catalyst PdCl$_2$(dppf) (379 mg, 0.519 mmol). The solution was heated to reflux (105° C.) under nitrogen, for 3 hours. Water (100 mL) was added to the mixture after cooling down to rt. Filtration gave 2.56 g of a black crude material. Purification via silica column chromatography eluting with dichloromethane gave methyl 3-(5-acetylfuran-2-yl)benzoate (1.58 g, 6.19 mmol, 61% yield) as a yellow solid. LCMS (ES): m/z 245 [M+1]+.

Example 29

Synthesis of 3-(5-acetylfuran-2-yl)benzoic acid

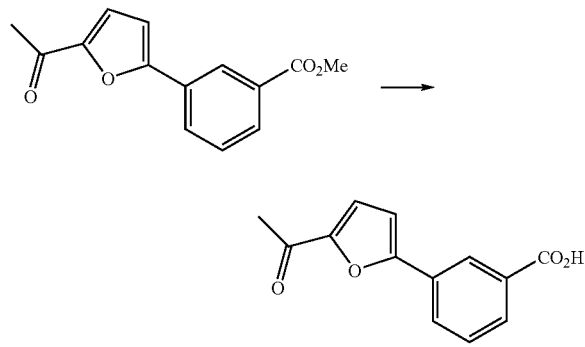

A solution of methyl 3-(5-acetylfuran-2-yl)benzoate (1.50 g, 6.1 mmol) in ethanol (15 mL), and sodium hydroxide (6N, 3 mL) was heated at 70° C. for 30 minutes. The reaction mixture was cooled to rt and pH was adjusted (pH=4) with HCl (6N). The resulting precipitate was collected by filtration to give the desired 3-(5-acetylfuran-2-yl)benzoic acid (1.10 g, 4.78 mmol, 77% yield) as a yellow/green solid. LCMS (ES): m/z 231 [M+1]$^+$.

Example 30

Synthesis of 1-(5-(3-(4-methyl-1,4-diazepane-1-carbonyl)phenyl)furan-2-yl)ethanone

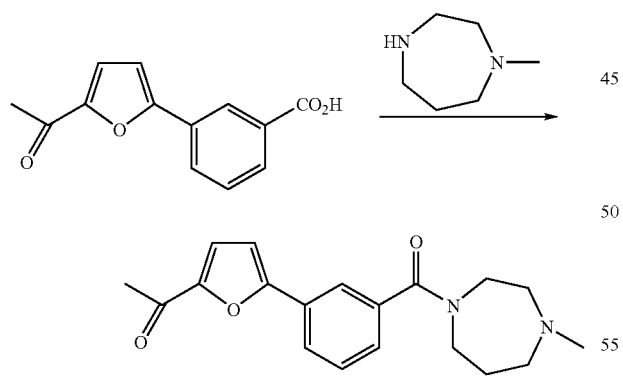

To a solution of 3-(5-acetylfuran-2-yl)benzoic acid (1.10 g, 4.78 mmol) and HOBt (1.29 g, 9.56 mmol) in DMF (10 mL) was added EDCI (1.83 g, 9.56 mmol). The reaction was stirred at rt for 10 min and then added 1-methylhomopiperazine (2.38 mL, 19.12 mmol) followed by DIEA (3.35 mL, 19.12 mmol). The reaction mixture was stirred at rt for 1 h and diluted with H$_2$O (50 mL). The mixture was extracted with DCM (3×50 mL), dried over Na$_2$SO$_4$ and concentrated to give brown oil (1.70 g). LCMS (ES): m/z 442 [M+1]$^+$.

Example 31

Synthesis of (E)-5-chloro-3-(1-(5-(3-(4-methyl-1,4-diazepane-1-carbonyl)phenyl)furan-2-yl)ethylidene)indolin-2-one

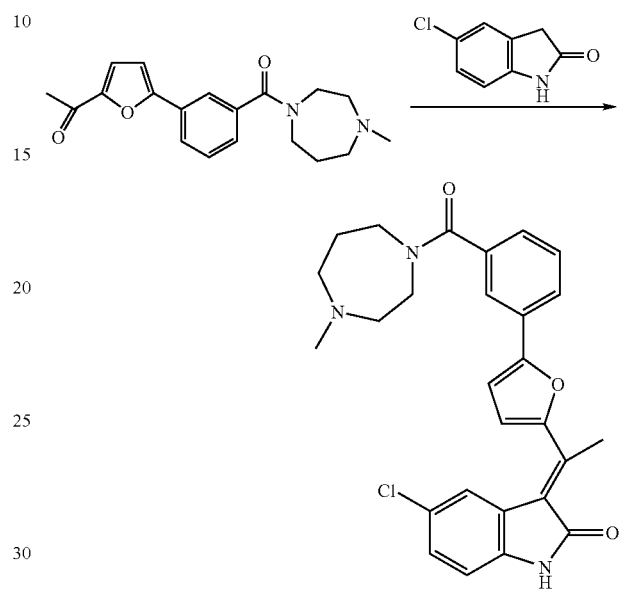

A solution of 5-chlorooxindole (668 mg, 4 mmol), 1-(5-(3-(4-methyl-1,4-diazepane-1-carbonyl)phenyl)furan-2-yl)ethanone (1.7 g of oil) and piperidine (394 µL, 4 mmol) in toluene (15 mL) was heated at reflux with a Dean-Stark receiver for 24 hours. After evaporation of the solvent, purification by silica column chromatography (methanol gradient in dichloromethane, 0 to 5% vol) gave (E)-5-chloro-3-(1-(5-(3-(4-methyl-1,4-diazepane-1-carbonyl)phenyl)furan-2-yl)ethylidene)indolin-2-one (800 mg) as a E:Z mixture. LCMS (ES): m/z 476 [M+1]$^+$.

Example 32

Synthesis of Compound 3

General Procedure

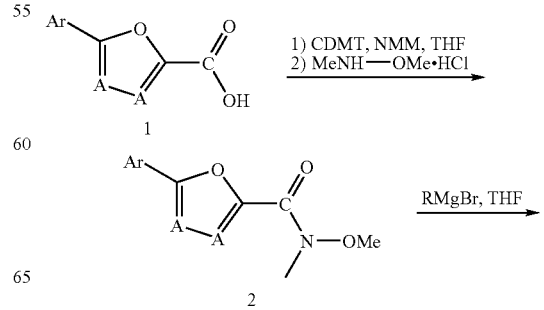

-continued

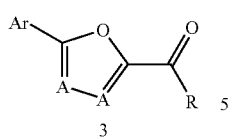

Compound 2 can be synthesized as described in Lidia De Luca et al., *J. Org. Chem.* 2001, 66, 2534-2537.

To a solution of the acid 1 (3.7 mmol) in THF (11 mL), at room temperature, were added 2-chloro-4,6-dimethoxy-[1,3,5]triazine (CDMT) (4.4 mmol) and N-methylmorpholine (NMM) (11.1 mmol). A precipitate was formed during stirring, and then N,O-dimethylhydroxylamine hydrochloride (3.7 mmol) was added. The mixture was stirred for additional 8 h and then quenched with 15 mL of water and extracted two times with 7 mL of diethyl ether. The combined organic phases were washed two times with 15 mL of a saturated solution of $Na_2CO_3$, followed by 15 mL of a solution 1 N HCl and brine. The organic layer was dried over anhydrous $Na_2SO_4$ to give, after evaporation of solvent, compound 2. A solution of compound 2 (2.5 mmol) in THF (10 mL) was added at room temperature to a THF solution (11 mL) of RMgBr (2.5 mmol), stirred for additional 0.5 h, and then quenched with aqueous saturated NH4Cl and extracted two times with 10 mL of diethyl ether. The combined organic phases were washed with 15 mL of a saturated solution of $Na_2CO_3$, followed by 15 mL of a solution 1 N HCl and brine. The organic layer was dried over anhydrous $Na_2SO_4$ to give, after evaporation of solvent, crude 3 that was further purified by flash-chromatography.

Example 33A

Synthesis of Compound 3

General Procedure

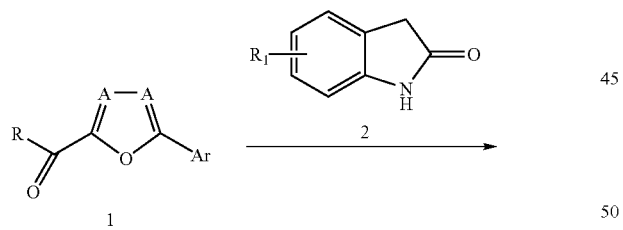

A solution of compound 2 (4 mmol) and compound 1 (4 mmol) and piperidine (394 μL, 4 mmol) in toluene (15 mL) was heated at reflux with a Dean-Stark receiver for 24 hours. After evaporation of the solvent, purification by silica column chromatography (methanol gradient in dichloromethane, 0 to 5% vol) gave compound 3.

Example 33B

Synthesis of Compound 3

General Procedure

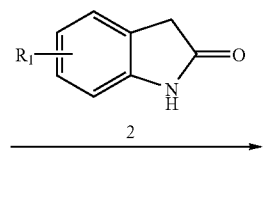

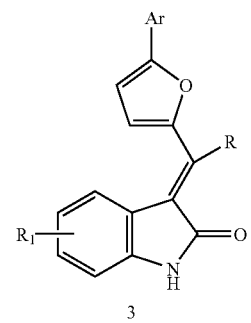

A solution of compound 2 (4 mmol) and compound 1 (4 mmol) and piperidine (394 μL, 4 mmol) in toluene (15 mL) was heated at reflux with a Dean-Stark receiver for 24 hours. After evaporation of the solvent, purification by silica column chromatography (methanol gradient in dichloromethane, 0 to 5% vol) gave compound 3.

Example 34

Synthesis of Oxindole 4

General Procedure

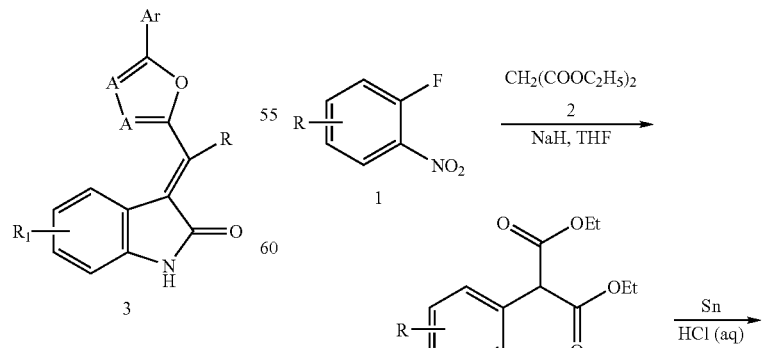

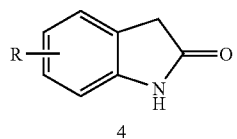

Oxindole 4 might be synthesized as described in Tian-Ming Yang et al., *J. Comb. Chem.* 2007, 9, 86-95 following the above scheme.

To the mixture of sodium hydride in 30 mL of THF was added dropwise a solution of 15 mmol of diethyl malonate 2 in 20 mL THF. The reaction mixture was continuously stirred for an additional 1 h at room temperature. Compound 1 (10 mmol) then was added, and the mixture was stirred for additional 30 min at room temperature. After the solvent was evaporated, water was added. The solution was neutralized to pH 2-3 with 2 M HCl and then extracted with ethyl acetate. The organic layer was washed with brine, dried over sodium sulfate, and concentrated under vacuum to give compound 3.

To a solution of 30 mmol of compound 3 in 50 mL of ethanol was added 15 equiv of 12 M HCl. Then tin powder (5 equiv) was partially and slowly added under strong stirring. After the completion of the addition of the tin powder, the reaction mixture was refluxed for additional 5 h. The solvent was then evaporated. The solution was stirred and neutralized with 40% NaOH until the mixture had a pH of ~7. The mixture was filtered. The water layer was extracted with ethyl acetate. The organic solvent was washed with brine, dried over sodium sulfate, and concentrated under vacuum. The residue was purified on silica gel to yield oxindole 4 being eluted by the ethyl acetate/petroleum ether system.

Example 35

Synthesis of (E)-3-((5-bromofuran-2-yl)methylene)indolin-2-one

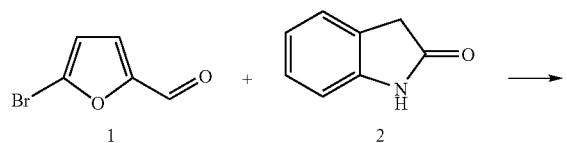

A solution of oxindole 2 (2.4 mmol), compound 1 (2.4 mmol) and piperidine (0.24 mL, 2.4 mmol) in EtOH (10 mL) was stirred at rt 30 min. The resulting precipitate was collected by filtration to yield desired (E)-3-((5-bromofuran-2-yl)methylene)indolin-2-one). LCMS (ES): m/z 291 [M+1]$^+$.

Example 36

Synthesis of (E)-3-((5-(6-(3-(dimethylamino)propoxy)pyridin-3-yl)furan-2-yl)methylene)indolin-2-one

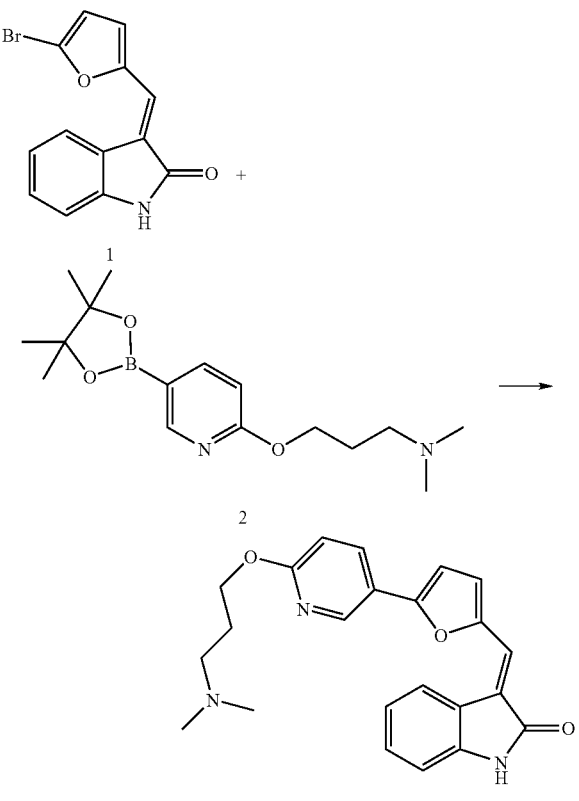

To a solution of compound 1 (50 mg, 0.173 mmol) and cesium carbonate (142 mg) in water/dioxane (150 μL/2 mL), flushed with nitrogen for 15 minutes, was added 3-boronic acid 2 (0.2 mmol), followed by catalyst PdCl$_2$(dppf) (8 mg). The solution was heated to reflux (105° C.) under nitrogen, for 3 hours. Water (100 mL) was added to the mixture after cooling to RT. The solid formed was isolated by filtration and purification via silica column chromatography eluting with dichloromethane gave compound 3. LCMS (ES): m/z 390 [M+1]$^+$.

Example 37

Synthesis of (E)-3-((5-(6-(4-methylpiperazin-1-yl)pyridin-3-yl)furan-2-yl)methylene)indolin-2-one

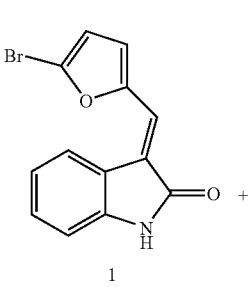

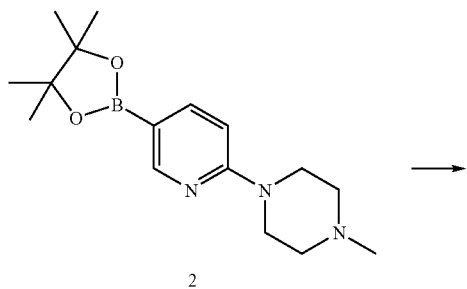

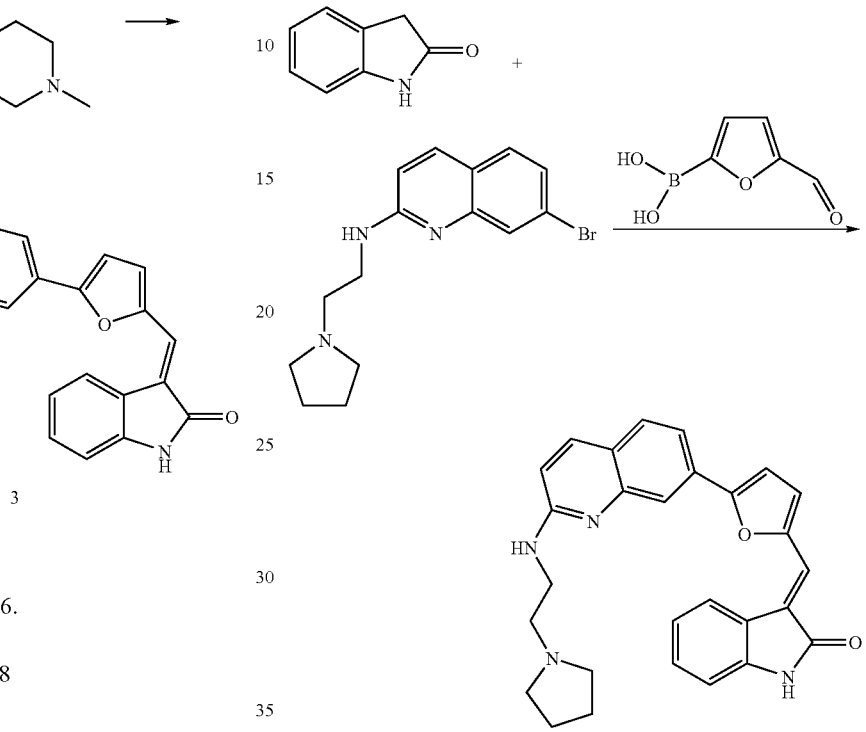

Same procedure as in example 36.

Example 38

Synthesis of 7-bromo-N-(2-(pyrrolidin-1-yl)ethyl)quinolin-2-amine

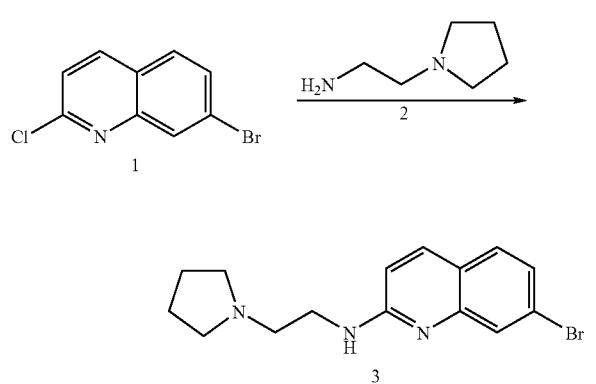

To 7-bromo-2-chloroquinoline 1 (107 mg, 0.44 mmol) and 2-(pyrrolidin-1-yl)ethanamine 2 (55.4 mg, 0.48 mmol) in 0.5 mL of dioxane was added p-toluene sulfonic acid (83 mg). The mixture was heated at 160° C. in microwave for 20 min. Water was added and the compound was extracted with dichloromethane and the organic layer was washed with brine, dried with sodium sulfate and concentrated under vacuum to give crude product 3.

Example 39

Synthesis of 3-((5-(2-(2-(pyrrolidin-1-yl)ethylamino)quinolin-7-yl)furan-2-yl)methylene)indolin-2-one To a solution of 7-bromo-N-(2-(pyrrolidin-1-yl)ethyl)quinolin-2-amine (70 mg, 0.219 mmol) 5-formylfuran-2-ylboronic acid (46 mg, 0.328 mmol) and cesium carbonate (214 mg, 0.656 mmol) in 5 mL dioxane was added PdCl$_2$(dppf) (8 mg, 0.011 mmol). This solution was heated at reflux under nitrogen for 10 hours. Monitoring by LC/MS showed completion of the Suzuki coupling.

Oxindole (44 mg, 0.328 mmol) was added to this solution, which was stirred at room temperature for 3 hours. The product was precipitated by adding water and filtered to give 60 mg of a brown solid. 3-((5-(2-(2-(pyrrolidin-1-yl)ethylamino)quinolin-7-yl)furan-2-yl)methylene)indolin-2-one was purified by preparative HPLC/MS. LCMS (ES): m/z 451 [M+1]$^+$.

Example 40

Synthesis of methyl 4-(5-acetylfuran-2-yl)benzoate

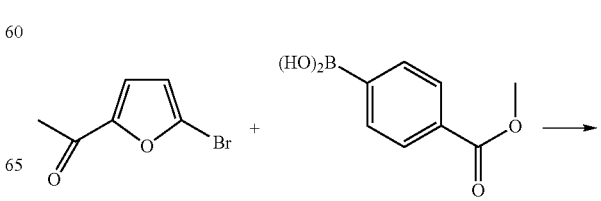

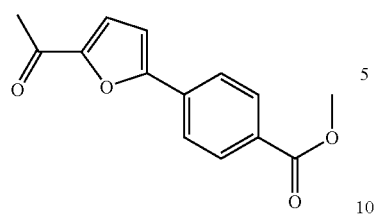

To a solution of 1-(5-bromofuran-2-yl)ethanone (963 mg, 5.09 mmol) and cesium carbonate (4.98 g, 15.27 mmol) in water/dioxane (5%, 20 mL), flushed with nitrogen for 15 minutes, was added 4-methoxycarbonylphenyl boronic acid (1.01 g, 5.60 mmol), followed by catalyst $PdCl_2$(dppf) (186 mg, 0.255 mmol). The solution was heated to reflux (105° C.) under nitrogen, for 16 hours. Water (50 mL) was added to the mixture after cooling to RT. Filtration gave 1.44 g of black crude material. Purification via silica column chromatography eluting with dichloromethane gave methyl 4-(5-acetyl-furan-2-yl)benzoate (580 g, 2.37 mmol, 47% yield) as a yellow solid. LCMS (ES): m/z 245 [M+1]$^+$.

Example 41

Synthesis of 4-(5-acetylfuran-2-yl)benzoic acid

A solution of methyl 4-(5-acetylfuran-2-yl)benzoate (580 mg, 2.37 mmol) in ethanol (5 mL), and sodium hydroxide (6N, 1 mL) was heated at 70° C. for 30 minutes. The reaction mixture was cooled to rt and pH was adjusted (pH=4) with HCl (6N). The resulting precipitate was collected by filtration to give the desired 4-(5-acetylfuran-2-yl)benzoic acid (500 mg, 2.17 mmol, 91% yield) as a yellow/green solid. LCMS (ES): m/z 231 [M+1]$^+$.

Example 42

Synthesis of 1-(5-(4-(4-methyl-1,4-diazepane-1-carbonyl)phenyl)furan-2-yl)ethanone

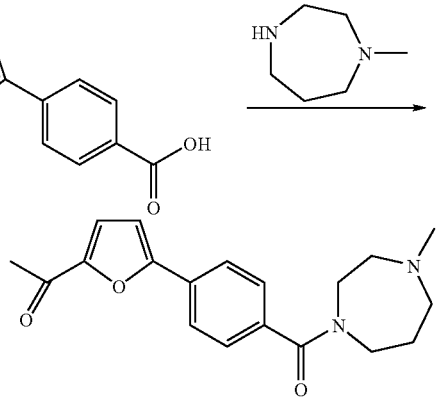

To a solution of 4-(5-acetylfuran-2-yl)benzoic acid (500 g, 2.17 mmol) and HOBt (587 mg, 4.35 mol) in DMF (5 mL) was added EDCI (835 mg, 4.35 mmol). The reaction was stirred at rt for 10 min and then 1-methylhomopiperazine (1.08 mL, 8.69 mol) was added, followed by DIEA (1.52 mL, 8.69 mmol). The reaction mixture was stirred at rt for 3 h and diluted with $H_2O$ (20 mL). The mixture was extracted with DCM (3×25 mL), washed with water (2×25 mL) then brine (25 mL), dried over $Na_2SO_4$ and concentrated to give brown oil (800 mg). LCMS (ES): m/z 442 [M+1]$^+$.

Example 43

Synthesis of 5-chloro-3-(1-(5-(4-(4-methyl-1,4-diazepane-1-carbonyl)phenyl)furan-2-yl)ethylidene)indolin-2-one

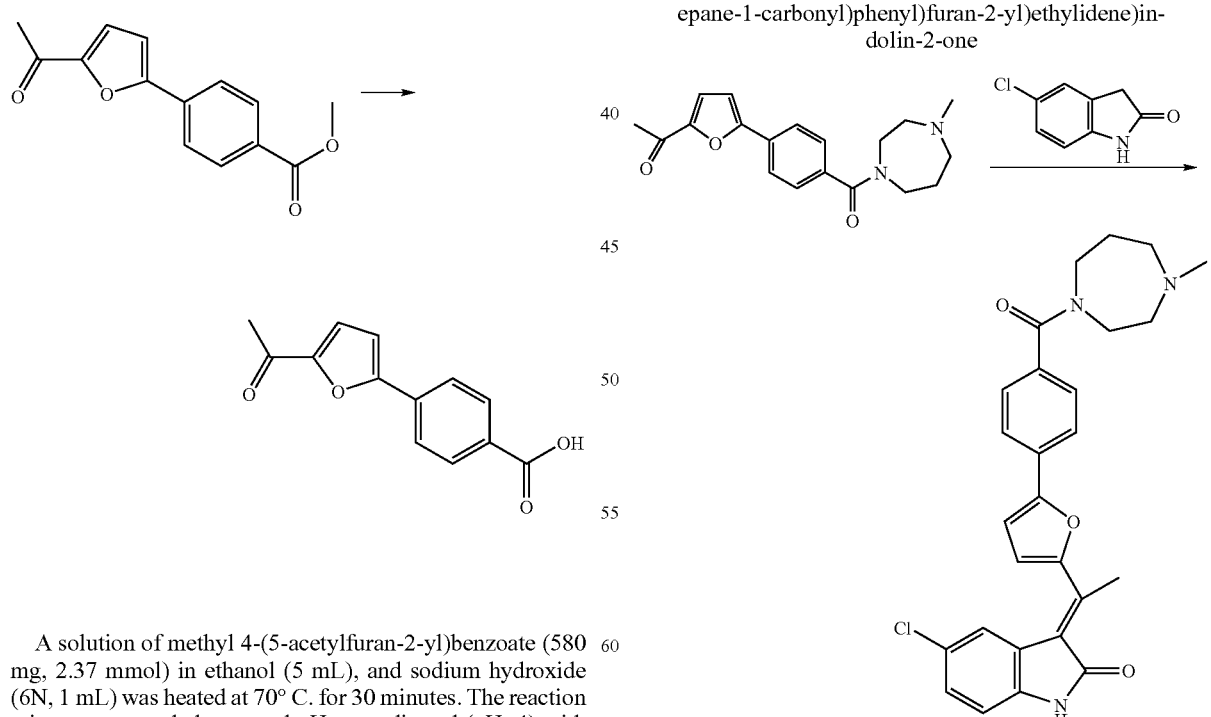

A solution of 5-chlorooxindole (362 mg, 2.17 mmol), 1-(5-(4-(4-methyl-1,4-diazepane-1-carbonyl)phenyl)furan-2-yl)

ethanone (800 mg of oil) and piperidine (214 µL, 2.17 mmol) in toluene (10 mL) was heated at reflux with a Dean-Stark receiver for 16 hours. After evaporation of the solvent, purification by silica column chromatography (methanol gradient in dichloromethane, 0 to 5% vol) gave 5-chloro-3-(1-(5-(4-(4-methyl-1,4-diazepane-1-carbonyl)phenyl)furan-2-yl)ethylidene)indolin-2-one (200 mg) as an E:Z mixture. LCMS (ES): m/z 476 [M+1]⁺.

Example 44

Synthesis of 5-((5-chloro-2-oxoindolin-3-ylidene)methyl)furan-2-ylboronic acid

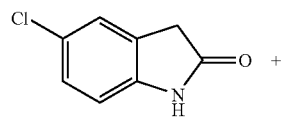

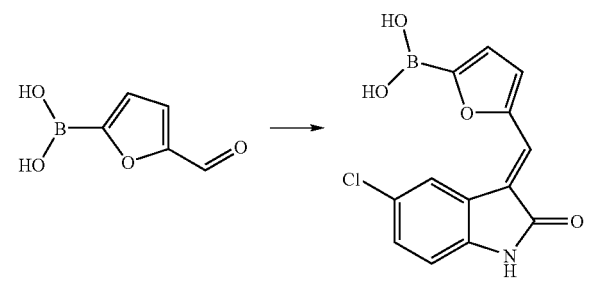

A solution of 5-chlorooxindole (999 mg, 5.98 mmol), 5-formylfuran-2-boronic acid (832 mg, 5.98 mmol) and piperidine (0.59 mL, 5.98 mmol) in EtOH (5.0 mL) was stirred at rt 90 min. The resulting precipitate was collected by filtration to yield the desired compound (354 mg). LCMS (ES): m/z 290 [M+1]⁺.

Example 45

Synthesis of 5-chloro-3-((5-(6-chloropyrazin-2-yl)furan-2-yl)methylene)indolin-2-one

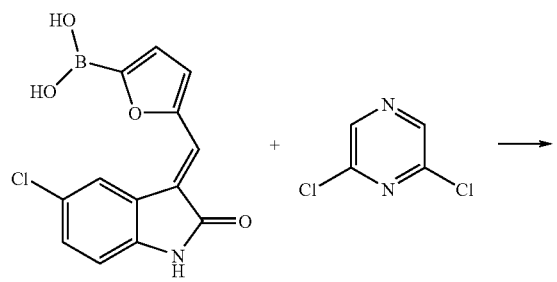

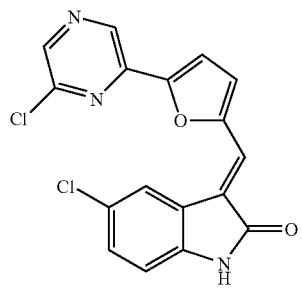

A solution of the product from the preceding Example (354 mg, 1.22 mmol), 2,6-dichloropyrazine (271 mg, 1.83 mmol), Cs₂CO₃ (1.196 g, 3.67 mmol) and PdCl₂(dppf) (44 mg, 0.06 mmol) in H₂O/dioxane (5%, 5 mL) was heated at reflux overnight. The reaction mixture was cooled to rt and diluted with H₂O (20 mL) and DCM (20 mL). The DCM layer was concentrated and precipitate collected by filtration (81 mg). The remaining precipitate in the aqueous layer was also collected by filtration to yield the desired compound (245 mg). LCMS (ES): m/z 358 [M+1]⁺.

Example 46

Synthesis of 5-chloro-3-((5-(6-(4-methyl-1,4-diazepan-1-yl)pyrazin-2-yl)furan-2-yl)methylene)indolin-2-one

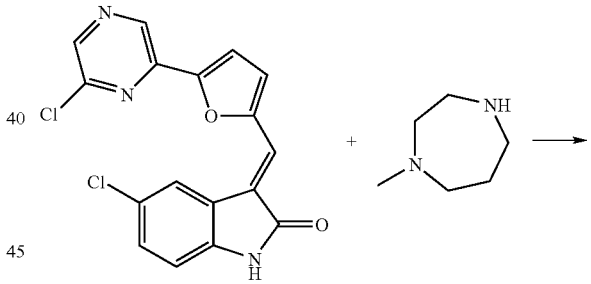

A solution of 5-chloro-3-((5-(6-chloropyrazin-2-yl)furan-2-yl)methylene)indolin-2-one (80 mg, 0.224 mmol), N-methylhomopiperazine (0.031 ml, 0.246 mmol), and triethylamine (0.035 ml, 0.246 mmol) in dioxane (0.4 mL) was prepared in a microwave tube. The reaction mixture was microwaved at 140° C. for 15 minutes. The solution was diluted with water, and the precipitate was collected by filtration to yield the desired product (40 mg). The precipitate was

Example 47

Synthesis of 5-chloro-3-((5-(6-((1-methylpiperidin-4-yl)methylamino)pyrazin-2-yl)furan-2-yl)methylene)indolin-2-one

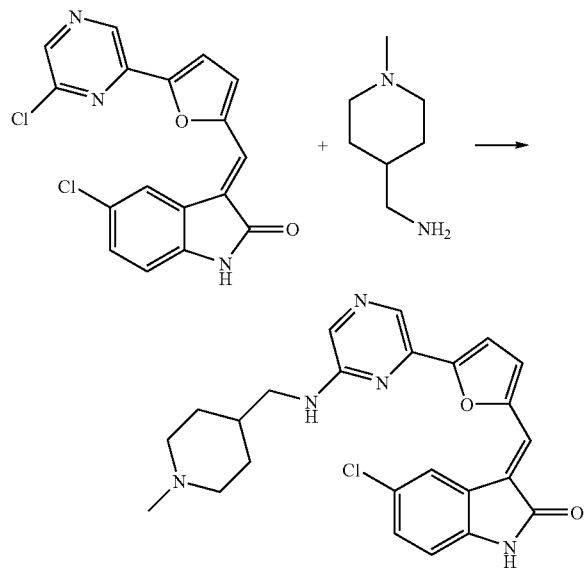

A solution of 5-chloro-3-((5-(6-chloropyrazin-2-yl)furan-2-yl)methylene)indolin-2-one (80 mg, 0.224 mmol), (1-methyl-4-piperidinyl)methanamine (32 mg, 0.246 mmol), and triethylamine (0.035 ml, 0.246 mmol) in dioxane (0.4 mL) was prepared in a microwave tube. The reaction mixture was microwaved at 140° C. for 15 minutes. The solution was diluted with water, and the precipitate was collected by filtration to yield the desired (70 mg). The precipitate was further purified by prep TLC eluting with 2% MeOH in dichloromethane. LCMS (ES): m/z 450 [M+1]$^+$.

Example 48

PIM-1 Assay Method

The following procedure was used to assay the PIM-1 kinase activity of compounds of the invention. Other methods for assaying PIM-1 and other PIM kinases, as well as methods to assay for activity against the various kinases in FIG. 1, are known in the art.

In a final reaction volume of 50 ul, recombinant PIM-1 (1 ng) was incubated with 12 mM MOPS pH 7.0, 0.4 mM EDTA, glycerol 1%, brij 35 0.002%, 2-mercaptoethanol 0.02%, BSA 0.2 mg/ml, 100 uM KKRNRTLTK, 10 mM MgAcetate, 15 uM ATP, [γ-$^{33}$P-ATP] (specific activity approx. 500 cpm/pmol), DMSO 4% and test inhibitor compound at the required concentration. The reaction was initiated by the addition of the Magnesium ATP mixture. After 40 min incubation at 23° C., the reactions were quenched by the addition of 100 ul 0.75% Phosphoric acid, and the labeled peptide collected by filtration through a phosphocellulose filter plate. The plate was washed 4 times with 0.075% phosphoric acid (100 ul per well) and then, after the addition of scintillation fluid (20 ul per well), the counts were measured by a scintillation counter.

Example 49

PIM-2 Assay Method

Test compounds dissolved and diluted in DMSO (2 ml) were added to a reaction mixture comprising 10 ml of 5× Reaction Buffer (40 mM MOPS pH 7.0, 5 mM EDTA), 10 ml of recombinant human PIM2 solution (4 ng PIM-2 dissolved in dilution buffer (20 mM MOPS pH 7.0; EDTA 1 mM; 5% Glycerol; 0.01% Brij 35; 0.1%; 0.1% 2-mercaptoethanol; 1 mg/ml BSA)) and 8 ul of water. Reactions were initiated by the addition of 10 ul of ATP Solution (49% (15 mM MgCl2; 75 uM ATP) 1% ([γ-33P]ATP: Stock 1 mCi/100 μl; 3000 Ci/mmol (Perkin Elmer)) and 10 ul of substrate peptide solution (RSRSSYPAGT, dissolved in water at a concentration of 1 mM), Reactions were maintained for 10 min at 30° C. The reactions were quenched with 100 ul of 0.75% Phosphoric acid, then transferred to and filtrered through a Phosphocellulose filter plate (Millipore, MSPH-N6B-50). After washing each well 4 times with 0.75% Phosphoric acid, scintillation fluid (20 uL) was added to each well and the residual radioactivity was measured using a Wallac luminescence counter.

Example 50

Cell Proliferation Modulatory Activity

A representative cell-proliferation assay protocol using Alamar Blue dye (stored at 4° C., use 20 ul per well) is described hereafter.

96-Well Plate Setup and Compound Treatment
  a. Split and trypsinize cells.
  b. Count cells using hemocytometer.
  c. Plate 4,000-5,000 cells per well in 100 μl of medium and seed into a 96-well plate according to the following plate layout. Add cell culture medium only to wells B10 to B12. Wells B1 to B9 have cells but no compound added.

| | 1 2 3 | 4 5 6 | 7 8 9 | 10 11 12 | |
|---|---|---|---|---|---|
| A | | EMPTY | | | |
| B | NO COMPOUND ADDED | | | Medium Only | |
| C | 10 nM | 100 nM | 1 uM | 10 uM | Control |
| D | 10 nM | 100 nM | 1 uM | 10 uM | Comp1 |
| E | 10 nM | 100 nM | 1 uM | 10 uM | Comp2 |
| F | 10 nM | 100 nM | 1 uM | 10 uM | Comp3 |
| G | 10 nM | 100 nM | 1 uM | 10 uM | Comp4 |
| H | | EMPTY | | | | d. Add 100 μl of 2× drug dilution to each well in a concentration shown in the plate layout above. At the same time, add 100 μl of media into the control wells (wells B10 to B12). Total volume is 200 μl/well.
  e. Incubate four (4) days at 37° C., 5% CO$_2$ in a humidified incubator.
  f. Add 20 μl Alamar Blue reagent to each well.
  g. Incubate for four (4) hours at 37° C., 5% CO$_2$ in a humidified incubator.
  h. Record fluorescence at an excitation wavelength of 544 nm and emission wavelength of 590 nm using a microplate reader.

In the assays, cells are cultured with a test compound for approximately four days, the dye is then added to the cells and fluorescence of non-reduced dye is detected after approximately four hours. Different types of cells can be utilized in the assays (e.g., HCT-116 human colorectal carcinoma cells, PC-3 human prostatic cancer cells and MiaPaca human pancreatic carcinoma cells).

Example 51

Modulation of FLT-3 Kinase Activity in Cell Free In Vitro Assay

FLT-3 Inhibition was determined by measuring the inhibition of recombinant human FLT-3 phosphorylation of the peptide EAIYAAPFAKKK using 10 uM ATP in a reaction mixture containing 20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, and 1% DMSO.

Example 52

Modulation of Protein Kinase Activity in Standardized Radiometric Kinase Assays

Compounds were tested further for activity against other protein kinases. Protein kinase inhibition IC50 data were determined using standardized radiometric kinase assays for each individual kinase, which entail filter binding of 33P labeled substrate proteins by the kinase of interest. Each IC50 value was determined over a range of 10 drug concentrations. Reaction conditions are available from the World Wide Web URL upstate.com/discovery/services/ic50_profiler.q.

Example 53

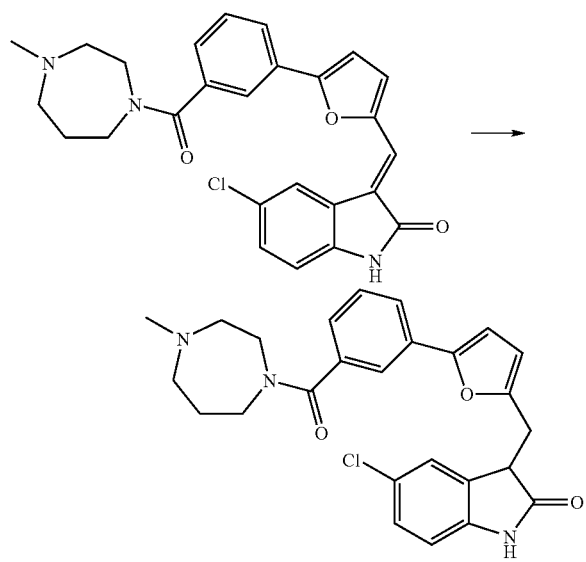

To 5-chloro-3-((5-(3-(4-methyl-1,4-diazepane-1-carbonyl)phenyl)furan-2-yl)methylene)indolin-2-one (24 mg) in methanol (4 ml) was added sodium borohydride (8 mg). The reaction was stirred at room temperature for 5 min. Water was added and the product was extracted with dichloromethane, dried with sodium sulfate and concentrated under vacuum to give 5-chloro-3-((5-(3-(4-methyl-1,4-diazepane-1-carbonyl) phenyl)furan-2-yl)methyl)indolin-2-one as orange powder. LCMS (ES): >95% pure, m/z 464 [M+1]⁺.

Example 54

Synthesis of 4-(5-((5-chloro-2-oxoindolin-3-ylidene) methyl)furan-2-yl)benzenesulfonamide

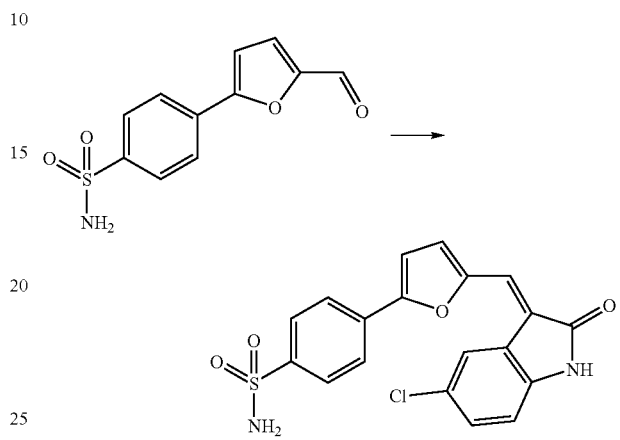

To 4-(5-formylfuran-2-yl)benzenesulfonamide (30 mg, 0.120 mmol) in EtOH was added 5-chlorooxindole (20 mg, 0.120 mmol) and piperidine (12 µL, 0.120 mmol). The mixture was stirred at 70° C. for several hours. The solid formed was isolated by filtration and air dried to yield 4-(5-((5-chloro-2-oxoindolin-3-ylidene)methyl)furan-2-yl)benzenesulfonamide. LC-MS (M+1=401).

Example 55

Synthesis of methyl 3-(5-((5-chloro-2-oxoindolin-3-ylidene)methyl)furan-2-yl)-4-fluorobenzoate

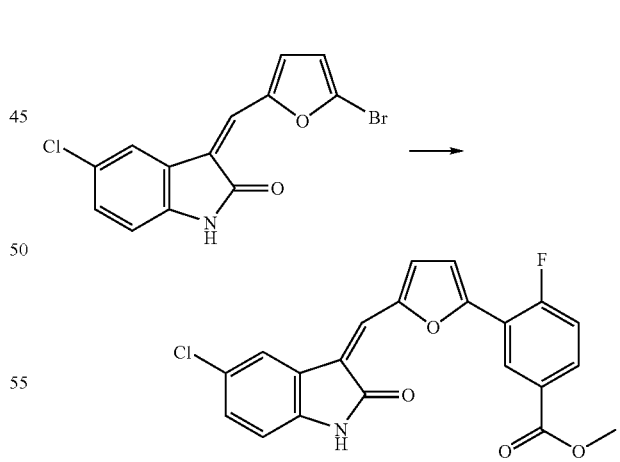

To 3-((5-bromofuran-2-yl)methylene)-5-chloroindolin-2-one (150 mg, 0.466 mmol) in dioxane/water (2850/150 µL) was added 2-fluoro-5-(methoxycarbonyl)phenylboronic acid (111 mg, 0.559 mmol) and $Cs_2CO_3$ (456 mg, 1.398 mmol). The mixture was degassed with nitrogen for 5 minutes, then $PdCl_2$ dppf (17 mg, 0.023 mmol) was added. The mixture was heated in microwave for 40 minutes at 110° C. Water was added and the solid formed was isolated by filtration to yield methyl 3-(5-((5-chloro-2-oxoindolin-3-ylidene)methyl)furan-2-yl)-4-fluorobenzoate. LCMS (M+1=398).

Example 56

Synthesis of methyl 4-(5-((5-chloro-2-oxoindolin-3-ylidene)methyl)furan-2-yl)-3-fluorobenzoate

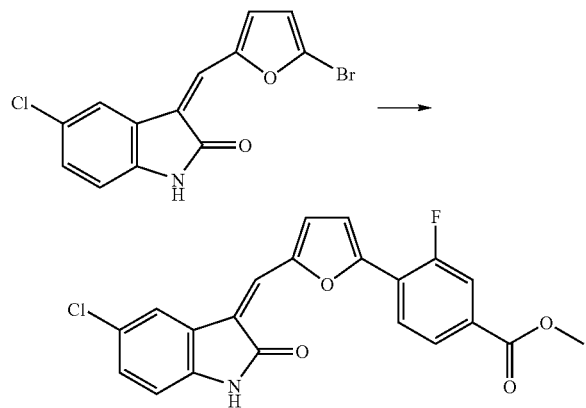

To 3-((5-bromofuran-2-yl)methylene)-5-chloroindolin-2-one (150 mg, 0.466 mmol) in dioxane/water (2850/150 µL) was added 2-fluoro-4-(methoxycarbonyl)phenylboronic acid (111 mg, 0.559 mmol) and Cs$_2$CO$_3$ (456 mg, 1.398 mmol). The mixture was degassed with nitrogen for 5 minutes, then PdCl$_2$ dppf (17 mg, 0.023 mmol) was added. The mixture was heated in microwave for 40 minutes at 110° C. Water was added and the solid formed was isolated by filtration to yield methyl 4-(5-((5-chloro-2-oxoindolin-3-ylidene)methyl)furan-2-yl)-3-fluorobenzoate. LCMS (M+1=398).

Example 57

Synthesis of 3-(5-((5-chloro-2-oxoindolin-3-ylidene)methyl)furan-2-yl)-4-fluorobenzoic acid

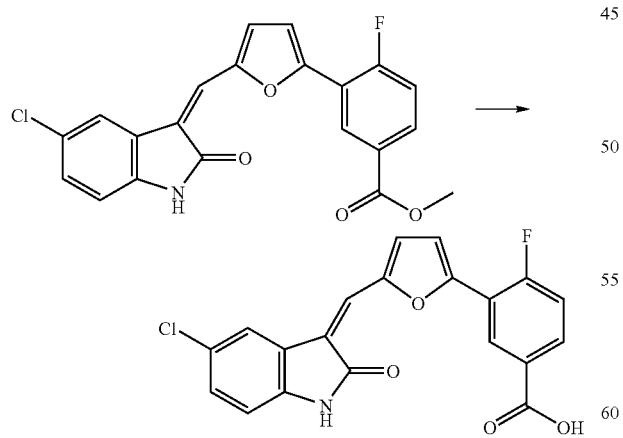

To methyl 3-(5-((5-chloro-2-oxoindolin-3-ylidene)methyl)furan-2-yl)-4-fluorobenzoate in EtOH was added 1.5 mL of 6M NaOH. The mixture was stirred at room temperature. EtOH was removed under reduced pressure. Water was added to the remaining solid and the mixture was sonicated. The solid was isolated by filtration and air dried to yield 3-(5-((5-chloro-2-oxoindolin-3-ylidene)methyl)furan-2-yl)-4-fluorobenzoic acid as sodium salt. LCMS (M+1=384).

Example 58

Synthesis of 4-(5-((5-chloro-2-oxoindolin-3-ylidene)methyl)furan-2-yl)-3-fluorobenzoic acid

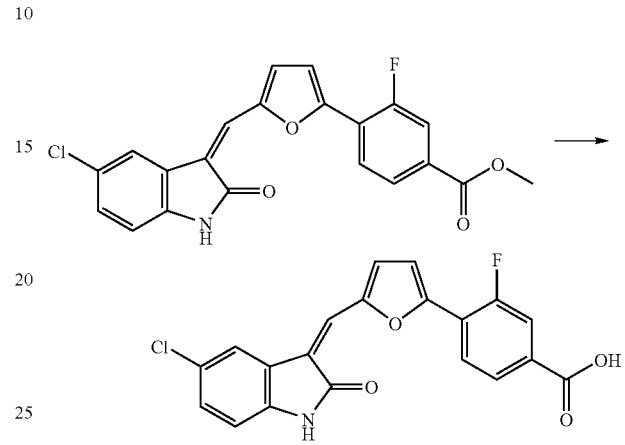

To methyl 4-(5-((5-chloro-2-oxoindolin-3-ylidene)methyl)furan-2-yl)-3-fluorobenzoate in EtOH was added 1.5 mL of 6M NaOH. The mixture was stirred at room temperature. EtOH was removed under reduced pressure. Water was added to the remaining solid and the mixture was sonicated. The solid was isolated by filtration and air dried to yield 4-(5-((5-chloro-2-oxoindolin-3-ylidene)methyl)furan-2-yl)-3-fluorobenzoic acid as sodium salt. LCMS (M+1=384).

Example 59

Synthesis of 5-chloro-3-((5-(2-fluoro-5-(4-methyl-1,4-diazepane-1-carbonyl)phenyl)-furan-2-yl)methylene)indolin-2-one

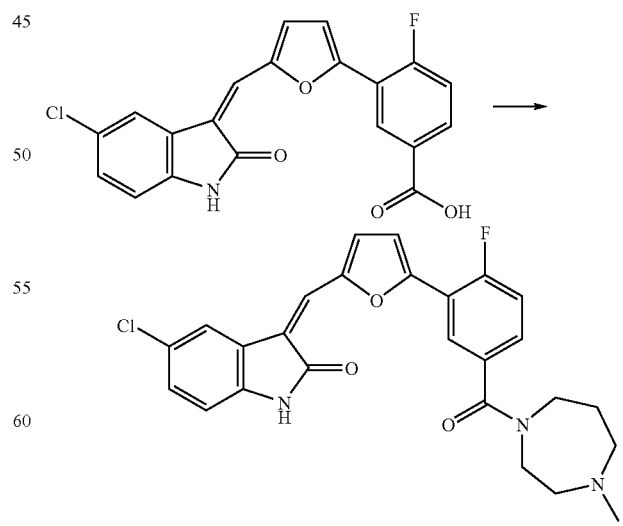

To 3-(5-((5-chloro-2-oxoindolin-3-ylidene)methyl)furan-2-yl)-4-fluorobenzoic acid (39 mg, 0.102 mmol) in DMF was added HBTU (58 mg, 0.153 mmol) and DIEA (53 µL, 0.306 mmol). The mixture was stirred at room temperature then was added 1-methylhomopiperazine (16 µL, 0.122 mmol) and allowed to stir at room temperature. The solid formed was isolated by filtration and purified by HPLC to yield 5-chloro-3-((5-(2-fluoro-5-(4-methyl-1,4-diazepane-1-carbonyl)phenyl)furan-2-yl)methylene)indolin-2-one. LCMS (M+1=480).

Example 60

Synthesis of 5-chloro-3-((5-(2-fluoro-4-(4-methyl-1,4-diazepane-1-carbonyl)phenyl)furan-2-yl)methylene)indolin-2-one

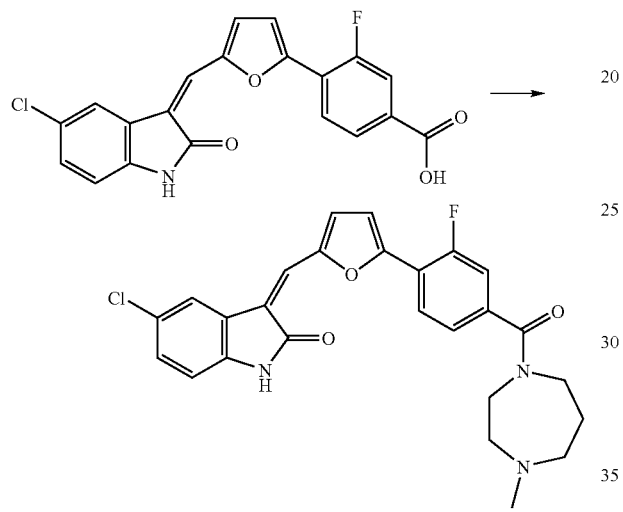

To 4-(5-((5-chloro-2-oxoindolin-3-ylidene)methyl)furan-2-yl)-3-fluorobenzoic acid (40 mg, 0.104 mmol) in DMF was added HBTU (60 mg, 0.157 mmol) and DIEA (55 µL, 0.313 mmol). The mixture was stirred at room temperature then was added 1-methylhomopiperazine (16 µL, 0.125 mmol) and allowed to stir at room temperature. The solid formed was isolated by filtration and purified by HPLC to yield 5-chloro-3-((5-(2-fluoro-4-(4-methyl-1,4-diazepane-1-carbonyl)phenyl)furan-2-yl)methylene)indolin-2-one. LCMS (M+1=480).

Example 61

Synthesis of 3-((5-(3-(4H-1,2,4-triazol-3-yl)phenyl)furan-2-yl)methylene)-5-chloroindolin-2-one

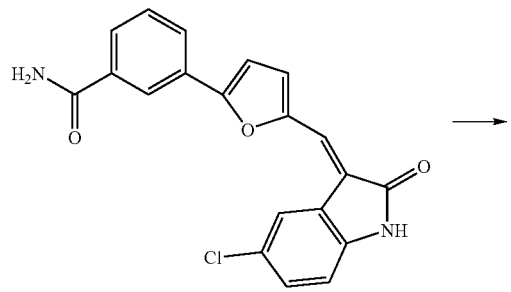

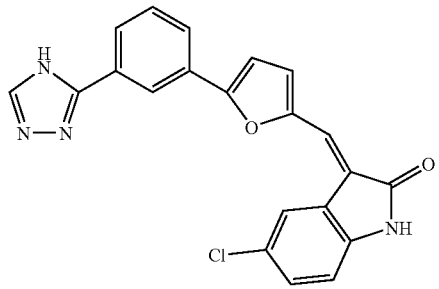

3-(5-((5-chloro-2-oxoindolin-3-ylidene)methyl)furan-2-yl)benzamide (100 mg, 0.275 mmol) in 5 mL DMF/DMA was stirred at 80° C. during 2 hr. DMF was evaporated and AcOH (10 mL) added. Hydrazine (1 mL) was added dropwise, the mixture was stirred during 10 minutes at R.T., then 45 minutes at 80° C. Water was added and the solid formed isolated by filtration and dried under vacuum. The product was purified by preparative TLC (DCM/MeOH 1%). LCMS (M+1)=389.

Example 62

Synthesis of 5-chloro-3-((5-(4-(3-morpholinopropoxy)phenyl)furan-2-yl)methylene)indolin-2-one

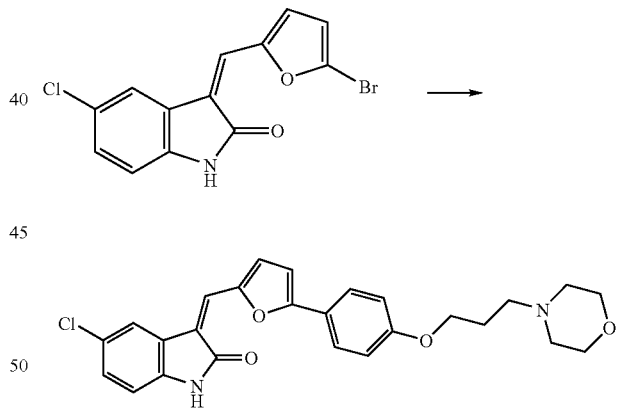

To 3-((5-bromofuran-2-yl)methylene)-5-chloroindolin-2-one (50 mg, 0.155 mmol) in dioxane/water (5% water) was added Cs$_2$CO$_3$ (152 mg, 0.466 mmol) and 4-(3-(4-(4,4,5,5-tetramethyl-1,3,2-dioxaborolan-2-yl)phenoxy)propyl)morpholine (65 mg, 0.186 mmol). The mixture was degassed with nitrogen for 5 minutes then heated in microwave for 20 minutes at 120° C. The solution was diluted with water and the solid formed was isolated by filtration. The solid was purified by HPLC to yield 5-chloro-3-((5-(4-(3-morpholinopropoxy)phenyl)furan-2-yl)methylene)indolin-2-one. LCMS (M+1=465).

Example 63

Synthesis of 5-chloro-3-((5-(3-(2-morpholinoethoxy)phenyl)furan-2-yl)methylene)indolin-2-one

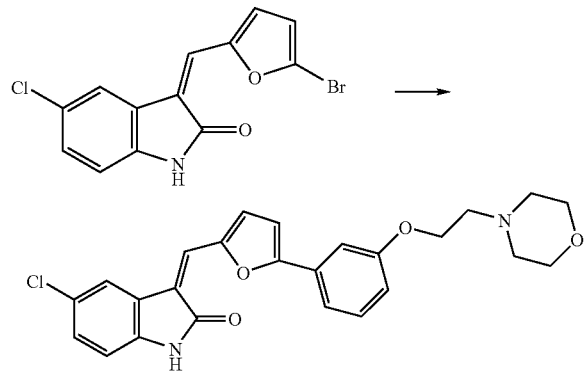

To 3-((5-bromofuran-2-yl)methylene)-5-chloroindolin-2-one (50 mg, 0.155 mmol) in dioxane/water (5% water) was added $Cs_2CO_3$ (152 mg, 0.466 mmol) and 4-(2-(3-(4,4,5,5-tetramethyl-1,3,2-dioxaborolan-2-yl)phenoxy)ethyl)morpholine (62 mg, 0.186 mmol). The mixture was degassed with nitrogen for 5 minutes then heated in microwave for 20 minutes at 120° C. The solution was diluted with water and the solid formed was isolated by filtration. The solid was purified by HPLC to yield 5-chloro-3-((5-(3-(2-morpholinoethoxy)phenyl)furan-2-yl)methylene)indolin-2-one. LCMS (M+1=451).

Example 64

Synthesis of 5-chloro-3-((5-(4-(2-morpholinoethoxy)phenyl)furan-2-yl)methylene)indolin-2-one

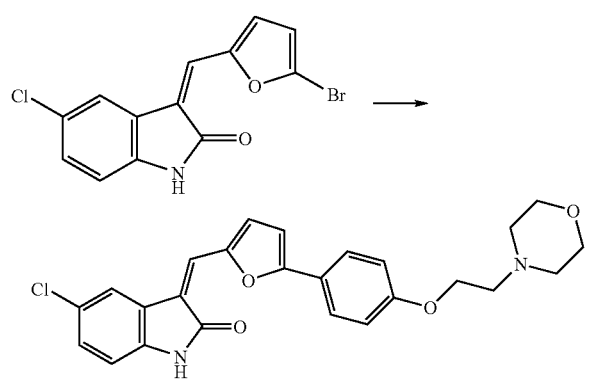

To 3-((5-bromofuran-2-yl)methylene)-5-chloroindolin-2-one (50 mg, 0.155 mmol) in dioxane/water (5% water) was added $Cs_2CO_3$ (152 mg, 0.466 mmol) and 4-(2-(4-(4,4,5,5-tetramethyl-1,3,2-dioxaborolan-2-yl)phenoxy)ethyl)morpholine (62 mg, 0.186 mmol). The mixture was degassed with nitrogen for 5 minutes then heated in microwave for 20 minutes at 120° C. The solution was diluted with water and the solid formed was isolated by filtration. The solid was purified by HPLC to yield 5-chloro-3-((5-(4-(2-morpholinoethoxy)phenyl)furan-2-yl)methylene)indolin-2-one. LCMS (M+1=451).

Example 65

Synthesis of 5-chloro-3-((5-(6-(2-morpholinoethylamino)pyridin-3-yl)furan-2-yl)methylene)indolin-2-one

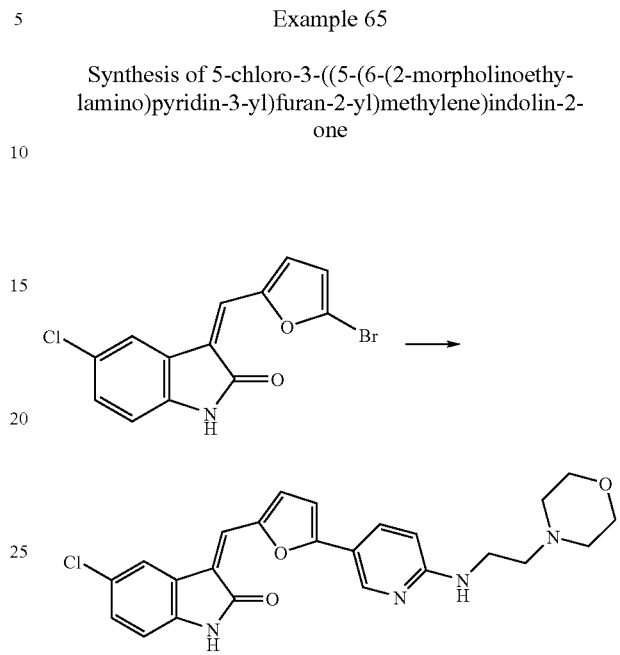

To 3-((5-bromofuran-2-yl)methylene)-5-chloroindolin-2-one (50 mg, 0.155 mmol) in dioxane/water (5% water) was added $Cs_2CO_3$ (152 mg, 0.466 mmol) and N-(2-morpholinoethyl)-5-(4,4,5,5-tetramethyl-1,3,2-dioxaborolan-2-yl)pyridin-2-amine (62 mg, 0.186 mmol). The mixture was degassed with nitrogen for 5 minutes then heated in microwave for 20 minutes at 120° C. The solution was diluted with water and the solid formed was isolated by filtration. The solid was purified by HPLC to yield 5-chloro-3-((5-(6-(2-morpholinoethylamino)pyridin-3-yl)furan-2-yl)methylene)indolin-2-one. LCMS (M+1=451).

Example 66

Synthesis of 5-chloro-3-((5-(6-(piperazin-1-yl)pyridin-3-yl)furan-2-yl)methylene)indolin-2-one

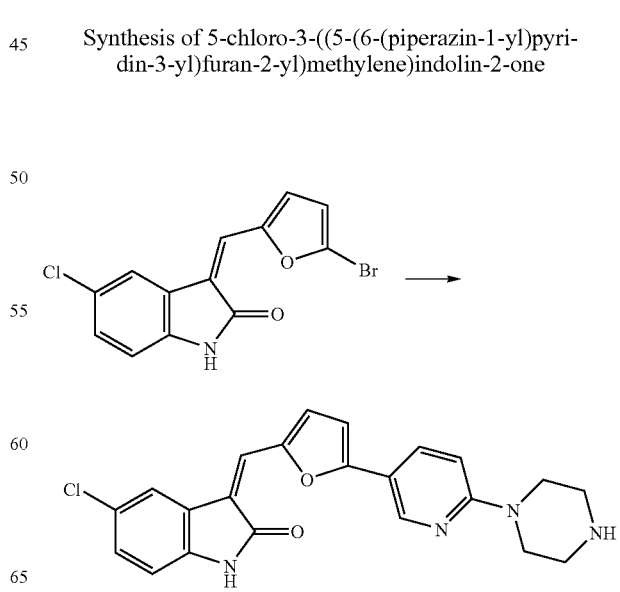

To 3-((5-bromofuran-2-yl)methylene)-5-chloroindolin-2-one (50 mg, 0.155 mmol) in dioxane/water (5% water) was added Cs₂CO₃ (152 mg, 0.466 mmol) and 1-(5-(4,4,5,5-tetramethyl-1,3,2-dioxaborolan-2-yl)pyridin-2-yl)piperazine (54 mg, 0.186 mmol). The mixture was degassed with nitrogen for 5 minutes then heated in microwave for 20 minutes at 120° C. The solution was diluted with water and the solid formed was isolated by filtration. The solid purified by HPLC to yield 5-chloro-3-((5-(6-(piperazin-1-yl)pyridin-3-yl)furan-2-yl)methylene)indolin-2-one. LCMS (M+1=407).

Example 67

Synthesis of 5-chloro-3-((5-(6-(dimethylamino)pyridin-3-yl)furan-2-yl)methylene)indolin-2-one

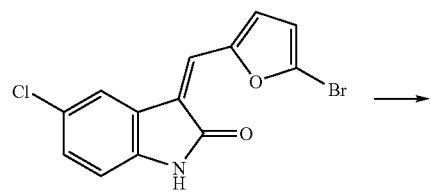

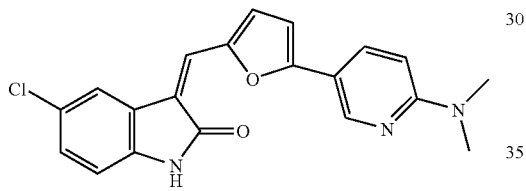

To 3-((5-bromofuran-2-yl)methylene)-5-chloroindolin-2-one (50 mg, 0.155 mmol) in dioxane/water (5% water) was added Cs₂CO₃ (152 mg, 0.466 mmol) and 6-(dimethylamino)pyridin-3-ylboronic acid (34 mg, 0.186 mmol). The mixture was degassed with nitrogen for 5 minutes then heated in microwave for 20 minutes at 120° C. The solution was diluted with water and the solid formed was isolated by filtration. The solid was purified by HPLC to yield 5-chloro-3-((5-(6-(dimethylamino)pyridin-3-yl)furan-2-yl)methylene)indolin-2-one. LCMS (M+1=366).

Example 68

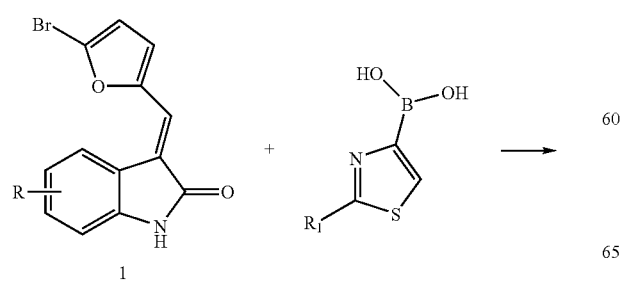

-continued

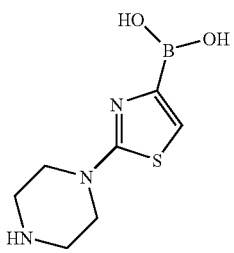

Compound 2 can be prepared via the Suzuki coupling reaction of compound 1 and the boronic acid as described in example 67. The following are examples of boronic acids that can be used:

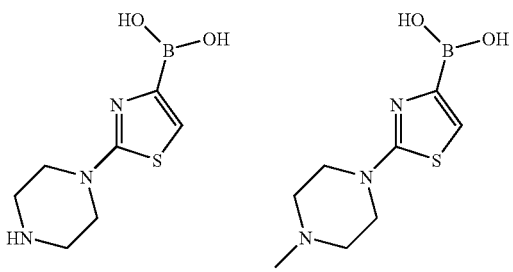

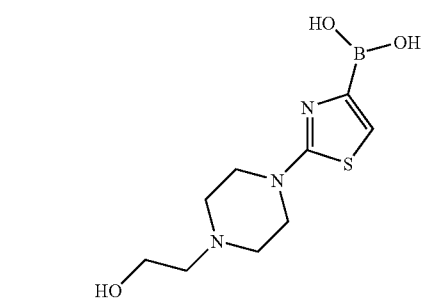

Example 69

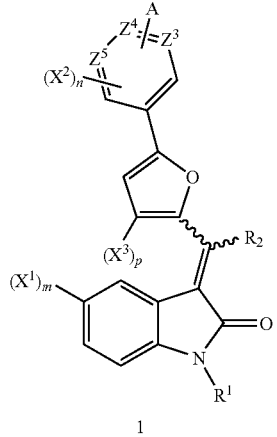

The following are methods that can be used to reduce compound 1 to compound 2.

Method A: Reduction using Pearlman's Catalyst. A solution of compound 1 in methanol is hydrogenated over Pearlman's catalyst at room temperature for ½-10 hours. The catalyst is removed by filtration, rinsed with methanol and the filtrate concentrated to give the reduced product 2.

Method B: Reduction using Palladium on Carbon. A solution of compound 1 in methanol containing a couple of drops of acetic acid is hydrogenated over palladium on carbon overnight at room temperature. The catalyst is removed by filtration, rinsed with methanol and the filtrate concentrated to give the reduced product 2.

Example 70

The following is a representative example of the synthesis of deuterated analogs:

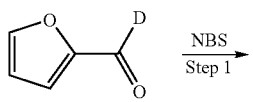

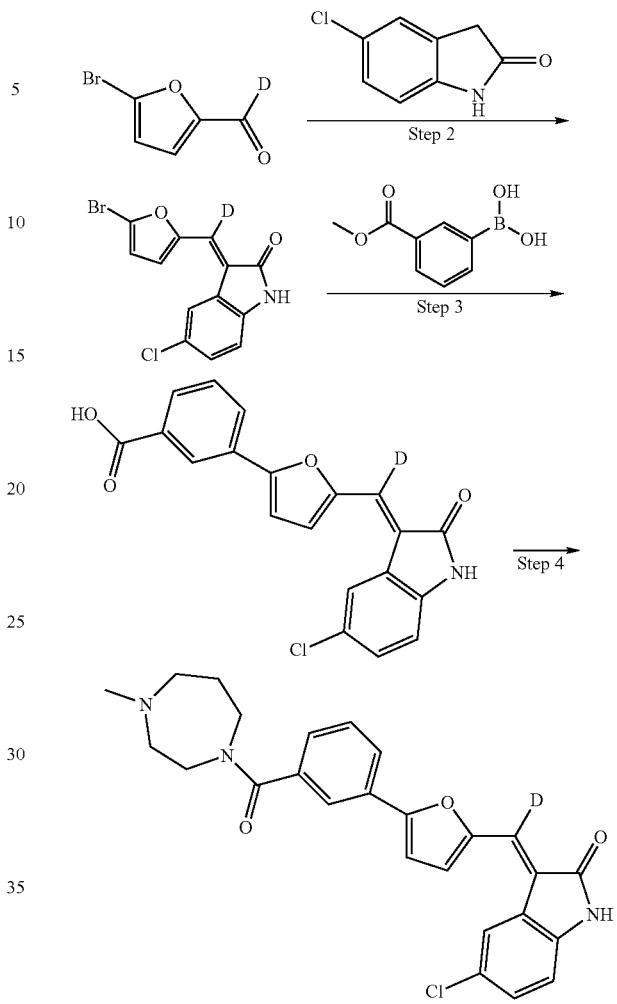

Step 1 can be done as described in Example 16.

Step 2 can be done as described in Example 7.

Step 3 can be performed as described in Example 17 for the Suzuki reaction followed by hydrolysis as described in Example 18.

Step 4 can be done as described in Example 8.

Example 71

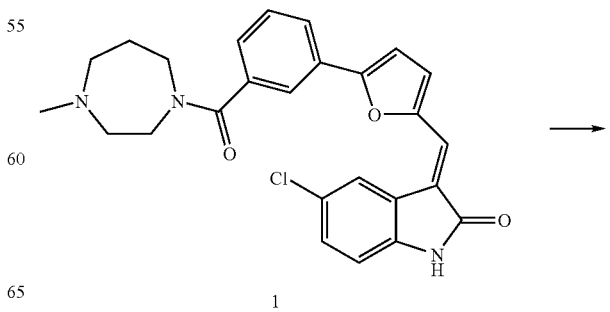

237
-continued

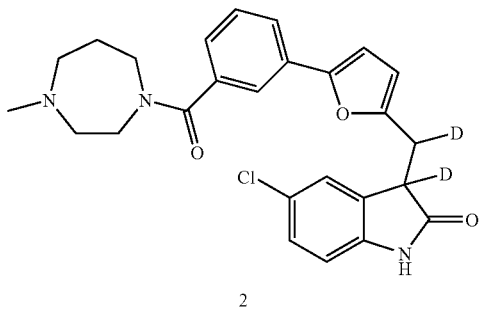

2

Compound 2 can be prepared from compound 1 by a reduction reaction with deuterated Raney nickel in tetrahydrofuran, as described in the literature (Pojer, P. M. *Tetrahedron Letters* (1984), 25: 2507-2508).

238

Example 72

PIM-3 Assay

The PIM-3 assay was run at Millopore. The following is the assay as described in the Millopore protocol guide. In a final reaction volume of 25 µL, Pim-3 (h) (5-10 mU) is incubated with 8 mM MOPS pH 7.0, 0.2 mM EDTA, 0.1% Triton X-100, 300 µM RSRHSSYPAGT, 10 mM MgAcetate and [g-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

The following table (Table 8) describes PIM2 and PIM3 $IC_{50}$ of selected compounds.

TABLE 8

PIM2 and PIM3 $IC_{50}$ of selected compounds in µM.

| Structure | PIM2 IC50 (µM) | PIM3 IC50 (µM) |
|---|---|---|
| 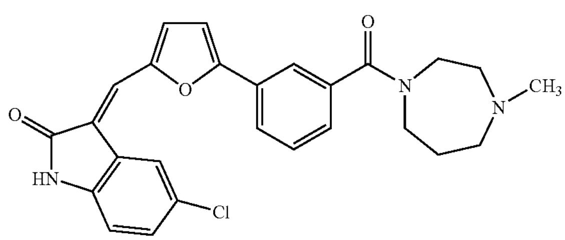 | <0.1 | <0.1 |
| 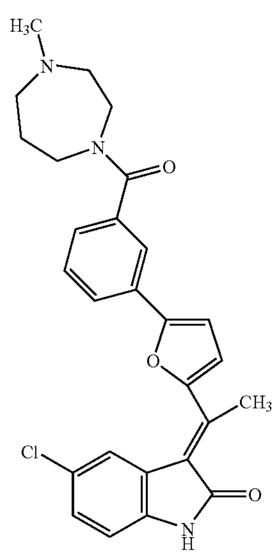 | <1 |  |

TABLE 8-continued

PIM2 and PIM3 IC$_{50}$ of selected compounds in μM.

| Structure | PIM2 IC50 (μM) | PIM3 IC50 (μM) |
|---|---|---|
| (structure) | <0.5 | <1 |
| (structure) | <0.5 | <1 |
| (structure) | <0.1 | <5 |

Example 73

MV4-11 Xenograft Model

Animal Studies: A compound of formula III was evaluated in the MV4-11 xenograft model of acute lymphocytic leukemia. Tumors were initiated by subcutaneous injection of MV4-11 tumor cells into the right hind flank in 5-7 week old female athymic mice (CrTac:Ncr-Foxn1$^{nu}$). When tumors reached a volume of 140±4.2 mm$^3$, mice were randomized and divided into groups of 10 mice per group. Vehicle (5% dextrose/water) or the test compound of Formula III was administered by oral gavage once daily at 50, 100 and 200 mg/kg. The dosing regimen was daily×10 days for the first 10 days followed by 5-2-5 regimen (once daily×5 days with 2 days no treatment) for 15 days. Tumor volumes and body weights were determined twice weekly. The tumor volume was determined by measuring in two directions with calipers and calculated using the following formula: tumor volume= (length×width$^2$)/2. Data were plotted as the median tumor volume in FIG. 2.

The invention claimed is:
1. A compound of Formula (I):

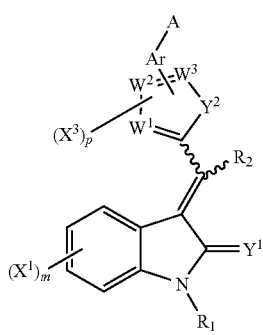

(I)

wherein:
R¹ is selected from H, alkyl, substituted alkyl;
R² is selected from H, alkyl, and substituted alkyl;
Y¹ is O or S;
Y² is O;
each X¹, X², and X³ is independently selected from halo, CN, CF₃, NO₂, alkyl, substituted alkyl, OR, and NR₂, COR, CONR, NRCONR, and NRC(O)OR;
m, n and p each independently represent 0, 1 or 2;
W¹, W² and W³ are each independently C, wherein each C is substituted with H or X³ or Ar, provided that either W² or W³ is the point of attachment for Ar;
Ar is a 5-10 membered aromatic or heteroaromatic group that is optionally substituted with (X²)ₙ;
A is selected from the group consisting of CH₂Q, —O—Z, —NRZ, NR—C(O)Z, NRC(O)—OZ, NRC(O)—NRZ, NRC(O)—OZ, OC(O)NRZ, and —C(=O)NRZ,
where Z is H, alkyl, substituted alkyl, heterocyclyl, substituted heterocyclyl, aryl, or substituted aryl,
and Q is OZ or NRZ;
R is independently selected at each occurrence from the group consisting of H, alkyl or substituted alkyl, and two R on NR₂ can cyclize to form a 5-7 membered ring that can be substituted and may optionally contain one additional heteroatom selected from N, O and S as a ring member, and R and Z, when both present on A or Q, can optionally cyclize to form a 5-7 membered ring that can be substituted and can include an additional O, N or S as a ring member; and
each q is independently 0, 1 or 2;
or a pharmaceutically acceptable salt thereof.

2. The compound of claim 1, wherein Y¹ is O.
3. The compound of claim 1, wherein R¹ is H or Me.
4. The compound of claim 1, wherein R² is H, Me, Et, Cyclopropyl, isopropyl or CH₂OH.
5. The compound of claim 1, wherein W¹ and W² are each independently CH or CMe.
6. The compound of claim 1, wherein m is 1 and X¹ is halo.
7. The compound of claim 1, wherein W³ is the point of attachment for Ar.
8. The compound of claim 1, wherein W² is the point of attachment for Ar.
9. The compound of claim 1, wherein Ar is phenyl or pyridyl, each of which can be substituted.
10. The compound of claim 9, wherein Ar is substituted with one group selected from halo, amino, alkyl, and hydroxyl, in addition to A.
11. The compound of claim 1, wherein A is —NR—C(O)Z or —C(=O)NRZ, wherein R is H or Me, or wherein R and Z can optionally cyclize to form a 5-7 membered ring that can be substituted and can include an additional O, N or S as a ring member.
12. The compound of claim 11, wherein Z is a group of the formula —(CH₂)ᵣZ', wherein r is 0, 1, 2, 3, or 4, and Z' is —NR¹R² or a 5-6 membered heteroaryl or heterocyclic ring containing at least one N as a ring member, and optionally substituted.
13. The compound of claim 1, wherein the compound is a compound of formula (II):

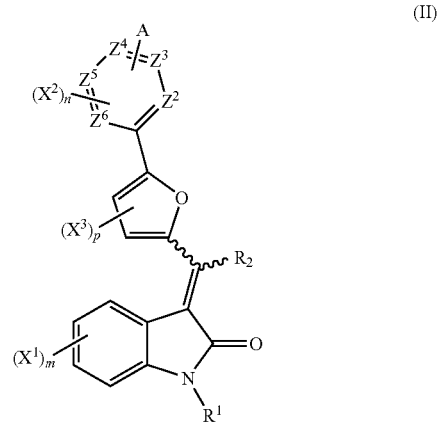

(II)

wherein A, R¹, R², X¹, X², X³, m, n, and p are as defined for Formula (I),
and each of Z², Z³, Z⁴, Z⁵ and Z⁶ is independently C or N, provided not more than two of Z², Z³, Z⁴, Z⁵ and Z⁶ are N, and wherein each C is CH or CX² or is the point of attachment for A;
or a pharmaceutically acceptable salt thereof.

14. The compound of claim 13, wherein A is —C(=O)—NRZ or —NRC(O)Z, wherein R is H or Me, or wherein R and Z can optionally cyclize to form a 5-7 membered ring that can be substituted and can include an additional O, N or S as a ring member.
15. The compound of claim 13, wherein m is 1 and X¹ is halo.
16. The compound of claim 13, wherein Z³ is C-A.
17. The compound of claim 13, wherein Z⁴ is C-A.
18. The compound of claim 13, which is a compound of the formula:

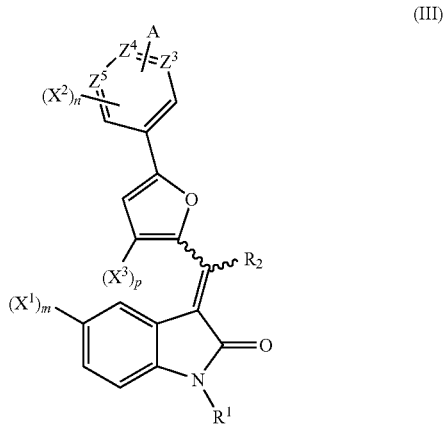

(III)

wherein

X¹ is Cl or F, and m is 0 or 1;

X² is halo, NH₂, OH, or CH₂OH, and n is 0 or 1;

X³ is Me, and p is 0 or 1;

R² is H, D, Me, Et, cyclopropyl, isopropyl or CH₂OH;

one of Z³ and Z⁴ is CH and the other of Z³ and Z⁴ is CA;

Z⁵ is N or CH, or Z⁵ can be CX² if n is 1;

R¹ is H;

A is OH, CH₂OH, NH₂, CONH₂, or a group of the formula -L-Az, wherein L is a linker selected from the group consisting of —C(O)—, —NRC(O)—, —C(O)NR—, NRC(O)—(CH₂)ᵣ— and —C(O)NR—(CH₂)ᵣ—, where each r is independently 1-3; each R is independently H, alkyl or substituted alkyl; and Az represents a 5-7-membered nitrogen-containing heterocyclic or heteroaryl group;

or a pharmaceutically acceptable salt thereof.

19. A compound of the formula (IIIa):

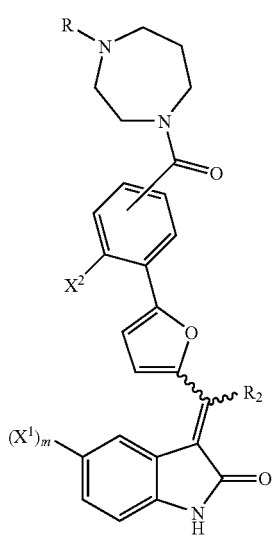

(IIIa)

wherein m is 1, and X¹ is Cl or F;

X² is selected from H, Cl, OH, OMe, NH₂, NHMe, Me, and F;

R² is H, D or Me; and

R is H, Me, Et, or isopropyl;

or a pharmaceutically acceptable salt thereof.

20. A pharmaceutical composition comprising at least one compound of formula (I) according to claim 1 admixed with at least one pharmaceutically acceptable excipient.

21. The compound of claim 1, which is selected from the group consisting of

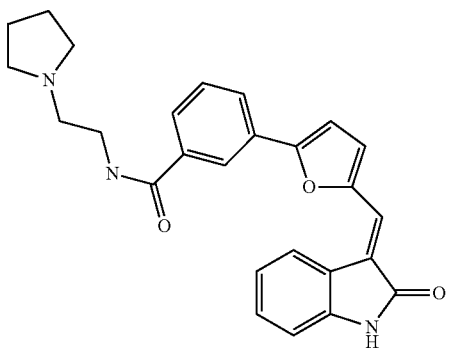

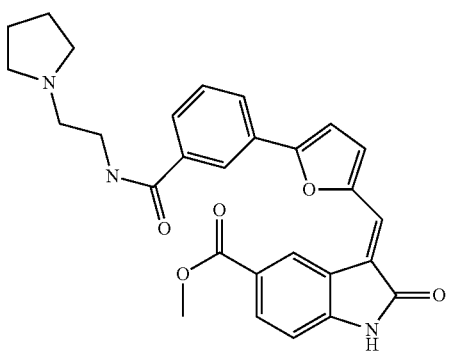

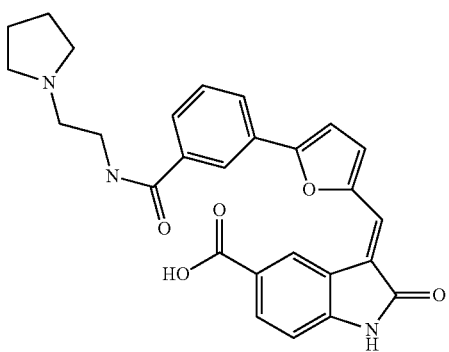

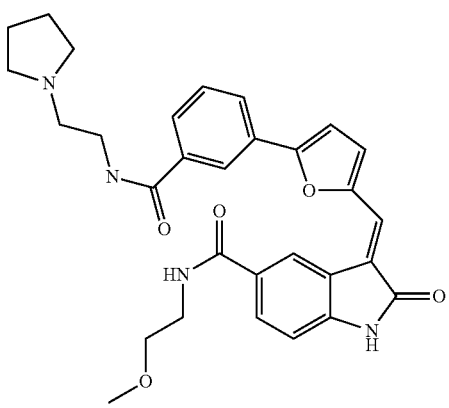

245
-continued
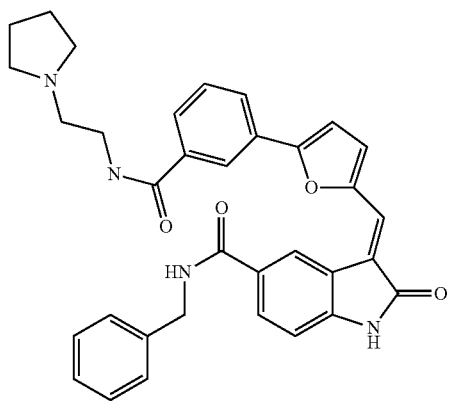
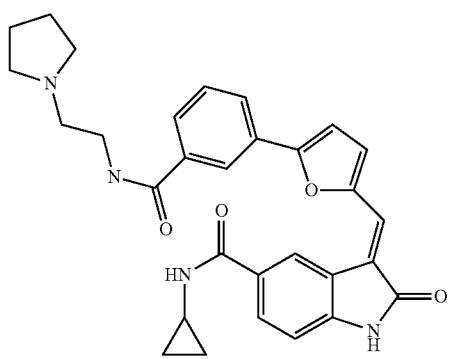
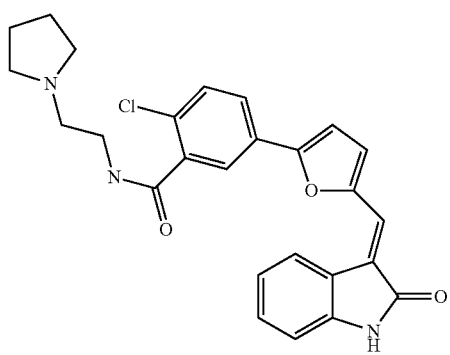
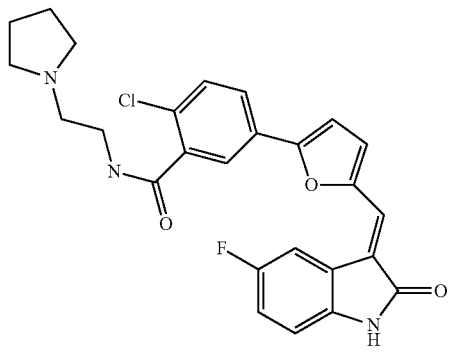
246
-continued
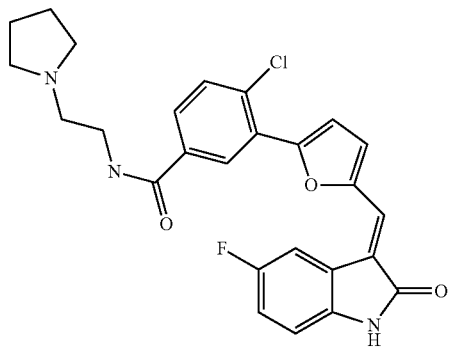
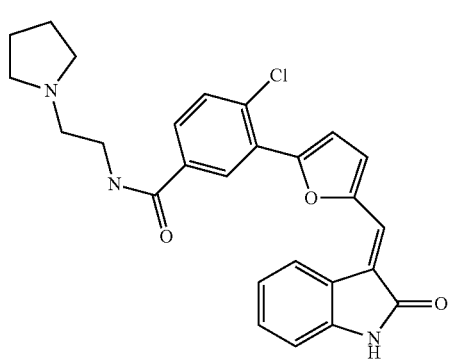
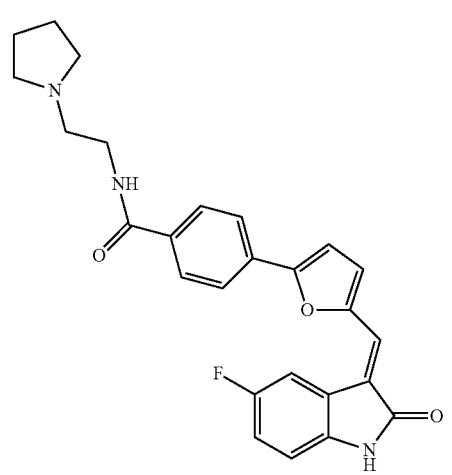
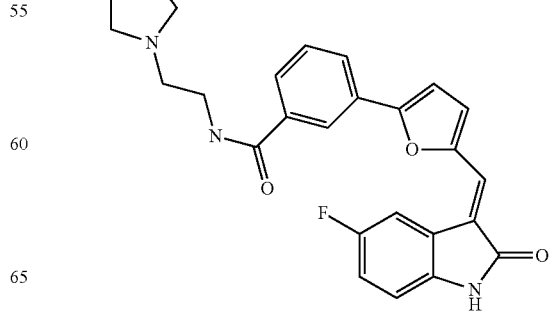

247
-continued
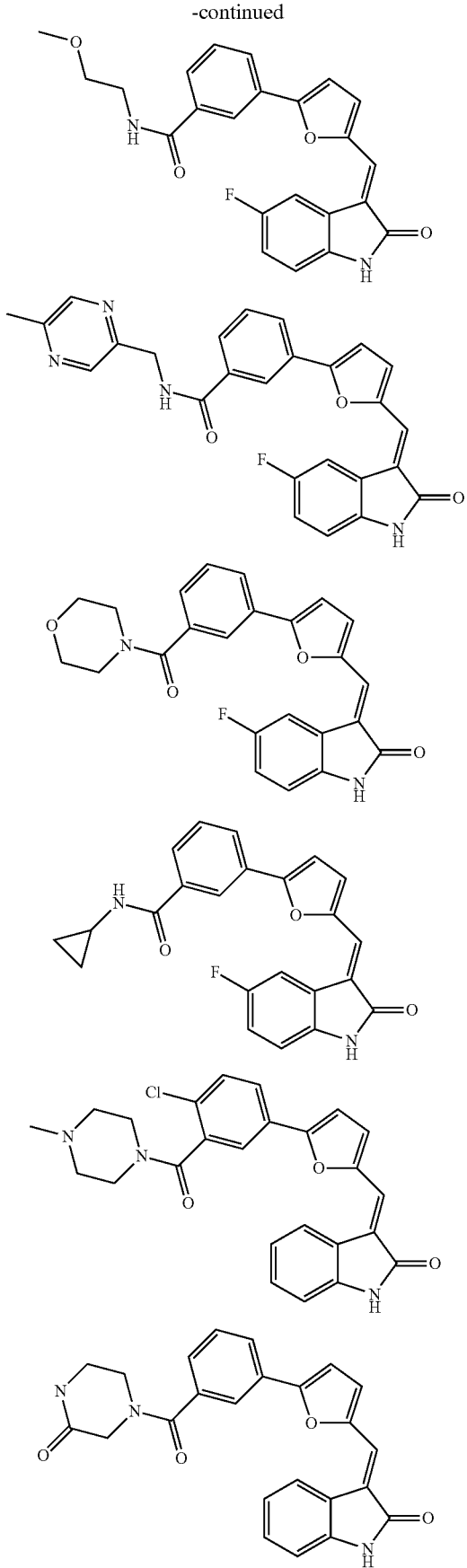
248
-continued
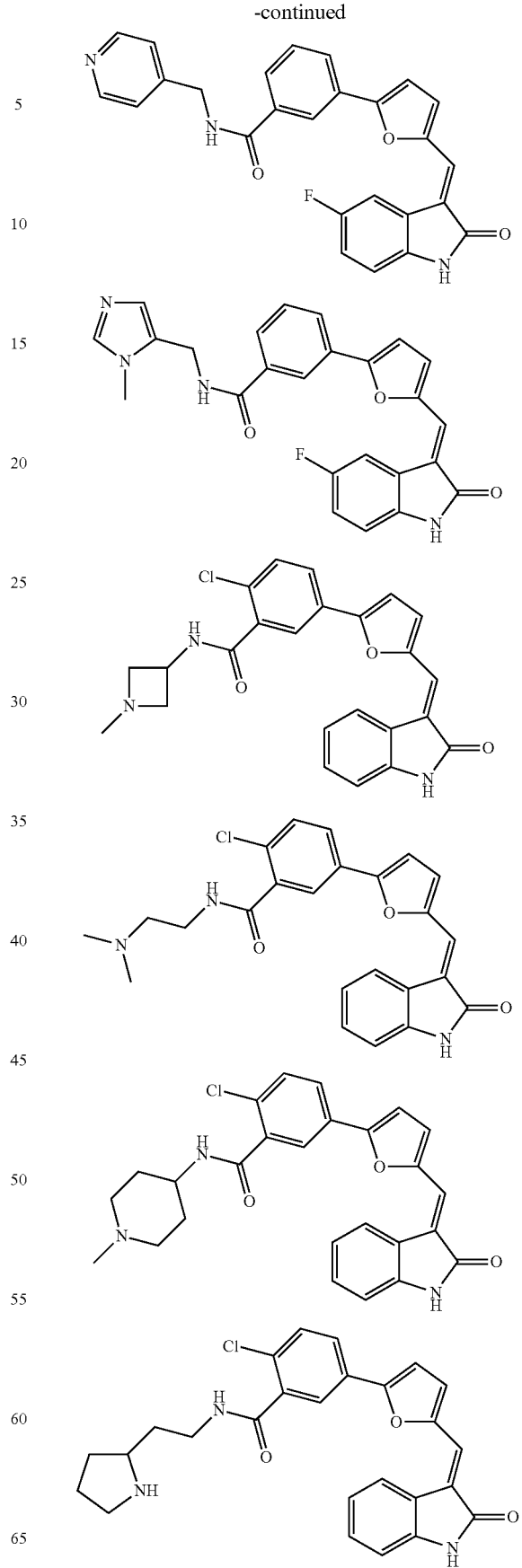

| 249 -continued | 250 -continued |
|---|---|
| 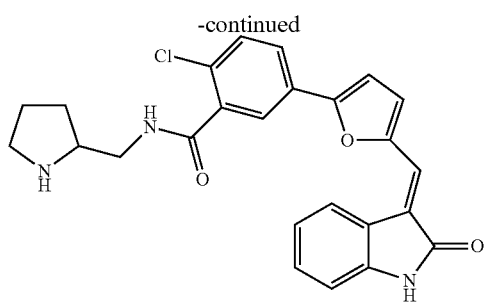 | 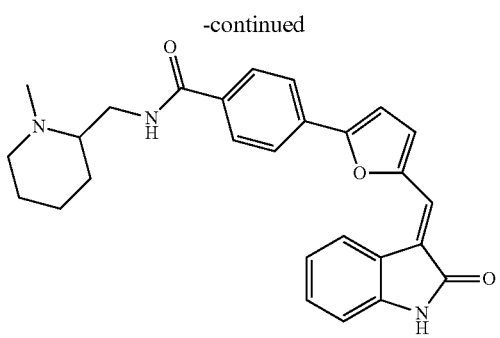 |
| 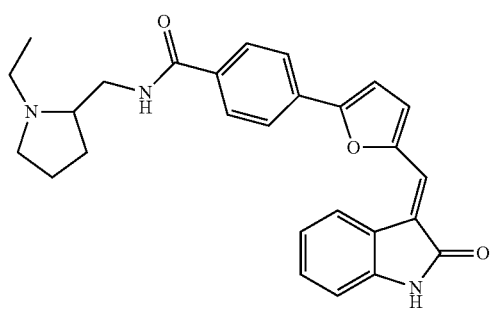 | 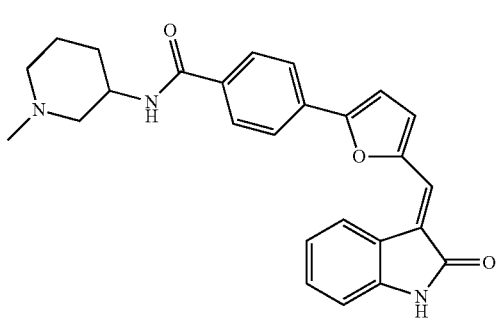 |
| 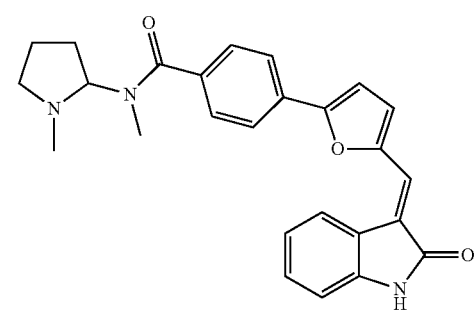 | 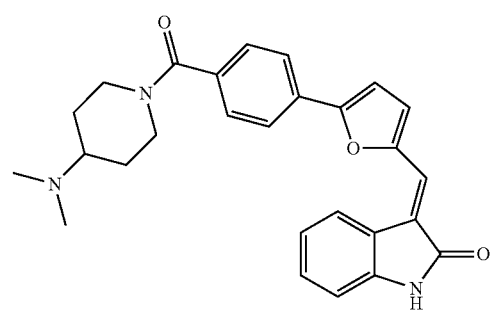 |
| 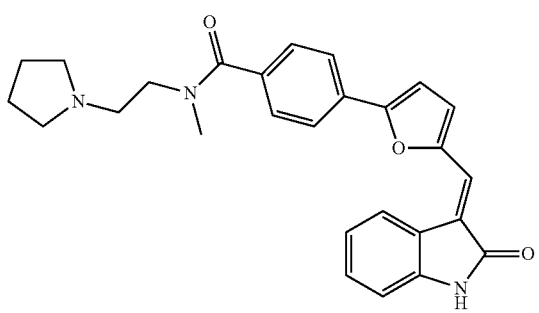 | 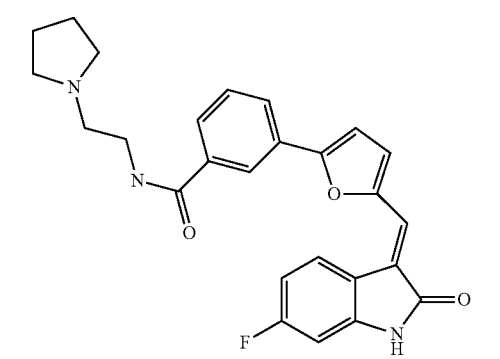 |
| 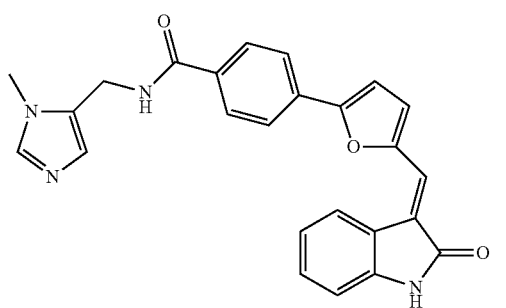 | 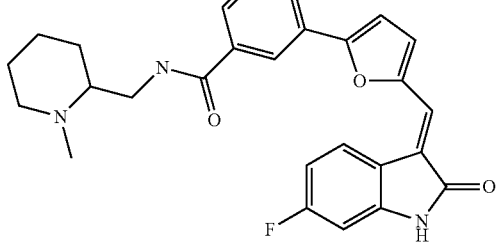 |

251
-continued
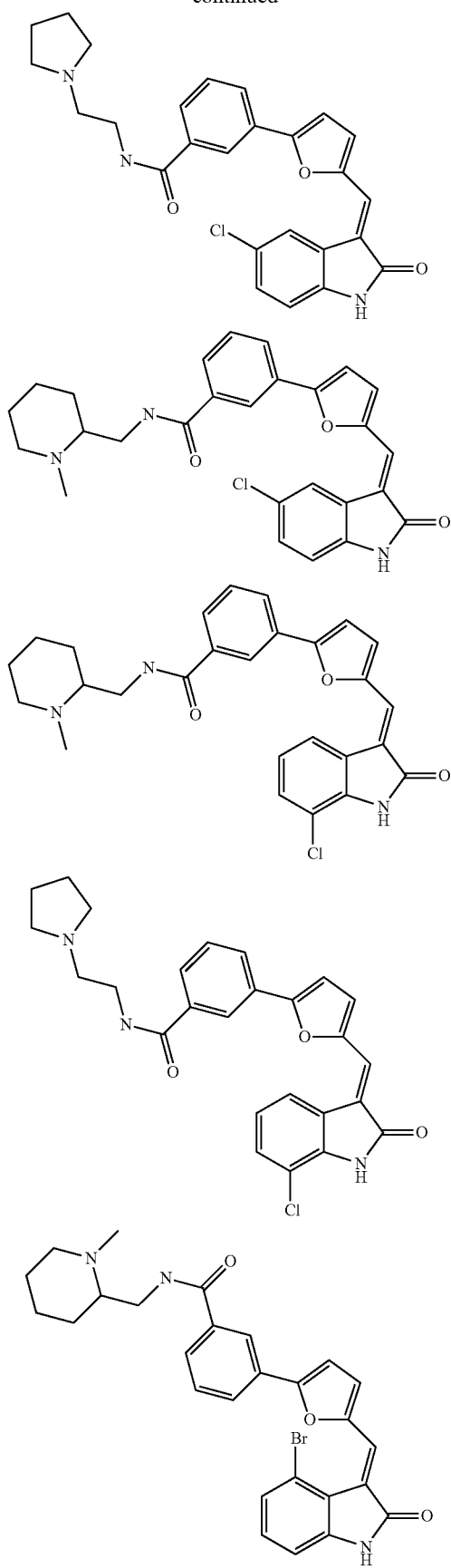
252
-continued
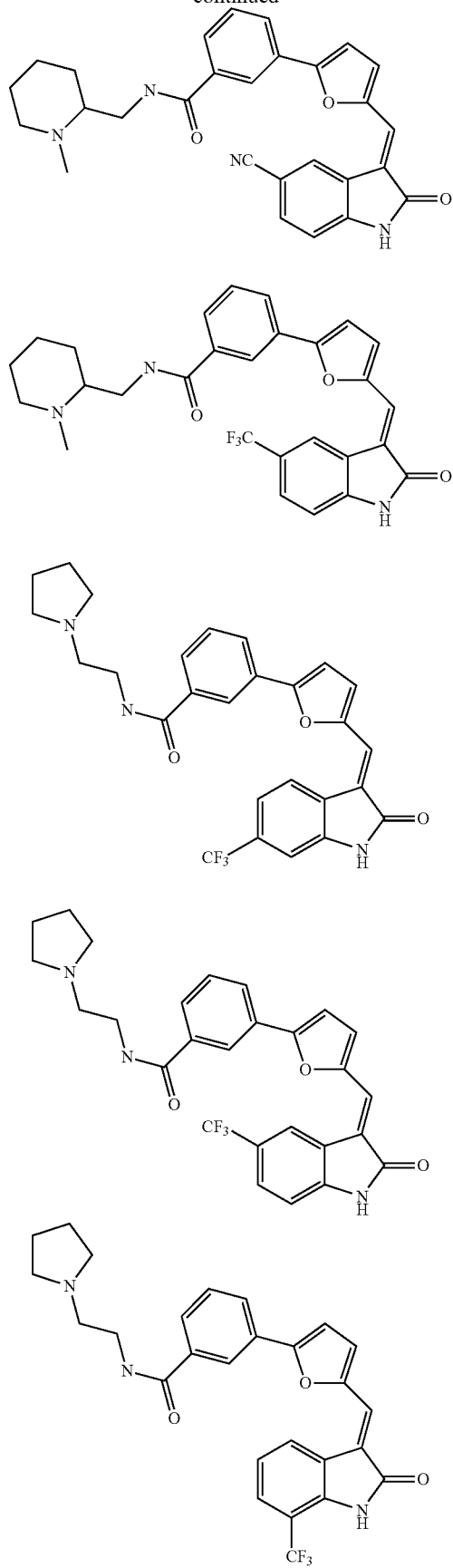

253
-continued
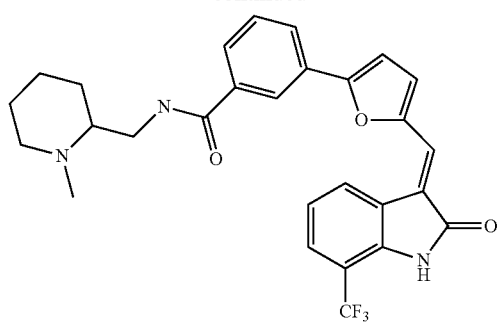
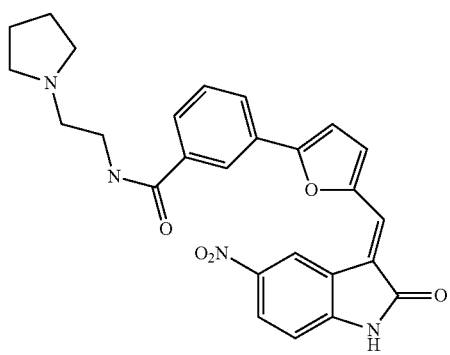
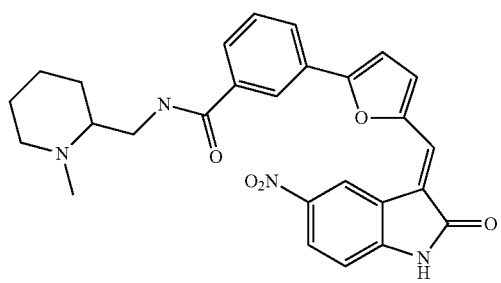
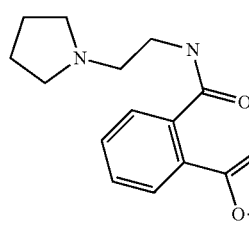
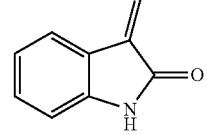
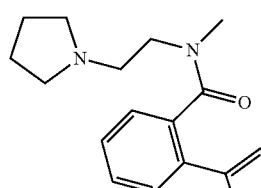
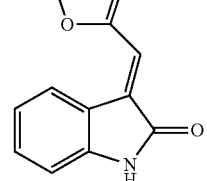
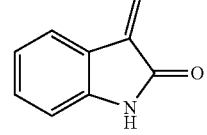
254
-continued
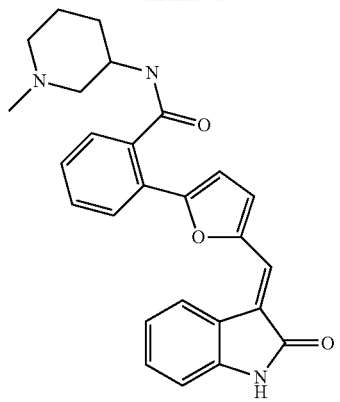
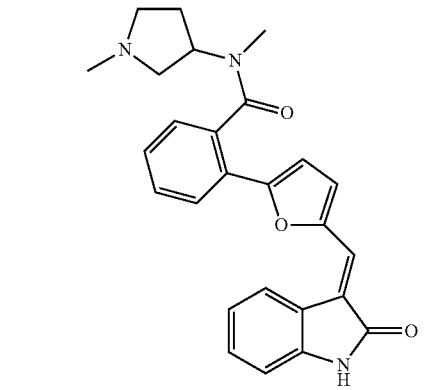
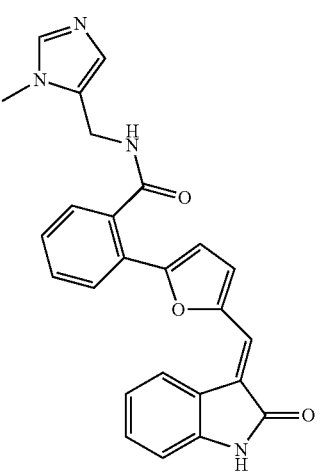

255
-continued
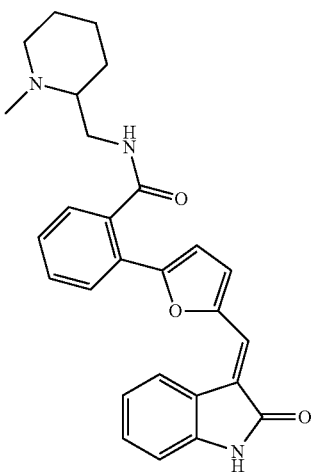
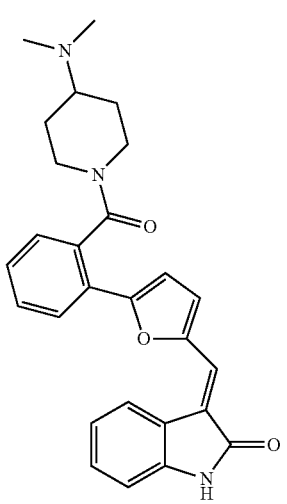
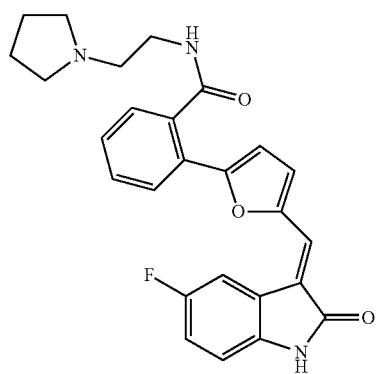
256
-continued
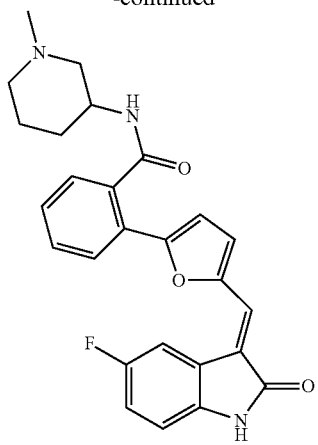
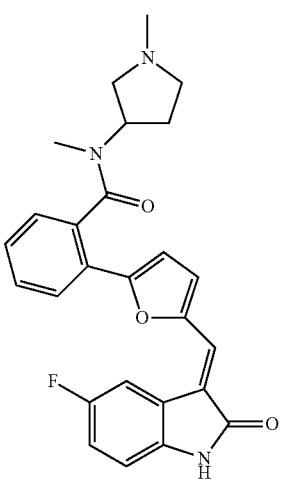
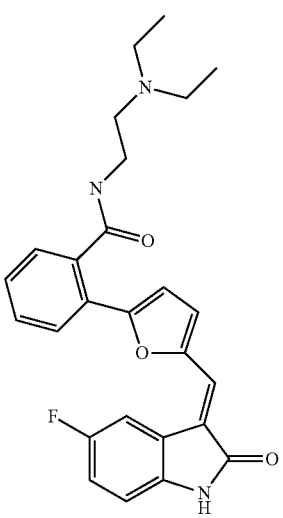

257
-continued
258
-continued
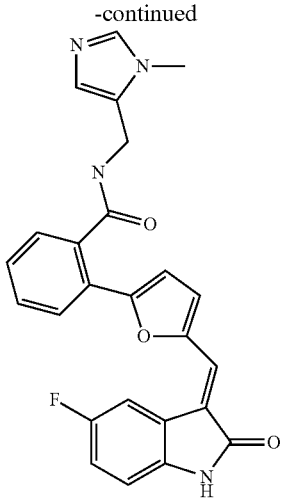
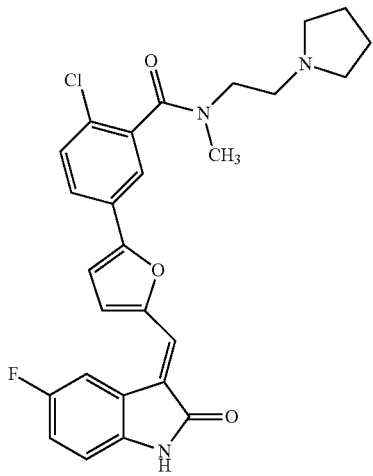

259
-continued
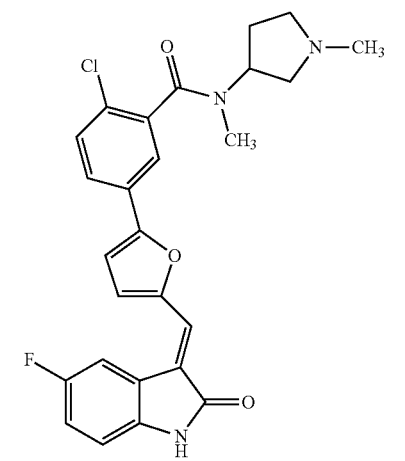
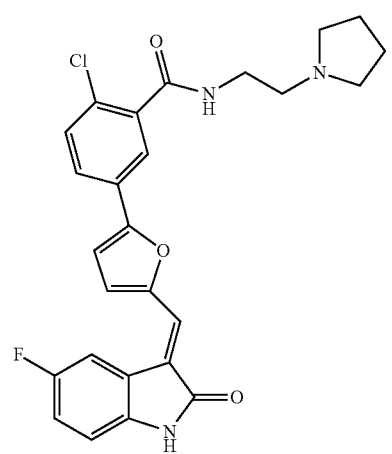
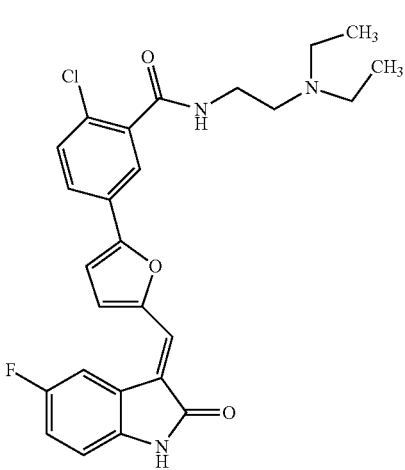
260
-continued
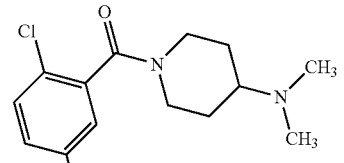
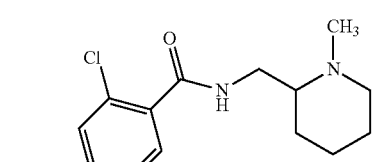
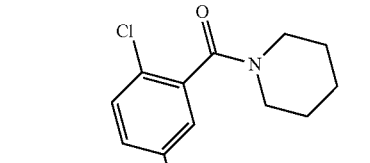
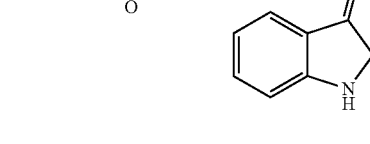

261
-continued
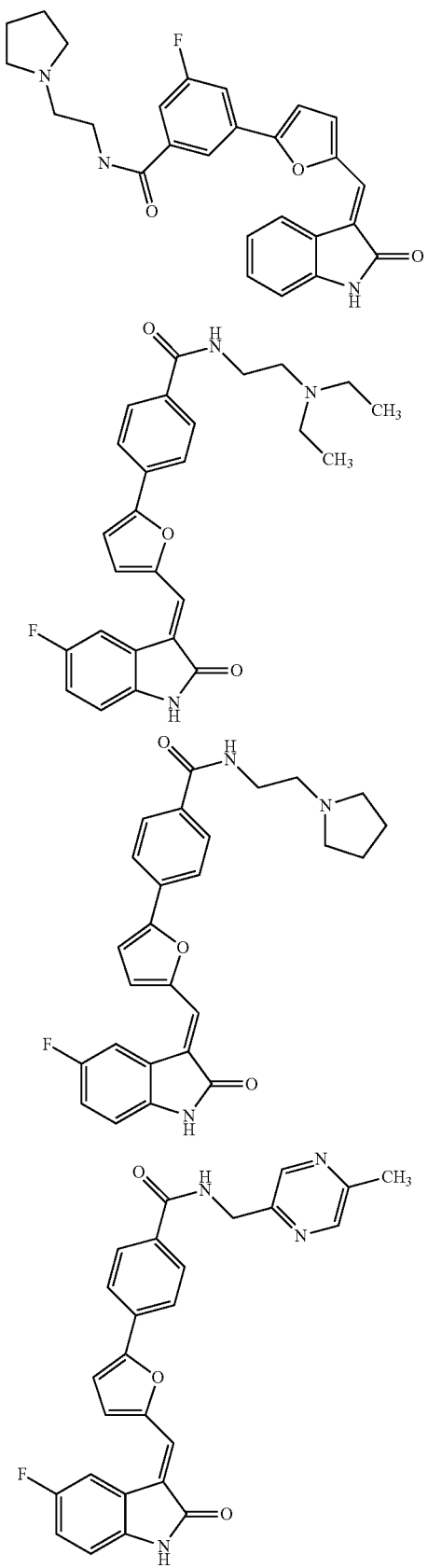
262
-continued
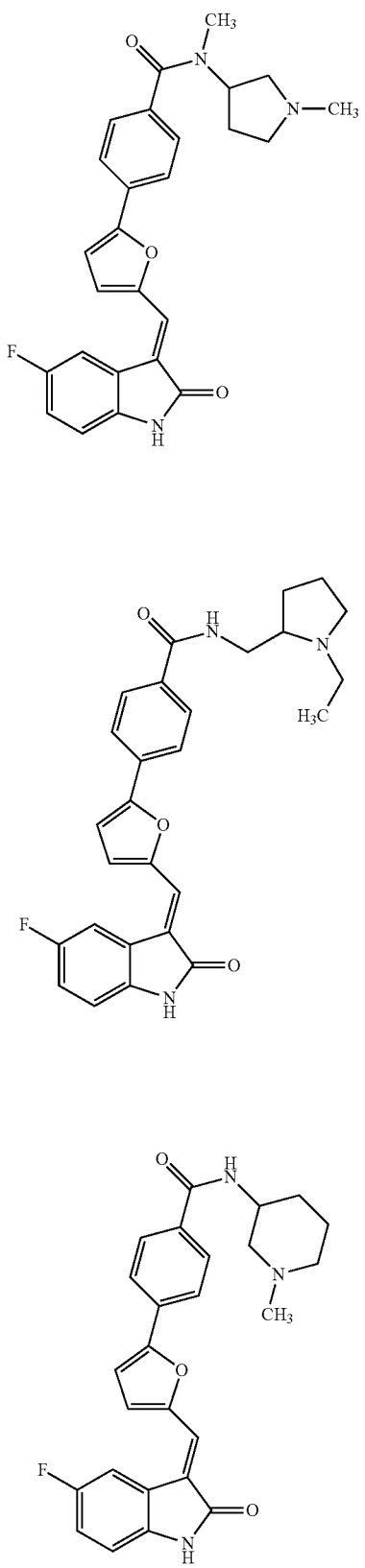

263
-continued
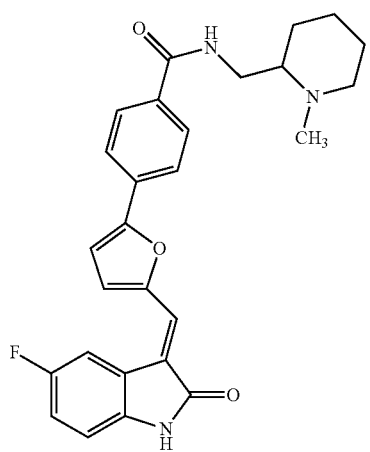
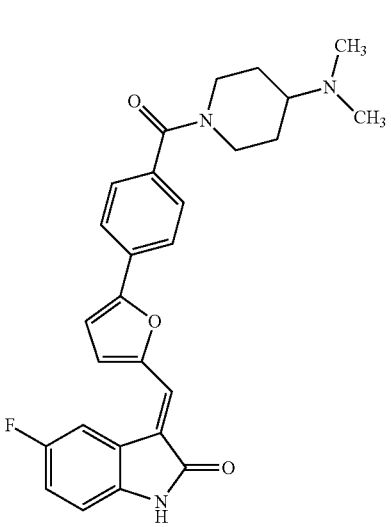
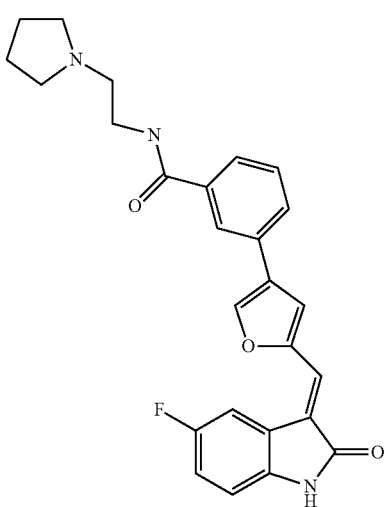
264
-continued
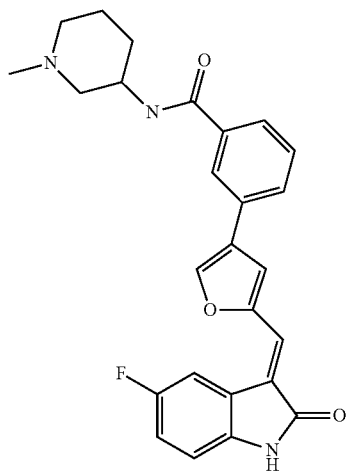
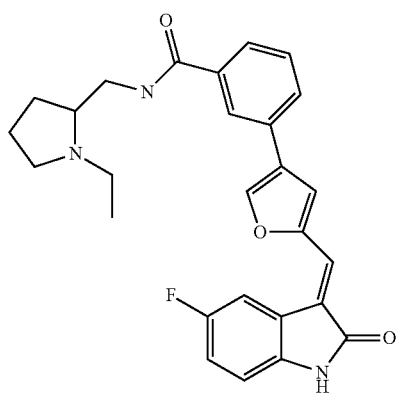
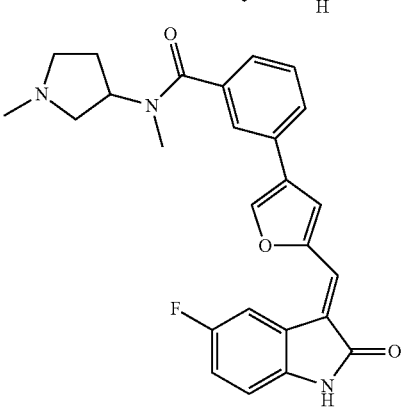
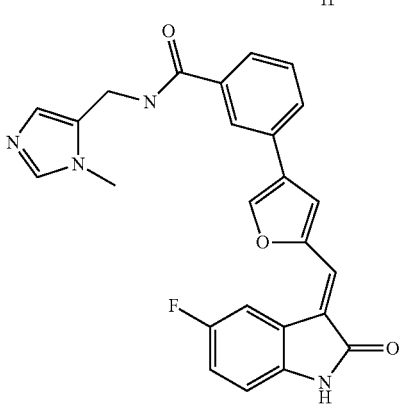

265
-continued
266
-continued
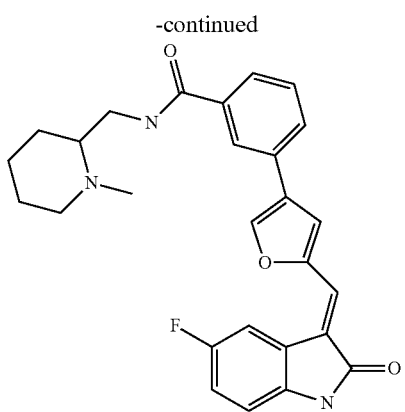
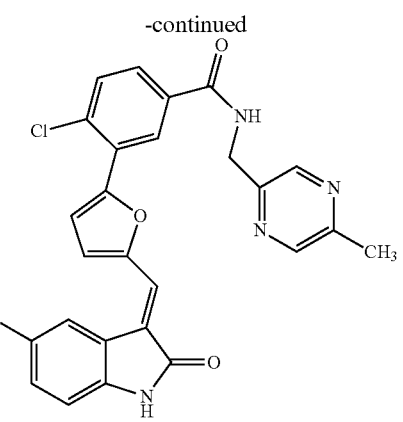

267
-continued
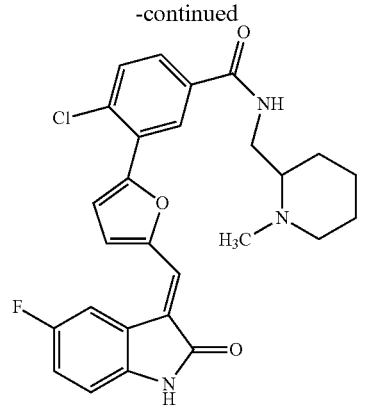
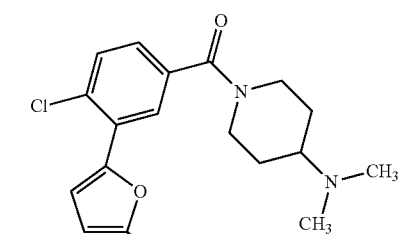
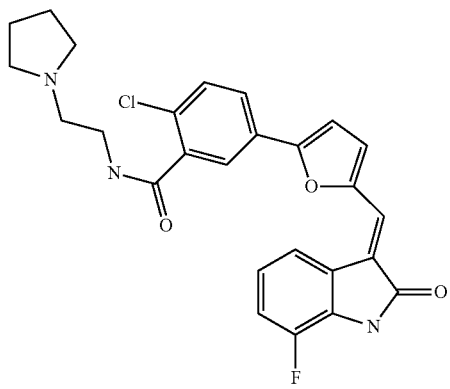
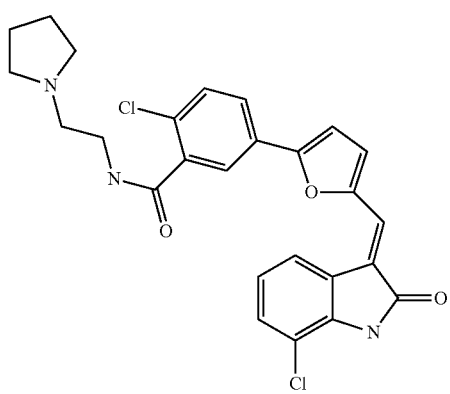
268
-continued
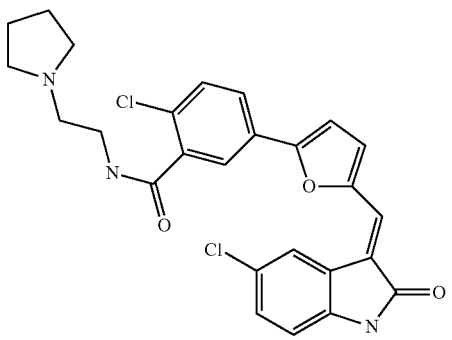
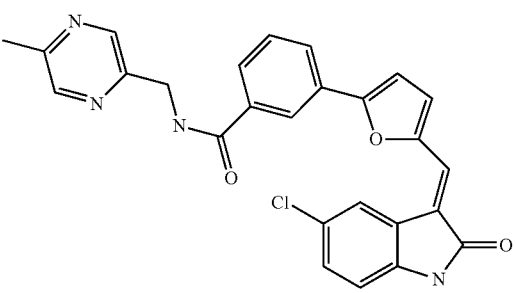
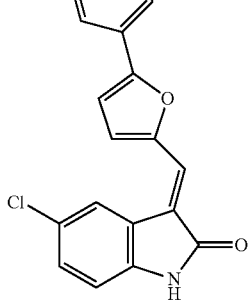
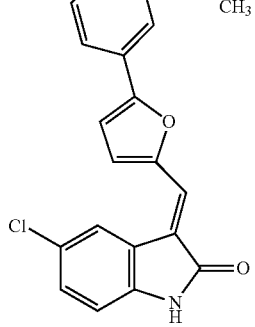

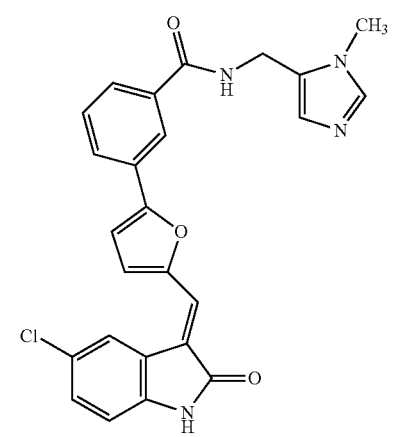
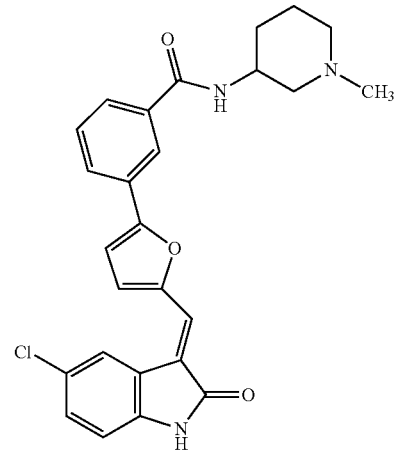
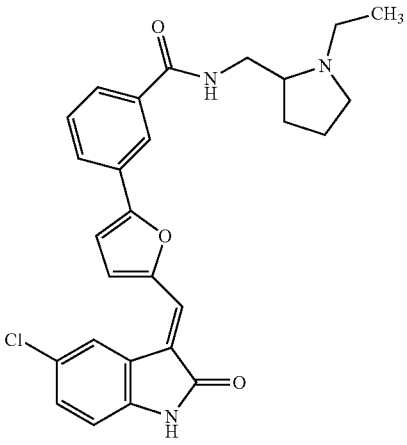
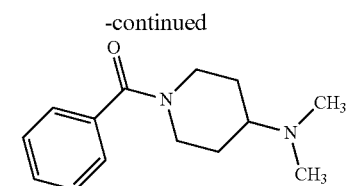
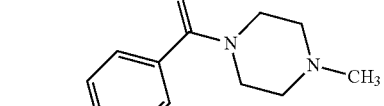
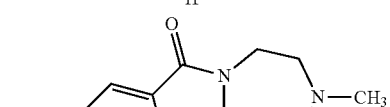
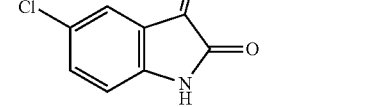

-continued
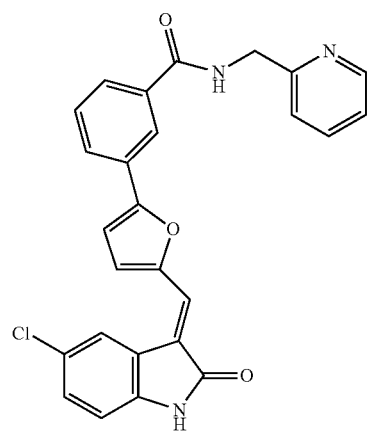
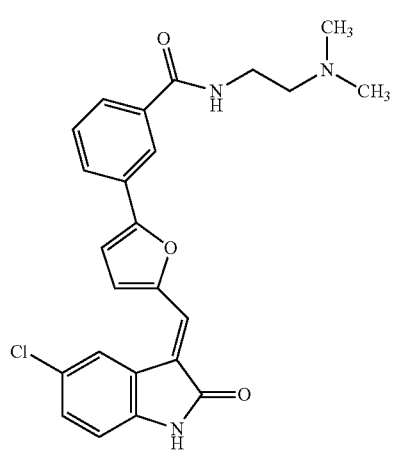
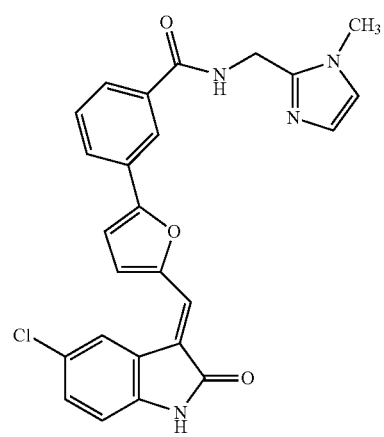
-continued
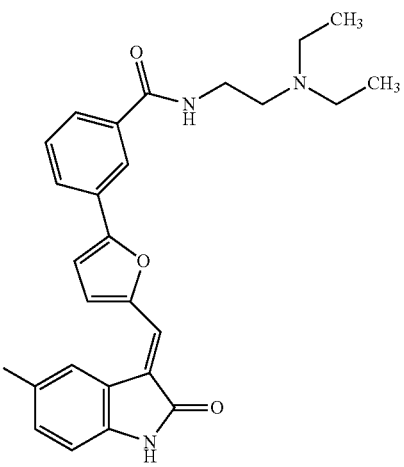
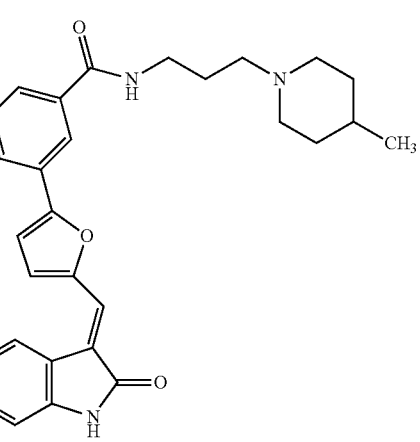
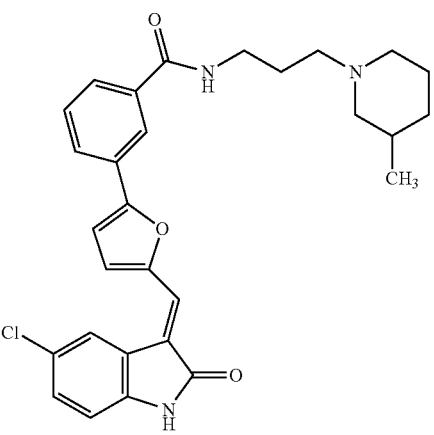

273
-continued
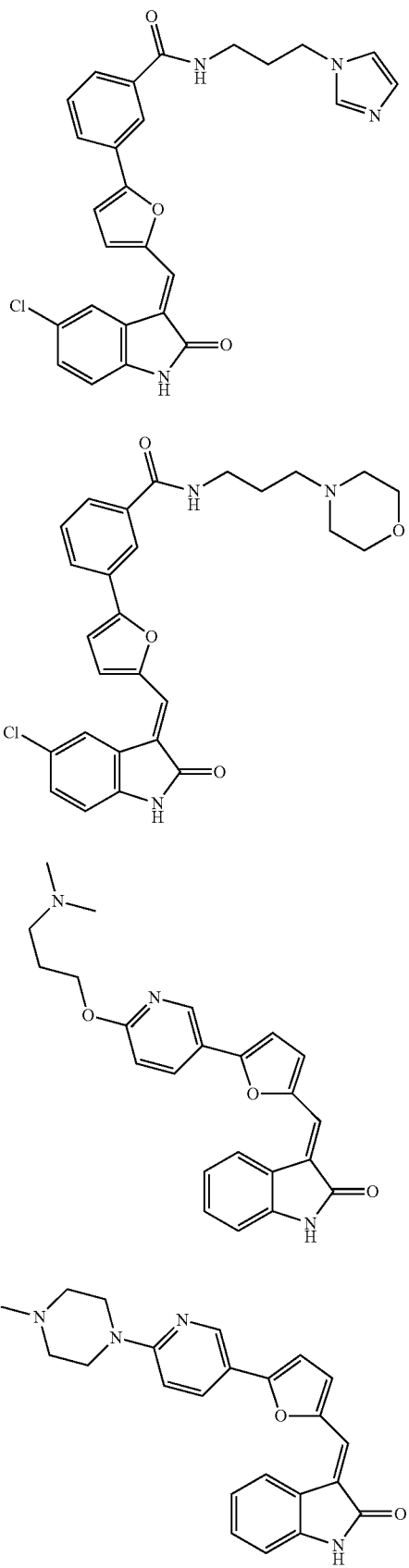
274
-continued
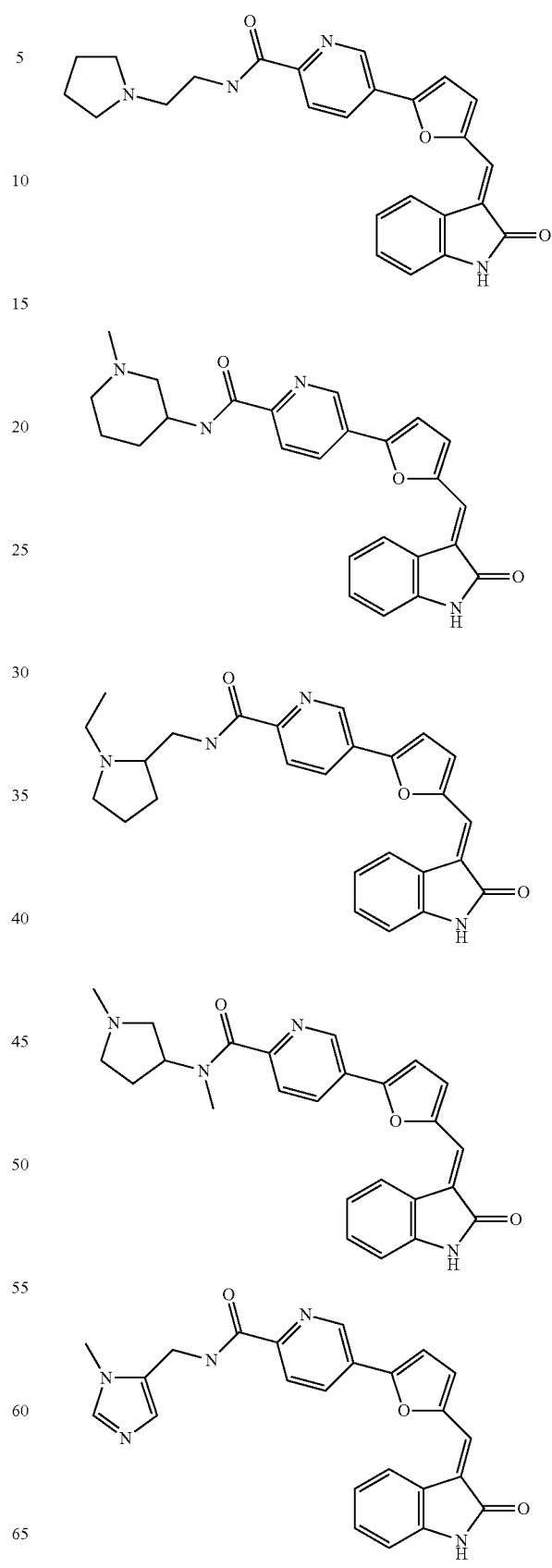

275
-continued
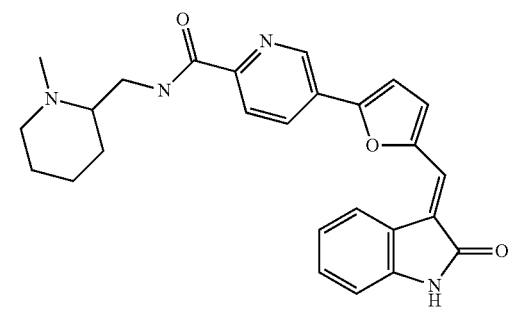
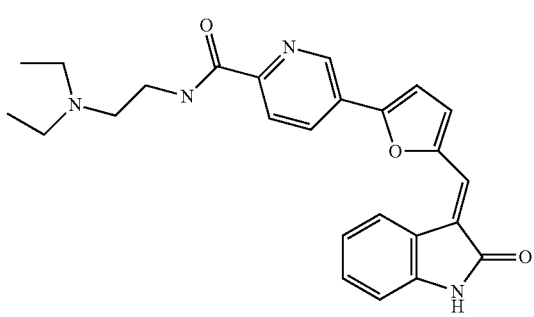
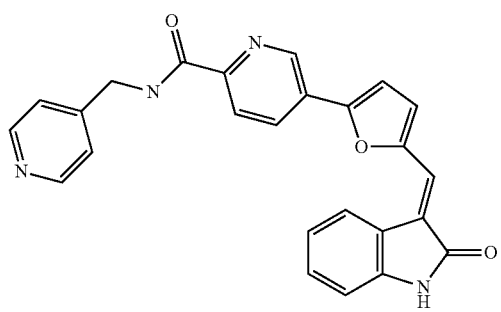
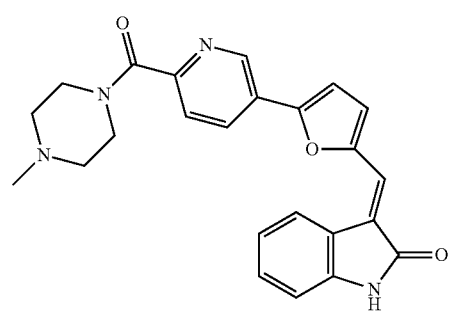
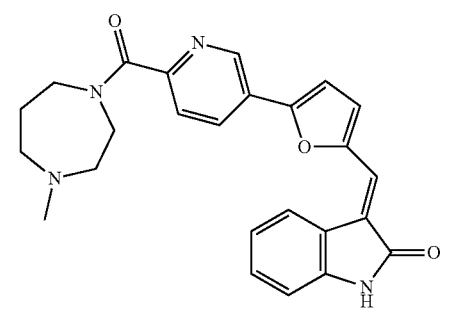
276
-continued
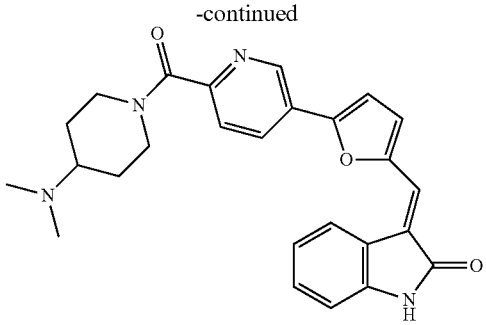
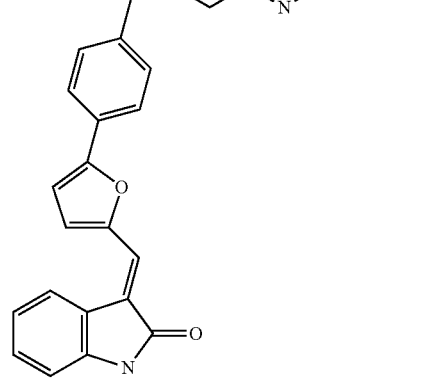

277
-continued
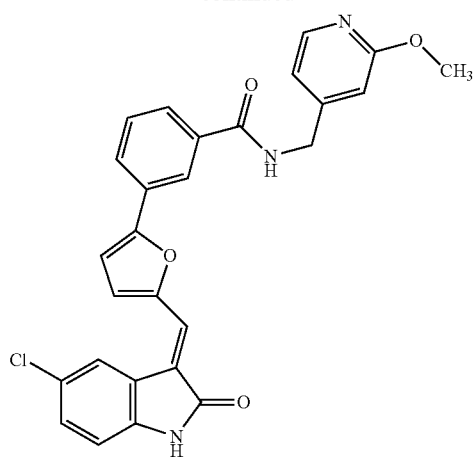
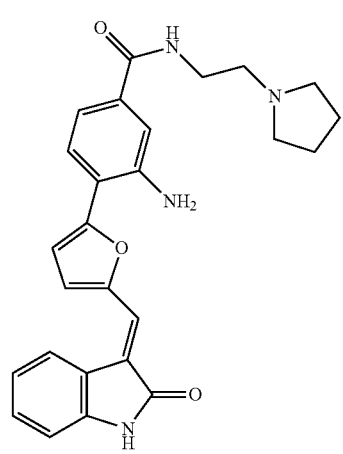
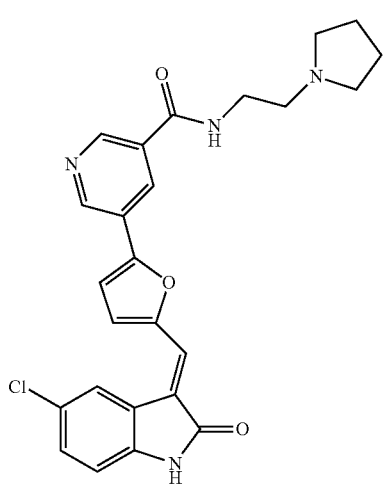
278
-continued
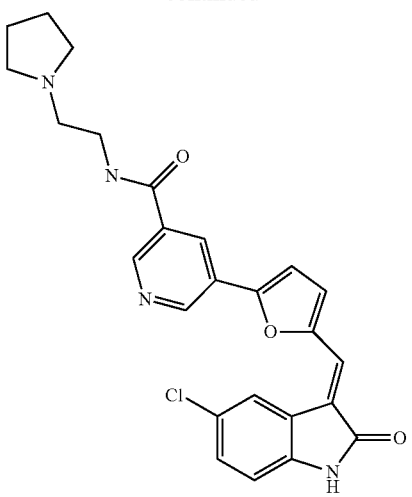
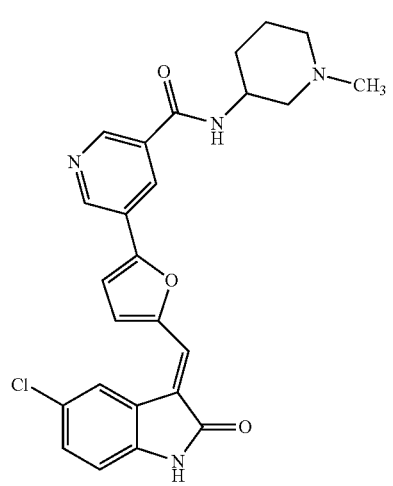
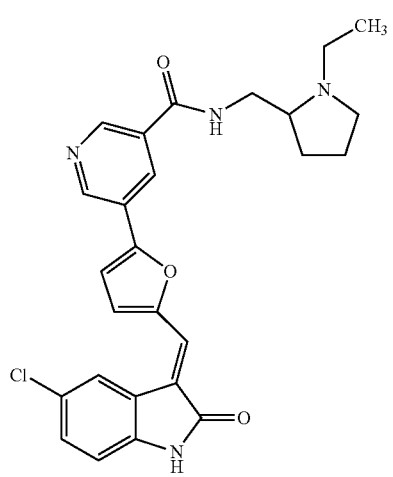

279
-continued
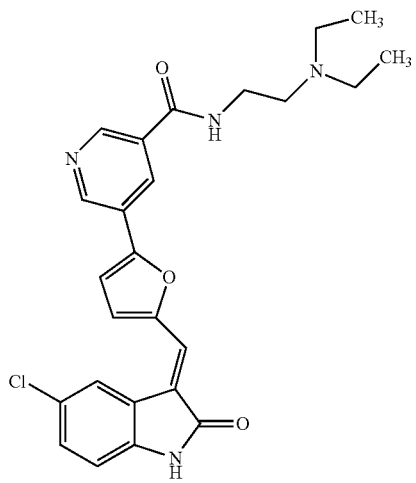
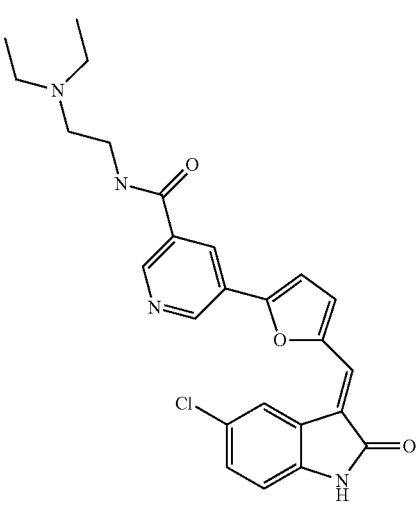
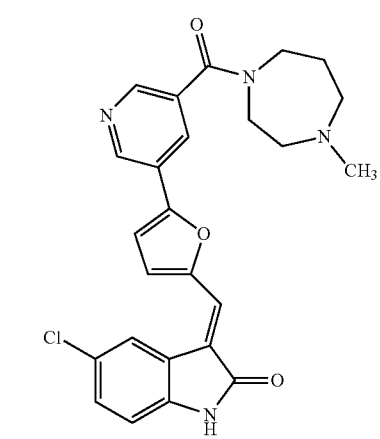
280
-continued
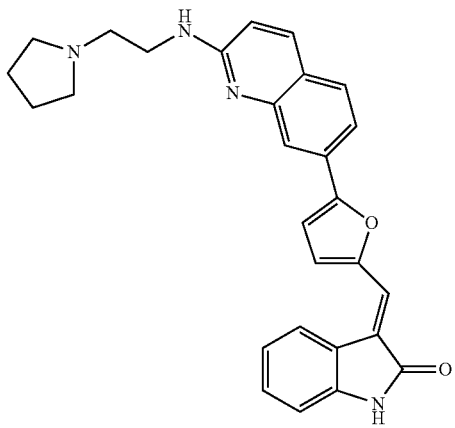
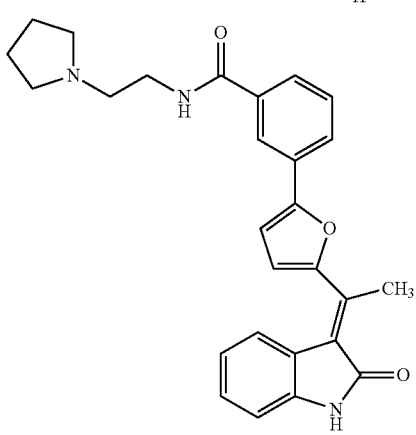
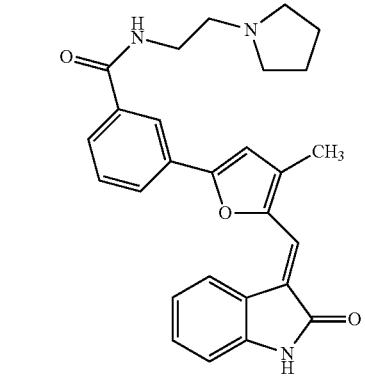
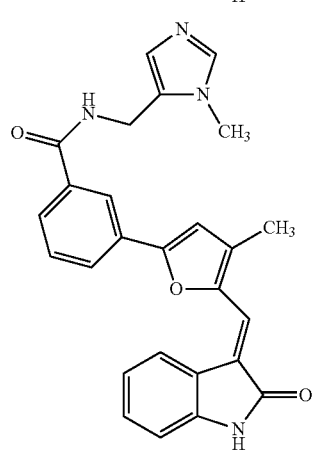

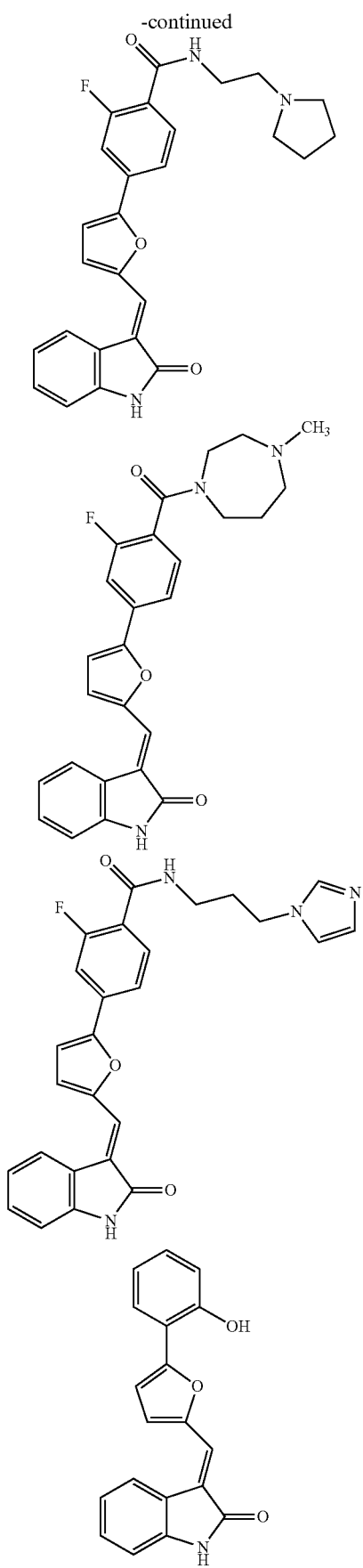
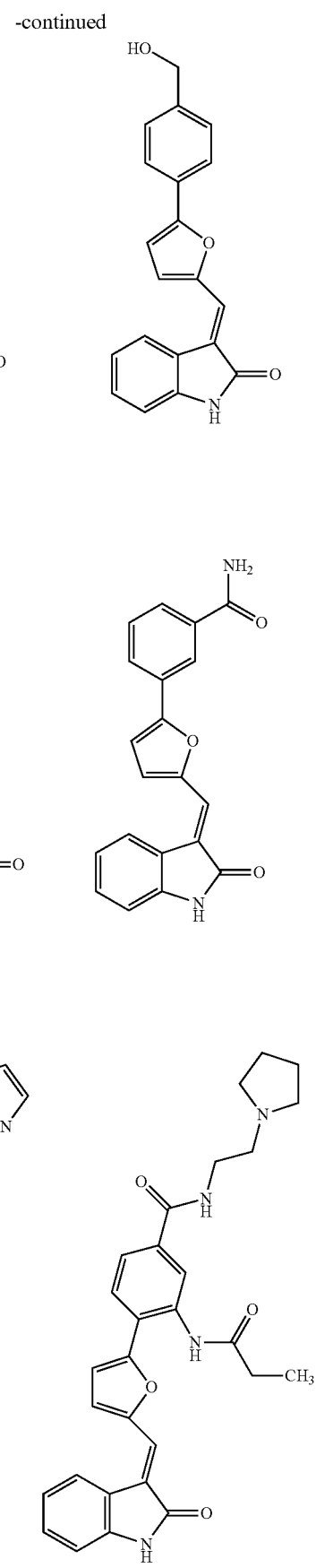

283
-continued
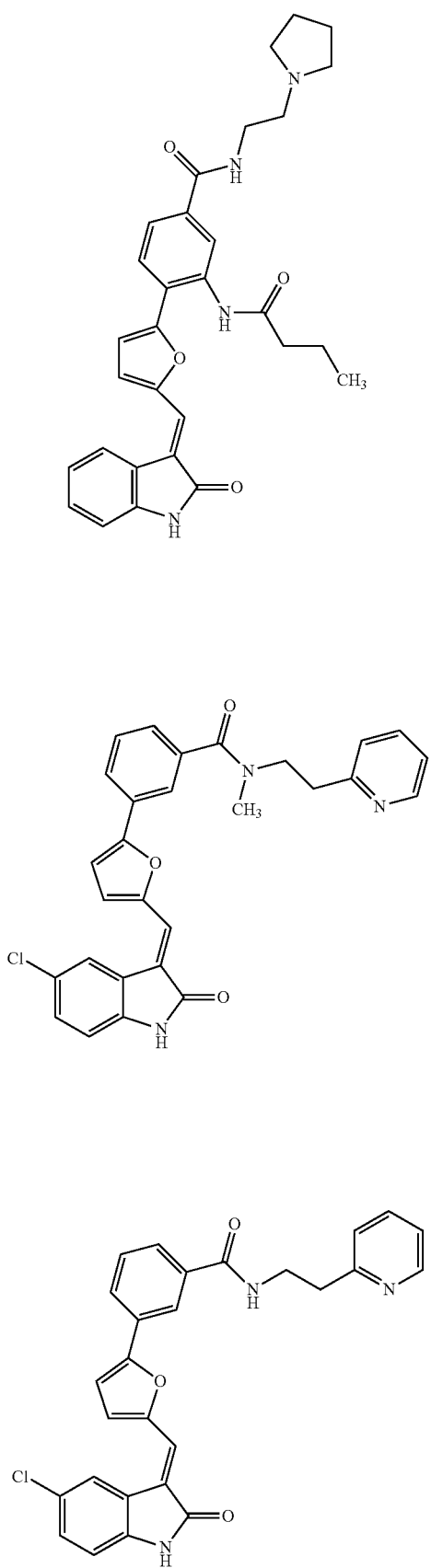
284
-continued
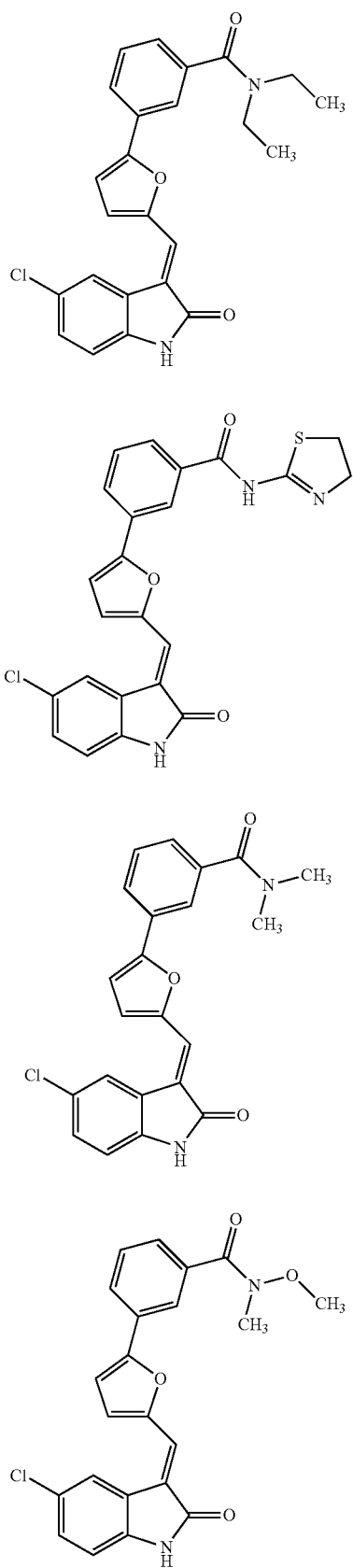

285
-continued
286
-continued
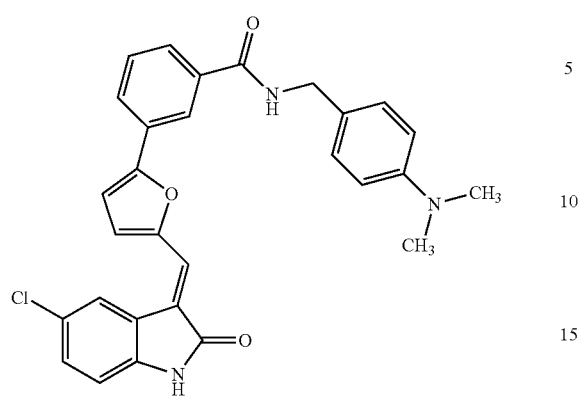
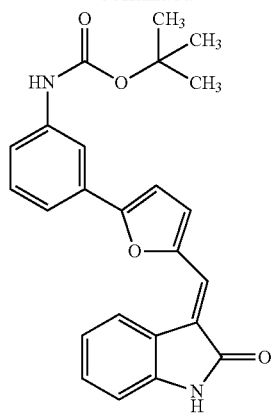
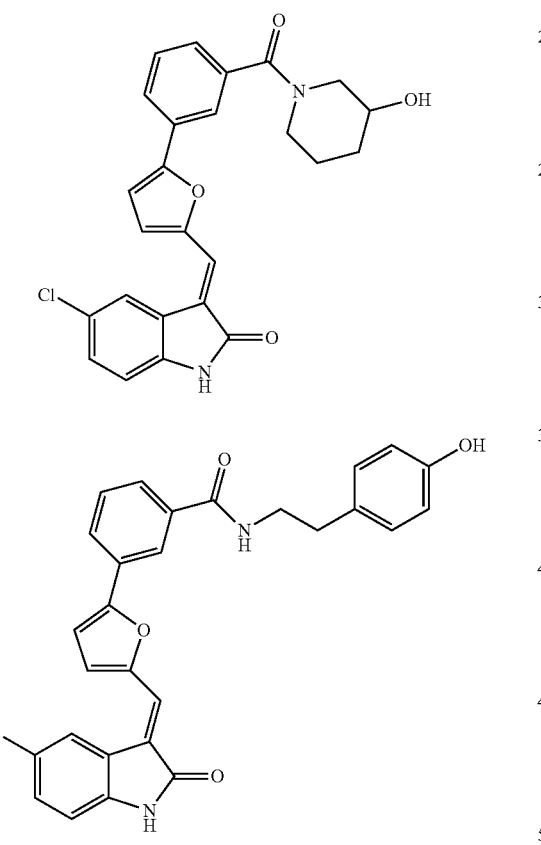
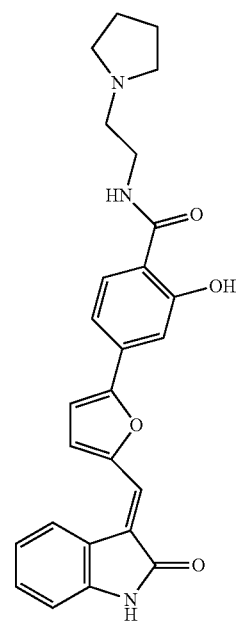
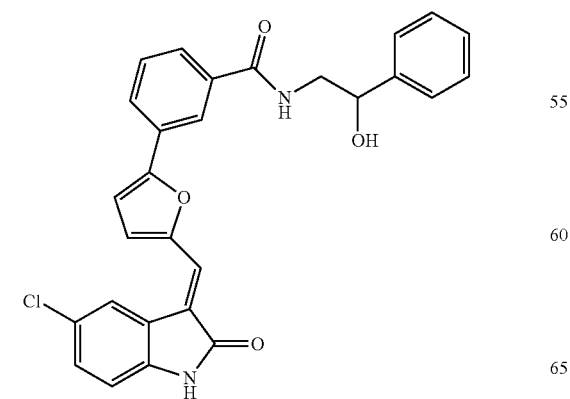
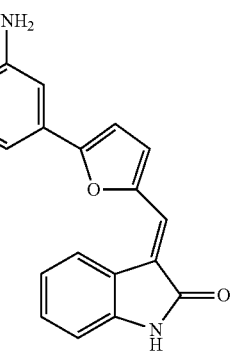

| 287 -continued | 288 -continued |
|---|---|
| 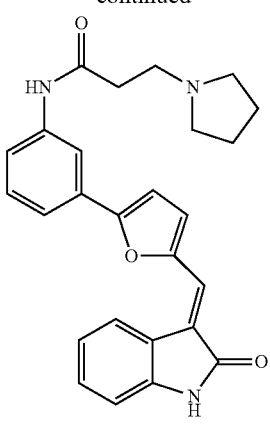 | 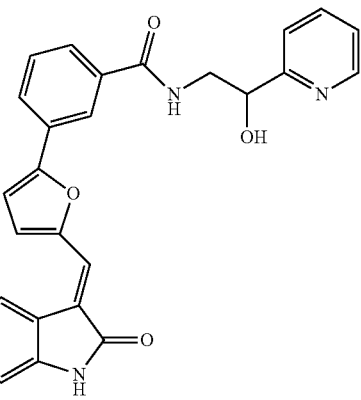 |
| 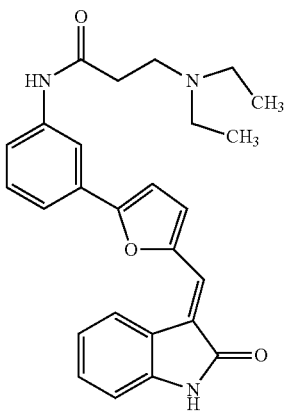 | 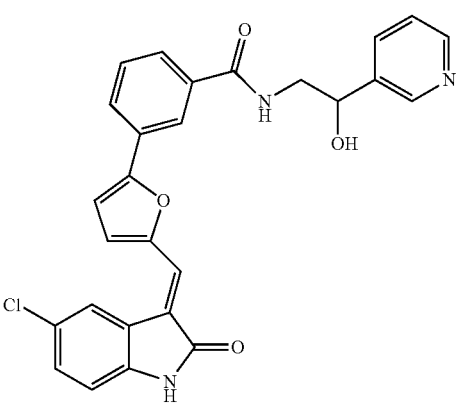 |
| 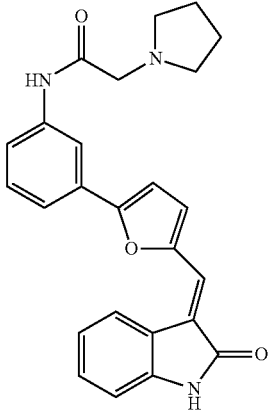 | 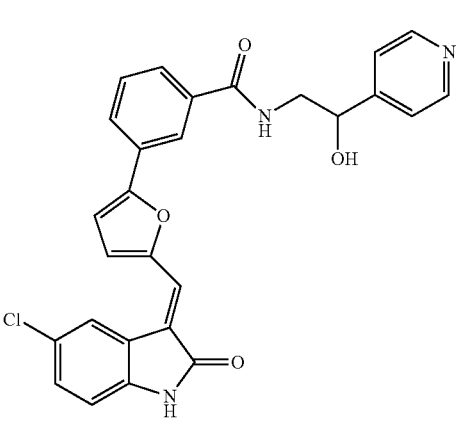 |
| 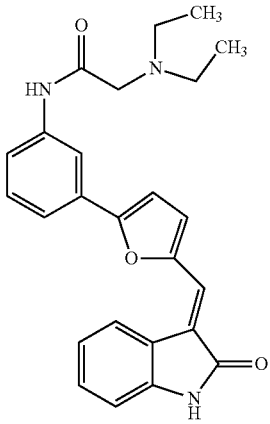 | 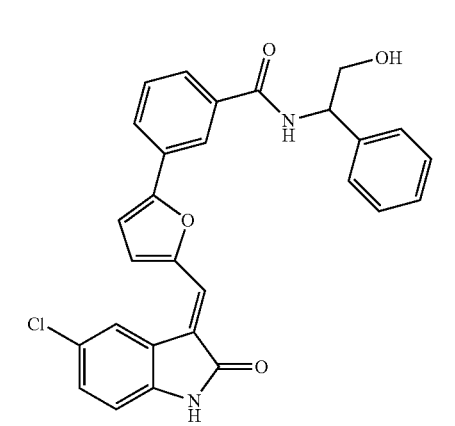 |

289
-continued
290
-continued
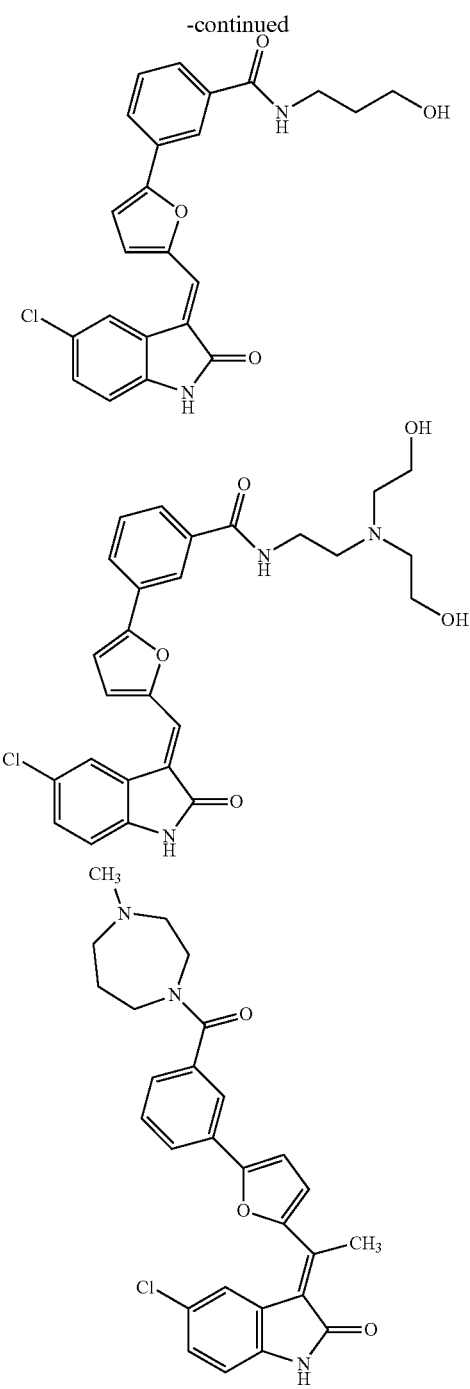
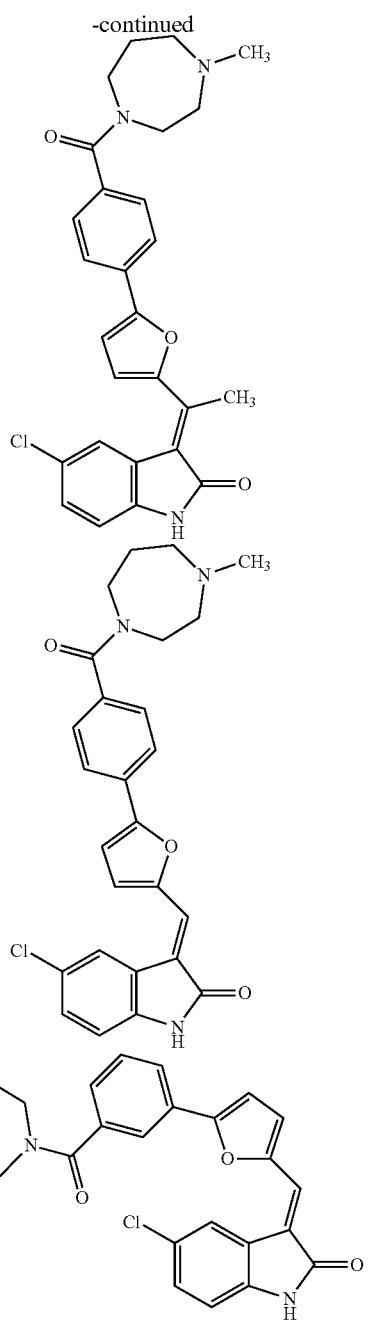
* * * * *